(12) United States Patent
Reinscheid et al.

(10) Patent No.: US 8,318,908 B2
(45) Date of Patent: Nov. 27, 2012

(54) NUCLEIC ACIDS CODING FOR ADHESION FACTOR OF GROUP B STREPTOCOCCUS, ADHESION FACTORS OF GROUP B STREPTOCOCCUS AND FURTHER USES THEREOF

(75) Inventors: Dieter J. Reinscheid, Neu-Ulm (DE); Heike Boisvert, Biberach (DE); Axel Schubert, Neu-Ulm (DE); Bernhard J. Eikmanns, Ulm (DE); Andreas Meinke, Pressbaum (AT)

(73) Assignee: Intercell AG, Vienna (AT)

( * ) Notice: Subject to any disclaimer, the term of this patent is extended or adjusted under 35 U.S.C. 154(b) by 0 days.

(21) Appl. No.: 13/114,615

(22) Filed: May 24, 2011

(65) Prior Publication Data

US 2011/0287013 A1 Nov. 24, 2011

Related U.S. Application Data

(60) Continuation of application No. 12/363,229, filed on Jan. 30, 2009, now Pat. No. 7,960,533, which is a division of application No. 10/531,659, filed as application No. PCT/EP03/11436 on Oct. 15, 2003, now Pat. No. 7,485,710.

(30) Foreign Application Priority Data

Oct. 15, 2002 (EP) .................................... 02023141
Mar. 20, 2003 (EP) .................................... 03006393

(51) Int. Cl.
*A61K 39/395* (2006.01)
*C07K 16/00* (2006.01)
*C12P 21/08* (2006.01)

(52) U.S. Cl. ............... 530/387.1; 530/387.9; 530/388.1; 530/388.2; 530/388.4; 424/130.1

(58) Field of Classification Search ........................ None
See application file for complete search history.

(56) References Cited

U.S. PATENT DOCUMENTS

| 6,191,270 B1 | 2/2001 | Druilhe et al. |
| 7,098,182 B2 | 8/2006 | Le Page et al. |
| 7,485,710 B2 | 2/2009 | Reinscheid et al. |
| 7,960,533 B2 | 6/2011 | Reinscheid et al. |

FOREIGN PATENT DOCUMENTS

| WO | WO-00/06736 A2 | | 2/2000 |
| WO | WO 02/34771 | * | 5/2002 |
| WO | WO-02/092818 A2 | | 11/2002 |

OTHER PUBLICATIONS

Databases EMBL 'Online!, Jul. 1, 2002, Telford et al.: "Nucleic acids and proteins from *Streptococcus* groups a & b," Database accession No. CQ655069.
Glaser et al., Genome sequence of *Streptococcus agalactia*, a pathogen causing invasive neonatal disease. Mol Microbiol. Sep. 2002; 45(6):1499-513.
Jacobsson, A novel family of fibrinogen-binding proteins in *Streptococcus agalactiae*. Vet Microbiol. Oct. 8, 2003;96(1):103-13.
Meehan et al., Affinity purification and characterization of a fibrinogen-binding protein complex which protects mice against lethal challenge with *Streptococcus equi* subsp. equi. Microbiology. Apr. 1998;144 ( Pt 4):993-1003.
Osaki et al., Characterization of *Streptococcus suis* genes encoding proteins homologous to sortase of gram-positive bacteria. J Bacteriol. Feb. 2002;184(4):971-82.
Schubert et al., A fibronogen receptor from group B *Streptococcus* interacts with fibrinogen by repetitive units with novel ligand binding sites. Mol. Microbiol. Oct. 2002;46(2):557-69.
Tettelin et al., Complete genome sequence and comparative genomic analysis of an emerging human pathogen, serotype V *Streptococcus agalactia*. Proc Natl Acad Sci U S A. Sep. 17, 2002;99(19):12391-6. Epub Aug. 28, 2002.

* cited by examiner

*Primary Examiner* — Albert Navarro
(74) *Attorney, Agent, or Firm* — Wolf, Greenfield & Sacks, P.C.

(57) ABSTRACT

The present invention is related to nucleic acids coding for adhesion factors of group B *streptococcus*, adhesion factors of group B *streptococcus* and uses thereof. More particularly, the present invention is related to a polypeptide being such adhesion factors and comprising an amino acid sequence, whereby the amino acid sequence is selected from the group comprising SEQ ID NO 11 to SEQ ID NO 20, and the use of such polypeptide for the manufacture of a vaccine.

9 Claims, 47 Drawing Sheets

```
1
GATCATTAAATAAATCAAGGTTAGTTAGCTTGAAAGATATAAATATATTCCAAAATTCCA
61
AAAAGTAATTGGCATAGTGACAAAAACTATTGCTCCCCTGCTTTAGAAATAATTTATTTT
121
TAATTTAATATTAAAAGTAAACTGAAGAATCTAGTTATATTTAAAAAGTAAAGGTTGCAT
181
TTTAACTAAATTATGTTAAACTACTGTTATGCGATGAGTCGATATGTGGTTTTACCACTA
241
TTGCGCAGGGAGATTATAAACGCAGGAGCGGATCTTGATAAGTTGTGTGAACCTTCTTGT
301
CACACTTGAAAAGGTGCCCTTAGCTTACTACTACTTGTAATTTCTTACAAATTGTGGTAA
361
GTAGCTGAAAAGCAAAAAAGAAAGAACCAGTTTGGTTCTTTCTTTTTTGCATAAATAAGT
421
CACAATTTCCTTCTTAAAATTATGTCTTTACTTAACTTTAATTGAATATGCTACCATCAC
481
ATTCTTTGTAAAATTTTTAAATAATCTAGTTTCTGATGGTTTAGATGAAGTATTAAAAAT
541
ATACTATTACCTCATTGTAAATCTTAATGTTAGTATGACTATCTATCATGCTTTATAATA
601
TTAAAGGAAAATTTAAAAATATCATGTTTTAGATATCAACTATTTAATTTTAAACATACA
661
AATTAATAATAAATTGCAACTAAATAATAAATTATCTTGACATAACTTATAAAATGTTTT
721
AATATATAATCTAAATAAAAGTAATAATAAAATGACTTTTAAAATTTAAAAAAAGTAAGG
                                                          RBS
781
AGAAAATTAATTGTTCAATAAAATAGGTTTTAGAACTTGGAAATCAGGAAAGCTTTGGCT
841         M  F  N  K  I  G  F  R  T  W  K  S  G  K  L  W  L
TTATATGGGAGTGCTAGGATCAACTATTATTTTAGGATCAAGTCCTGTATCTGCTATGGA
     Y  M  G  V  L  G  S  T  I  I  L  G  S  S  P  V  S  A  M  D
901                           Repeat 1 (SEQ ID 21)
TAGTGTTGGAAATCAAAGTCAGGGCAATGTTTTAGAGCGTCGTCAACGTGATGCAGAAAA
     S  V  G  N  Q  S  Q  G  N  V  L  E  R  R  Q  R  D  A  E  N
961          Repeat 2 (SEQ ID 22)                    Repeat 3 (SEQ ID 23)
CAGAAGCCAAGGCAATGTTCTAGAGCGTCGTCAACGCGATGTTGAGAATAAGAGCCAAGG
     R  S  Q  G  N  V  L  E  R  R  Q  R  D  V  E  N  K  S  Q  G
1021                               Repeat 4 (SEQ ID 24)
CAATGTTTTAGAGCGTCGTCAACGTGATGCGGAAAACAAGAGCCAAGGCAATGTTTTAGA
     N  V  L  E  R  R  Q  R  D  A  E  N  K  S  Q  G  N  V  L  E
1081                     Repeat 5 (SEQ ID 25)
GCGTCGTCAACGTGATGCAGAAAACAGAAGCCAAGGCAATGTTCTAGAGCGTCGTCAACG
     R  R  Q  R  D  A  E  N  R  S  Q  G  N  V  L  E  R  R  Q  R
1141                 Repeat 6 (SEQ ID 26)
TGATGCAGAAAACAGAAGCCAAGGCAATGTTCTAGAGCGTCGTCAACGCGATGCAGAAAA
```

Fig. 1-1

```
         D   A   E   N   R   S   Q   G   N   V   L   E   R   R   Q   R   D   A   E   N
1201                    Repeat 7 (SEQ ID 27)                              Repeat 8 (SEQ ID 28)
      CAGAAGCCAAGGTAATGTTCTAGAGCGTCGTCAACGTGATGCAGAAAACAGAAGCCAAGG
         R   S   Q   G   N   V   L   E   R   R   Q   R   D   A   E   N   R   S   Q   G
1261                                         Repeat 9 (SEQ ID 29)
      TAATGTTCTAGAGCGTCGTCAACGTGATGCAGAAAACAGAAGCCAAGGTAATGTTCTAGA
         N   V   L   E   R   R   Q   R   D   A   E   N   R   S   Q   G   N   V   L   E
1321                    Repeat 10 (SEQ ID 30)
      GCGTCGTCAACGCGATGTTGAGAATAAGAGCCAAGGCAATGTTTTAGAGCGTCGTCAACG
         R   R   Q   R   D   V   E   N   K   S   Q   G   N   V   L   E   R   R   Q   R
1381           Repeat 11 (SEQ ID 31)
      TGATGCGGAAAACAAGAGCCAAGGCAATGTTTTAGAGCGTCGTCAACGTGATGCAGAAAA
         D   A   E   N   K   S   Q   G   N   V   L   E   R   R   Q   R   D   A   E   N
1441             Repeat 12 (SEQ ID 32)                                    Repeat 13 (SEQ ID 33)
      CAGAAGCCAAGGCAATGTTTTAGAGCGTCGTCAACGTGATGCAGAAAACAGAAGCCAAGG
         R   S   Q   G   N   V   L   E   R   R   Q   R   D   A   E   N   R   S   Q   G
1501                                         Repeat 14 (SEQ ID 34)
      CAATGTTCTAGAGCGTCGTCAACGTGATGCAGAAAACAGAAGCCAAGGCAATGTTCTAGA
         N   V   L   E   R   R   Q   R   D   A   E   N   R   S   Q   G   N   V   L   E
1561                    Repeat 15 (SEQ ID 35)
      GCGTCGTCAACGTGATGCAGAAAACAGAAGCCAAGGCAATGTTCTAGAGCGTCGTCAACG
         R   R   Q   R   D   A   E   N   R   S   Q   G   N   V   L   E   R   R   Q   R
1621           Repeat 16 (SEQ ID 36)
      CGATGCAGAAAACAGAAGCCAAGGTAATGTTCTAGAGCGTCGTCAACGTGATGCAGAAAA
         D   A   E   N   R   S   Q   G   N   V   L   E   R   R   Q   R   D   A   E   N
1681                  Repeat 17 (SEQ ID 37)                               Repeat 18 (SEQ ID 38)
      CAGAAGCCAAGGCAATGTTTTAGAGCGTCGTCAACGTGATGCAGAAAACAGAAGCCAAGG
         R   S   Q   G   N   V   L   E   R   R   Q   R   D   A   E   N   R   S   Q   G
1741                                            Repeat 19 (SEQ ID 39)
      CAATGTTTTAGAGCGTCGTCAACGTGATGCAGAAAACAGAAGCCAAGGCAATGTTTTAGA
         N   V   L   E   R   R   Q   R   D   A   E   N   R   S   Q   G   N   V   L   E
1801
      GCGTCGTCAACGTGATGCGGAAAACAAGAGCCAAGTAGGTCAACTTATAGGGAAAAATCC
         R   R   Q   R   D   A   E   N   K   S   Q   V   G   Q   L   I   G   K   N   P
1861
      ACTTCTTTCAAAGTCAATTATATCTAGAGAAAATAATCACTCGAGTCAAGGTGACTCTAA
         L   L   S   K   S   I   I   S   R   E   N   N   H   S   S   Q   G   D   S   N
1921
      CAAACAGTCATTCTCTAAAAAAGTATCTCAGGTTACTAATGTAGCTAATAGACCGATGTT
         K   Q   S   F   S   K   K   V   S   Q   V   T   N   V   A   N   R   P   M   L
1981
      AACTAATAATTCTAGAACAATTTCAGTGATAAATAAATTACCTAAAACAGGTGATGATCA
         T   N   N   S   R   T   I   S   V   I   N   K   L   P   K   T   G   D   D   Q
2041
```

Fig. 1-2

```
AAATGTCATTTTTAAACTTGTAGGTTTTGGTTTAATTTTGTTAACAAGTCGCTGCGGTTT
   N  V  I  F  K  L  V  G  F  G  L  I  L  L  T  S  R  C  G  L
2101
GAGACGCAATGAAAATTAAGTATAATCAATCATTTAGTAACTATATATAATGATATATGC
   R  R  N  E  N  *
2161
AATCAATAAAAAGGAATCGGATACGAGATTCCTTTTTATAATTAGGTTGGTTAGGGTGAC
2221
TTTTTTCATTTGGCTATTCTTGAAAGTTTATAAAAATGTAGTTATAATAGTCACATTAAA
2281
ATGTTTTGAAAATATTGATGAACAACATCAACAAATAGAGGTCATTATATGGGATATACC
2341
GTTGCTATCGTAGGTGCTACAGGTGCCGTAGGAACACAAATGATTCGTCAATTAGAACAA
2401
TCGAATTTACCAATAGAACAAGTGAAACTTTTATCATCAAGTCGCTCAGCAGGTAAAATT
2461
TTACATTTTAAAGATGAGGCTATACGTGTTGAAGAGACAACAAAAGAATCATTTTACGAT
2521
GTTGATATTGCCTTGTTTTCAGCTGGTGGATC
```

Fig. 1-3

```
1
GCATAAATAAGTCACAATTTCCTTCTTAAAATTATGTCTTTACTTAACTTTAATTGAATA
61
TGCTACCATCACATTCTTTGTAAAATTTTTAAATAATCTAGTTTCTGATGGTTTAGATGA
121
AGTATTAAAAATATACTATTACCTCATTGTAAATCTTAATGTTAGTATGACTATCTATCA
181
TGCTTTATAATATTAAAGGAAAATTTAAAAATATCATGTTTTAGATATCAACTATTTAAT
241
TTTAAACATACAAATTAATAATAAATTGCAACTAAATAATAAATTATCTTGACATAACTT
301
ATAAAATGTTTTAATATATAATCTAAATAAAAGTAATAATAAAATGACTTTTAAAATTTA
361
AAAAAAGTAAGGAGAAAATTAATTGTTCAATAAAATAGGTTTTAGAACTTGGAAATCAGG
421          RBS              M  F  N  K  I  G  F  R  T  W  K  S  G
AAAGCTTTGGCTTTATATGGGAGTGCTAGGATCAACTATTATTTTAGGATCAAGTTCTGT
    K  L  W  L  Y  M  G  V  L  G  S  T  I  I  L  G  S  S  S  V
481                      Repeat 1 (SEQ ID 40)
ATCTGCTATGGATAGTGTTGGAAATCAAAGTCAGGGCAATGTTTTAGAGCGTCGTCAACG
    S  A  M  D  S  V  G  N  Q  S  Q  G  N  V  L  E  R  R  Q  R
541              Repeat 2 (SEQ ID 41)
CGATGCAGAAAACAGAAGCCAAGGCAATGTTTTAGAGCGTCGTCAACGTGATGCAGAAAA
    D  A  E  N  R  S  Q  G  N  V  L  E  R  R  Q  R  D  A  E  N
                  Repeat 3 (SEQ ID 42)                  Repeat 4 (SEQ ID 43)
601
CAGAAGCCAAGGCAATGTTTTAGAGCGTCGTCAACGTGATGCAGAAAACAGAAGCCAAGG
    R  S  Q  G  N  V  L  E  R  R  Q  R  D  A  E  N  R  S  Q  G
661                                    Repeat 5 (SEQ ID 44)
TAATGTTCTAGAGCGTCGTCAACGCGATGTTGAAAATAAAAGCCAAGGCAATGTTTTAGA
    N  V  L  E  R  R  Q  R  D  V  E  N  K  S  Q  G  N  V  L  E
721                            Repeat 6 (SEQ ID 45)
GCGTCGTCAACGTGATGCAGAAAACAGAAGCCAAGGTAATGTTCTAGAGCGTCGTCAACG
    R  R  Q  R  D  A  E  N  R  S  Q  G  N  V  L  E  R  R  Q  R
781          Repeat 7 (SEQ ID 46)
CGATGTTGAAAATAAAAGCCAAGGCAATGTTTTAGAGCGTCGTCAACGTGATGCAGAAAA
    D  V  E  N  K  S  Q  G  N  V  L  E  R  R  Q  R  D  A  E  N
841          Repeat 8 (SEQ ID 47)                        Repeat 9 (SEQ ID 48)
CAGAAGCCAAGGTAATGTTCTAGAGCGTCGTCAACGTGATGCAGAAAACAGAAGCCAAGG
    R  S  Q  G  N  V  L  E  R  R  Q  R  D  A  E  N  R  S  Q  G
901                                    Repeat 10 (SEQ ID 49)
CAATGTTTTAGAGCGTCGTCAACGCGATGCAGAAAACAGAAGCCAAGGCAATGTTCTAGA
    N  V  L  E  R  R  Q  R  D  A  E  N  R  S  Q  G  N  V  L  E
```

Fig. 3-1

```
961                           Repeat 11 (SEQ ID 50)
GCGTCGTCAACGTGATGCTGAAAACAAAAGCCAAGGCAATGTTTTAGAGCGTCGTCAACG
   R  R  Q  R  D  A  E  N  K  S  Q  G  N  V  L  E  R  R  Q  R
1021         Repeat 12 (SEQ ID 51)
TGATGCAGAAAACAGAAGCCAAGGCAATGTTTTAGAGCGTCGTCAACGTGATGCTGAAAA
   D  A  E  N  R  S  Q  G  N  V  L  E  R  R  Q  R  D  A  E  N
1081           Repeat 13 (SEQ ID 52)              Repeat 14 (SEQ ID 53)
CAGAAGCCAAGGCAATGTTTTAGAGCGTCGTCAACGCGATGCAGAAAACAGAAGCCAAGG
   R  S  Q  G  N  V  L  E  R  R  Q  R  D  A  E  N  R  S  Q  G
1141                                    Repeat 15 (SEQ ID 54)
TAATGTTCTAGAGCGTCGTCAACGTGATGCGGAAAACAAGAGCCAAGGCAATGTTTTAGA
   N  V  L  E  R  R  Q  R  D  A  E  N  K  S  Q  G  N  V  L  E
1201                      Repeat 16 (SEQ ID 55)
GCGTCGTCAACGTGATGCAGAAAACAGAAGCCAAGGCAATGTTTTAGAGCGTCGTCAACG
   R  R  Q  R  D  A  E  N  R  S  Q  G  N  V  L  E  R  R  Q  R
1261         Repeat 17 (SEQ ID 56)
CGATGTTGAGAATAAGAGCCAAGGCAATGTTTTAGAGCGTCGTCAACGTGATGCGGAAAA
   D  V  E  N  K  S  Q  G  N  V  L  E  R  R  Q  R  D  A  E  N
1321
CAAGAGCCAAGTAGGTCAACTTATAGGGAAAAATCCACTTCTTTCAAAGTCAATTATATC
   K  S  Q  V  G  Q  L  I  G  K  N  P  L  L  S  K  S  I  I  S
1381
TAGAGAAAATAATCACTCTAGTCAAGGTGACTCTAACAAACAGTCATTCTCTAAAAAAGT
   R  E  N  N  H  S  S  Q  G  D  S  N  K  Q  S  F  S  K  K  V
1441
ATCTCAGGTTACTAATGTAGCTAATAGACCGATGTTAACTAATAATTCTAGAACAATTTC
   S  Q  V  T  N  V  A  N  R  P  M  L  T  N  N  S  R  T  I  S
1501
AGTGATAAATAAATTACCTAAAACAGGTGATGATCAAAATGTCATTTTTAAACTTGTAGG
   V  I  N  K  L  P  K  T  G  D  D  Q  N  V  I  F  K  L  V  G
1561
TTTTGGTTTAATTTTGTTAACAAGTCGCTGCGGTTTGAGACGCAATGAAAATTAAGTATA
   F  G  L  I  L  L  T  S  R  C  G  L  R  R  N  E  N  *
1621
ATCAATCATTTAGTAACTATATATAATGATATATGCAATCAATAAAAAGGAATCGGATAC
GAGATTCCTTTTTATAATTAGGTTGGTTAGGGTGACTTTTTTCATTTGGCTATTCTTGAA
1741            1761              1781
AGTTTATAAAAATGTAGTATAATAGTCACATTAAAATGTTTTGAAAATATTGATGAACAA
1801
CATCAACAAATAGAGGTCAT
```

Fig. 3-2

1
GCATAAATAAGTCACAATTTCCTTCTAAAAATTATGTCTTTACTTAACTTTAATTGAATA
61
TGCTACCATCACATTCTTTGTAAAATTTTTAAATAATCTAGTTTCTGATGGTTTAGATGA
121
AGTATTAAAAATATACTATTATCTCATTGTAAATCCTAATGTTAGTATGACTATCTATCA
181
TGTTTTATAATATTGAAGGAAAATTTAAAAATATCATGTTTTAGATATCAACTATTTAAT
241
TTAAACATACAAATTAATAATAAATTGCAATTAAATAACAAATTACCTTGACATAAATT
301
ATAAAATGTTTTAATATATATAATCTAAATAAAAATAATAATAAAATGACTTTTAAAATT
361
TAAAAAAGTAAGGAGAAAATTAATTGTTCAATAAAATAGGTTTTAGAACTTGGAAATCA
421        RBS        *M  F  N  K  I  G  F  R  T  W  K  S*
GGAAAGCTTTGGCTTTATATGGGAGTGCTAGGATCAACTATTATTTTAGGATCAAGTCCT
 *G  K  L  W  L  Y  M  G  V  L  G  S  T  I  I  L  G  S  S  P*
481                        Repeat 1 (SEQ ID 57) →
GTATCTGCTATGGATAGTGTTGGAAATCAAAGTCAAGGTAATGTTCTAGAGCGTCGTCAA
 *V  S  A  M  D  S  V  G  N  Q  S  Q  G  N  V  L  E  R  R  Q*
541         Repeat 2 (SEQ ID 58) →
CGTGATGCGGATAACAAGAGCCAAGGCAATGTTCTAGAACGTCGTCAACGCGATGTAGAA
  R  D  A  D  N  K  S  Q  G  N  V  L  E  R  R  Q  R  D  V  E
601            → Repeat 3 (SEQ ID 59)
AACAGAAGCCAAGGCAATGTTCTAGAGCGTCGTCAACGCGATGCGGATAACAAGAGCCAA
  N  R  S  Q  G  N  V  L  E  R  R  Q  R  D  A  D  N  K  S  Q
          → Repeat 4 (SEQ ID 60)                Repeat 5 (SEQ ID 61)  →
GGCAATGTTTTAGAGCGCCGCCAACGCGATGCAGAAAACAAAAGTCAGGCAATGTTCTA
  G  N  V  L  E  R  R  Q  R  D  A  E  N  K  S  Q  G  N  V  L
721              Repeat 6 (SEQ ID 62) →
GAACGTCGTCAACGTGATGTTGAGAATAAGAGCCAAGGCAATGTTCTAGAGCGTCGCCAA
  E  R  R  Q  R  D  V  E  N  K  S  Q  G  N  V  L  E  R  R  Q
781         Repeat 7 (SEQ ID 63) →
CGTGATGCAGAAAACAAAAGTCAGGGTAATGTTCTAGAGCGTCGTCAACGCGATGCAGAT
  R  D  A  E  N  K  S  Q  G  N  V  L  E  R  R  Q  R  D  A  D
841              → Repeat 8 (SEQ ID 64)
AACAAGAGCCAAGGTAATGTTCTAGAACGTCGTCAACGCGATGTGGAAAACAAAAGTCAG
  N  K  S  Q  G  N  V  L  E  R  R  Q  R  D  V  E  N  K  S  Q
       → Repeat 9 (SEQ ID 65)                  Repeat 10 (SEQ ID 66) →
GGCAATGTTCTAGAACGTCGTCAACGTGATGTTGAGAATAAGAGCCAAGGCAATGTTCTA
  G  N  V  L  E  R  R  Q  R  D  V  E  N  K  S  Q  G  N  V  L
961              Repeat 11 (SEQ ID 67) →
GAGCGTCGCCAACGTGATGCAGAAAACAAAAGTCAGGGTAATGTTCTAGAGCGTCGTCAA
  E  R  R  Q  R  D  A  E  N  K  S  Q  G  N  V  L  E  R  R  Q

Fig. 4-1

```
1021        Repeat 12 (SEQ ID 68)
CGCGATGCAGATAACAAGAGCCAAGGTAATGTTCTAGAACGTCGTCAACGCGATGTGGAA
 R   D   A   D   N   K   S   Q   G   N   V   L   E   R   R   Q   R   D   V   E
1081                  Repeat 13 (SEQ ID 69)
AACAAAAGTCAGGGCAATGTTCTAGAGCGTCGCCAACGTGATGTTGAGAACAAGAGCCAA
 N   K   S   Q   G   N   V   L   E   R   R   Q   R   D   V   E   N   K   S   Q
1141
GTAGGTCAACTTATAGGGAAAAATCCACTTCTTTCAAAGTCAACTATATCTAGAGAAAAT
 V   G   Q   L   I   G   K   N   P   L   L   S   K   S   T   I   S   R   E   N
1201
AATCACTCTAGTCAAGGTGACTCTAACAAACAGTCATTCTCTAAAAAAGTATCTCAGGTT
 N   H   S   Q   G   D   S   N   K   Q   S   F   S   K   K   V   S   Q   V
1261
ACTAATGTAGCTAATAGACCAATGTTAACTAATAATTCTAGAACAATTTCAGTGATAAAT
 T   N   V   A   N   R   P   M   L   T   N   N   S   R   T   I   S   V   I   N
1321
AAATTACCTAAAACAGGTGATGATCAAAATGTCATTTTTAAACTTGTAGGTTTTGGTTTA
 K   L   P   K   T   G   D   D   Q   N   V   I   F   K   L   V   G   F   G   L
1381
ATTTTGTTAACAAGTCGCTGCGGTTTGAGACGCAATGAAAATTAAGTATAATCAATCATT
 I   L   L   T   S   R   C   G   L   R   R   N   E   N   *
1441
TAGTAACTATTATAATGATATATGCAATCAATAAAAAGGAATCGGATACAAGATTCCTTT TTATAATTAGGTTGGTTAGGGTGACTTTTTCATTTGGCTATTCTTGAAAGTTTATAAAAA
1561
TGTAGTATAATAGTCACATTAAAATGTTTTGAAAATATTGATGAACAACATCAACAAATA
1621
GAGGTCAT
```

Fig. 4-2

```
1
GCATAAATAAGTCACCAATTTCCCTTCTTAAAATTATGTCTTTACTTAACTTTAATTGAA
61
TATGCTACCATCACATTCTTTGTAAAATTTTTAAATAATCTAGTTTCTGATGGTTTAGAT
121
GAAGTATTAAAAATATACTATTACCTCATTGTAAATCTTAATGTTAGTATGACTATCTAT
181
CATGCTTTATAATATTAAAGGAAAATTTAAAAATATCATGTTTTAGATATCAACTATTTA
241
ATTTTAAACATACAAATTAATAATAAATTGCAACTAAATAATAAATTATCTTGACATAAC
301
TTATAAAATGTTTTAATATATAATCTAAATAAAAGTAATAATAAAATGACTTTTAAAATT
361
TAAAAAAGTAAGGAGAAAATTAATTGTTCAATAAAATAGGTTTTAGAACTTGGAAATCA
421            RBS             M  F  N  K  I  G  F  R  T  W  K  S
GGAAAGCTTTGGCTTTATATGGGAGTGCTAGGATCAACTATTATTTTAGGATCAAGTCCT
    G  K  L  W  L  Y  M  G  V  L  G  S  T  I  I  L  G  S  S  P
481                         Repeat 1 (SEQ ID 70)
GTATCTGCTATGGATAGTGTTGGAAATCAAAGTCAGGGCAATGTTTTAGAGCGTCGTCAA
    V  S  A  M  D  S  V  G  N  Q  S  Q  G  N  V  L  E  R  R  Q
541          Repeat 2 (SEQ ID 71)
CGCGATGCAGAAAACAGAAGCCAAGGTAATGTTCTAGAGCGTCGTCAACGCGATGCAGAA
    R  D  A  E  N  R  S  Q  G  N  V  L  E  R  R  Q  R  D  A  E
601              Repeat 3 (SEQ ID 72)
AACAGAAGCCAAGGTAATGTTCTAGAGCGTCGTCAACGTGATGCGGAAAACAAGAGCCAA
    N  R  S  Q  G  N  V  L  E  R  R  Q  R  D  A  E  N  K  S  Q
661
GTAGGTCAACTTATAGGGAAAAATCCACTTCTTTCAAAGTCAATTATATCTAGAGAAAAT
    V  G  Q  L  I  G  K  N  P  L  L  S  K  S  I  I  S  R  E  N
721
AATCACTCTAGTCAAGGTGACTCTAACAAACAGTCATTCTCTAAAAAAGTATCTCAGGTT
    N  H  S  S  Q  G  D  S  N  K  Q  S  F  S  K  K  V  S  Q  V
781
ACTAATGTAGCTAATAGACCGATGTTAACTAATAATTCTAGAACAATTTCAGTGATAAAT
    T  N  V  A  N  R  P  M  L  T  N  N  S  R  T  I  S  V  I  N
841
AAATTACCTAAAACAGGTGATGATCAAAATGTCATTTTTAAACTTGTAGGTTTTGGTTTA
    K  L  P  K  T  G  D  D  Q  N  V  I  F  K  L  V  G  F  G  L
901
ATTTTGTTAACAAGTCGCTGCGGTTTGAGACGCAATGAAAATTAAGTATAATCAATCATT
    I  L  L  T  S  R  C  G  L  R  R  N  E  N  *
961
TAGTAACTATATATAATGATATATGCAATCAATAAAAAGGAATCGGATACGAGATTCCTT TTTATAATTAGGTTGGTTAGGGTGACTTTTTTCATTTGGCTATTCTTGAAAGTTTATAAA
1081
AATGTAGTATAATAGTCACATTAAAATGTTTTGAAAATATTGATGAACAACATCAACAAA
1141
TAGAGGTCAT
```

Fig. 5

1
GCATAAATAAGTCACAATTTCCTTCTTAAAATTATGTCTTTACTTAACTTTAATTGAATA
61
TGCTACCATCACATTCTTTGTAAAATTTTTAAATAATCTAGTTTCTGATGGTTTAGATGA
121
AGTATTAAAAATATACTATTACCTCATTGTAAATCTTAATGTTAGTATGACTATCTATCA
181
TGCTTTATAATATTAAAGGAAAATTTAAAAATATCATGTTTTAGATATCAACTATTTAAT
241
TTTAAACATACAAATTAATAATAAATTGCAACTAAATAATAAATTATCTTGACATAACTT
301
ATAAAATGTTTTAATATATAATCTAAATAAAAGTAATAATAAAATGACTTTTAAAATTTA
361
AAAAAAGTAAGGAGAAAATTAATTGTTCAATAAAATAGGTTTTAGAACTTGGAAATCAGG
421    RBS         *M  F  N  K  I  G  F  R  T  W  K  S  G*
AAAGCTTTGGCTTTATATGGGAGTGCTAGGATCAACTATTATTTTAGGATCAAGTCCTGT
       *K  L  W  L  Y  M  G  V  L  G  S  T  I  I  L  G  S  S  P  V*
481                    Repeat 1 (SEQ ID 73) ⟶
ATCTGCTATGGATAGTGTTGGAAATCAAAGCCAAGGCAATGTTCTAGAGCGTCGTCAACG
   *S  A  M  D  S  V  G  N  Q  S  Q  G  N  V  L  E  R  R  Q  R*
541                Repeat 2 (SEQ ID 74) ⟶
CGATGCAGAAAACAGAAGCCAAGGTAATGTTTTAGAACGTCGTCAACGCGATGTTGAGAA
    *D  A  E  N  R  S  Q  G  N  V  L  E  R  R  Q  R  D  V  E  N*
601          ⟶ Repeat 3 (SEQ ID 75)                    Repeat 4 (SEQ ID 76)  ⟶
CAAGAGCCAAGGTAATGTTTTAGAGCGTCGCCAACGTGATGCGGAAAACAAAAGTCAGGG
    *K  S  Q  G  N  V  L  E  R  R  Q  R  D  A  E  N  K  S  Q  G*
661                            Repeat 5 (SEQ ID 77) ⟶
CAATGTTTTAGAGCGTCGTCAACGTGATGCAGAAAACAGAAGCCAAGGTAATGTTCTAGA
    *N  V  L  E  R  R  Q  R  D  A  E  N  R  S  Q  G  N  V  L  E*
721                Repeat 6 (SEQ ID 78) ⟶
GCGTCGTCAACGCGATGTTGAGAATAAGAGCCAAGGCAATGTTCTAGAGCGTCGTCAACG
    *R  R  Q  R  D  V  E  N  K  S  Q  G  N  V  L  E  R  R  Q  R*
781        Repeat 7 (SEQ ID 79) ⟶
CGATGTTGAGAATAAGAGCCAAGGTAATGTTCTAGAGCGTCGTCAACGCGATGTTGAGAA
    *D  V  E  N  K  S  Q  G  N  V  L  E  R  R  Q  R  D  V  E  N*
841          ⟶ Repeat 8 (SEQ ID 80)                   Repeat 9 (SEQ ID 81)  ⟶
TAAGAGCCAAGGTAATGTTCTAGAGCGTCGTCAACGTGATGCGGAAAACAAGAGCCAAGG
    *K  S  Q  G  N  V  L  E  R  R  Q  R  D  A  E  N  K  S  Q  G*
901                           Repeat 10 (SEQ ID 82) ⟶
CAATGTTCTAGAGCGTCGTCAACGCGATGCAGAAAACAGAAGCCAAGGTAATGTTTTAGA
    *N  V  L  E  R  R  Q  R  D  A  E  N  R  S  Q  G  N  V  L  E*
961
GCGTCGCCAACATGATGTTGAGAATAAGAGTCAAGTAGGTCAACTTATAGGGAAAAATCC
    *R  R  Q  H  D  V  E  N  K  S  Q  V  G  Q  L  I  G  K  N  P*
1021
ACTTTTTTCAAAGTCAACTGTATCTAGAGAAAATAATCACTCTAGTCAAGGTGACTCTAA
    *L  F  S  K  S  T  V  S  R  E  N  N  H  S  S  Q  G  D  S  N*
1081

Fig. 6-1

```
CAAACAGTCATTCTCTAAAAAAGTATCTCAGGTTACTAATGTAGCTAATAGACCGATGTT
  K  Q  S  F  S  K  K  V  S  Q  V  T  N  V  A  N  R  P  M  L
1141
AACTAATAATTCTAGAACAATTTCAGTGATAAATAAATTACCTAAAACAGGTGATGATCA
  T  N  N  S  R  T  I  S  V  I  N  K  L  P  K  T  G  D  D  Q
1201
AAATGTCATTTTTAAACTTGTAGGTTTTGGTTTAATTTTATTAACAAGTCTCTGCGGTTT
  N  V  I  F  K  L  V  G  F  G  L  I  L  L  T  S  L  C  G  L
1261
GAGACGCAATGAAAATTAAGTATAATCAACCATTTAGTAACTATTATAATGATATATGCA
  R  R  N  E  N  *
1321
ATCAATAAAAAGGAATCGAATACGAGATTCCTTTTTATAATTAGGTTGGTTAGGGTGAC
1381
TTTTTTCATTTGGCTATTCTTGAAAGTTTATAAAAATGTAGTATAATAGTCACATTAAAA
1441
TGTTTTGAAAATATTGATGAACAACATCATCAAATAGAGGTCAT
```

Fig. 6-2

```
1
GCATAAATAAGTCACAATTTCCTTCTAAAAATTATGTCTTTACTTAACTTTAATTGAATA
61
TGCTACCATCACATTCTTTGTAAAATTTTTAAATAACCTAGTTTCTGATGGTTTAGATGA
121
AGTATTAAAAATATACTATTATCTCATTGTAAATCCTAATGTTAGTATGACTATCTATCA
181
TGTTTTATAATATTGAAGGAAAATTTAAAAATATCATGTTTTAGATATCAACTATTTAAT
241
TTTAAACATACAAATTAATAATAAATTGCAATTAAATAACAAATTACCTTGACATAAATT
301
ATAAAATGATTTAATATATATAATCTAAATAAAAATAATAATAAAATGACTTTTAAAATT
361
TAAAAAAGTAAGGAGAAAATTAATTGTTCAATAAAATAGGTTTTAGAACTTGGAAATCA
421            RBS           M  F  N  K  I  G  F  R  T  W  K  S
GGAAAGCTTTGGCTTTATATGGGAGTGCTAGGATCAACTATTATTTAGGATCAAGTCCT
       G  K  L  W  L  Y  M  G  V  L  G  S  T  I  I  L  G  S  S  P
481                           Repeat 1 (SEQ ID 83)
GTATCTGCTATGGATAGTGTTGGAAATCAAAGTCAAGGTAATGTTCTAGAGCGTCGCCAA
       V  S  A  M  D  S  V  G  N  Q  S  Q  G  N  V  L  E  R  R  Q
541            Repeat 2 (SEQ ID 84)
CGTGATGCGGATAACAAGAGCCAAGGTAATGTTTTAGAGCGTCGCCAACGTGATGCAGAT
       R  D  A  D  N  K  S  Q  G  N  V  L  E  R  R  Q  R  D  A  D
601                    Repeat 3 (SEQ ID 85)
AACAAAAGTCAGGGCAATGTTCTAGAACGTCGCCAACGTGATGTTGATAACAAGAGCCAA
       N  K  S  Q  G  N  V  L  E  R  R  Q  R  D  V  D  N  K  S  Q
       Repeat 4 (SEQ ID 86)                    Repeat 5 (SEQ ID 87)
GGTAACGTTCTAGAGCGTCGCCAACGCGATGCTGATAACAAGAGCCAAGGTAATGTTTTA
       G  N  V  L  E  R  R  Q  R  D  A  D  N  K  S  Q  G  N  V  L
721                           Repeat 6 (SEQ ID 88)
GAGCGCCGCCAACGCGATGCAGATAACAAAAGTCAAGGTAATGTTCTAGAGCGTCGCCAA
       E  R  R  Q  R  D  A  D  N  K  S  Q  G  N  V  L  E  R  R  Q
781            Repeat 7 (SEQ ID 89)
CGCGATGTTGATAACAAGAGCCAGGGTAATGTTTTAGAGCGTCGCCAACGCGATGCAGAT
       R  D  V  D  N  K  S  Q  G  N  V  L  E  R  R  Q  R  D  A  D
841                    Repeat 8 (SEQ ID 90)
AACAAAAGTCAGGGTAATGTTTAGAGCGTCGCCAACGCGATGTTGATAACAAAAGCCAA
       N  K  S  Q  G  N  V  L  E  R  R  Q  R  D  V  D  N  K  S  Q
       Repeat 9 (SEQ ID 91)                    Repeat 10 (SEQ ID 92)
GGTAATGTTTTAGAGCGTCGCCAACGTGATGCTGATAACAAAAGTCAGGGCAATGTTCTA
       G  N  V  L  E  R  R  Q  R  D  A  D  N  K  S  Q  G  N  V  L
961                    Repeat 11 (SEQ ID 93)
GAGCGTCGCCAACGTGATGCGGATAACAAAAGCCAAGGTAATGTTCTAGAGCGTCGCCAA
       E  R  R  Q  R  D  A  D  N  K  S  Q  G  N  V  L  E  R  R  Q
1021           Repeat 12 (SEQ ID 94)
CGCGATGCGGATAACAAAAGTCAGGGCAATGTTTAGAGCGTCGCCAACGTGATGCTGAT
       R  D  A  D  N  K  S  Q  G  N  V  L  E  R  R  Q  R  D  A  D
```

Fig. 7-1

```
1081                        Repeat 13  (SEQ ID 95)
AACAAAAGTCAAGGTAATGTTCTAGAGCGTCGCCAACGCGATGCAGATAACAAAAGCCAA
 N   K   S   Q   G   N   V   L   E   R   R   Q   R   D   A   D   N   K   S   Q
       Repeat 14  (SEQ ID 96)                          Repeat 15  (SEQ ID 97)
GGTAATGTTCTAGAGCGTCGCCAACGCGATGCTGATAACAAAAGTCAAGGTAATGTTCTA
 G   N   V   L   E   R   R   Q   R   D   A   D   N   K   S   Q   G   N   V   L
1201                                        Repeat 16  (SEQ ID 98)
GAGCGTCGCCAACGTGATGCTGATAACAAGAGCCAAGGCAATGTTCTTGAGCGTCGTCAA
 E   R   R   Q   R   D   A   D   N   K   S   Q   G   N   V   L   E   R   R   Q
1261           Repeat 17  (SEQ ID 99)
CGCGATGTCGATAACAAAAGTCAGGGTAATGTTTTAGAGCGTCGCCAACGTGATGCGGAT
 R   D   V   D   N   K   S   Q   G   N   V   L   E   R   R   Q   R   D   A   D
1321                Repeat 18  (SEQ ID 100)
AACAAGAGTCAAGGTAATGTTTTAGAGCGTCGCCAACGCGATGCGGATAACAAGAGCCAA
 N   K   S   Q   G   N   V   L   E   R   R   Q   R   D   A   D   N   K   S   Q
       Repeat 19  (SEQ ID 101)                         Repeat 20  (SEQ ID 102)
GGTAATGTTTTAGAGCGTCGCCAACGCGATGCGGATAACAAGAGTCAAGGTAATGTTTTA
 G   N   V   L   E   R   R   Q   R   D   A   D   N   K   S   Q   G   N   V   L
1441                                 Repeat 21  (SEQ ID 103)
GAGCGTCGCCAACGCGATGCGGATAACAAGAGCCAAGGTAATGTTTTAGAGCGTCGCCAA
 E   R   R   Q   R   D   A   D   N   K   S   Q   G   N   V   L   E   R   R   Q
1501          Repeat 22  (SEQ ID 104)
CGCGATGCAGATAACAAAAGTCAAGGTAATGTTTTAGAGCGTCGCCAACGCGATGCTGAT
 R   D   A   D   N   K   S   Q   G   N   V   L   E   R   R   Q   R   D   A   D
1561              Repeat 23  (SEQ ID 105)
AACAAGAGCCAAGGTAATGTTTTAGAGCGTCGTCAACGTGATGCAGATAACAAAAGTCAG
 N   K   S   Q   G   N   V   L   E   R   R   Q   R   D   A   D   N   K   S   Q
       Repeat 24  (SEQ ID 106)                         Repeat 25  (SEQ ID 107)
GGCAATGTTTTAGAGCGTCGTCAACGTGATGCGGATAACAAGAGCCAAGGTAATGTTTTA
 G   N   V   L   E   R   R   Q   R   D   A   D   N   K   S   Q   G   N   V   L
1681                                 Repeat 26  (SEQ ID 108)
GAGCGTCGCCAACGTGATGCGGATAACAAGAGCCAGGGCAATGTTCTAGAACGTCGTCAA
 E   R   R   Q   R   D   A   D   N   K   S   Q   G   N   V   L   E   R   R   Q
1741          Repeat 27  (SEQ ID 109)
CGTGATGCGGATAACAAGAGCCAAGGTAACGTTTTAGAGCGTCGCCAACGTGATGCGGAT
 R   D   A   D   N   K   S   Q   G   N   V   L   E   R   R   Q   R   D   A   D
1801                   Repeat 28  (SEQ ID 110)
AACAAGAGCCAGGGCAATGTTTTAGAGCGCCGCCAACGCGATGCAGATAACAAAAGTCAA
 N   K   S   Q   G   N   V   L   E   R   R   Q   R   D   A   D   N   K   S   Q
       Repeat 29  (SEQ ID 111)                         Repeat 30  (SEQ ID 112)
GGTAATGTTCTAGAGCGTCGCCAACGCGATGCAGATAACAAGAGCCAGGGTAATGTTCTA
 G   N   V   L   E   R   R   Q   R   D   A   D   N   K   S   Q   G   N   V   L
1921
GAGCGTCGCCAACGCGATGCGGAAAACAAAGTCAAGTAGGTCAACTTATAGGGAAAAAT
 E   R   R   Q   R   D   A   E   N   K   S   Q   V   G   Q   L   I   G   K   N
1981
```

Fig. 7-2

```
CCACTTTTTTCAAAGTCAACTGTATCTAGAGAAAATAATCACTCTAGTCAAGGTGACTCT
  P  L  F  S  K  S  T  V  S  R  E  N  N  H  S  S  Q  G  D  S
2041
AACAAACAGTCATTCTCTAAAAAAATATCTCAGGTTACTAATGTAGCTAATGGACCGATG
  N  K  Q  S  F  S  K  K  I  S  Q  V  T  N  V  A  N  G  P  M
2101
TTAACTAATAATTCTAGAACAATTTCAGTGATAAATAAATTACCTAAAACAGGTGATGAT
  L  T  N  N  S  R  T  I  S  V  I  N  K  L  P  K  T  G  D  D
2161
CAAAATGTCATTTTTAAACTTGTAGGTTTTGGTTTAATTTTGTTAACAAGTCTCTGCGGT
  Q  N  V  I  F  K  L  V  G  F  G  L  I  L  L  T  S  L  C  G
2221
TTGAGACGCAATGAAAATTAAGTATAATCAACCATTTAGTAACTATTATAATGATATATG
  L  R  R  N  E  N  *
2281           ──────────────────→ ←──────────────
CAATCAATAAAAAGGAATCGAATACGAGATTCCTTTTTATAATTAGGTTGGTTAGGGTG
2341                2361                2381
ACTTTTTTCATTTGGCTATTCTTGAAAGTTTATAAAAATGTAGTATAATAGTCACATTAA
2401                2421                2441
AATGTTTTGAAAATATTGATGAACAACATCATCAAATAGAGGTCAT
```

Fig. 7-3

GNVLERRQRDAENRSQ (SeqID 204)
GLSQNRDVRENQRARE (SeqID205)
GNVLERRQRDAENRSQ
GLSQNRDVRENQRARE
ANVLERRQRDAENRSQ (SeqID 206)
GAVLERRQRDAENRSQ (SeqID 207)
GNALERRQRDAENRSQ (SeqID 208)
GNVAERRQRDAENRSQ (SeqID 209)
GNVLARRQRDAENRSQ (SeqID 210)
GNVLEARQRDAENRSQ (SeqID 211)
GNVLERAQRDAENRSQ (SeqID 212)
GNVLERRARDAENRSQ (SeqID 213)
GNVLERRQADAENRSQ (SeqID 214)
GNVLERRQRAAENRSQ (SeqID 215)
GNVLERRQRDAENRSQ (SeqID 216)
GNVLERRQRDAANRSQ (SeqID 217)
GNVLERRQRDAEARSQ (SeqID 218)
GNVLERRQRDAENASQ (SeqID 219)
GNVLERRQRDAENRAQ (SeqID 220)
GNVLERRQRDAENRSA (SeqID 221)
GNVLERRQRDAENRSQ
GLSQNRDVRENQRARE
GNVLERRQRDAENRSQ
GLSQNRDVRENQRARE

Fig. 11

1
ATTTTTAAGCAATATTTTAAAACATAAAAAAGAAAAATCAACTACTTAAGCTAATTGAA
61
GTATTTCTAAGATAATAAAAAATAAGATTATCAAATAAAAAGAAAAATCATTCAAAAATT
121
GGGAAAAAACTTTAAAATTCCATACCTTATAATAAGAAATTATTGATATCATAATAAGTG
181
ATAGTTTGTATATTCTAGGATATTCTGTATCTGATCTTAGATTTAGAAACGACATTTCGG
241
CACAATAGGAGTTGTAAAATGAGAAAATACCAAAAATTTTCTAAAATATTGACGTTAAGT
301 <u>RBS</u>        *M   R   K   Y   Q   K   F   S   K   I   L   T   L   S*
CTTTTTTGTTTGTCGCAAATACCGCTTAATACCAATGTTTTAGGGGAAAGTACCGTACCG
 *L   F   C   L   S   Q   I   P   L   N   T   N   V   L   G   E   S   T   V   P*
361
GAAAATGGTGCTAAAGGAAAGTTAGTTGTTAAAAAGACAGATGACCAGAACAAACCACTT
  E   N   G   A   K   G   K   L   V   V   K   K   T   D   D   Q   N   K   P   L
421
TCAAAAGCTACCTTTGTTTTAAAAACTACTGCTCATCCAGAAAGTAAAATAGAAAAAGTA
  S   K   A   T   F   V   L   K   T   T   A   H   P   E   S   K   I   E   K   V
481
ACTGCTGAGCTAACAGGTGAAGCTACTTTTGATAATCTCATACCTGGAGATTATACTTTA
  T   A   E   L   T   G   E   A   T   F   D   N   L   I   P   G   D   Y   T   L
541
TCAGAAGAAACAGCGCCCGAAGGTTATAAAAAGACTAACCAGACTTGGCAAGTTAAGGTT
  S   E   E   T   A   P   E   G   Y   K   K   T   N   Q   T   W   Q   V   K   V
601
GAGAGTAATGGAAAAACTACGATACAAAATAGTGGTGATAAAAATTCCACAATTGGACAA
  E   S   N   G   K   T   T   I   Q   N   S   G   D   K   N   S   T   I   G   Q
661
AATCACGAAGAACTAGATAAGCAGTATCCCCCCACAGGAATTTATGAAGATACAAAGGAA
  N   H   E   E   L   D   K   Q   Y   P   P   T   G   I   Y   E   D   T   K   E
721
TCTTATAAACTTGAGCATGTTAAAGGTTCAGTTCCAAATGGAAAGTCAGAGGCAAAAGCA
  S   Y   K   L   E   H   V   K   G   S   V   P   N   G   K   S   E   A   K   A
781
GTTAACCCATATTCAAGTGAAGGTGAGCATATAAGAGAAATTCCAGAGGGAACATTATCT
  V   N   P   Y   S   S   E   G   E   H   I   R   E   I   P   E   G   T   L   S
841
AAACGTATTTCAGAAGTAGGTGATTTAGCTCATAATAAATATAAAATTGAGTTAACTGTC
  K   R   I   S   E   V   G   D   L   A   H   N   K   Y   K   I   E   L   T   V
901
AGTGGAAAAACCATAGTAAAACCAGTGGACAAACAAAAGCCGTTAGATGTTGTCTTCGTA
  S   G   K   T   I   V   K   P   V   D   K   Q   K   P   L   D   V   V   F   V
961
CTCGATAATTCTAACTCAATGAATAACGATGGCCCAAATTTTCAAAGGCATAATAAAGCC
  L   D   N   S   N   S   M   N   N   D   G   P   N   F   Q   R   H   N   K   A
1021

Fig. 16-1

```
AAGAAAGCTGCCGAAGCTCTTGGGACCGCAGTAAAAGATATTTTAGGAGCAAACAGTGAT
  K  K  A  A  E  A  L  G  T  A  V  K  D  I  L  G  A  N  S  D
1081
AATAGGGTTGCATTAGTTACCTATGGTTCAGATATTTTTGATGGTAGGAGTGTAGATGTC
  N  R  V  A  L  V  T  Y  G  S  D  I  F  D  G  R  S  V  D  V

1141
GTAAAAGGATTTAAAGAAGATGATAAATATTATGGCCTTCAAACTAAGTTCACAATTCAG
  V  K  G  F  K  E  D  D  K  Y  Y  G  L  Q  T  K  F  T  I  Q
1201
ACAGAGAATTATAGTCATAAACAATTAACAAATAATGCTGAAGAGATTATAAAAAGGATT
  T  E  N  Y  S  H  K  Q  L  T  N  N  A  E  E  I  I  K  R  I
1261
CCTACAGAAGCTCCTAGAGCTAAATGGGGATCAACTACAAACGGACTTACTCCAGAGCAA
  P  T  E  A  P  R  A  K  W  G  S  T  T  N  G  L  T  P  E  Q
1321
CAAAAGCAGTACTATCTTAGTAAAGTAGGGGAAACATTTACTATGAAAGCCTTCATGGAG
  Q  K  Q  Y  Y  L  S  K  V  G  E  T  F  T  M  K  A  F  M  E
1381
GCAGATGATATTTTGAGTCAAGTAGATCGAAATAGTCAAAAAATTATTGTTCATATAACT
  A  D  D  I  L  S  Q  V  D  R  N  S  Q  K  I  I  V  H  I  T
1441
GATGGTGTTCCAACAAGATCATATGCTATTAATAATTTTAAATTGGGTGCATCATATGAA
  D  G  V  P  T  R  S  Y  A  I  N  N  F  K  L  G  A  S  Y  E
1501
AGCCAATTTGAACAAATGAAAAAAAATGGATATCTAAATAAAAGTAATTTTCTACTTACT
  S  Q  F  E  Q  M  K  K  N  G  Y  L  N  K  S  N  F  L  L  T
1561
GATAAGCCCGAGGATATAAAAGGAAATGGGGAGAGTTACTTTTTGTTTCCCTTAGATAGT
  D  K  P  E  D  I  K  G  N  G  E  S  Y  F  L  F  P  L  D  S
1621
TATCAAACACAGATAATCTCTGGAAACTTACAAAAACTTCATTATTTAGATTTAAATCTT
  Y  Q  T  Q  I  I  S  G  N  L  Q  K  L  H  Y  L  D  L  N  L
1681
AATTACCCTAAAGGTACAATTTATCGAAATGGACCAGTAAGAGAACATGGAACACCAACC
  N  Y  P  K  G  T  I  Y  R  N  G  P  V  R  E  H  G  T  P  T
1741
AAACTTTATATAAATAGTTTAAAACAGAAAAATTATGACATCTTTAATTTTGGTATAGAT
  K  L  Y  I  N  S  L  K  Q  K  N  Y  D  I  F  N  F  G  I  D
1801
ATATCTGCTTTTAGACAAGTTTATAATGAGGATTATAAGAAAAATCAAGATGGTACTTTT
  I  S  A  F  R  Q  V  Y  N  E  D  Y  K  K  N  Q  D  G  T  F
1861
CAAAAATTGAAAGAGGAAGCTTTTGAACTTTCAGATGGGGAAATAACAGAACTAATGAAG
  Q  K  L  K  E  E  A  F  E  L  S  D  G  E  I  T  E  L  M  K
1921
TCATTCTCTTCTAAACCTGAGTATTATACCCCGATAGTAACTTCATCCGATGCATCTAAC
  S  F  S  S  K  P  E  Y  Y  T  P  I  V  T  S  S  D  A  S  N
1981
```

Fig. 16-2

```
AATGAAATTTTATCTAAAATTCAGCAACAATTTGAAAAGGTTTTAACAAAAGAAAACTCA
 N  E  I  L  S  K  I  Q  Q  Q  F  E  K  V  L  T  K  E  N  S
2041
ATTGTTAATGGAACTATAGAAGATCCTATGGGTGACAAAATCAATTTACAGCTTGGCAAC
 I  V  N  G  T  I  E  D  P  M  G  D  K  I  N  L  Q  L  G  N
2101
GGACAAACATTGCAACCAAGTGATTATACTTTACAGGGAAATGATGGAAGTATAATGAAA
 G  Q  T  L  Q  P  S  D  Y  T  L  Q  G  N  D  G  S  I  M  K
2161
GATAGCATTGCAACTGGTGGGCCTAATAATGATGGTGGAATACTTAAAGGGGTTAAATTA
 D  S  I  A  T  G  G  P  N  N  D  G  G  I  L  K  G  V  K  L
2221
GAATACATCAAAAATAAACTCTACGTTAGAGGTTTGAACTTAGGGGAGGGACAAAAAGTA
 E  Y  I  K  N  K  L  Y  V  R  G  L  N  L  G  E  G  Q  K  V
2281
ACACTCACATATGATGTGAAACTAGATGACAGTTTTATAAGTAACAAATTCTATGACACT
 T  L  T  Y  D  V  K  L  D  D  S  F  I  S  N  K  F  Y  D  T
2341
AATGGTAGAACAACATTGAATCCTAAATCAGAGGATCCTAATACACTTAGAGATTTTCCA
 N  G  R  T  T  L  N  P  K  S  E  D  P  N  T  L  R  D  F  P
2401
ATCCCTAAAATTCGTGATGTGAGAGAATATCCTACAATAACGATTAAAAACGAGAAGAAG
 I  P  K  I  R  D  V  R  E  Y  P  T  I  T  I  K  N  E  K  K
2461
TTAGGTGAAATTGAATTTACAAAAGTTGATAAAGATAATAATAAGTTGCTTCTCAAAGGA
 L  G  E  I  E  F  T  K  V  D  K  D  N  N  K  L  L  L  K  G
2521
GCTACGTTTGAACTTCAAGAATTTAATGAAGATTATAAACTTTATTTACCAATAAAAAAT
 A  T  F  E  L  Q  E  F  N  E  D  Y  K  L  Y  L  P  I  K  N
2581
AATAATTCAAAAGTAGTGACGGGAGAAAACGGCAAAATTTCTTACAAAGATTTGAAAGAT
 N  N  S  K  V  V  T  G  E  N  G  K  I  S  Y  K  D  L  K  D
2641
GGCAAATATCAGTTAATAGAAGCAGTTTCGCCGAAGGATTATCAAAAAATTACTAATAAA
 G  K  Y  Q  L  I  E  A  V  S  P  K  D  Y  Q  K  I  T  N  K
2701
CCAATTTTAACTTTTGAAGTTGTTAAAGGATCGATACAAAATATAATAGCTGTTAATAAA
 P  I  L  T  F  E  V  V  K  G  S  I  Q  N  I  I  A  V  N  K
2761
CAGATTTCTGAATATCATGAGGAAGGTGACAAGCATTTAATTACCAACACGCATATTCCA
 Q  I  S  E  Y  H  E  E  G  D  K  H  L  I  T  N  T  H  I  P
2821
CCAAAAGGAATTATTCCGATGACAGGTGGGAAGGAATTCTATCTTTCATTTTAATAGGT
 P  K  G  I  I  P  M  T  G  K  G  I  L  S  F  I  L  I  G
2881
GGATCTATGATGTCTATTGCAGGTGGAATTTATATTTGGAAAAGATATAAGAAATCTAGT
 G  S  M  M  S  I  A  G  G  I  Y  I  W  K  R  Y  K  K  S  S
2941
```

Fig. 16-3

```
GATATATCTAGAGAAAAAGATTAAGAATCATGTGTTTTAGTATTCTTAATTAATTAAATA
 D   I   S   R   E   K   D   *
3001
TAATTCGAAAGGAGTGGTGCTGCGGTAATATTATAATCCGTATATTATTATCTATGTTGA
3061
TTAACTAGAATAAGAAGGAGATAGAAATGAAAAAAATCAACAAATGTCTTACAGTGTTCT
3121              RBS        M   K   K   I   N   K   C   L   T   V   F
CGACACTGCTATTGATCTTAACGTCACTATTCTCAGTTGCACCAGCGTTTGCGGACGACG
 S   T   L   L   I   L   T   S   L   F   S   V   A   P   A   F   A   D   D
3181
TAACAACTGATACTGTGACCTTGCACAAGATTGTCATGCCACAAGCTGCATTTGATAACT
 V   T   T   D   T   V   T   L   H   K   I   V   M   P   Q   A   A   F   D   N
3241
TTACTGAAGGTACAAAAGGTAAGAATGATAGCGATTATGTTGGTAAACAAATTAATGACC
 F   T   E   G   T   K   G   K   N   D   S   D   Y   V   G   K   Q   I   N   D
3301
TTAAATCTTATTTTGGCTCAACCGATGCTAAAGAAATTAAGGGTGCTTTCTTTGTTTTCA
 L   K   S   Y   F   G   S   T   D   A   K   E   I   K   G   A   F   F   V   F
3361
AAAATGAAACTGGTACAAAATTCATTACTGAAAATGGTAAGGAAGTCGATACTTTGGAAG
 K   N   E   T   G   T   K   F   I   T   E   N   G   K   E   V   D   T   L   E
3421
CTAAAGATGCTGAAGGTGGTGCTGTTCTTTCAGGGTTAACAAAAGACACTGGTTTTGCTT
 A   K   D   A   E   G   G   A   V   L   S   G   L   T   K   D   T   G   F   A
3481
TTAACACTGCTAAGTTAAAAGGAACTTACCAAATCGTTGAATTGAAAGAAAAATCAAACT
 F   N   T   A   K   L   K   G   T   Y   Q   I   V   E   L   K   E   K   S   N
3541
ACGATAACAACGGTTCTATCTTGGCTGATTCAAAAGCAGTTCCAGTTAAAATCACTCTGC
 Y   D   N   N   G   S   I   L   A   D   S   K   A   V   P   V   K   I   T   L
3601
CATTGGTAAACAACCAAGGTGTTGTTAAAGATGCTCACATTTATCCAAAGAATACTGAAA
 P   L   V   N   N   Q   G   V   V   K   D   A   H   I   Y   P   K   N   T   E
3661
CAAAACCACAAGTAGATAAGAACTTTGCAGATAAAGATCTTGATTATACTGACAACCGAA
 T   K   P   Q   V   D   K   N   F   A   D   K   D   L   D   Y   T   D   N   R
3721
AAGACAAAGGTGTTGTCTCAGCGACAGTTGGTGACAAAAAGAATACATAGTTGGAACAA
 K   D   K   G   V   V   S   A   T   V   G   D   K   E   Y   I   V   G   T
3781
AAATTCTTAAAGGCTCAGACTATAAGAAACTGGTTTGGACTGATAGCATGACTAAAGGTT
 K   I   L   K   G   S   D   Y   K   K   L   V   W   T   D   S   M   T   K   G
3841
TGACGTTCAACAACAACGTTAAAGTAACATTGGATGGTAAAGATTTTCCTGTTTTAAACT
 L   T   F   N   N   N   V   K   V   T   L   D   G   K   D   F   P   V   L   N
3901
ACAAACTCGTAACAGATGACCAAGGTTTCCGTCTTGCCTTGAATGCAACAGGTCTTGCAG
 Y   K   L   V   T   D   D   Q   G   F   R   L   A   L   N   A   T   G   L   A
3961
```

Fig. 16-4

```
CAGTAGCAGCTGCTGCAAAAGACAAAGATGTTGAAATCAAGATCACTTACTCAGCTACGG
 A  V  A  A  A  A  K  D  K  D  V  E  I  K  I  T  Y  S  A  T
4021
TGAACGGCTCCACTACTGTTGAAGTTCCAGAAACCAATGATGTTAAATTGGACTATGGTA
 V  N  G  S  T  T  V  E  V  P  E  T  N  D  V  K  L  D  Y  G
4081
ATAACCCAACGGAAGAAAGTGAACCACAAGAAGGTACTCCAGCTAACCAAGAAATTAAAG
 N  N  P  T  E  E  S  E  P  Q  E  G  T  P  A  N  Q  E  I  K
4141
TCATTAAAGACTGGGCAGTAGATGGTACAATTACTGATGTTAATGTTGCAGTTAAAGCTA
 V  I  K  D  W  A  V  D  G  T  I  T  D  V  N  V  A  V  K  A
4201
TCTTTACCTTGCAAGAAAAACAAACGGATGGTACATGGGTGAACGTTGCTTCACACGAAG
 I  F  T  L  Q  E  K  Q  T  D  G  T  W  V  N  V  A  S  H  E
4261
CAACAAAACCATCACGCTTTGAACATACTTTCACAGGTTTGGATAATACTAAAACTTACC
 A  T  K  P  S  R  F  E  H  T  F  T  G  L  D  N  T  K  T  Y
4321
GCGTTGTCGAACGTGTTAGCGGCTACACTCCAGAATATGTATCATTTAAAAATGGTGTTG
 R  V  V  E  R  V  S  G  Y  T  P  E  Y  V  S  F  K  N  G  V
4381
TGACTATCAAGAACAACAAAAACTCAAATGATCCAACTCCAATCAACCCATCAGAACCAA
 V  T  I  K  N  N  K  N  S  N  D  P  T  P  I  N  P  S  E  P
4441
AAGTGGTGACTTATGGACGTAAATTTGTGAAAACAAATCAAGCTAACACTGAACGCTTGG
 K  V  V  T  Y  G  R  K  F  V  K  T  N  Q  A  N  T  E  R  L
4501
CAGGAGCTACCTTCCTTGTTAAGAAAGAAGGAAAATACTTGGCACGTAAAGCAGGTGCAG
 A  G  A  T  F  L  V  K  K  E  G  K  Y  L  A  R  K  A  G  A
4561
CAACTGCTGAAGCAAAGGCAGCTGTAAAAACTGCTAAACTAGCATTGGATGAAGCTGTTA
 A  T  A  E  A  K  A  A  V  K  T  A  K  L  A  L  D  E  A  V
4621
AAGCTTATAACGACTTGACTAAAGAAAAACAAGAAGGCCAAGAAGGTAAAACAGCATTGG
 K  A  Y  N  D  L  T  K  E  K  Q  E  G  Q  E  G  K  T  A  L
4681
CTACTGTTGATCAAAAACAAAAAGCTTACAATGACGCTTTTGTTAAAGCTAACTACTCAT
 A  T  V  D  Q  K  Q  K  A  Y  N  D  A  F  V  K  A  N  Y  S
4741
ATGAATGGGTTGCAGATAAAAAGGCTGATAATGTTGTTAAATTGATCTCTAACGCCGGTG
 Y  E  W  V  A  D  K  K  A  D  N  V  V  K  L  I  S  N  A  G
4801
GTCAATTTGAAATTACTGGTTTGGATAAAGGCACTTATAGCTTGGAAGAAACTCAAGCAC
 G  Q  F  E  I  T  G  L  D  K  G  T  Y  S  L  E  E  T  Q  A
4861
CAGCAGGTTATGCGACATTGTCAGGTGATGTAAACTTTGAAGTAACTGCCACATCATATA
 P  A  G  Y  A  T  L  S  G  D  V  N  F  E  V  T  A  T  S  Y
4921
```

Fig. 16-5

```
GCAAAGGGGCTACAACTGACATCGCATATGATAAAGGATCTGTAAAAAAGATGCCCAAC
 S   K   G   A   T   T   D   I   A   Y   D   K   G   S   V   K   K   D   A   Q
4981
AAGTTCAAAACAAAAAGTAACCATCCCACAAACAGGTGGTATTGGTACAATTCTTTTCA
 Q   V   Q   N   K   K   V   T   I   P   Q   T   G   G   I   G   T   I   L   F
5041
CAATTATTGGTTTAAGCATTATGCTTGGAGCAGTAGTTGTCATGAAAAAACGTCAATCAG
 T   I   I   G   L   S   I   M   L   G   A   V   V   V   M   K   K   R   Q   S
5101
AGGAAGCTTAAGGCTAGTCTTTGATGGTGTATAAGCACAGTTAAAGCTGTGCTTATGATC
 E   E   A   *
5161
TAAGGGTATTTCAGTAGAAGTACTCTTAGATCATAAGCAAGAGCCATTATTTAGGAGATG
5221
ACGTGAAGACTAAAAATATCAACAAAAAAACTAAAAAGAAGAAGTCAAATCTTCCTTTTA
5281
TCATTCTTTTTCTAATAGGTCTATCTATTTTATTGTATCCAGTGGTATCACGTTTTTACT
5341
ATACGATAGAATCTAATAATCAAACACAGGATTTTGAGAGAG
```

Fig. 16-6

```
1
GCTCATGATAATTTATAGAACATTTATAAAATCTTATAATAAACTGGTTAAGTATAGGAA
61
ATACTGCATATTTCTTGAAAATATGGTGTATATTGTGAATAAAATGATGACCAAGTTAAT
121
TGAATTTTCCTATCGAAAAATTTTTCAAAAAAATAATTTCACGCTCAAATCATTTGATT
181
GTCAAATAAATAGAGCCTTTATAAAAATATTATATAAGTATAAATGTAAAAAAATAAAA
241
AAATGATATTTTATTTGATTCAAATGTATTTAATAAAAATACAAAGTTTCTAAAAAAGT
301
AAAAATTCCATCTCAATAAACAGCGTTAGTTATTATAACCGAACATTATTGTCCTTAAAA
361
CATTAAAACAAAAACAAAAGTTCGTAATTTAATTAATTTGTCATGTTACTAATCTTATGC
421
TAATATATTATCTCGTGATAAGTTTTTGATGTAAAAATTATCATGAAAAAGAAAAGAGAG
                                                         RBS
481
ATGGAAATGAAAAAACAATTTTTAAAATCAGCAGCGATTCTATCGCTAGCAGTAACAGCA
541     M  K  K  Q  F  L  K  S  A  A  I  L  S  L  A  V  T  A
GTATCTACAAGTCAGCCGGTAGCCGGGATAACTAAAGATTATAATAACCGAAATGAAAAA
        V  S  T  S  Q  P  V  A  G  I  T  K  D  Y  N  N  R  N  E  K
601
GTAAAAAAGTATTTACAAGAAAATAATTTCGGTCATAAAATAGCGTATGGATGGAAAAAT
   V  K  K  Y  L  Q  E  N  N  F  G  H  K  I  A  Y  G  W  K  N
661
AAAGTAGAATTTGATTTTCGTTATTTATTGGATACTGCTAAATATTTAGTAAATAAAGAA
   K  V  E  F  D  F  R  Y  L  L  D  T  A  K  Y  L  V  N  K  E
721
GAATTTCAAGATCCTTTATATAATGATGCGCGCGAAGAATTGATAAGTTTTATTTTTCCT
   E  F  Q  D  P  L  Y  N  D  A  R  E  E  L  I  S  F  I  F  P
781
TATGAGAAATTTTTAATTAACAATCGTGACATAACTAAATTAACAGTTAATCAGTATGAA
   Y  E  K  F  L  I  N  N  R  D  I  T  K  L  T  V  N  Q  Y  E
841
GCGATTGTGAATAGAATGAGTGTTGCTTTACAAAAATTTTCAAAGAATATTTTTGAGAAA
   A  I  V  N  R  M  S  V  A  L  Q  K  F  S  K  N  I  F  E  K
901
CAGAAAGTAAATAAAGATTTAATCCCTATTGCGTTTTGGATTGAGAAAAGTTACAGAACT
   Q  K  V  N  K  D  L  I  P  I  A  F  W  I  E  K  S  Y  R  T
961
GTTGGAACGAATGAAATCGCCGCTTCTGTAGGCATTCAAGGAGGATTTTATCAAAACTTC
   V  G  T  N  E  I  A  A  S  V  G  I  Q  G  G  F  Y  Q  N  F
1021
CATGATTATTATAATTATTCATATCTATTAAATTCTTTATGGCATGAAGGAAATGTAAAA
   H  D  Y  Y  N  Y  S  Y  L  L  N  S  L  W  H  E  G  N  V  K
1081
GAAGTAGTTAAGGATTATGAAAACACTATTCGTCAAATACTATCTAAAAAGCATGAGATT
   E  V  V  K  D  Y  E  N  T  I  R  Q  I  L  S  K  K  H  E  I
1141
```

Fig. 17-1

```
GAAAAAATTCTTAATCAGAGCACTTCTGATATCTCTATAGATGATGATGATTACGAAAAA
 E  K  I  L  N  Q  S  T  S  D  I  S  I  D  D  D  D  Y  E  K
1201
GGAAATAAAGAATTGCTAAGGGAAAAATTAAATATTATTCTAAATCTTTCAAAGAGAGAT
 G  N  K  E  L  L  R  E  K  L  N  I  I  L  N  L  S  K  R  D
1261
TACAGAGTAACTCCATACTATGAAGTGAATAAACTACATACAGGGCTTATTTTATTGGAG
 Y  R  V  T  P  Y  Y  E  V  N  K  L  H  T  G  L  I  L  L  E
1321
GATGTCCCTAATTTAAAGATTGCTAAGGATAAGTTGTTCTCATTAGAGAATTCTTTAAAG
 D  V  P  N  L  K  I  A  K  D  K  L  F  S  L  E  N  S  L  K
1381
GAATACAAAGGAGAGAAAGTTAATTATGAGGAACTAAGATTCAATACGGAACCTTTAACT
 E  Y  K  G  E  K  V  N  Y  E  E  L  R  F  N  T  E  P  L  T
1441
AGTTACTTAGAAAATAAAGAAAAATTTTTAGTCCCCAATATTCCATATAAAAATAAATTA
 S  Y  L  E  N  K  E  K  F  L  V  P  N  I  P  Y  K  N  K  L
1501
ATTTTAAGGGAAGAAGATAAATATAGTTTTGAAGATGATGAAGAAGAGTTTGGAAATGAA
 I  L  R  E  E  D  K  Y  S  F  E  D  D  E  E  E  F  G  N  E
1561
CTTCTAAGTTACAATAAGCTTAAGAATGAAGTTTTACCTGTTAATATTACAACTTCTACT
 L  L  S  Y  N  K  L  K  N  E  V  L  P  V  N  I  T  T  S  T
1621
ATATTAAAACCGTTTGAACAGAAGAAAATTGTGGAAGATTTTAATCCTTATTCTAATTTA
 I  L  K  P  F  E  Q  K  K  I  V  E  D  F  N  P  Y  S  N  L
1681
GACAATTTAGAAATAAAAAAAATAAGGTTGAATGGCTCCCAAAAACAAAAAGTAGAACAG
 D  N  L  E  I  K  K  I  R  L  N  G  S  Q  K  Q  K  V  E  Q
1741
GAAAAAACTAAATCGCCAACTCCTCAAAAAGAGACTGTGAAAGAACAAACTGAGCAAAAA
 E  K  T  K  S  P  T  P  Q  K  E  T  V  K  E  Q  T  E  Q  K
1801
GTATCTGGAAATACTCAAGAGGTAGAAAAGAAATCTGAAACTGTGGCAACTTCACAACAA
 V  S  G  N  T  Q  E  V  E  K  K  S  E  T  V  A  T  S  Q  Q
1861
AGTTCAGTTGCGCAAACTTCTGTCCAACAGCCGGCTCCGGTTCAATCAGTTGTTCAAGAA
 S  S  V  A  Q  T  S  V  Q  Q  P  A  P  V  Q  S  V  V  Q  E
1921
TCCAAAGCTTCTCAAGAGGAGATTAATGCAGCACACGATGCTATTTCGGCGTATAAATCA
 S  K  A  S  Q  E  E  I  N  A  A  H  D  A  I  S  A  Y  K  S
1981
ACAGTCAATATTGCTAATACAGCCGGTGTAACAACTGCGGAAATGACCACGCTCATTAAT
 T  V  N  I  A  N  T  A  G  V  T  T  A  E  M  T  T  L  I  N
2041
ACTCAAACTTCTAATCTTTCTGATGTTGAGAAAGCTTTAGGAAATAATAAGGTTAATAAT
 T  Q  T  S  N  L  S  D  V  E  K  A  L  G  N  N  K  V  N  N
2101
GGTGCAGTCAATGTATTGAGAGAAGATACAGCTCGTCTTGAGAATATGATTTGGAATCGT
 G  A  V  N  V  L  R  E  D  T  A  R  L  E  N  M  I  W  N  R
2161               Fig. 17-2
```

```
GCTTACCAAGCTATTGAAGAATTCAACGTCGCTCGTAATACTTATAATAACCAAATCAAG
 A  Y  Q  A  I  E  E  F  N  V  A  R  N  T  Y  N  N  Q  I  K
2221
ACAGAAACAGTTCCAGTTGATAATGATATTGAAGCTATTTTAGCAGGTTCTCAAGCTAAA
 T  E  T  V  P  V  D  N  D  I  E  A  I  L  A  G  S  Q  A  K
2281
ATTAGCCATTTGGACAATCGTATCGGAGCGCGCCACATGGATCAAGCTTTTGTAGCTAGT
 I  S  H  L  D  N  R  I  G  A  R  H  M  D  Q  A  F  V  A  S
2341
TTATTAGAAGTTACTGAGATGAGTAAATCAATCTCATCGCGTATAAAAGAGTAGACACTG
 L  L  E  V  T  E  M  S  K  S  I  S  S  R  I  K  E  *
2401
CTATCAAGGCGATCTTAAACTTTTGTATTAAACTAACCTAAAAGATAGAAAGAGACTAAT
2461                                          RBS
ATGAAAAAAATAACAACTTTAATCTTAGCTAGTAGCTTATTACTAGTTGCAACGACATCG
 M  K  K  I  T  T  L  I  L  A  S  S  L  L  L  V  A  T  T  S
2521
GTTAAAGCTGATGATAACTTTGAAATGCCAACGCGTTATGTTAAAATGAGTGAAAAATCA
 V  K  A  D  D  N  F  E  M  P  T  R  Y  V  K  M  S  E  K  S
2581
AAAGCATTTTATCAAAGACTACAAGAAAAACAACGTAAGGCACATACTACTGTGAAGACT
 K  A  F  Y  Q  R  L  Q  E  K  Q  R  K  A  H  T  T  V  K  T
2641
TTTAATAATTCAGAAATAAGGCATCAACTACCTCTTAAACAAGAAAAGGCTAGAAATGAT
 F  N  N  S  E  I  R  H  Q  L  P  L  K  Q  E  K  A  R  N  D
2701
ATCTACAATTTAGGCATTCTTATTTCTCAGGAGTCTAAAGGGTTCATCCAACGTATTGAT
 I  Y  N  L  G  I  L  I  S  Q  E  S  K  G  F  I  Q  R  I  D
2761
AATGCCTATTCTTTGGAAAATGTCTCAGATATTGTTAATGAAGCTCAGGCTTTGTATAAA
 N  A  Y  S  L  E  N  V  S  D  I  V  N  E  A  Q  A  L  Y  K
2821
CGTAACTATGATTTATTTGAAAAAATCAAATCTACACGTGATAAGGTTCAAGTCTTACTT
 R  N  Y  D  L  F  E  K  I  K  S  T  R  D  K  V  Q  V  L  L
2881
GCATCGCATCAAGATAATACAGACTTAAAAAACTTTTATGCTGAGTTAGATGATATGTAT
 A  S  H  Q  D  N  T  D  L  K  N  F  Y  A  E  L  D  D  M  Y
2941
GAACATGTTTATCTCAATGAAAGTAGAGTGGAGGCGATAAACAGAAATATCCAAAAATAT
 E  H  V  Y  L  N  E  S  R  V  E  A  I  N  R  N  I  Q  K  Y
3001
AATTAGTTTCTAAACTAACAAACATTCCTAAATATAAGATATTAAACCCTACTTATTGAT
 N  *
3061
TAGTGAGTAGGGTTTTACTGTTTTAAATAGCTTTCTGCTCAGAATGTAAGCCTTGTCATT
3121
TCAAAGGAACTATGTTATTATTCTTAAGTAAATTAAATAGGACATTTGGGGTGCGTAACA
3181
GCTGAGATTATACCCATTGA
```

NUCLEIC ACIDS CODING FOR ADHESION FACTOR OF GROUP B STREPTOCOCCUS, ADHESION FACTORS OF GROUP B STREPTOCOCCUS AND FURTHER USES THEREOF

RELATED APPLICATIONS

This application is a continuation application of U.S. application Ser. No. 12/363,229 now U.S. Pat. No. 7,960,533, filed Jan. 30, 2009, which is a divisional of U.S. application Ser. No. 10/531,659 now U.S. Pat. No. 7,485,710, filed Jan. 26, 2006, which is national stage filing under 35 U.S.C. §371 of international application PCT/EP03/11436, filed Oct. 15, 2003, the entire disclosure of each of which is incorporated herein by reference.

The present invention relates to isolated nucleic acid molecules which code for bacterial adhesion factors, the bacterial adhesion factors and various uses thereof.

BACKGROUND OF THE INVENTION

*Streptococcus agalactiae*, or group B *streptococcus* (GBS), is a leading cause of infant mortality. GBS encompasses an estimated prevalence of several thousand cases per year resulting in an annual mortality rate in the United States between about 10% and 15% (Schuchat, 1998). Studies from the USA demonstrated a risk of 1-2 cases per 1000 live births (Zangwill et al., 1992) and incidence rates for different European countries vary between 0.24 and 1.26 per 1000 live births (Carstensen et al., 1985; Faxelius et al., 1988). In the United States, up to 30% of pregnant women carry GBS at least temporarily in the vagina or rectum without symptoms (Schuchat, 1998). Infants born to these women become colonized with GBS during delivery (Baker and Edwards, 1995). Aspiration of infected amniotic fluid or vaginal secretions allows GBS to gain access to the lungs. Common manifestations of this infection include bacteraemia, pneumonia, and meningitis (Spellerberg, 2000). Even infant survivors of GBS meningitis suffer from neurologic sequelae ranging from deafness, learning disabilities, as well as motor, sensory, and cognitive impairment (Baker and Edwards, 1995). Currently, antibiotic prophylaxis in parturients is the recommended approach for the prevention of neonatal disease by GBS (Baker et al., 1999); however, with the resurgence of antibiotic resistance in other streptococcal species, a similar plight in GBS may occur.

In addition to infant infections, GBS is also an important pathogen in the elderly and in immunocompromised persons, in which the incidence of invasive GBS disease is about 9 in 100,000 (Farley et al., 1993). Of these infections, the mortality rate can be as high as 30%.

An important GBS virulence determinant is the type-specific capsular polysaccharide, which prevents the deposition of host complement factor C3b and thereby inhibits opsonophagocytosis of the bacteria (Rubens et al., 1987). Nine distinct capsular serotypes, Ia, Ib, and II to VIII, have been identified so far in GBS (Wessels, 1997). Efforts are currently under way to develop a multivalent conjugate vaccine against GBS based on the capsule polysaccharides of the clinically relevant serotypes (Paoletti et al., 1999; Baker et al., 1999; Baker et al., 2000; Paoletti and Kasper, 2002). However, there are a number of technical difficulties to overcome with capsule-containing conjugate vaccines: multiple serotypes are needed, an appropriate protein conjugate needs to be identified and validated, and potential cross-reaction with human tissues needs to be addressed (Korzeniowska-Kowal et al., 2001). The use of cell surface proteins from GBS represents an attractive alternative to capsule polysaccharides for the development of a vaccine against these bacteria. The surface proteins Sip, Rib, α and β from GBS have already been shown to confer protective immunity in mice against GBS infections (Madoff et al., 1992; Larsson et al., 1997; Larsson et al., 1999; Brodeur et al., 2000). Also two unique surface proteins from a serotype V strain were shown in a mouse model to protect against GBS infection (Areschoug et al., 1999). Finally, antibodies against C5a peptidase from GBS were found to inititate macrophage killing of the bacteria (Cheng et al., 2001).

The interaction of GBS with its host is a complex process involving the colonization and penetration of epithelial and endothelial surfaces and the evasion of the immune defence (Spellerberg, 2000). In streptococci, fibrinogen binding has been shown to play a significant role in the adhesion to host surfaces (Courtney et al., 1994; Cheung et al., 1991; Ni et al., 1998; Pei and Flock, 2001) and the protection from the immune system (Courtney et al., 1997; Thern et al., 1998; Ringdahl et al., 2000). Therefore, several studies have addressed the molecular basis of fibrinogen binding in streptococci of the serological groups A, C and G (Fischetti, 1989; Meehan et al., 1998; Vasi et al., 2000).

Fibrinogen is a 330 kDa glycoprotein found in high concentrations in blood plasma (Fuss et al., 2001; Mosesson et al., 2001). It is a hexamer composed of each of two Aα-, Bβ-, and γ-chains linked together by disulfide bonds. Fibrinogen is a key player in haemostasis and mediates platelet adherence and aggregation at sites of injury. Furthermore, it is cleaved by thrombin to form fibrin, which is the major component of blood clots. Fibrinogen also plays a role in opsonophagocytosis. It has been shown to inhibit the binding of the activated complement factor C3b, thereby blocking the activation of the alternative complement pathway (Whitnack et al., 1984; Whitnack and Beachey, 1985). The newborn's unique susceptibility for disseminated GBS infections has been associated with a relative complement deficiency (Mills et al., 1979; Edwards et al., 1983). Fibrinogen binding of GBS may thus play an important role in the inhibition of the residual complement activity in the newborn (Noel et al., 1991).

In several studies, the interaction of GBS with human fibrinogen has been demonstrated (Schonbeck et al., 1981; Lammler et al., 1983; Chhatwal et al., 1984; Spellerberg et al., 2002). However, the molecular basis of fibrinogen binding in GBS remained unknown.

GBS has been demonstrated to bind to and invade epithelial and endothelial cells (Gibson et al., 1993; La Penta et al., 1997; Winram et al, 1998). Treatment of GBS with the protease trypsin abolishes the adhesive and invasive properties of the bacteria (Valentin-Weigand and Chhatwal, 1995; Winram et al., 1998), indicating a proteinacious nature of the adhesins and invasins in GBS. As adhesins and invasins are located on the surface of the bacteria and are important for the virulence of GBS, they represent ideal targets for the development of a GBS vaccine.

The problem underlying the present invention was to provide means for the development of medicaments such as vaccines against bacterial infections. More particularly, the problem was to provide new adhesions factors of GBS which can be used for the manufacture of said medicaments.

The problem is solved in a first aspect by an isolated nucleic acid molecule, preferably encoding a fibrinogen-binding-polypeptide or such protein or a fragment thereof, comprising a nucleic acid sequence which is selected from the group comprising

3 a) a nucleic acid having at least 70% identity to a nucleic acid sequence which is selected from the group comprising SEQ ID NO 1 to SEQ ID NO 6,
b) a nucleic acid which is essentially complementary to the nucleic acid of a),
c) a nucleic acid comprising at least 15 sequential bases of the nucleic acid of a) or b),
d) a nucleic acid which anneals under stringent hybridisation conditions to the polynucleotide of a), b) or c), and
e) a nucleic acid which, but for the degeneracy of the genetic code, would hybridize to the nucleic acid defined in a), b), c) or d).

The problem is solved in a second aspect by an isolated nucleic acid molecule, preferably encoding an adhesion factor or a fragment thereof, comprising a nucleic acid sequence which is selected from the group comprising
a) a nucleic acid having at least 70% identity to a nucleic acid sequence set forth in SeqID NO 7, SeqID NO 8, SeqID NO 9 or SeqID NO 10.
b) a nucleic acid which is essentially complementary to the nucleic acid of a),
c) a nucleic acid comprising at least 15 sequential bases of the nucleic acid of a) or b),
d) a nucleic acid which anneals under stringent hybridisation conditions to the nucleic acid of a), b) or c), and
e) a nucleic acid which, but for the degeneracy of the genetic code, would hybridize to the nucleic acid defined in a), b), c) or d).

In an embodiment of both aspects of the present invention the identity is at least 80%, preferably at least 90%, more preferably 100%.

In a further embodiment of both aspects of the present invention the nucleic acid is DNA.

In a still further embodiment of both aspects of the present invention the nucleic acid is RNA.

In a preferred embodiment of both aspects of the present invention the nucleic acid molecule is isolated from a bacterium.

In a more preferred embodiment of both aspects of the present invention the bacterium is a species selected from the group comprising Streptococci, Staphylococci, and Lactococci.

In an even more preferred embodiment of both aspects of the present invention the bacterium is a species which is selected from the group comprising *Streptococcus agalactiae, Streptococcus pyogenes, Streptococcus pneumoniae* and *Streptococcus mutans*.

In a most preferred embodiment of both aspects of the present invention the bacterium is *Streptococcus agalactiae*.

In an embodiment of the first aspect of the present invention the nucleic acid molecule encodes a fibrinogen-binding-protein comprising at least one repeat of an amino acid motive comprising 16 amino acids.

In an embodiment of the second aspect of the present invention the nucleic acid molecule encodes an adhesion factor which interacts with epithelial cells.

In a preferred embodiment of the first aspect of the present invention the encoded fibrinogen-binding-protein comprises 19 repeats of the amino acid motive whereby the amino acid motive is any one of the ones specified or disclosed herein.

In a more preferred embodiment of the first aspect of the present invention the repeats are encoded by a polynucleotide selected from the group comprising SEQ ID NO 21 to SEQ ID NO 112.

In a third aspect the problem underlying the present invention is solved by an isolated nucleic acid molecule comprising

4 a nucleic acid sequence, whereby the nucleic acid sequence is selected from the group comprising SEQ ID NO 21 to SEQ ID NO 21 to 112.

In a fourth aspect the problem underlying the present invention is solved by an isolated nucleic acid molecule encoding for a polypeptide whereby the polypeptide comprises an amino acid motive, whereby the amino acid motive is G-N/S/T-V-L-A/E/M/Q-R-R-X-K/R/W-A/D/E/N/Q-A/F/I/L/V/Y-X-X-K/R-X-X (SEQ ID NO 222).

In a preferred embodiment of any of the aspects 1 to 4 of the present invention the nucleic acid is DNA, RNA or mixtures thereof, preferably the nucleic acid molecule is isolated from a genomic DNA.

In a fifth aspect the problem underlying the present invention is solved by a vector comprising a nucleic acid molecule according to any aspect of the present invention.

In a preferred embodiment the vector is adapted for recombinant expression of the polypeptide encoded by any of the nucleic acid molecules according to any aspect of the present invention.

In a sixth aspect the problem underlying the present invention is solved by a cell comprising the vector according to the present invention.

In a preferred embodiment the cell is a host cell.

In a seventh aspect the problem underlying the present invention is solved by a polypeptide, preferably a fibrinogen-binding-polypeptide and/or an adhesion factor, comprising an amino acid sequence, whereby the amino acid sequence is encoded by a nucleic acid molecule according to any aspect of the present invention, and fragments of said polypeptide.

In an eighth aspect the problem underlying the present invention is solved by a polypeptide, preferably a fibrinogen-binding-polypeptide and/or an adhesion factor, comprising an amino acid sequence, whereby the amino acid sequence is selected from the group comprising SEQ ID NO 11 to SEQ ID NO 20.

In an embodiment of this aspect of the present invention the polypeptide, preferably a fibrinogen-binding-polypeptide and/or an adhesion factor, having an amino acid sequence according to any of SEQ ID NO 11 to 16 is a fibrinogen-binding protein.

In a further embodiment of this aspect of the present invention the polypeptide is an adhesion factor which interacts with epithelial cells. In an even more preferred embodiment the epithelial cells are human epithelial cells.

In a ninth aspect the problem underlying the present invention is solved by a polypeptide comprising an amino acid sequence, whereby the amino acid sequence is selected from the group comprising SEQ ID NO 113 to SEQ ID NO 205. In an embodiment the polypeptide comprises at least one of the amino acid sequence according to SEQ ID NO 113 to SEQ ID NO 225 in combination with at least one other amino acid sequence. More preferable this at least one other amino acid sequence is an amino acid sequence according to any of SEQ ID NO 113 to SEQ ID NO 205.

In a tenth aspect the problem underlying the present invention is solved by a polypeptide comprising an amino acid motive, whereby the polypeptide comprises an amino acid motive, whereby the amino acid motive is G-N/S/T-V-L-A/E/M/Q-R-R-X-K/R/W-A/D/E/N/Q-A/F/I/L/V/Y-X-X-K/R-X-X (SEQ ID NO 222).

In an eleventh aspect the problem underlying the present invention is solved by a process for producing a polypeptide according to any aspect of the present invention comprising expressing the nucleic acid molecule according to any aspect of the present invention.

In a twelfth aspect the problem underlying the present invention is solved by a process for producing a cell which expresses a polypeptide according to any aspect of the present invention or a fragment thereof, comprising transforming or transfecting a suitable host cell with the vector according to the present invention such that the transformed or transfected cell expresses the polypeptide encoded by the polynucleotide contained in the vector.

In a thirteenth aspect the problem underlying the present invention is solved by a pharmaceutical composition, especially a vaccine, comprising a polypeptide or a fragment thereof, as defined in any aspect of the present invention or a nucleic acid molecule according to any aspect of the present invention.

In a preferred embodiment the pharmaceutical composition comprises an immunostimulatory substance, whereby the immunostimulatory substance is preferably selected from the group comprising polycationic polymers, immunostimulatory deoxynucleotides (ODNs), synthetic KLK peptides, neuroactive compounds, alumn, Freund's complete or incomplete adjuvants or combinations thereof.

In a preferred embodiment the immunostimulatory substance is a combination of either a polycationic anion and immunostimulatory deoxynucleotides or of synthetic KLK peptides and immunostimulatory deoxynucleotides.

In a more preferred embodiment the polycationic polymer is a polycationic peptide and/or whereby the neuroactive compound is human growth hormone.

In a fourteenth aspect the problem underlying the present invention is solved by the use of a polypeptide according to any aspect of the present invention or a fragment thereof for the manufacture of a medicament, especially for the manufacture of a vaccine against bacterial infection.

In a preferred embodiment the bacterial infection is a bacterial infection of *Streptococcus agalactiae*.

In a fifteenth aspect the problem underlying the present invention is solved by the use of molecules which inhibit the binding of a polypeptide according to any aspect of the present invention to fibrinogen for the manufacture of a medicament to prevent and treat bacterial infection. Preferably, the bacterial infection is a *Streptococcus agalactiae* infection.

In a further embodiment the molecules are selected from the group comprising fibrinogen receptor antibodies, fibrinogen receptor mimotopes and fibrinogen receptor antagonists binding to a polypeptide according to any aspect of the present invention.

In a sixteenth aspect the problem underlying the present invention is solved by the use of molecules which inhibit the binding of a polypeptide according to any aspect of the present invention to epithelial cells, preferably human epithelial cells.

In a seventeenth aspect the problem underlying the present invention is solved by an antibody, or at least an effective part thereof, which binds at least to a selective part of the polypeptide or a fragment thereof according to any aspect of the present invention.

In an embodiment the antibody is a monoclonal antibody.

In a further embodiment said effective part comprises Fab fragments.

In a still further embodiment the antibody is a chimeric antibody.

In a preferred embodiment the antibody is a humanized antibody.

In an eighteenth aspect the problem underlying the present invention is solved by a hybridoma cell line, which produces the antibody according to the present invention.

In a nineteenth aspect the problem underlying the present invention is solved by the use of the antibody according to the present invention for the preparation of a medicament for treating or preventing bacterial infections, especially *Streptococcus agalactiae* infections.

In a twentieth aspect the problem underlying the present invention is solved by an antagonist which reduces or inhibits the activity of the polypeptide or a fragment thereof according to any aspects of the present invention.

In a twenty-first aspect the problem underlying the present invention is solved by a method for identifying an antagonist capable of reducing or inhibiting the activity of the polypeptide or fragment thereof according to any aspect of the present invention comprising:
  a) contacting an isolated or immobilized polypeptide according to any of the aspects of the present invention or a fragment thereof with a candidate antagonist under conditions to permit binding of said candidate antagonist to said polypeptide or fragment thereof, in the presence of a component capable of providing a detectable signal in response to the binding of the candidate antagonist to said polypeptide or fragment thereof; and
  b) detecting the presence or absence of a signal generated in response to the binding of the antagonist to the polypeptide or fragment thereof, preferably the presence of a signal indicating a compound capable of inhibiting or reducing the activity of the polypeptide or fragment thereof.

In a twenty-second aspect the problem underlying the present invention is solved by a method for identifying an antagonist capable of reducing or inhibiting the activity of a polypeptide or a fragment thereof according to any the aspects of the present invention comprising;
  a) providing the polypeptide according to any aspect of the present invention or a fragment thereof,
  b) providing an interaction partner of the polypeptide according to any aspect of the present invention, preferably the antibody according to the present invention,
  c) providing a candidate antagonist,
  d) reacting the polypeptide, the interaction partner of the polypeptide and the candidate antagonist, and
  e) determining whether the candidate antagonist inhibits or reduces the activity of the polypeptide.

In a twenty-third aspect the problem underlying the present invention is solved by a method for identifying an antagonist capable of reducing or inhibiting the interaction activity of the polypeptide according to the present invention or a fragment thereof to its interaction partner comprising:
  a) providing the polypeptide according to the present invention or a fragment thereof,
  b) providing an interaction partner to said polypeptide or a fragment thereof, preferably an antibody according to the present invention,
  c) allowing interaction of said polypeptide or fragment thereof to said interaction partner to form an interaction complex,
  d) providing a candidate antagonist,
  e) allowing a competition reaction to occur between the candidate antagonist and the interaction complex, and
  f) determining whether the candidate antagonist inhibits or reduces the interaction activities of the polypeptide or the fragment thereof with the interaction partner.

In a twenty-fourth aspect the problem underlying the present invention is solved by an antagonist identified or identifiable by a method according to the twenty-second or twenty-third aspect of the present invention.

In a twenty-fifth aspect the problem underlying the present invention is solved by a process for in vitro diagnosis of a disease related to expression of the polypeptide or a fragment thereof according to any aspect of the present invention comprising determining the presence of a polynucleotide sequence encoding said polypeptide or the presence of a polypeptide according to any aspect of the present invention.

In a twenty-sixth aspect the problem underlying the present invention is solved by a process for in vitro diagnosing a disease related to expression of the polypeptide according to the present invention or a fragment thereof, comprising determining the presence of a nucleic acid sequence encoding said polypeptide or a fragment thereof according to the present invention, or the presence of the polypeptide according to the present invention or a fragment thereof.

In a twenty-seventh aspect the problem underlying the present invention is solved by a process for in vitro diagnosis of a bacterial infection, preferably *Streptococcus agalactiae* infection, comprising the step of determining the presence of a nucleic acid molecule according to any aspect of the present invention, or of a polypeptide according to any aspect of the present invention.

In a preferred embodiment of the latter three aspects of the present invention the presence is determined in a sample which is preferably derived from a host organism.

In a twenty-eighth aspect the problem underlying the present invention is solved by an affinity device comprising a support material and immobilized to said support material a polypeptide according to any aspect of the present invention or a nucleic acid molecule according to any aspect according to the present invention.

In a twenty-ninth aspect the problem underlying the present invention is solved by the use of a polypeptide according to any aspect of the present invention for the isolation and/or purification and/or identification of an interaction partner of said polypeptide.

In a thirtieth aspect the problem underlying the present invention is solved by the use of any of the polypeptides according to any aspect of the present invention for the generation of a peptide binding to said polypeptide.

In a preferred embodiment the peptide is selected from the group comprising anticalines.

In a thirty-first aspect the problem underlying the present invention is solved by the use of a polypeptide according to any aspect of the present invention for the manufacture of a functional nucleic acid, whereby the functional nucleic acid is selected from the group comprising aptamers and spiegelmers.

In a thirty-second aspect the problem underlying the present invention is solved by the use of a nucleic acid molecule according to any aspect of the present invention for the manufacture of a functional ribonucleic acid, whereby the functional ribonucleic acid is selected from the group comprising ribozymes, antisense nucleic acids and siRNA.

In a thirty-third aspect the problem underlying the present invention is solved by the use of a polypeptide according to the present invention or a fragment thereof as an antigen.

In a thirty-fourth aspect the problem underlying the present invention is solved by the use of a nucleic acid according to any aspect of the present invention for the manufacture or generation of a functional nucleic acid, preferably a ribonucleic acid, wherein the functional ribonucleic acid is selected from the group comprising ribozymes, antisense nucleic acids and siRNA.

In a thirty-fifth aspect the problem underlying the present invention is solved by the use of the polypeptides according to the present invention or any fragment thereof for the generation or manufacture of an antibody.

As used herein the term SEQ ID NO X to SEQ ID NO Y is an abbreviation for any of the SEQ ID Nos comprised by X and Y including X and Y.

The present inventors have surprisingly found that the genomes of GBS comprises a variety of adhesion factors which share a common amino acid motive. This amino acid motive is responsible for the binding of the adhesion factor to fibrinogen. As used herein, an adhesion factor is a factor, preferable a peptide or a protein which mediates the binding of a microorganism to a substrate. Preferably, the microorganism is GBS. More preferably, the substrate is fibrinogen and a host cell, respectively. The adhesion factor as used herein can be an adhesin or an invasin. The common amino acid motive can be described as follows using the one letter code for amino acids:

(SEQ ID NO 222)
G-N/S/T-V-L-A/E/M/Q-R-R-X-K/R/W-A/D/E/N/Q-A/F/I/L/V/Y-X-X-K/R-X-X.

As may be taken from the above sequence the amino acid motive comprises a total of 16 positions. Some of the positions have to be occupied by a distinct amino acid such as, e.g., position 1 or 3 or 4. Other positions such as positions 15 or 16 may be occupied by any amino acid, preferably by a naturally occurring amino acid. These positions are marked in the above sequence with an 'X'. Still further positions can be occupied by different amino acids. These different amino acids are indicated in the above motive, whereby the various amino acids are separated by '/'. Accordingly, at position 2 N, S or T may be present. Any permutations of the above sequence of amino acids can be realized by the one skilled in the art, which are thus within the scope of the present invention.

The present invention is thus related in one aspect to the above amino acid motive. More particularly, the present invention is related to any peptide or polypeptide which comprises this amino acid motive. It is to be understood that the terms peptide and polypeptide are used in a synonymous way if not indicated to the contrary.

Polypeptides, as used herein, include all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, unless otherwise indicated, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, $2^{nd}$ Ed., T. E. Creighton, W.H. Freeman and Company, New York (1993). Many detailed reviews are available on this subject, such as, for example, those provided by Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York (1983); Seifter et al., *Meth. Enzymol.* 182:626-646 (1990) and Rattan et al., *Protein Synthesis: Posttranslational Modification and Aging*, Ann. N.Y. Acad. Sci. 663:48-62 (1992). It will be appreciated, as is well known and as noted above, that polypeptides are not always entirely linear. For instance, polypeptides may be generally as a result of posttranslational event, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During posttranslational modification of the peptide, a methionine residue at the $NH_2$-terminus may be deleted. Accordingly, this invention contemplates the use of both the methionine-containing and the methionineless amino terminal variant of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, *E. coli*. Accordingly, when glycosylation is desired, a polypeptide should be expressed in glycosylating host, generally a eukaryotic cell. Insect cells often carry out the same posttranslational glycosylations as mammalian cells and, for this reason, insect cell expression systems have been developed to express efficiently mammalian proteins having native patterns of glycosylation, inter alia.

Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

Any polypeptide comprising the amino acid motive is regarded as a polypeptide according to the present invention. As explained in greater detail in the examples, the present inventors have found that GBS comprises a number of adhesion factors which comprise not only one copy of the amino acid motive but a number thereof. Thus any polypeptide comprising a plurality or being composed of a plurality of the amino acid motive is a polypeptide according to the present invention. For example, the adhesion factor referred to herein as FbsA may comprise as little as one unit of the amino acid motive to as much as 19 copies thereof.

Other adhesion factors according to the present invention are those referred to herein as PabA, PabB, PabC and PabD. It is to be understood that the term polypeptides according to the present invention also comprise any fragment, derivative or analog thereof. Further preferred polypeptides according to the present invention are those the amino acid sequence of which corresponds to SEQ ID 11 to 20.

The fragment, derivative or analog of the polypeptide of the present invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides set forth in the Sequence Listing, variants, analogs, derivatives and fragments thereof, and variants, analogs and derivatives of the fragments. Additionally, fusion polypeptides comprising such polypeptides, variants, analogs, derivatives and fragments thereof, and variants, analogs and derivatives of the fragments, in addition to a heterologous polypeptide, are contemplated by the present invention. Such fusion polypeptides and proteins, as well as polynucleotides encoding them, can readily be made using standard techniques, including standard recombinant techniques for producing and expressing a recombinant polynucleic acid encoding a fusion protein.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further particularly preferred in this regard are variants, analogs, derivatives and fragments, and variants, analogs and derivatives of the fragment, having the amino acid sequence of any polypeptide set forth in the Sequence Listing, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the polypeptide of the present invention. Also especially preferred in this regard are conservative substitutions. Most highly preferred polypeptides having an amino acid sequence set forth in the Sequence Listing without substitutions.

The polypeptides and polynucleotides of the present invention are preferably provided in an isolated form, and preferably are purified to homogeneity. Also the polypeptides according to the present invention are preferably isolated polypeptides.

The polypeptides of the present invention include any polypeptide set forth in the Sequence Listing (in particular a mature polypeptide) as well as polypeptides which have at least 70% identity to a polypeptide set forth in the Sequence Listing, preferably at least 80% or 85% identity to a polypeptide set forth in the Sequence Listing, and more preferably at least 90% similarity (more preferably at least 90% identity) to a polypeptide set forth in the Sequence Listing and still more preferably at least 95%, 96%, 97%, 98%, 99%, or 99.5% similarity (still more preferably at least 95%, 96%, 97%, 98%, 99%, or 99.5% identity) to a polypeptide set forth in the Sequence Listing and also include portions of such polypeptides with such portion of the polypeptide generally containing at least 5 amino acids and more preferably at least 10, 15 or 16 or multiples thereof Preferably, the multiples are multiples of a repeat of 16 amino acids, whereby the 16 amino acids correspond to the amino acid motive as disclosed herein.

Fragments or portions of the polypeptides of the present invention may be employed for producing the corresponding full-length polypeptide by peptide synthesis; therefore, the fragments may be employed as intermediates for producing the full-length polypeptides.

Fragments or portions of the polynucleotides of the present invention may be used to synthesize full-length polynucleotides of the present invention.

Also among preferred embodiments of this aspect of the present invention are polypeptides comprising fragments of the polypeptide having the amino acid sequence set forth in the Sequence Listing, and fragments of variants and derivatives of the polypeptides set forth in the Sequence Listing.

As used herein a fragment is a polypeptide having an amino acid sequence that entirely is the same as part but not all of the amino acid sequence of the aforementioned S. agalactiae polypeptides and variants or derivatives thereof.

Such fragments may be "free-standing", i. e., not part of or fused to another amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a polypeptide of the present invention comprised within a precursor polypeptide designed for expression in a host and having heterologous pre and pro-polypeptide regions fused to the amino terminus of the fragment and an additional region fused to the carboxyl terminus of the fragment. Therefore, fragments in one aspect of the meaning intended herein, refers to the portion or portions of a fusion polypeptide or fusion protein derived from a polypeptide of the present invention.

Representative examples of polypeptide fragments of the invention, include, for example, in any selected polypeptide, fragments from about amino acid number 45-60, 61-76, 77-92, 93-108, 109-124, 125-140, 141-156, 157-172, 173-188, 189-204, 205-220, 221-236, 237-252, 253-268, 269-284, 285-300, 301-316, 317-332, 333-348, 410-414 of the amino acid sequences disclosed herein, or any of the repeats, either alone or in combination with one or several of the ones mentioned in the following tables 1 and 2, optionally combined with the signal peptide or the LPXTG motif.

TABLE 1

| FbsA of GBS strain 6313 | FbsA of GBS strain 706 S2 |
|---|---|
| 1-35 signal peptide | 1-35 signal peptide |
| 45-60 repeat 1 (SEQ ID 113) | 45-60 repeat 1 (SEQ ID 132) |
| 61-76 repeat 2 (SEQ ID 114) | 61-76 repeat 2 (SEQ ID 133) |
| 77-92 repeat 3 (SEQ ID 115) | 77-92 repeat 3 (SEQ ID 134) |
| 93-108 repeat 4 (SEQ ID 116) | 93-108 repeat 4 (SEQ ID 135) |
| 109-124 repeat 5 (SEQ ID 117) | 109-124 repeat 5 (SEQ ID 136) |
| 125-140 repeat 6 (SEQ ID 118) | 125-140 repeat 6 (SEQ ID 137) |
| 141-156 repeat 7 (SEQ ID 119) | 141-156 repeat 7 (SEQ ID 138) |
| 157-172 repeat 8 (SEQ ID 120) | 157-172 repeat 8 (SEQ ID 139) |
| 173-188 repeat 9 (SEQ ID 121) | 173-188 repeat 9 (SEQ ID 140) |
| 189-204 repeat 10 (SEQ ID 122) | 189-204 repeat 10 (SEQ ID 141) |
| 205-220 repeat 11 (SEQ ID 123) | 205-220 repeat 11 (SEQ ID 142) |
| 221-236 repeat 12 (SEQ ID 124) | 221-236 repeat 12 (SEQ ID 143) |
| 237-252 repeat 13 (SEQ ID 125) | 237-252 repeat 13 (SEQ ID 144) |
| 253-268 repeat 14 (SEQ ID 126) | 253-268 repeat 14 (SEQ ID 145) |
| 269-284 repeat 15 (SEQ ID 127) | 269-284 repeat 15 (SEQ ID 146) |
| 285-300 repeat 16 (SEQ ID 128) | 285-300 repeat 16 (SEQ ID 147) |
| 301-316 repeat 17 (SEQ ID 129) | 301-316 repeat 17 (SEQ ID 148) |
| 317-332 repeat 18 (SEQ ID 130) | 378-382 LPXTG motif |
| 333-348 repeat 19 (SEQ ID 131) | |
| 410-414 LPXTG motif | |

TABLE 2

| FbsA of GBS strain 33 H1A | FbsA of GBS strain 176 H4A |
|---|---|
| 1-35 signal peptide | 1-35 signal peptide |
| 45-60 repeat 1 (SEQ ID 149) | 45-60 repeat 1 (SEQ ID 162) |
| 61-76 repeat 2 (SEQ ID 150) | 61-76 repeat 2 (SEQ ID 163) |
| 77-92 repeat 3 (SEQ ID 151) | 77-92 repeat 3 (SEQ ID 164) |
| 93-108 repeat 4 (SEQ ID 152) | 154-158 LPXTG motif |
| 109-124 repeat 5 (SEQ ID 153) | |
| 125-140 repeat 6 (SEQ ID 154) | |
| 141-156 repeat 7 (SEQ ID 155) | |
| 157-172 repeat 8 (SEQ ID 156) | |
| 173-188 repeat 9 (SEQ ID 157) | |
| 189-204 repeat 10 (SEQ ID 158) | |
| 205-220 repeat 11 (SEQ ID 159) | |
| 221-236 repeat 12 (SEQ ID 160) | |
| 237-252 repeat 13 (SEQ ID 161) | |
| 314-318 LPXTG motif | |

TABLE 3

| FbsA of GBS strain O90R | FbsA of GBS strain SS1169 |
|---|---|
| 1-35 signal peptide | 1-34 signal peptide |
| 45-60 repeat 1 (SEQ ID 165) | 45-60 repeat 1 (SEQ ID 175) |
| 61-76 repeat 2 (SEQ ID 166) | 61-76 repeat 2 (SEQ ID 176) |
| 77-92 repeat 3 (SEQ ID 167) | 77-92 repeat 3 (SEQ ID 177) |
| 93-108 repeat 4 (SEQ ID 168) | 93-108 repeat 4 (SEQ ID 178) |
| 109-124 repeat 5 (SEQ ID 169) | 109-124 repeat 5 (SEQ ID 179) |
| 125-140 repeat 6 (SEQ ID 170) | 125-140 repeat 6 (SEQ ID 180) |
| 141-156 repeat 7 (SEQ ID 171) | 141-156 repeat 7 (SEQ ID 181) |
| 157-172 repeat 8 (SEQ ID 172) | 157-172 repeat 8 (SEQ ID 182) |
| 173-188 repeat 9 (SEQ ID 173) | 173-188 repeat 9 (SEQ ID 183) |

TABLE 3-continued

| FbsA of GBS strain O90R | FbsA of GBS strain SS1169 |
|---|---|
| 189-204 repeat 10 (SEQ ID 174) | 189-204 repeat 10 (SEQ ID 184) |
| 267-270 LPXTG motif | 205-220 repeat 11 (SEQ ID 185) |
| | 221-236 repeat 12 (SEQ ID 186) |
| | 237-252 repeat 13 (SEQ ID 187) |
| | 253-268 repeat 14 (SEQ ID 188) |
| | 269-284 repeat 15 (SEQ ID 189) |
| | 285-300 repeat 16 (SEQ ID 190) |
| | 301-316 repeat 17 (SEQ ID 191) |
| | 317-332 repeat 18 (SEQ ID 192) |
| | 333-348 repeat 19 (SEQ ID 193) |
| | 349-364 repeat 20 (SEQ ID 194) |
| | 365-380 repeat 21 (SEQ ID 195) |
| | 381-396 repeat 22 (SEQ ID 196) |
| | 397-412 repeat 23 (SEQ ID 197) |
| | 413-428 repeat 24 (SEQ ID 198) |
| | 429-444 repeat 25 (SEQ ID 199) |
| | 445-460 repeat 26 (SEQ ID 200) |
| | 461-476 repeat 27 (SEQ ID 201) |
| | 477-492 repeat 28 (SEQ ID 202) |
| | 493-508 repeat 29 (SEQ ID 203) |
| | 509-524 repeat 30 (SEQ ID 204) |
| | 586-590 LPXTG motif |

As used herein "about" includes the particularly recited ranges larger or smaller by several, a few, 5, 4, 3, 2 or 1 amino acid at either extreme or at both extremes.

Preferred fragments of the invention include, for example, truncation polypeptides including polypeptides having an amino acid sequence set forth in the Sequence Listing, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out above also are preferred embodiments of truncation fragments, which are especially preferred among fragments generally. Degradation forms of the polypeptides of the invention in a host cell are also preferred.

Also preferred in this aspect of the invention are fragments characterized by structural or functional attributes of the polypeptide of the present invention. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions of the polypeptide of the present invention, and combinations of such fragments.

Preferred regions are those that mediate activities of the polypeptide of the present invention. Most highly preferred in this regard are fragments that have a chemical, biological or other activity of the polypeptide of the present invention, including those with a similar activity or an improved activity, or with a decreased undesirable activity. Particularly preferred are fragments comprising a receptor activity for such as, e.g., fibrinogen in case of FbsA or the host cell in case of PabA, PabB, PabC and PabD that confer a function essential for the ability of S. agalactiae to cause disease in humans and/or that are able to mediate the adherence and/or invasion of S. agalactiae to or into epithelial cells, more preferably human epithelial cells. Further preferred polypeptide fragments are those that comprise or contain antigenic or immunogenic determinants in an animal, especially in a human. A host cell as used herein is a cell which is capable of uptaking of GBS in the natural host or in an internalization assay such as, e.g., the one as described in example 1.

The polypeptides according to the present invention may be used for the detection of the organism or organisms in a sample containing these polypeptides. Preferably such detection is for diagnosis, more preferable for the diagnosis of a disease, most preferably for the diagnosis of a disease related or linked to the presence or abundance of Gram-positive bacteria, especially bacteria selected from the group comprising streptococci, staphylococci and lactococci. More preferably, the microorganisms are selected from the group comprising *Streptococcus agalactiae*, *Streptococcus pyogenes*, *Streptococcus pneumoniae* and *Streptococcus mutans*.

The present invention also relates to diagnostic assays such as quantitative and diagnostic assays for detecting levels of the polypeptide of the present invention in cells and tissues, including determination of normal and abnormal levels. Thus, for instance, a diagnostic assay in accordance with the invention for detecting over-expression of the polypeptide compared to normal control tissue samples may be used to detect the presence of an infection, for example, and to identify the infecting organism. Assay techniques that can be used to determine levels of a polypeptide, in a sample derived from a host are well-known to those of skill in the art. Such assay methods include radioimmunoassays, competitive-binding assays, Western Blot analysis and ELISA assays. Among these, ELISAs frequently are preferred. An ELISA assay initially comprises preparing an antibody specific to the polypeptide, preferably a monoclonal antibody. In addition, a reporter antibody generally is prepared which binds to the monoclonal antibody. The reporter antibody is attached to a detectable reagent such as radioactive, fluorescent or enzymatic reagent, such as horseradish peroxidase enzyme.

The polypeptides according to the present invention may also be used for the purpose of or in connection with an array. More particularly, at least one of the polypeptides according to the present invention may be immobilized on a support. Said support typically comprises a variety of polypeptides whereby the variety may be created by using one or several of the polypeptides according to the present invention and/or polypeptides being different therefrom. The characterizing feature of such array as well as of any array in general is the fact that at a distinct or predefined region or position on said support or a surface thereof, a distinct polypeptide is immobilized. Because of this any activity at a distinct position or region of an array can be correlated with a specific polypeptide. The number of different polypeptides immobilized on a support may range from as little as 10 to several 1000 different polypeptides. The density of polypeptides per $cm^2$ is in a preferred embodiment as little as 10 oligonucleotides per $cm^2$ to at least 400 different polynucleotides per $cm^2$ and more particularly at least 1000 different polypeptides per $cm^2$.

The manufacture of such arrays is known to the one skilled in the art and, for example, described in U.S. Pat. No. 5,744,309. The array preferably comprises a planar, porous or non-porous solid support having at least a first surface. The polypeptides as disclosed herein, are immobilized on said surface. Preferred support materials are, among others, glass or cellulose. It is also within the present invention that the array is used for any of the diagnostic applications described herein. Apart from the polypeptides according to the present invention also the nucleic acid molecules according to the present invention may be used for the generation of an array as described above. This applies as well to an array made of antibodies, preferably monoclonal antibodies as, among others, described herein.

The isolated nucleic acid molecule according to the present invention, also referred to herein as the nucleic acid (molecule) according to the present invention, codes for the amino acid motive and the polypeptides according to the present invention. The nucleic acid molecule according to the present invention can in a first alternative be a nucleic acid (molecule) which has an identity of at least 70% to a nucleic acid molecule which has the nucleic acid sequence as specified in SEQ ID No.1 to 10. It is also within the present invention that the isolated nucleic acid molecule has a similarity of at least 70% of any sequence, which encodes any of the polypeptides of the present invention. Preferably, the identity is at least 80% and more preferably the identity is at least 90%. Identity may also be 95%, 96%, 97%, 98%, 99% or 99.5%.

Identity, as known in the art and used herein, is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the mach between strings of such sequences. Identity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or two polypeptide sequences, the term is well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., SIAM J. *Applied Math.*, 48: 1073 (1988)). Preferred methods to determine identity are designed to give the largest match between the sequences tested. Methods to determine identity are codified in computer programs. Preferred computer program methods to determine identity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403 (1990)).

The nucleic acid according to the present invention can as a second alternative also be a nucleic acid which is at least essentially complementary to the nucleic acid described as the first alternative above. As used herein complementary means that a nucleic acid strand is base pairing via Watson-Crick base pairing with a second nucleic acid strand. Essentially complementary as used herein means that the base pairing is not occurring for all of the bases of the respective strands but leaves a certain number or percentage of the bases unpaired or wrongly paired. The percentage of correctly pairing bases is preferably at least 70%, more preferably 80%, even more preferably 90% and most preferably any percentage higher than 90%. It is to be noted that a percentage of 70% matching bases is considered as homology and the hybridization having this extent of matching base pairs is considered as stringent. Hybridization conditions for this kind of stringent hybridization may be taken from Current Protocols in Molecular Biology, John Wiley and Sons, Inc., 1987. More particularly, the hybridization conditions can be as follows:

Hybridization performed e.g. in 5× SSPE, 5× Denhardt's reagent, 0.1% SDS, 100 g/mL sheared DNA at 68° C.
Moderate stringency wash in 0.2×SSC, 0.1% SDS at 42° C.
High stringency wash in 0.1×SSC, 0.1% SDS at 68° C.

Genomic DNA with a GC content of 50% has an approximate $T_M$ of 96° C. For 1% mismatch, the $T_M$ is reduced by approximately 1° C.

In addition, any of the further hybridization conditions described herein are in principle applicable as well.

The nucleic acid according to the present invention can as a third alternative also be a nucleic acid which comprises a stretch of at least 15 bases of the nucleic acid according to the first and second alternative of the nucleic acid molecule according to the present invention as outlined above. Preferably, the bases form a contiguous stretch of bases. However, it is also within the present invention that the stretch consists of two or more moieties which are separated by a number of bases.

The nucleic acid according to the present invention can as a fourth alternative also be a nucleic acid which anneals under stringent hybridisation conditions to any of the nucleic acids of the present invention according to the above outlined first, second, and third alternative. Stringent hybridisation conditions are typically those described herein.

Finally, the nucleic acid according to the present invention can as a fifth alternative also be a nucleic acid which, but for the degeneracy of the genetic code, would hybridise to any of the nucleic acids according to any of the nucleic acids of the present invention according to the first, second, third, and fourth alternative as outlined above. This kind of nucleic acid refers to the fact that preferably the nucleic acids according to the present invention code for the polypeptides according to the present invention and thus for adhesins and invasions, respectively. This kind of nucleic acid is particularly useful in the detection and thus diagnosis of the nucleic acid molecules according to the present invention and thus of the respective microorganisms such as GBS and any disease or diseased condition where this kind of microorganims is involved. Preferably, the hybridisation would occur or be preformed under stringent conditions as described in connection with the fourth alternative described above.

Polynulceotide(s) as used herein generally refer to any polyribonucleotide or polydeoxribonucleotide, which may be unmodified RNA or DNA or modified RNA or DNA. Thus, for instance, polynucleotides as used herein refers to, among other, single-and double-stranded DNA, DNA that is a mixture of single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. The term polynucleotide also embraces short polynucleotides often referred to as oligonucleotide(s). "Polynucleotide" and "nucleic acid" or "nucleic acid molecule" are often used interchangeably herein.

Using the information provided herein and known, standard methods, such as those for cloning and sequencing and those for synthesizing polynucleotides and polypeptides (see, e.g., Sambrook et al., *Molecular Cloning: A Laboratory Manual*, 2$^{nd}$ Ed., Cold Spring Harbor Laboratory Press, Cold Spring Harbor, N.Y. (1989)), one can generate numerous unique fragments, both longer and shorter than the polynucleotides and polypeptides set forth in the Sequence Listing, of the *S. agalactiae* genome and the *S. agalactiae* coding regions, which are encompassed by the present invention. To be unique, a fragment must be of sufficient size to distinguish it from other known nucleic acid sequences, most readily determined by comparing any selected *S. agalactiae* fragment to the nucleotide sequences in computer databases such as GenBank. Such comparative searches are standard in the art. Many unique fragments will be *S. agalactiae*-specific. Typically, a unique fragment useful as a primer or probe will be at least about 20 to 25 nucleotides in length, depending upon the specific nucleotide content of the sequence. Additionally, fragments can be, for example, at least about 30, 40, 50, 60, 75, 80, 90, 100, 150, 200, 250, 300, 400, 500 or more nucleotides in length. The nucleic acid fragment can be single, double or triple stranded, depending upon the purpose for which it is intended.

Additionally, as discussed above and below, modifications can be made to the *S. agalactiae* polynucleotides and polypeptides that are encompassed by the present invention. For example, nucleotide substitutions can be made which do not affect the polypeptide encoded by the nucleic acid, and thus any polynucleotide which encodes the polypeptides of this invention is within the present invention. Additionally, certain amino acid substitutions (and corresponding nucleotide substitutions to encode them) can be made which are known in the art to be neutral (Robinson W. E. Jr. and Mitchell, W. m., *AIDS* 4: S141-S162 (1990)). Such variations may arise naturally as allelic variations (e. g. clue to genetic polymorphism) or may be produced by human intervention (e. g. by mutagenesis of cloned DNA sequences), such as induced point, deletion, insertion and substitution mutations. Minor changes in amino acid sequences are generally preferred, such as conservative amino acid replacements, small internal deletions or insertions, and additions or deletions at the ends of the molecules. Substitutions may be designed based on, for example, the model of Dayhoff, et al. (in *Atlas of Protein Sequence and Structure* 1978, Nat'l Biomed. Res. Found., Washington D.C.). These modifications can result in changes in the amino acid sequence, provide silent mutations, modify a restriction site, or provide other specific mutations. Likewise, such amino acid changes result in a different nucleic acid encoding the polypeptides and proteins. Thus, alternative polynucleotides, which are within the parameters of the present invention, are contemplated by such modifications.

Furthermore, some of the polynucleotide sequences set forth in the Sequence Listing are open reading frames (ORFs), i. e. coding regions of *S. agalactiae*. The polypeptide encoded by each open reading frame can be deduced, and the molecular weight of the polypeptide thus calculated using amino acid residue molecular weight values well known in the art. Any selected coding region can be functionally linked, using standard techniques such as standard subcloning techniques, to any desired regulatory sequence, whether a *S. agalactiae* regulatory sequence or a heterologous regulatory sequence, or to a heterologous coding sequence to create a fusion protein, as further described herein.

Polynucleotides of the present invention may be in the form of RNA, such as mRNA or cRNA, or in the form of DNA, including, for instance, cDNA and genomic DNA obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand.

The coding sequence which encodes a *S. agalactiae* polypeptide of this invention may be identical to the coding sequence of a polynucleotide set forth in the sequence listing. It also may be a polynucleotide with a different sequence which, as a result of the redundancy (degeneracy) of the genetic code, encodes a *S. agalactiae* polypeptide set forth in the sequence listing.

Polynucleotides of the present invention which encode a *S. agalactiae* polypeptide as disclosed herein, including those set forth in the sequence listing may include, but are not limited to, the coding sequence for a mature polypeptide, by itself; the coding sequence for a mature polypeptide and additional coding sequences, such as those encoding a leader or secretory sequence, such as a pre-, or pro- or prepro-protein sequence; the coding sequence of a mature polypeptide, with or without the aforementioned additional coding sequences, together with additional, non-coding sequences, including for example, but not limited to non-coding 5' and 3' sequences, such as the transcribed, non-translated sequences that play a role in transcription (including termination signals, for example), ribosome binding, mRNA stability elements, and additional coding sequence which encode additional amino acids, such as those which provide additional functionalities. Thus, for instance, a polypeptide may be fused to a marker sequence, such as a peptide, which facilitates purification of the fused polypeptide. In certain embodiments of this aspect of the invention, the marker sequence is a hexa-histidine peptide, such as the tag provided in the pQE vector (Qiagen, Inc.), among others, many of which are commercially available. As described in Gentz et al., *Proc. Natl. Acad. Sci., USA* 86: 821-824 (1989), for instance, hexa-histidine provides for convenient purificaion of the fusion protein. The HA tag may also be used to create fusion proteins and corresponds to an epitope derived of influenza hermagglutinin protein, which has been described by Wilson et al., *Cell* 37:767 (1984), for instance. Polynucleotides of the invention also include, but are not limited to, polynucleotides comprising a structural gene and its naturally associated genetic elements.

In accordance with the foregoing, the term "polynucleotide encoding a polypeptide" as used herein encompasses polynucleotides which include a sequence encoding a polypeptide of the present invention, particularly a polypeptide having a *S. agalactiae* amino acid sequence set forth in the Sequence Listing. The term encompasses polynucleotides that include a single continuous region or discontinuous regions encoding the polypeptide (for example, interrupted by integrated phage or insertion sequence or editing) together with additional regions, that also may contain coding and/or non-coding sequences.

The present invention further relates to variants of the herein above described polynucleotides which encode for fragments, analogs and derivatives of the polypeptide having a deducted *S. agalactiae* amino acid sequence set forth in the Sequence Listing. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the ,aforementioned polynucleotides by nucleotide substitutions, deletions or additions. The substitutions, deletions or additions may involve one or more nucleotides. The variants may be altered in coding or on-coding regions or both. Alterations in the coding regions may produce conservative or non-conservative amino acid substitutions, deletions or additions. Preferred are polynucleotides encoding a variant, analog, derivative or fragment, or a variant, analogue or derivative of a fragment, which have a S. agalactiae sequence as set forth in the Sequence Listing, in which several, a few, 5 to 10, 1 to 5, 1 to 3, 2, 1 or no amino acid(s) is substituted, deleted or added, in any combination. Especially preferred among these are silent substitutions, additions and deletions, which do not alter the properties and activities of the S. agalactiae polypeptides set forth in the Sequence Listing. Also especially preferred in this regard are conservative substitutions.

Further preferred embodiments of the invention are polynucleotides that are at least 70% identical over their entire length to a polynucleotide encoding a polypeptide according to the present invention and more particularly those polypeptides having an amino acid sequence set forth in the Sequence Listing, and polynucleotides which are complementary to such polynucleotides. Alternatively, most highly preferred are polynucleotides that comprise a region that is at least 80% or at least 85% identical over their entire length to a polynucleotide encoding a S. agalactiae polypeptide according to the present invention and more particularly those polypeptides set forth in the Sequence Listing, including complementary polynucleotides. In this regard, polynucleotides at least 90%, 91%, 92%, 93%, 94%, 95%, or 96% identical over their entire length to the same are particularly preferred, and among these particularly preferred polypeptides, those with at least 95% are especially preferred. Furthermore, those with at least 97% are highly preferred among those with at least 95%, and among these, those with at least 98% and at least 99% are particularly highly preferred, with at least 99% or 99.5% being the more preferred.

Preferred embodiments in this respect, moreover, are polynucleotides which encode polypeptides which retain substantially the same biological function or activity as the mature polypeptide encoded by the DNA set forth in the Sequence Listing.

The present invention further relates to polynucleotides that hybridize to the herein above-described sequences. In this regard, the present invention especially relates to polynucleotides which hybridize under stringent conditions to the herein above-described polynucleotides. Stringent conditions are typically selective conditions. As herein used, the term "stringent conditions" means hybridization will occur only if there is at least 95% and preferably at least 97% identity between the sequences. For a specific sequence, stringent conditions can be determined empirically according to the nucleotide content, as is known in the art and also exemplified herein. For example, a typical example of stringent conditions is hybridization of a 48mer having 55% GC content at 42° C. in 50% formamide and 750 mM NaCl followed by washing at 55° C. in 15 mM NaCl and 0.1% SDS.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding polypeptides of the present invention and to isolate cDNA and genomic clones of other genes that have a high sequence similarity to the polynucleotides of the present invention. Such probes generally will comprise at least 15 bases. Preferably, such probes will have at least 20, at least 25 or at least 30 bases, and may have at least 50 bases. Particularly preferred probes will have at least 30 bases, and will have 50 bases or less, such as 30, 35, 40, 45, or 50 bases.

For example, the coding region of the polynucleotide of the present invention may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine to which members of the library the probe hybridizes.

The polynucleotides and polypeptides of the present invention may be employed as reagents and materials for development of treatments of and diagnostics for disease, particularly human disease, as further discussed herein relating to polynucleotide assays, inter alia.

The polynucleotides of the present invention that are oligonucleotides can be used in the processes herein as described, but preferably fol PCR, to determine whether or not the S. agalactiae genes identified herein in whole or in part are present and/or transcribed in infected tissue such as blood. It is recognized that such sequences will also have utility in diagnosis of the stage of infection and type of infection the pathogen has attained. For this and other purposes the arrays comprising at least one of the nucleic acids according to the present invention as described herein, may be used.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

The present invention additionally contemplates polynucleotides functionally encoding fusion polypeptides wherein the fusion polypeptide comprises a fragment of a S. agalactiae polypeptide and one or more polypeptide(s) derived from another S. agalactiae polypeptide or from another organism or a synthetic polyamino acid sequence. Such polynucleotides may or may not encode amino acid sequences to facilitate cleavage of the S. agalactiae polypeptide from the other polypeptide(s) under appropriate conditions.

In sum, a polynucleotide of the present invention may preferably encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Isolated as used herein means separated "by the hand of man" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the term is employed herein. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

The nucleic acids according to the present invention may be chemically synthesized. Alternatively, the nucleic acids can be isolated from various microorganisms by methods known to the one skilled in the art. Appropriate sources are, e.g. *Streptococcus agalactiae, Streptococcus pyogenes, Streptococcus mutans* and *Streptococcus pneumoniae*.

The nucleic acids according to the present invention may be used for the detection of nucleic acids and organisms or samples containing these nucleic acids. Preferably such detection is for diagnosis, more preferable for the diagosis of a disease, most preferably for the diagnosis of a disease related or linked to the present or abundance of *S. agalactiae*.

*S. agalactiae* bacteria, which have infected eukaryotes (herein also "individual(s)"), particularly mammals, and especially humans, may be detected at the DNA level by a variety of techniques. By selecting regions of nucleic acids that vary among strains of *S. agalactiae*, preferred candidates for distinguishing a specific strain of *S. agalactiae* can be obtained. Furthermore, by selecting regions of nucleic acids that vary between *S. agalactiae* and other organisms, preferred candidates for distinguishing *S. agalactiae* from other organisms can be obtained. Nucleic acids for diagnosis may be obtained from an infected individual's cells and tissues, such as bone, blood, muscle, cartilage, and skin. Genomic DNA may be used directly for detection or may be amplified enzymatically by using PCR (Saiki et al., *Nature*, 324: 163-166 (1986) prior to analysis. RNA or cDNA may also be used in the same ways. As an example, PCR primers complementary to the nucleic acid forming part of the polynucleotide of the present invention can be used to identify and analyze for its presence and/or expression. Using PCR, characterization of the strain of *S. agalactiae* present in a mammal, and especially a human, may be made by an analysis of the genotype of the prokaryote gene. For example, deletions and insertions can be detected by a change in size of the amplified product in comparison to the genotype of a reference sequence. Point mutations can be identified by hybridising amplified DNA to radiolabeled RNA or alternatively, radiolabeled antisense DNA sequences. Perfectly matched sequences can be distinguished form mismatched duplexes by Rnase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer can be used with double-stranded PCR product or a single-stranded template molecule generated by a modified PCR. The sequence determination is performed by conventional procedures with radiolabled nucleotide or by automatic sequencing procedures with fluorescent-tags.

Genetic characterization based on DNA sequence differences may be achieved by detection of alteration in electrophoretic mobility of DNA fragments in gels, with or without denaturing agents. Small sequence deletions and insertions can be visualised by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g. Myers et al., *Science*, 230: 1242 (1985)).

Sequence changes at specific locations also may be revealed by nuclease protection assays, such as Rnase and S1 protection or the chemical cleavage method (e. g., Cotton et al., *Proc. Natl. Acad. Sci., USA*, 85: 4397-4401 (1985)).

Thus, the detection of a specific DNA sequence may be achieved by methods such as hybridization, Rnase protection, chemical cleavage, direct DNA sequencing or the use of restriction enzymes, e. g., restriction fragment length polymorphisms (RFLP) and Southern blotting of genomic DNA.

In addition to more conventional gel-electrophoresis and DNA sequencing, mutations also can be detected by in situ analysis.

Cells carrying mutations or polymorphisms in the gene of the present invention may also be detected at the DNA level by a variety of techniques, to allow for serotyping, for example. For example, RT-PCR can be used to detect mutations. It is particularly preferred to use RT-PCR in conjunction with automated detection systems, such as, for example, GeneScan. RNA or cDNA may also be used for the same purpose, PCR or RT-PCR. As an example, PCR primers complementary to the nucleic acid encoding the polypeptide of the present invention can be used to identify and analyse mutations. The primers may be used to amplify the gene isolated from the individual such that the gene may then be subject to various techniques for elucidation of the DNA sequence. In this way, mutations in the DNA sequence may be diagnosed.

The invention provides a process for diagnosing disease, arising from infection with *S. agalactiae*, comprising determining from a sample isolated or derived from an individual an increased level of expression of a polynucleotide having the sequence of a polynucleotide set forth in the Sequence Listing. Expression of polynucleotide can be measured using any one of the methods well known in the art for the quantitation of polynucleotides, such as, for example, PCR, RT-PCR, Rnase protection, Northern blotting, other hybridisation methods and the arrays described herein.

The present invention also relates to vectors which comprise a polynucleotide or polynucleotides of the present invention, host cells which are genetically engineered with vectors of the invention and the production of polypeptides of the invention by recombinant techniques.

Cells can be genetically engineered to incorporate polynucleotides and express polypeptides of the present invention. Introduction of polynucleotides into the host cell can be effected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis et al., BASIC METHODS IN MOLECULAR BIOLOGY, (1986) and Sambrook et al., MOLECULAR CLONONG: A LABORATORY MANUAL, $2^{nd}$ Ed., Cold Spring Harbor Laboratory Press, Cold Spring Harbor, N.Y. (1989).

Polynucleotide constructs in cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al, MOLECULAR CLONING: A LABORATORY MANUAL, $2^{nd}$ Ed., Cold Spring Harbor Laboratory Press, Cold Spring Harbor, N.Y. (1989).

In accordance with this aspect of the invention the vector may be, for example, a plasmid vector, a single or double-stranded phage vector, a single or double-stranded RNA or DNA viral vector, a single or double-stranded RNA or DNA viral vector. Plasmids generally are designated herein by a lower case p preceded and/or followed by capital letters and/or number, in accordance with standard naming conventions that are familiar to those of skill in the art. Starting plasmids disclosed herein are either commercially available, publicly available, or can be constructed from available plasmids by routine application of well known, published procedures, given the teachings herein. Many plasmids and other cloning and expression vectors that can be used in accordance with the present invention are well known and readily available to those of skill in the art.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic cells, are well known and employed routinely by those of skill in the art.

A great variety of expression vectors can be used to express a polypeptide of the invention. Such vectors include, among other, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for experssion in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques, such as, for example, those set forth in Sambrook et al., MOLECULAR CLONING, A LABORATORY MANUAL, $2^{nd}$ Ed.; Cold Spring Harbor Laboratory Press, Cold Spring Harbor, N.Y. (1989).

The DNA sequence in the expression vector is operatively linked to appropriate expression control sequence(s), including, for instance, a promoter to direct mRNA transcription. Representatives of such promoters include, but are not limited to, the phage lambda PL promoter, the *E. coli* lac, trp and tac promoters, the SV40 early and late promoters and promoters of retroviral LTRs.

In general, expression constructs will contain sites for transcription initiation and termination, and, in the transcribed region, a ribosome binding site for translation. The coding portion of the mature transcripts expressed by the constructs will include a translation initiating AUG or others such as GUG and UUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination, among other.

Vectors for propagation and expression generally will include selectable markers and amplification regions, such as, for example, those set forth in Sambrook et al., MOLECULAR CLONONG, A LABORATORY MANUAL, $2^{nd}$ Ed.; Cold Spring Harbor Laboratory Press, Cold Spring Harbor, N.Y. (1989)

Representative examples of appropriate cells which host said vectors include bacterial cells, such as streptococci, staphylococci, *E. coli*, streptomyces and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, Pkk233-3, pDR540, pRIT5 available from Pharmacia, and pBR322 (ATCC 37017). Among preferred eukaryotic vectors are pWLNEO, pSV2CAT, pOG44, PXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides of the present invention include not only well known and readily available promoters, but also promoters that readily may be obtained by the foregoing technique, using a reporter gene.

Among known prokaryotic promoters suitable for expression of polynucleotides and polypeptides in accordance with the present invention are the *E. coli* lacI and lacZ and promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus "(RSV")", and metallothionein promoters, such as the mouse metallothionein-I promoter.

Recombinant expression vectors will include, for example, origins of replication, a promoter preferably derived from a highly-expressed gene to direct transcription of a downstream structural sequence, and a selectable marker to permit isolation of vector containing cells after exposure to the vector.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. A transcription termination signal appropriately disposed at the 3'end of the transcribed region may also be included in the polynucleotide construct.

For secretion of the translated protein into the lumen of the endoplasmic reticulum, into the periplasmic space or into the extracellular environment, appropriate secretion signals may be incorporated into the expressed polypeptide.

These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N- or C-terminus of the polypeptide to improve stability and persistence in the host cell, during purification or during subsequent handling and storage. Also, regions may be added to the polypeptide to facilitate purification. Such regions may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from immunoglobulin that is useful to solubilize or purify polypeptides. For example, EP-A-0 464 533 (Canadian counterpart 2045869) discloses fusion proteins comprising various portions of constant region of immunoglobin molecules together with another protein or part thereof. In drug discovery, for example, proteins have been fused with antibody Fc portions for the purpose of high-throughput screening assays to identify antagonists. See, D. Bennett et al., *Journal of Molecular Recognition*, Vol. 8 52-58 (1995) and K. Johanson et al., *The Journal of Biological Chemistry*, Vol. 270, No. 16, pp 9459-9471 (1995).

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents; such methods are well known to those skilled in the art.

Mammalian expression vectors may comprise expression sequences, such as an origin of replication, a suitable promoter and enhancer, and also any necessary ribosome binding sites, polyadenylation regions, splice donor and acceptor sites, transcriptional termination sequences, and 5' flanking non-transcribed sequences that are useful or necessary for expression.

The polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well-known techniques for refolding protein may be employed to regenerate the active conformation when the polypeptide is denatured during isolation and or purification.

The polypeptides according to the present invention can be produced by chemical synthesis as well as by biotechnological means. The latter comprise the transfection or transformation of a host cell with a vector containing a nucleic acid according to the present invention and the cultivation of the transfected or transformed host cell under conditions, which are known to the ones skilled in the art. The production method may also comprise a purification step in order to purify or isolate the polypeptide to be manufactured. In a preferred embodiment the vector is a vector according to the present invention.

In a further aspect the present invention relates to an antibody directed to any of the polypeptides, derivatives or fragments thereof according to the present invention. The present invention includes, for example, monoclonal and polyclonal antibodies, chimeric, single chain, and humanized antibodies, as well as Fab fragments, or the product of a Fab expression library. It is within the present invention that the antibody may be chimeric, i. e. that different parts thereof stem from different species or at least the respective sequences are taken from different species.

Antibodies generated against the polypeptides corresponding to a sequence of the present invention can be obtained by direct injection of the polypeptides into an animal or by administering the polypeptides to an animal, preferably a non-human. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique known in the art, which provides antibodies produced by continuous cell line cultures can be used. Examples include various techniques, such as those in Kohler, G. and Milstein, C., Nature 256: 495-497 (1975); Kozbor et al., Immunology Today 4: 72 (1983); Cole et al., pg. 77-96 in MONOCLONAL ANTIBODIES AND CANCER THERAPY, Alan R. Liss, Inc. (1985); U.S. Pat. Nos 5,545,403; 5,545,405; 5,654,403; 5,792,838; 5,316,938; 5,633,162; 5,644,036; 5,858,725.

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

Alternatively, phage display technology could be utilized to select antibody genes with binding activities towards the polypeptide either from repertoires of PCR amplified v-genes of lymphocytes from humans screened for possessing anti-Fab or from naïve libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

If two antigen binding domains are present, each domain may be directed against a different epitope—termed 'bispecific' antibodies.

The above-described antibodies may be employed to isolate or to identify clones expressing the polypeptide or purify the polypeptide of the present invention by attachment of the antibody to a solid support for isolation and/or purification by affinity chromatography.

Thus, among others, antibodies against the polypeptide of the present invention may be employed to inhibit and/or treat infections, particularly bacterial infections and especially infections arising from *S. agalactiae*.

Polypeptide derivatives include antigenically, epitopically or immunologically equivalent derivatives which form a particular aspect of this invention. The term "antigenically equivalent derivative" as used herein encompasses a polypeptide or its equivalent which will be specifically recognized by certain antibodies which, when raised to the protein or polypeptide according to the present invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof can be used as an antigen to immunize a mouse or other animal such as a rat or chicken. The fusion protein may provide stability to the polypeptide. The antigen may be associated, for example by conjugation, with an immunogenic carrier protein, for example bovine serum albumin (BSA) or keyhole limpet haemocyanin (KLH). Alternatively, a multiple antigenic peptide comprising multiple copies of the protein or polypeptide, or an antigenically or immunologically equivalent polypeptide thereof, may be sufficiently antigenic to improve immunogenicity so as to obviate the use of a carrier.

Preferably the antibody or derivative thereof is modified to make it less immunogenic in the individual. For example, if the individual is human the antibody may most preferably be "humanized", wherein the complimentarity determining region(s) of the hybridoma-derived antibody has been transplanted into a human monoclonal antibody, for example as described in Jones, P. et al. (1986), Nature 321, 522-525 or Tempest at al., (1991) Biotechnology 9, 266-273.

The use of a polynucleotide of the invention in genetic immunization will preferably employ a suitable delivery method such as direct injection of plasmid DNA into muscle (Wolff et al., (1992) Hum. Mol. Genet. 1, 363; Manthorpe et al., (1963) Hum. Gene Ther. 4, 419) delivery of DNA complexed with specific protein carriers (Wu et al., (1989) J Biol. Chem. 264, 16985), coprecipitation of DNA with calcium phosphate (Benvenisty & Reshef (1986) PNAS 83, 9551), encapsulation of DNA in various forms of liposomes (Kaneda et al., (1989) Science 243, 375), particle bombardment (Tang et al., (1992) Nature 356, 152; Eisenbraun et al., (1993) DNA Cell. Biol. 12, 791) and in vivo infection using cloned retroviral vectors (Seeger et al., (1984) PNAS 81, 5849).

In a further aspect the present invention relates to a peptide binding to any of the polypeptides according to the present invention, and a method for the manufacture of such peptides whereby the method is characterized by the use of the polypeptides according to the present invention and the basic steps are known to the one skilled in the art.

Such peptides may be generated by using methods according to the state of the art such as phage display or ribosome display. In case of phage display, basically a library of peptide is generated, such as in form of phages, and this kind of libraries is contacted with the target molecule, in the present case the polypeptides according to the present invention. Those peptides binding to the target molecule are subsequently removed, preferably as a complex with the target molecule, from the respective reaction. It is known to the one skilled in the art that the binding characteristics, at least to a certain extend, depend on the particularly realized experimental set-up such as the salt concentration and the like. After separating those peptides binding to the target molecule with a higher affinity or a bigger force, from the non-binding members of the library, and optionally also after removal of the target molecule from the complex of target molecule and peptide, the respective peptide(s) may subsequently be characterised. Prior to the characterisation optionally an amplification step is realized such as, e. g. by propagating the peptide coding phages. The characterisation preferably comprises the sequencing of the target binding peptides. Basically, the peptides are not limited in their lengths, however, preferably peptides having a lengths from about 8 to 20 amino acids are preferably obtained in the respective methods. The size of the libraries may be about $10^2$ to $10^{18}$, preferably $10^8$ to $10^{15}$ different peptides, however, is not limited thereto.

A particular form of target binding polypeptides are the so-called "anticalines" which are, among others, described in German patent application DE 197 42 706.

In a further aspect the present invention relates to functional nucleic acids interacting with any of the polypeptides according to the present invention, and a method for the manufacture of such functional nucleic acids whereby the method is characterized by the use of the polypeptides according to the present invention and the basic steps are known to the one skilled in the art. The functional nucleic acids are preferably aptamers and spiegelmers.

Aptamers are D-nucleic acids, which are either single stranded or double stranded and which specifically interact with a target molecule. The manufacture or selection of aptamers is, e. g., described in European patent EP 0 533 838. Basically the following steps are realized. First, a mixture of nucleic acids, i. e. potential aptamers, is provided whereby each nucleic acid typically comprises a segment of several, preferably at least eight subsequent randomised nucleotides. This mixture is subsequently contacted with the target molecule whereby the nucleic acid(s) binds to the target molecule, such as based on an increased affinity towards the target or with a bigger force thereto, compared to the candidate mixture. The binding nucleic acid(s) are/is subsequently separated from the remainder of the mixture. Optionally, the thus obtained nucleic acid(s) is amplified using, e.g. polymerase chain reaction. These steps may be repeated several times giving at the end a mixture having an increased ratio of nucleic acids specifically binding to the target from which the final binding nucleic acid is then optionally selected. These specifically binding nucleic acid(s) are referred to as aptamers. It is obvious that at any stage of the method for the generation or identification of the aptamers samples of the mixture of individual nucleic acids may be taken to determine the sequence thereof using standard techniques. It is within the present invention that the aptamers may be stabilized such as, e. g., by introducing defined chemical groups which are known to the one skilled in the art of generating aptamers. Such modification may for example reside in the introduction of an amino group at the 2'-position of the sugar moiety of the nucleotides. Aptamers are currently used as therapeutical agens. However, it is also within the present invention that the thus selected or generated aptamers may be used for target validation and/or as lead substance for the development of medicaments, preferably of medicaments based on small molecules. This is actually done by a competition assay whereby the specific interaction between the target molecule and the aptamer is inhibited by a candidate drug whereby upon replacement of the aptamer from the complex of target and aptamer it may be assumed that the respective drug candidate allows a specific inhibition of the interaction between target and aptamer, and if the interaction is specific, said candidate drug will, at least in principle, be suitable to block the target and thus decrease its biological availability or activity in a respective system comprising such target. The thus obtained small molecule may then be subject to further derivatisation and modification to optimise its physical, chemical, biological and/or medical characteristics such as toxicity, specificity, biodegradability and bioavailability.

Spiegelmers and their generation or manufacture is based on a similar principle. The manufacture of spiegelmers is described in international patent application WO 98/08856. Spiegelmers are L-nucleic acids, which means that they are composed of L-nucleotides rather than D-nucleotides as aptamers are. Spiegelmers are characterized by the fact that they have a very high stability in biological systems and, comparable to aptamers, specifically interact with the target molecule against which they are directed. In the process of generating spiegelmers, a heterogeneous population of D-nucleic acids is created and this population is contacted with the optical antipode of the target molecule, in the present case for example with the D-enantiomer of the naturally occurring L-enantiomer of the polypeptides according to the present invention. Subsequently, those D-nucleic acids are separated which do not interact with the optical antipode of the target molecule. But those D-nucleic acids interacting with the optical antipode of the target molecule are separated, optionally determined and/or sequenced and subsequently the corresponding L-nucleic acids are synthesized based on the nucleic acid sequence information obtained from the D-nucleic acids. These L-nucleic acids, which are identical in terms of sequence with the aforementioned D-nucleic acids interacting with the optical antipode of the target molecule, will specifically interact with the naturally occurring target molecule rather than with the optical antipode thereof. Similar to the method for the generation of aptamers it is also possible to repeat the various steps several times and thus to enrich those nucleic acids specifically interacting with the optical antipode of the target molecule.

In a further aspect the present invention relates to functional nucleic acids interacting with any of the nucleic acid molecules according to the present invention, and a method for the manufacture of such functional nucleic acids whereby the method is characterized by the use of the nucleic acid molecules and their respective sequences according to the present invention and the basic steps are known to the one skilled in the art. The functional nucleic acids are preferably ribozymes, antisense oligonucleotides and siRNA.

Ribozymes are catalytically active nucleic acids, which preferably consist of RNA which basically comprises two moieties. The first moiety shows a catalytic activity whereas the second moiety is responsible for the specific interaction with the target nucleic acid, in the present case the nucleic acid coding for the polypeptides according to the present invention. Upon interaction between the target nucleic acid and the second moiety of the ribozyme, typically by hybridisation and Watson-Crick base pairing of essentially complementary stretches of bases on the two hybridising strands, the catalytically active moiety may become active which means that it catalyses, either intramolecularly or intermolecularly, the target nucleic acid in case the catalytic activity of the ribozyme is a phosphodiesterase activity. Subsequently, there may be a further degradation of the target nucleic acid which in the end results in the degradation of the target nucleic acid as well as the protein derived from the said target nucleic acid. Ribozymes, their use and design principles are known to the one skilled in the art, and, for example described in Doherty and Doudna ((2001) Ribozym structures and mechanism. Annu. Rev. Biophys. Biomolstruct. 30, 457-475) and Lewin and Hauswirth (Ribozyme Gene Therapy: Applications for molecular medicine. 2001 7: 221-8).

The activity and design of antisense oligonucleotides for the manufacture of a medicament and as a diagnostic agent, respectively, is based on a similar mode of action. Basically, antisense oligonucleotides hybridise based on base complementarity, with a target RNA, preferably with a mRNA, thereby activate RNase H. RNase H is activated by both phosphodiester and phosphorothioate-coupled DNA. Phosphodiester-coupled DNA, however, is rapidly degraded by cellular nucleases with the exception of phosphorothioate-coupled DNA_ These resistant, non-naturally occurring DNA derivatives do not inhibit RNase H upon hybridisation with RNA. In other words, antisense polynucleotides are only effective as DNA RNA hybride complexes. Examples for this kind of antisense oligonucleotides are described, among others, in U.S. Pat. Nos. 5,849,902 and 5,989,912. In other words, based on the nucleic acid sequence of the target molecule which in the present case are the nucleic acid molecules for the polypeptides according to the present invention, either from the target protein from which a respective nucleic acid sequence may in principle be deduced, or by knowing the nucleic acid sequence as such, particularly the mRNA, suitable antisense oligonucleotides may be designed based on the principle of base complementarity.

Particularly preferred are antisense-oligonucleotides, which have a short stretch of phosphorothioate DNA (3 to 9 bases). A minimum of 3 DNA bases is required for activation of bacterial RNase H and a minimum of 5 bases is required for mammalian RNase H activation. In these chimeric oligonucleotides there is a central region that forms a substrate for RNase H that is flanked by hybridising "arms" comprised of modified nucleotides that do not form substrates for RNase H. The hybridising arms of the chimeric oligonucleotides may be modified such as by 2'-O-methyl or 2'-fluoro. Alternative approaches used methylphosphonate or phosphoramidate linkages in said arms. Further embodiments of the antisense oligonucleotide useful in the practice of the present invention are P-methoxyoligonucleotides, partial P-methoxyoligodeoxyribonucleotides or P-methoxyoligonucleotides.

Of particular relevance and usefulness for the present invention are those antisense oligonucleotides as more particularly described in the above two mentioned US patents. These oligonucleotides contain no naturally occurring 5'3'-linked nucleotides. Rather the oligonucleotides have two types of nucleotides: 2'-deoxyphosphorothioate, which activate RNase H, and 2'-modified nucleotides, which do not. The linkages between the 2'-modified nucleotides can be phosphodiesters, phosphorothioate or P-ethoxyphosphodiester. Activation of RNase H is accomplished by a contiguous RNase H-activating region, which contains between 3 and 5 2'-deoxyphosphorothioate nucleotides to activate bacterial RNase H and between 5 and 10 2'-deoxyphosphorothioate nucleotides to activate eucaryotic and, particularly, mammalian RNase H. Protection from degradation is accomplished by making the 5' and 3' terminal bases highly nuclease resistant and, optionally, by placing a 3' terminal blocking group.

More particularly, the antisense oligonucleotide comprises a 5' terminus and a 3' terminus; and from 11 to 59 5' 3'-linked nucleotides independently selected from the group consisting of 2'-modified phosphodiester nucleotides and 2'-modified P-alkyloxyphosphotriester nucleotides; and wherein the 5'-terminal nucleoside is attached to an RNase H-activating region of between three and ten contiguous phosphorothioate-linked deoxyribonucleotides, and wherein the 3'-terminus of said oligonucleotide is selected from the group consisting of an inverted deoxyribonucleotide, a contiguous stretch of one to three phosphorothioate 2'-modified ribonucleotides, a biotin group and a P-alkyloxyphosphotriester nucleotide.

Also an antisense oligonucleotide may be used wherein not the 5' terminal nucleoside is attached to an RNase H-activating region but the 3' terminal nucleoside as specified above. Also, the 5' terminus is selected from the particular group rather than the 3' terminus of said oligonucleotide.

The nucleic acids as well as the polypeptides according to the present invention may be used as or for the manufacture of vaccines. Preferably such vaccine is for the prevention or treatment of diseases caused by, related to or associated with GBS. In so far another aspect of the invention relates to a method for inducing an immunological response in an individual, particularly a mammal, which comprises inoculating the individual with the polypeptide of the invention, or a fragment or variant thereof, adequate to produce antibody to protect said individual from infection, particularly bacterial infection and most particularly *Streptococcus* infections.

Yet another aspect of the invention relates to a method of inducing immunological response in an individual which comprises, through gene therapy or otherwise, delivering a nucleic acid functionally encoding the polypeptide, or a fragment or a variant thereof, for expressing the polypeptide, or a fragment or a variant thereof in vivo in order to induce an immunological response to produce antibodies or a cell mediated T cell response, either cytokine-producing T cells or cytotoxic T cells, to protect said individual from disease, whether that disease is already established within the individual or not. One way of administering the gene is by accelerating it into the desired cells as a coating on particles or otherwise.

A further aspect of the invention relates to an immunological composition which, when introduced into a host capable of having induced within it an immunological response, induces an immunological response in such host, wherein the composition comprises recombinant DNA which codes for and expresses an antigen of the polypeptide of the present invention. The immunological response may be used therapeutically or prophylactically and may take the form of antibody immunity or cellular immunity such as that arising from CTL or CD4+ T cells.

The polypeptide of the invention or a fragment thereof may be fused with co-protein, which may not by itself produce antibodies, but is capable of stabilizing the first protein and producing a fused protein, which will have immunogenic and protective properties. This fused recombinant protein preferably further comprises an antigenic co-protein, such as Glutathione-S-transferase (GST) or beta-galactosidase, relatively large co-proteins which solubilise the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al., Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *S. agalactiae*. Such fragments will be particularly useful for identifying protein epitopes able to provoke a prophylactic or therapeutic immune response. This approach can allow for the subsequent preparation of monoclonal antibodies of particular value from the requisite organ of the animal successfully resisting or clearing infection for the development of prophylactic agents or therapeutic treatments of *S. agalactiae* infection in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused e.g. by mechanical, chemical or thermal damage or by implantation of indwelling devices, or wounds in the mucous membranes, such as the mouth, mammary glands, urethra or vagina.

The present invention also includes a vaccine formulation, which comprises the immunogenic recombinant protein together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials, and may be stored in a freeze-dried condition requiring only the addition of the sterile liquid carrier immediately prior to use. The vaccine formulation may also include adjuvant systems for enhancing the immunogenicity of the formulation, such as oil-in-water systems and other systems known in the art. The dosage will depend on the specific activity of the vaccine and can be readily determined by routine experimentation.

It is also within the present invention that the vaccine comprises apart from the polypeptide and/or nucleic acid molecule according to the present invention other compounds, which are biologically or pharmaceutically active. Preferably, the vaccine composition comprises at least one polycationic peptide. The polycationic compound(s) to be used according to the present invention may be any polycationic compound, which shows the characteristic effects according to the WO 97/30721. Preferred polycationic compounds are selected from basic polypeptides, organic polycations, basic polyamino acids or mixtures thereof. These polyamino acids should have a chain length of at least 4 amino acid residues (WO 97/30721). Especially preferred are substances like polylysine, polyarginine and polypeptides containing more than 20%, especially more than 50% of basic amino acids in a range of more than 8, especially more than 20, amino acid residues or mixtures thereof. Other preferred polycations and their pharmaceutical compositions are described in WO 97/30721 (e. g. polyethyleneimine) and WO 99/38528. Preferably these polypeptides contain between 20 and 500 amino acid residues, especially between 30 and 200 residues.

These polycationic compounds may be produced chemically or recombinantly or may be derived from natural sources.

Cationic (poly)peptides may also be anti-microbial with properties as reviewed in Ganz et al., 1999; Hancock, 1999. These (poly)peptides may be of prokaryotic or animal or plant origin or may be produced chemically or recombinantly (WO 02/13857). Peptides may also belong to the class of defensins (WO 02/13857). Sequences of such peptides can, for example, be found in the Antimicrobial Sequences Database under the following interne address:

http://www.bbcm.univ.trieste.it/~tossi/pag2.html

Such host defence peptides or defensives are also a preferred form of the polycationic polymer according to the present invention. Generally, a compound allowing as an end product activation (or down-regulation) of the adaptive immune system, preferably mediated by APCs (including dendritic cells) is used as polycationic polymer.

Especially preferred for use as polycationic substances in the present invention are cathelicidin derived antimicrobial peptides or derivatives thereof (International patent application WO 02/13857, incorporated herein by reference), especially antimicrobial peptides derived from mammal cathelicidin, preferably from human, bovine or mouse.

Polycationic compounds derived from natural sources include HIV-REV or HIV-TAT (derived cationic peptides, antennapedia peptides, chitosan or other derivatives of chitin) or other peptides derived from these peptides or proteins by biochemical or recombinant production. Other preferred polycationic compounds are cathelin or related or derived substances from cathelin. For example, mouse cathelin is a peptide, which has the amino acid sequence $NH_2$-RLAGLL-RKGGEKIGEKLKKIGOKIKNFFQKLVPQPE-COOH.

Related or derived cathelin substances contain the whole or parts of the cathelin sequence with at least 15-20 amino acid residues. Derivations may include the substitution or modification of the natural amino acids by amino acids which are not among the 20 standard amino acids. Moreover, further cationic residues may be introduced into such cathelin molecules. These cathelin molecules are preferred to be combined with the antigen. These cathelin molecules surprisingly have turned out to be also effective as an adjuvant for an antigen without the addition of further adjuvants. It is therefore possible to use such cathelin molecules as efficient adjuvants in vaccine formulations with or without further immunactivating substances.

Another preferred polycationic substance to be used according to the present invention is a synthetic peptide containing at least 2 KLK-motifs separated by a linker of 3 to 7 hydrophobic amino acids (International patent application WO 02/32451, incorporated herein by reference).

The pharmaceutical composition of the present invention may further comprise Immunostimulatory nucleic acid(s). Immunostimulatory nucleic acids are e.g. neutral or artificial CpG containing nucleic acids, short stretches of nucleic acid derived from non-vertebrates or in form of short oligonucleotides (ODNs) containing non-methylated cytosine-guanine di-nucleotides (CpG) in a certain base context (e.g. described in WO 96/02555). Alternatively, also nucleic acids based on inosine and cytidine as e.g. described in the WO 01/93903, or deoxynucleic acids containing deoxy-inosine and/or deoxyuridine residues (described in WO 01/93905 and PCT/EP 02/05448, incorporated herein by reference) may preferably be used as immunostimulatory nucleic acids for the present invention. Preferably, the mixtures of different immunostimulatory nucleic acids may be used according to the present invention.

It is also within the present invention that any of the aforementioned polycationic compounds is combined with any of the immunostimulatory nucleic acids as aforementioned. Preferably, such combinations are according to the ones as described in WO 01/93905, WO 02/32451, WO 01/54720, WO 01/93903, WO 02/13857 and PCT/EP 02/05448 and the Austrian patent application A 1924/2001, incorporated herein by reference.

In addition or alternatively such vaccine composition may comprise apart from the polypeptide/nucleic acid molecules according to the present invention a neuroactive compound. Preferably, the neuroactive compound is human growth factor as, e.g. described in WO 01/24822. Also preferably, the neuroactive compound is combined with any of the polycationic compounds and/or immunostimulatory nucleic acids as aforementioned.

In a further aspect the present invention is related to a pharmaceutical composition. Such pharmaceutical composition is, for example, the vaccine described herein. Also a pharmaceutical composition is a pharmaceutical composition which comprises any of the following compounds or combinations threreof: the nucleic acids according to the present invention, the polypeptides according to the present invention, the vector according to the present invention, the cells according to the present invention, the antibody according to the present invention, the functional nucleic acids according to the present invention and the binding peptides such as the anticalines according to the present invention, any agonists and antagonists screened as described herein. In connection therewith any of these compounds may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of active agent of at least about 10 μg/kg body weight. In most cases they will be administered in one or more doses in an amount not in excess of about 8 mg/kg body weight per day. Preferably, in most cases, dose is from about 10 μg/kg to about 1 mg/kg body weight, daily. For administration particularly to mammals, and particularly humans, it is expected that the daily dosage level of the active agent will be from 0.01 mg/kg to 10 mg/kg and typically around 1 mg/kg. For example, a dose may be 1 mg/kg daily. It will be appreciated that optimum dosage will be determined by standard methods for each treatment modality and indication, taking into account the indication, its severity, route of administration, complicating conditions. and the like. The physician in any event will determine the actual dosage, which will be most suitable for an individual and will vary with the age, weight and response of the particular individual. The above dosages are exemplary of the average case. There can, of course, be individual instances where higher or lower dosage ranges are merited, and such are within the scope of this invention.

In therapy or as a prophylactic, the active agent may be administered to an individual as an injectable composition, for example as a sterile aqueous dispersion, preferably isotonic.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

The pharmaceutical composition may be administered in conjunction with an in-dwelling device. In-dwelling devices include surgical implants, prosthetic devices and catheters, i. e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systematic effect against relevant bacteria shortly before insertion of an in-dwelling device. Treatment may be continued after surgery during the in-body time of the device. In addition, the composition could also be used to broaden perioperative cover for any surgical technique to prevent *Streptococcus* infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 μg/ml to 10 mg/ml for bathing of wounds or indwelling devices.

A vaccine composition is conveniently in injectable form. Conventional adjuvants may be employed to enhance the immune response. A suitable unit dose for vaccination is 0.5-5 μg/kg of antigen, and such dose is preferably administered 1-3 times and with an interval of 1-3 weeks.

With the indicated dose range, no adverse toxicological effects should be observed with the compounds of the invention, which would preclude their administration to suitable individuals.

The antibodies described above may also be used as diagnostic reagents to detect the presence of bacteria containing the polypeptides according to the present invention.

In a further embodiment the present invention relates to diagnostic and pharmaceutical packs and kits comprising one or more containers filled with one or more of the ingredients of the aforementioned compositions of the invention. The ingredient(s) can be present in a useful amount, dosage, formulation or combination. Associated with such container(s) can be a notice in the form prescribed by a governmental agency regulating the manufacture, use or sale of pharmaceuticals or biological products, reflecting approval by the agency of the manufacture, use or sale of the product for human administration.

In connection with the present invention any disease related use as disclosed herein such as, e. g. use of the pharmaceutical composition or vaccine, is particularly a disease or diseased condition which is caused, linked or associated with Gram-positive bacteria, more particularly bacteria selected from the group comprising Streptococci, Staphylococci and Lactococci. More preferably, the microorganisms are selected from the group comprising *S. agalactiae, S. pyogenes, S. pneumoniae* and *S. mutans*. In connection therewith it is to be noted that *S. agalactiae* comprises several strains including those disclosed herein. Also, the disease may be particularly a disease occurring in any patient selected from the group comprising people with chronic illness such as diabetes mellitus and liver failure, pregnant women, the fetus and the newborn. A disease related, caused or associated with the bacterial infection to be prevented and/or treated according to the present invention includes in neonates sepsis, pneumonia and meningitis, and in adults sepsis and soft tissue infections. Pregnancy-related infections are sepsis, amnionitis, urinary tract infection and stillbirth.

In a still further embodiment the present invention is related to a screening method using any of the polypeptides or nucleic acids according to the present invention. Screening methods as such are known to the one skilled in the art and can be designed such that an agonist or an antagonist is screened. Preferably an antagonist is screened which in the present case inhibits or prevents the binding of any polypeptide according to the present invention to an interaction partner. Such interaction partner can be a naturally occurring interaction partner or a non-naturally occurring interaction partner. Preferable the interaction partner is fibrinogen or a fragment thereof in case of FbsA or any host cell in case of PabA, PabB, PabC, and PabD, including epithelial cells, preferably human epithelial cells.

The invention also provides a method of screening compounds to identify those, which enhance (agonist) or block (antagonist) the function of polypeptides or polynucleotides of the present invention, such as its interaction with a binding molecule. The method of screening may involve high-throughput.

For example, to screen for agonists or antagonists, the interaction partner of the polynucleotide and nucleic acid, respectively, according to the present invention, a synthetic reaction mix, a cellular compartment, such as a membrane, cell envelope or cell wall, or a preparation of any thereof, may be prepared from a cell that expresses a molecule that binds to the polypeptide of the present invention. The preparation is incubated with labelled polypeptide in the absence or the presence of a candidate molecule, which may be an agonist or antagonist. The ability of the candidate molecule to bind the binding molecule is reflected in decreased binding of the labelled ligand. Molecules, which bind gratuitously, i. e., without inducing the functional effects of the polypeptide, are most likely to be good antagonists. Molecules that bind well and elicit functional effects that are the same as or closely related to the polypeptide are good agonists.

The functional effects of potential agonists and antagonists may by measured, for instance, by determining activity of a reporter system following interaction of the candidate molecule with a cell or appropriate cell preparation, and comparing the effect with that of the polypeptide of the present invention or molecules that elicit the same effects as the polypeptide. Reporter systems that may be useful in the regard include but are not limited to colorimetric labelled substrate converted into product, a reporter gene that is responsive to changes in the functional activity of the polypeptide, and binding assays known in the art.

Another example of an assay for antagonists is a competitive assay that combines the polypeptide of the present invention and a potential antagonist with membrane-bound binding molecules, recombinant binding molecules, natural substrates or ligands, or substrate or ligand mimetics, under appropriate conditions for a competitive inhibition assay. The polypeptide can be labelled such as by radioactivity or a colorimetric compound, such that the number of polypeptide molecules bound to a binding molecule or converted to product can be determined accurately to assess the effectiveness of the potential antagonist.

Potential antagonists include small organic molecules, peptides, polypeptides and antibodies that bind to a polypeptide of the invention and thereby inhibit or extinguish its acitivity. Potential antagonists also may be small organic molecules, a peptide, a polypeptide such as a closely related protein or antibody that binds to the same sites on a binding molecule without inducing functional activity of the polypeptide of the invention.

Potential antagonists include a small molecule, which binds to and occupies the binding site of the polypeptide thereby preventing binding to cellular binding molecules, such that normal biological activity is prevented. Examples of small molecules include but are not limited to small organic molecules, peptides or peptide-like molecules.

Other potential antagonists include antisense molecules (see Okano, J. Neurochem. 56:560 (1991); OLIGODEOXY-NUCLEOTIDES AS ANTISENSE INHIBITORS OF GENE EXPRESSION; CRC Press, Boca Raton, Fla. (1988), for a description of these molecules).

Preferred potential antagonists include derivatives of the polypeptides of the invention.

As used herein the activity of a polypeptide according to the present invention is its capability to bind to any of its interaction partner or the extent of such capability of its binding to its or any interaction partner.

In a particular aspect, the invention provides the use of the polypeptide, polynucleotide or inhibitor of the invention to interfere with the initial physical interaction between a pathogen and mammalian host responsible for sequelae of infection. In particular the molecules of the invention may be used: i) in the prevention of adhesion of S. agalactiae to mammalian extracellular matrix proteins on in-dwelling devices or to extracellular matrix proteins in wounds; ii) to block protein mediated mammalian cell invasion by, for example, initiating phosphorylation of mammalian tyrosine kinases (Rosenshire et al., Infect. Immun. 60:2211 (1992)). iii) to block bacterial adhesion between mammalian extracellular matrix proteins and bacterial proteins which mediate tissue damage; iv) to block the normal progression of pathogenesis in infections initiated other than by the implantation of in-dwelling devices or by other surgical techniques.

Each of the DNA coding sequence provided herein may be used in the discovery and development of antibacterial compounds. The encoded protein upon expression can be used as a target for the screening of antibacterial drugs. Additionally, the DNA sequences encoding the amino terminal regions of the encoded protein or Shine-Delgamo or other translation facilitating sequences of the respective mRNA can be used to construct antisense sequences to control the expression of the coding sequence of interest.

The antagonists and agonists may be employed, for instance, to inhibit diseases arising from infection with Streptococcus, especially S. agalactiae, such as sepsis.

In a still further aspect the present invention is related to an affinity device such affinity device comprises at least a support material and any of the polypeptides according to the present invention, which is attached to the support material. Because of the specificity of the polypeptides according to the present invention for their target cells or target molecules or their interaction partners, the polypeptides allow a selective removal of their interaction partner(s) from any kind of sample applied to the support material provided that the conditions for binding are met. The sample may be a biological or medical sample, including but not limited to, fermentation broth, cell debris, cell preparation, tissue preparation, organ preparation, blood, urine, lymph liquid, liquor and the like.

The polypeptide may be attached to the matrix in a covalent or non-covalent manner. Suitable support material is known to the one skilled in the art and can be selected from the group comprising cellulose, silicon, glass, aluminium, paramagnetic beads, starch and dextrane.

The present invention is further illustrated by the following figures, examples and the sequence listing from which further features, embodiments, and advantages may be taken. It is to be understood that the present examples are give by way of illustration only and not by way of limitation of the disclosure.

In connection with the present invention

FIG. 1 shows the DNA sequence of the fbsA-encoding region and the deduced FbsA protein from the serotype III GBS strain 6313;

FIG. 2 the result of a Southern Blot analysis;

FIG. 3 the DNA sequence of the fbsA-encoding region and the deduced FbsA protein from the serotype Ia GBS strain 706 S2;

FIG. 4 the DNA sequence of the fbsA-encoding region and the deduced FbsA protein from the serotype Ib GBS strain 33H1A;

FIG. 5 the DNA sequence of the fbsA-encoding region and the deduced FbsA protein from the serotype Ii GBS strain 176 H4A;

FIG. 6 the DNA sequence of the fbsA-encoding region and the deduced FbsA protein from the capsule GBS mutant O90R;

FIG. 7 the DNA sequence of the fbsA-encoding region and the deduced FbsA protein from the serotype V GBS strain SS1169;

FIG. 8 a schematic comparison of the FbsA proteins from the GBS strains 6313 (serotype III), 706 S2 (serotype Ia), 33H1A (serotype Ib), O176 H4A (serotype II), O90R (derived from serotype Ia) and SS1169 (serotype V), respectively;

FIG. 9 the result of a Western blot analysis of truncated FbsA derivatives to identify the fibrinogen binding domain in FbsA;

FIG. 10 a diagram illustrating the competitive inhibition of fibrinogen binding to GBS 6313 by the purified fusion proteins FbsA-19, FbsA-9 and Bsp, respectively;

FIG. 11 the result of a spot membrane analysis of fibrinogen binding by synthetic peptides derived from the repeat unit of FbsA;

FIG. 12 the result of a spot membrane analysis of the fibrinogen binding repeat unit;

FIG. 13 a diagram illustrating the competitive inhibition of fibrinogen binding to GBS 6313 by synthetic peptides;

FIG. 14 a diagram illustrating eukaryotic cell adherence (A) and invasion (B) of GBS strains 6313, 706 S2, and O90R and their respective fbsA deletion mutants;

FIG. 15 the result of a peptide ELISA of FbsA peptides with human sera;

FIG. 16 the DNA sequence of the pabA/B-encoding region and the deduced PabA (nt 319-2964) and PabB (nt 3087-5111) proteins from GBS 6313;

FIG. 17 the DNA sequence of the pabC/D-encoding region and the deduced PabC (nt 487-2394) and PabD (nt 2461-3006) proteins from GBS 6313;

FIG. 18 a picture from a scanning electron microscopy of A549 cells;

FIG. 19 a diagram illustrating the adherence of GBS 6313 to and invasion of A549 cells in the presence of 100 µg/ml of PabA, PabB, PabC or PabD fusion proteins;

FIG. 20 a diagram illurstrating eukaryotic cell adherence and internalization by GBS 6313 and its pabA and pabB deletion mutants;

FIG. 21 the result of a Western Blot testing anti-PabA, anti-PabB, and anti-PabD antisera for their sensitivity;

FIG. 22 a Western blot analysis of culture supernatant of different S. agalactiae strains and their isogenic fbsA deletion mutants for the presence of fibrinogen binding proteins;

FIG. 23 the binding of different S. agalactiae strains and their fbsA deletion mutants to immobilized fibrinogen;

FIG. 24 the adherence and internalization of different S. agalactiae strains and their isogenic fbsA mutants into the lung epithelial cell line A549;

FIG. 25 the adherence and internalization of the S. agalactiae strains 6313 and 6313ΔfbsA into the fibroblast cell line HEL299;

FIG. 26 the influence of FbsA protein on the adherence of S. agalactiae to A549 cells;

FIG. 27 the binding of FbA-coated latex beads to human A549 cells;

FIG. 28 the transcriptional organization of the pabC-encoding region of S. agalactiae;

FIG. 29 the PCR-analysis of GBS strains for the presence of pabC and pabD genes;

FIG. 30 the comparison of the amino acid sequences of the PabC proteins from different S. agalactiae strains;

FIG. 31 the restriction map of the pabC-encoding region, the Western blot analysis of PabC and Gbs0851 fusion proteins for fibrinogen-binding and the identification of the FbsA and PabC-binding sites within human fibrinogen;

FIG. 32 the binding of recombinant PabC fusion proteins to immobilized fibrinogen by ELISA, and FIG. 33 the adherence and invasion of the lung epithelial cell line A549 by the S. agalactiae pabC strains.

The figures to which it might be referred to in the specification are described in the following in more detail.

FIG. 1 shows the DNA sequence of the fbsA-encoding region and the deduced FbsA protein from the serotype III GBS strain 6313. The putative ribosomal binding site (RBS) is underlined and the potential transcriptional terminator is indicated by antiparallel arrows. Within the deduced FbsA protein, letters in bold and italic indicate the putative signal peptide sequence and letters in bold and underlined mark the cell wall anchor motif LPKTG. Repeats in FbsA are numbered and marked by arrows.

FIG. 2 shows a Southern blot analysis to determine the presence of the fbsA gene in different clinical isolates of GBS. Chromosomal DNA from different GBS strains belonging to serotypes Ia, Ib, II, III, IV, and V, respectively was digested with HindIII and, after size separation and blotting onto nylon membrane, hybridised with a digoxigenin-labelled fbsA-specific DNA probe.

FIG. 3 shows the DNA sequence of the fbsA-encoding region and the deduced FbsA protein from the serotype Ia GBS strain 706 S2. The putative ribosomal binding site (RBS) is underlined and the potential transcriptional terminator is indicated by antiparallel arrows. Within the deduced FbsA protein, letters in bold and italic indicate the putative signal peptide sequence and letters in bold and underlined mark the cell wall anchor motif LPKTG. Repeats in FbsA are numbered and marked by arrows.

FIG. 4 shows the DNA sequence of the fbsA-encoding region and the deduced FbsA protein from the serotype Ib GBS strain 33H1A. The putative ribosomal binding site (RBS) is underlined and the potential transcriptional terminator is indicated by antiparallel arrows. Within the deduced FbsA protein, letters in bold and italic indicate the putative signal peptide sequence and letters in bold and underlined mark the cell wall anchor motif LPKTG. Repeats in FbsA are numbered and marked by arrows.

FIG. 5 shows the DNA sequence of the fbsA-encoding region and the deduced FbsA protein from the serotype II GBS strain 176 1-14A. The putative ribosomal binding site (RBS) is underlined and the potential transcriptional terminator is indicated by antiparallel arrows. Within the deduced FbsA protein, letters in bold and italic indicate the putative signal peptide sequence and letters in bold and underlined mark the cell wall anchor motif LPKTG. Repeats in FbsA are numbered and marked by arrows.

FIG. 6 shows the DNA sequence of the fbsA-encoding region and the deduced FbsA protein from the capsule GBS mutant O90R. The putative ribosomal binding site (RBS) is underlined and the potential transcriptional terminator is indicated by antiparallel arrows. Within the deduced FbsA protein, letters in bold and italic indicate the putative signal peptide sequence and letters in bold and underlined mark the cell wall anchor motif LPKTG. Repeats in FbsA are numbered and marked by arrows.

FIG. 7 shows the DNA sequence of the fbsA-encoding region and the deduced FbsA protein from the serotype V GBS strain SS1169. The putative ribosomal binding site (RBS) is underlined and the potential transcriptional terminator is indicated by antiparallel arrows. Within the deduced FbsA protein, letters in bold and italic indicate the putative signal peptide sequence and letters in bold and underlined mark the cell wall anchor motif LPKTG. Repeats in FbsA are numbered and marked by arrows.

FIG. 8 shows a schematic comparison of the FbsA proteins from the GBS strains 6313 (serotype III), 706 S2 (serotype Ia), 33H1A (serotype Ib), O176 H4A (serotype II), O90R (derived from serotype Ia) and SS1169 (serotype V), respectively. Indicated are the locations of the signal peptide (black box), the wall-spanning region (WSR; boxes with vertical bars), the cell wall anchor motif (LPKTG), and the membrane-spanning region (MSR; boxes with diagonal bars). The number of individual repeats is indicated for each protein. Grey boxes represent a repeat with the sequence motif 'GNVLERRQRDAENRSQ', boxes with horizontal bars represent repeats with an R14K substitution and dotted boxes show the location of repeats with both an A11V and R14K substitution. Repeats that carry an E12D substitution are indicated below the FbsA proteins from GBS strains 33H1A and SS1169. Above FbsA from 33H1A, a repeat carrying a single A11V substitution is indicated.

FIG. 9 shows a Western blot analysis of truncated FbsA derivatives to identify the fibrinogen-binding domain in FbsA. Hexahistidyl-tagged fusion proteins, representing the mature FbsA protein (FbsA-19), the N-terminal repeat-containing region (FbsA-N) or the C-terminal part (FbsA-C) of FbsA were separated by SDS-PAGE, blotted onto nitrocellulose and tested for their binding to human fibrinogen. The fibrinogen binding activity of the three proteins encoded by different constructs are indicated below the schematic FbsA drawing.

FIG. 10 shows the competitive inhibition of fibrinogen binding to GBS 6313 by the purified fusion proteins FbsA-19, FbsA-9 and Bsp, respectively. FbsA-9 differs from FbsA-19 in that it contains only 9 repeats in its repeat domain. The binding assay was performed with $^{125}$I-labelled fibrinogen in the presence of different concentrations of each fusion protein. Each experiment was performed at least in triplicate.

FIG. 11 shows a spot membrane analysis of fibrinogen binding by synthetic peptides derived from the repeat unit of FbsA. Fibrinogen binding was tested with peptides carrying the FbsA repeat motif 'GNVLERRQRDAENRSQ' (SEQ ID 113) and with peptides containing the scrambled sequence 'GLSQNRDVRENQRARE'. (SEQ ID 205) Synthetic peptides, which differed from the repeat motif in that single amino acids had been replaced by alanine, were probed for fibrinogen binding. Beside the spot membrane, the sequence of each synthetic peptide is listed. Bold and underlined letters indicate amino acid substitutions within the repeat motif.

FIG. 12 shows a spot membrane analysis of the fibrinogen binding repeat unit. Synthetic peptides were tested for fibrinogen binding, in which each of the amino acids of the fibrinogen-binding repeat was replaced by each of the 20 amino acids. The vertical letters, printed in bold, represent the FbsA-derived fibrinogen binding sequence 'GNVLERRQRDAENRSQ'. The horizontal letters represent those amino acids that were introduced in the synthetic peptides instead of the original amino acid in the respective position.

FIG. 13 shows the competitive inhibition of fibrinogen binding to GBS 6313 by synthetic peptides. The binding assay was performed with $^{125}$I-labelled fibrinogen in the presence of different concentrations of the peptides pep_FbsA (SEQ ID 211), carrying an FbsA-derived repeat unit, and pep_R6A, possessing an R6A substitution within the repeat unit. Each experiment was performed at least in triplicate.

FIG. 14 shows eukaryotic cell adherence (A) and invasion (B) of GBS strains 6313, 706 S2, and O90R and their respective fbsA deletion mutants. The values represent the result of at least four independent experiments performed in triplicate. Error bars are indicated.

FIG. 15. shows a peptide ELISA of FbsA peptides with human sera. The 5 biotinylated peptides (wild type <1>: GNVLERRQRDAENRSQ SEQ ID No. 113; alanine mutant peptides: <2> GAVLERRQRDAENRSQ SEQ ID No. 207, <3> GNALERRQRDAENRSQ SEQ ID No. 208, <4> GNVLEARQRDAENRSQ SEQ ID No. 211, <5> GNVLERAQRDAENRSQ SEQ ID No. 212; see also FIG. 11) were coated on Streptavidin-coated ELISA plates and analysed using 5 sera from patients infected with GBS. The patient sera were applied in a dilution of 1:200 and 1:1,000. IgG (A) and IgA (3) antibodies were detected with secondary anti-human antibodies coupled to Horse Radish Peroxidase and ABTS as substrate.

FIG. 16 shows the DNA sequence of the pabA/B-encoding region and the deduced PabA (nt 319-2964) and PabB (nt3087-5111) proteins from GBS 6313. Putative ribosomal binding sites (RBS) are underlined. Letters in bold and italics indicate the putative signal peptides of the deduced PabA and PabB proteins and letters in bold and underlined mark the region with high identity to the cell wall anchor motif from Gram positive bacteria.

FIG. 17 shows the DNA sequence of the pabC/D-encoding region and the deduced PabC (nt 487-2394) and PabD (nt 2461-3006) proteins from GBS 6313. Putative ribosomal binding sites (RBS) are underlined. Letters in bold and italics indicate the putative signal peptides of the deduced PabC and PabD proteins.

FIG. 18 shows a scanning electron microscopy of A549 cells incubated for two hours with latex beads coated with PabA, PabB, PabC, PabD, respectively. BSA-coated latex beads were used as a control.

FIG. 19 shows the adherence of GBS 6313 to and invasion of A549 cells in the presence of 100 µg/ml of PabA, PabB, PabC or PabD fusion proteins. The adherence of GBS 6313 to A549 cells (A) and its internalization into these cells (B) was arbitrarily set to 100% and the results obtained in the presence of the different fusion proteins was related to these values. Each experiment was performed at least three times in triplicate.

FIG. 20 shows eukaryotic cell adherence and internalization by GBS 6313 and its pabA and pabB deletion mutants. The adherence of GBS 6313 to A549 cells (A) and its internalization into these cells (B) was arbitrarily set to 100% and the results obtained with the GBS mutants 6313ΔpabA and 6313ΔpabB were related to these values. Each experiment was performed at least three times in triplicate.

FIG. 21 shows the testing of anti-PabA, anti-PabB, and anti-PabD antisera for their sensitivity in detecting their respective antigens. Serial dilutions of the fusion proteins PabA, PabB, and PabD were spotted onto nitrocellulose and probed with a 1:1000 dilution of the mice sera against the respective proteins. Bound antibodies were labelled with an anti-mouse-HRP conjugate and visualized by chemiluminescence.

FIG. 22 shows a Western blot analysis of culture supernatant of different *S. agalactiae* strains and their isogenic fbsA deletion mutants for the presence of fibrinogen binding proteins. 15 µg of proteins from concentrated culture supernatant of the different *S. agalactiae* strains and their fbsA deletion mutants was size separated by SDS-PAGE, blotted onto nitrocellulose and tested for the interaction with human fibrinogen. Bound fibrinogen was detected by incubating the blot with rabbit anti-fibrinogen antibodies followed by an incubation with goat anti-rabbit antibodies coupled to horseradish peroxidase. For the detection of fibrinogen-antibody complexes, chemiluminescence was used.

FIG. 23 shows the binding of different *S. agalactiae* strains and their fbsA deletion mutants to immobilized fibrinogen. Similar cell numbers of the different strains were incubated with fibrinogen, which was immobilized to Terasaki plates. The number of bacteria bound to fibrinogen was related to the number of input bacteria into the assay.

Figure 28:
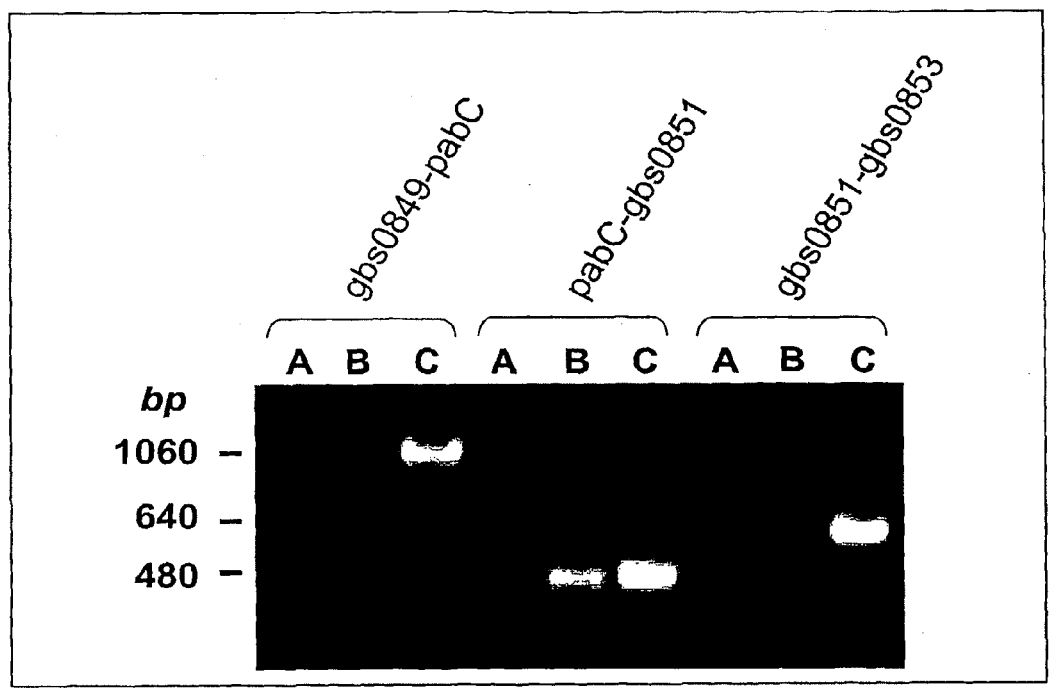

FIG. 28: shows the transcriptional organization of the pabC-encoding region in *S. agalactiae*. The names on top of the figure indicate the genes to which the primer pairs annealed during PCR with total RNA (A), RT-PCR with total RNA (B) or PCR with chromosomal DNA (C) from *S. agalactiae* 6313.

Figure 29:
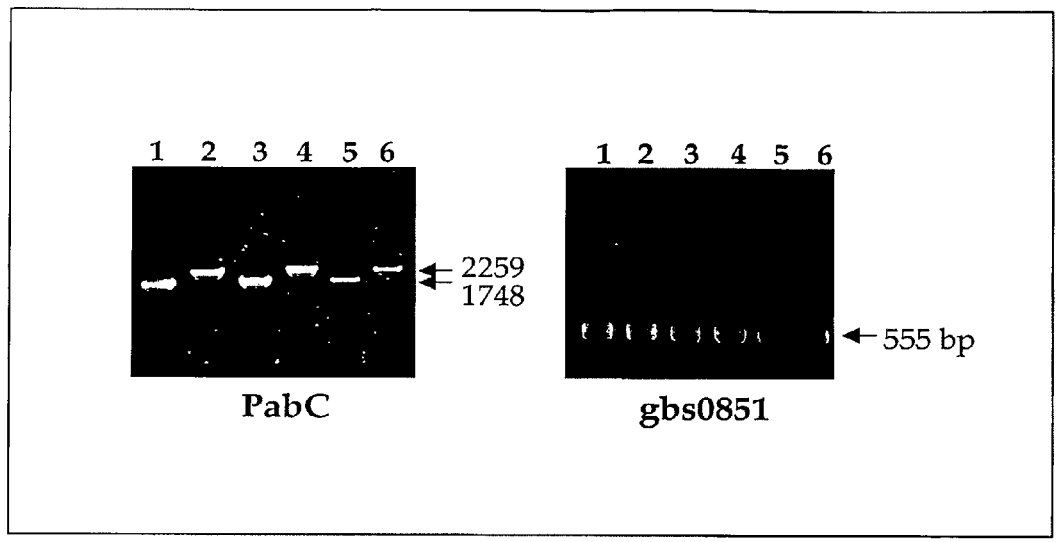

FIG. 29: shows the PCR-analysis of GBS strains for the presence of pabC and pabD genes. The following strains were used for the PCR: 1, *S. agalactiae* 1137 (Ia); 2, *S. agalactiae* A90/14 (Ib); 3, *S. agalactiae* 6313 (II); 4, *S. agalactiae* 4416 S3 (111); 5, *S. agalactiae* 4357 (V); 6, *S. agalactiae* 4327 (V).

Figure 30:
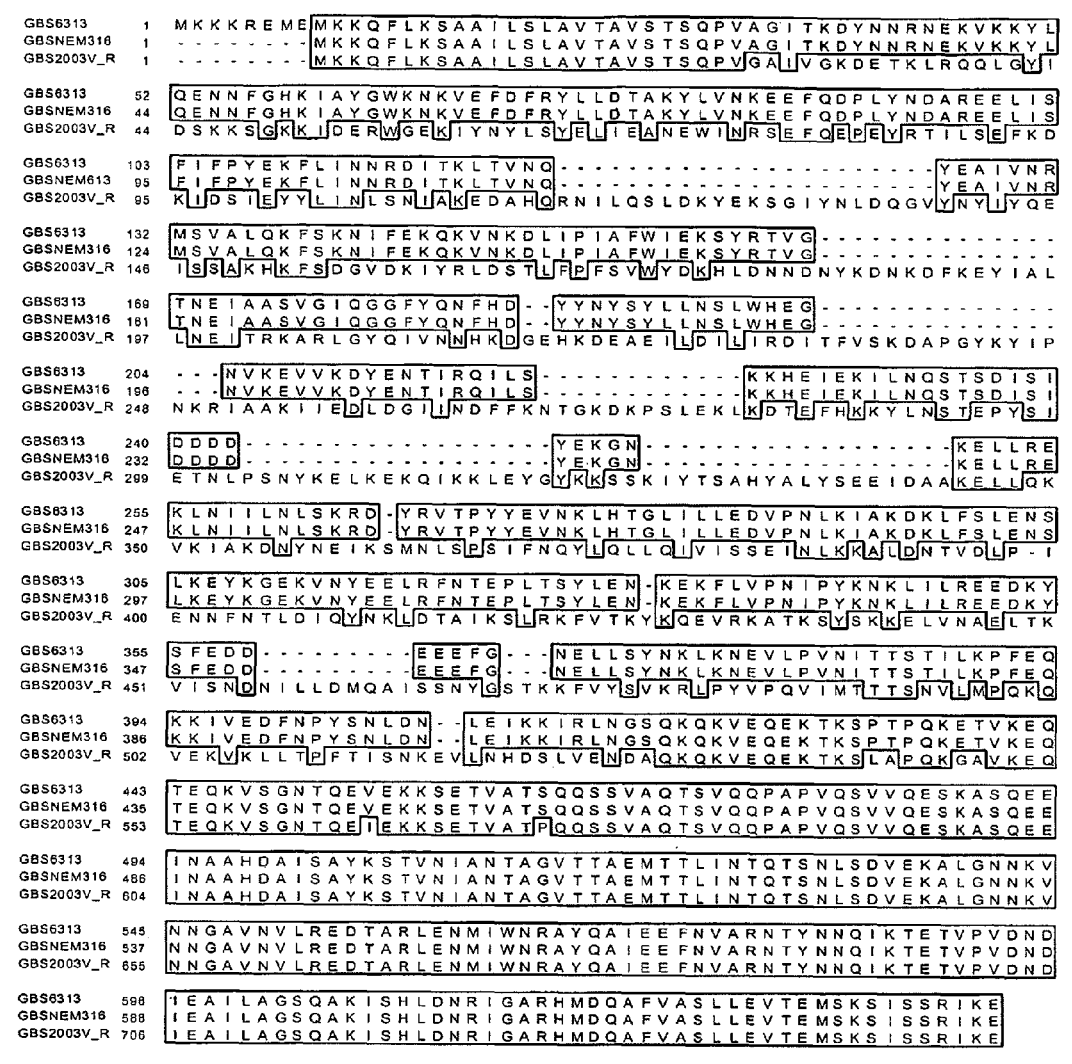

FIG. 30: shows the comparison of the amino acid sequences of the PabC proteins from *S. agalactiae* 6313, *S. agalactiae* NEM316, and *S. agalactiae* 2003V_R.

Figure 31:
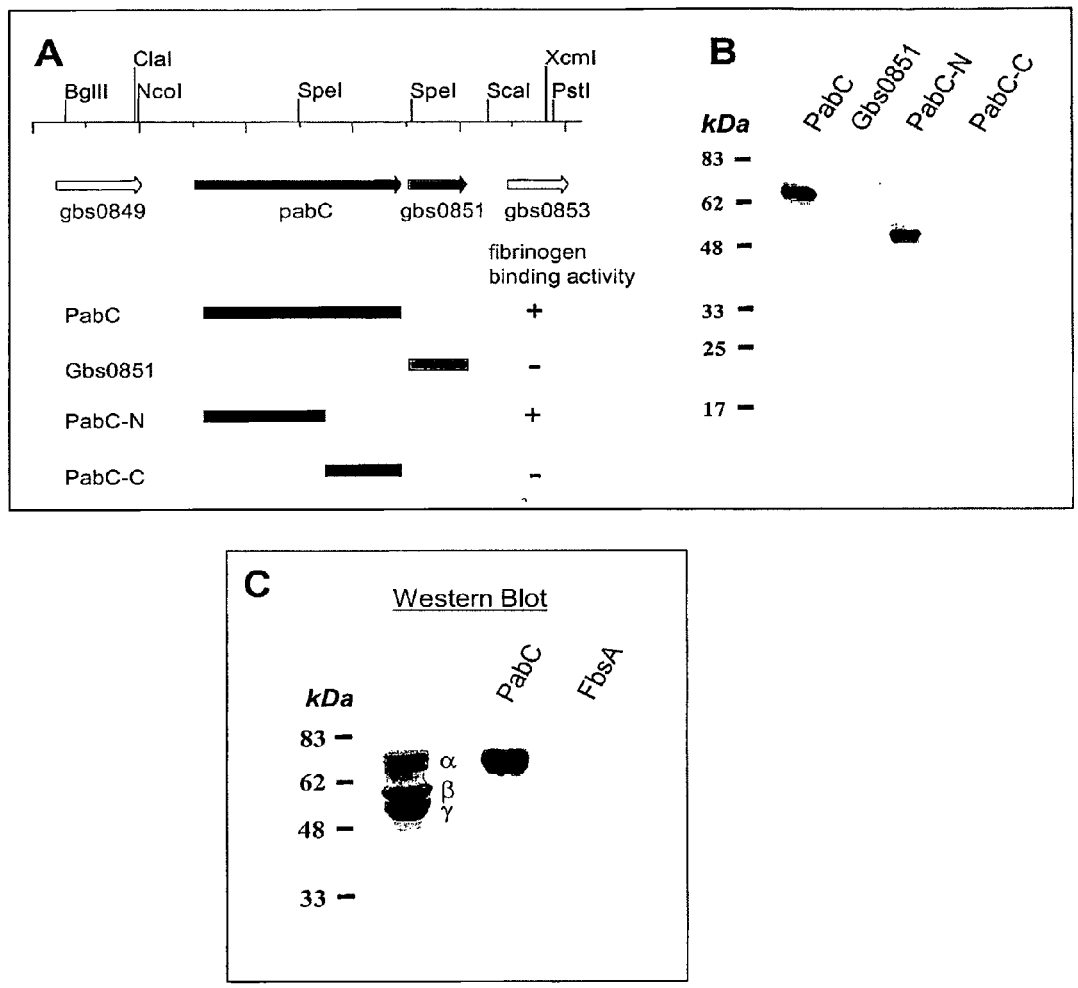

FIG. 31: shows (A) the restriction map of the pabC-encoding region in *S. agalactiae* and (B) the Western blot analysis of PabC and Gbs0851 fusion proteins for fibrinogen-binding. The fusion proteins were size-separated by SDS-PAGE, transferred onto a nitrocellulose membrane and tested for fibrinogen binding by Western blotting. Bound fibrinogen was detected with rabbit anti-fibrinogen antibodies, followed by peroxidase-labelled goat anti-rabbit antibodies, and visualized by chemiluminescence. PabC and Gbs0851: full-length fusion proteins; PabC-N: N-terminal 388 amino acids of PabC; PabC-C: C-terminal 222 amino acids of PabC. (C) Identification of the FbsA and PabC-binding sites within human fibrinogen by Western blot analysis. Human fibrinogen was size separated by SDS-PAGE and either Coomassie stained (left lane) or transferred onto nitrocellulose and tested for FbsA- or PabC-binding by Western blotting. Bound fusion proteins were detected with mouse anti-HisTag antibodies, followed by peroxidase-conjugated goat anti-mouse IgG fab fragments and visualized by chemiluminescence.

Figure 32:
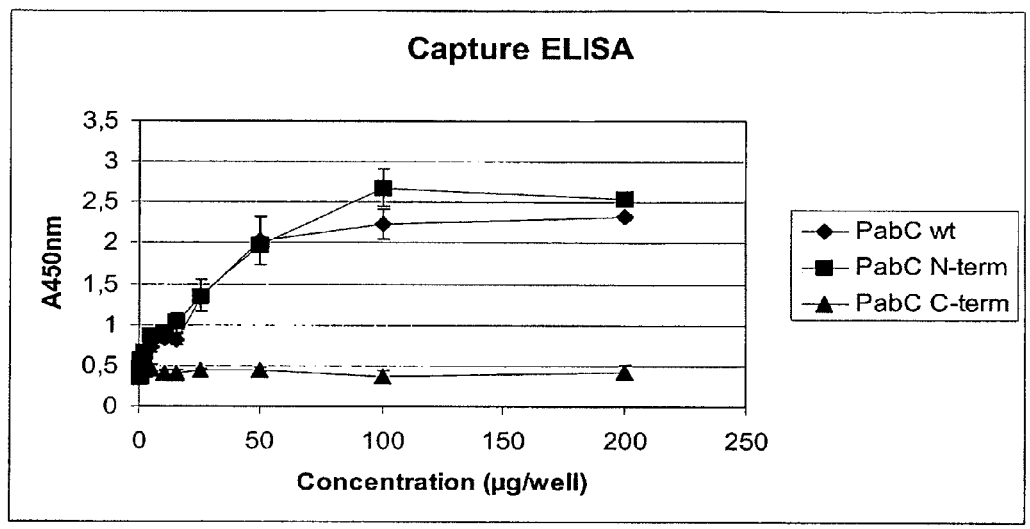

FIG. 32: shows the binding of recombinant PabC fusion proteins to immobilized fibrinogen in a capture ELISA assay. Microtiter wells were coated with a fixed amount of human fibrinogen, followed by the addition of increasing concentrations of the different PabC fusion proteins. Bound fusion protein was detected with mouse anti-HisTag antibodies and peroxidase-conjugated goat anti-mouse IgG fab fragments. Colour development was initiated by the addition of tetramethyl-benzidine substrate and stopped with $H_2SO_4$. The absorbance of the microtiter wells was read at 450 nm. Values represent the means of three independent experiments, each performed in triplicate.

Figure 33:
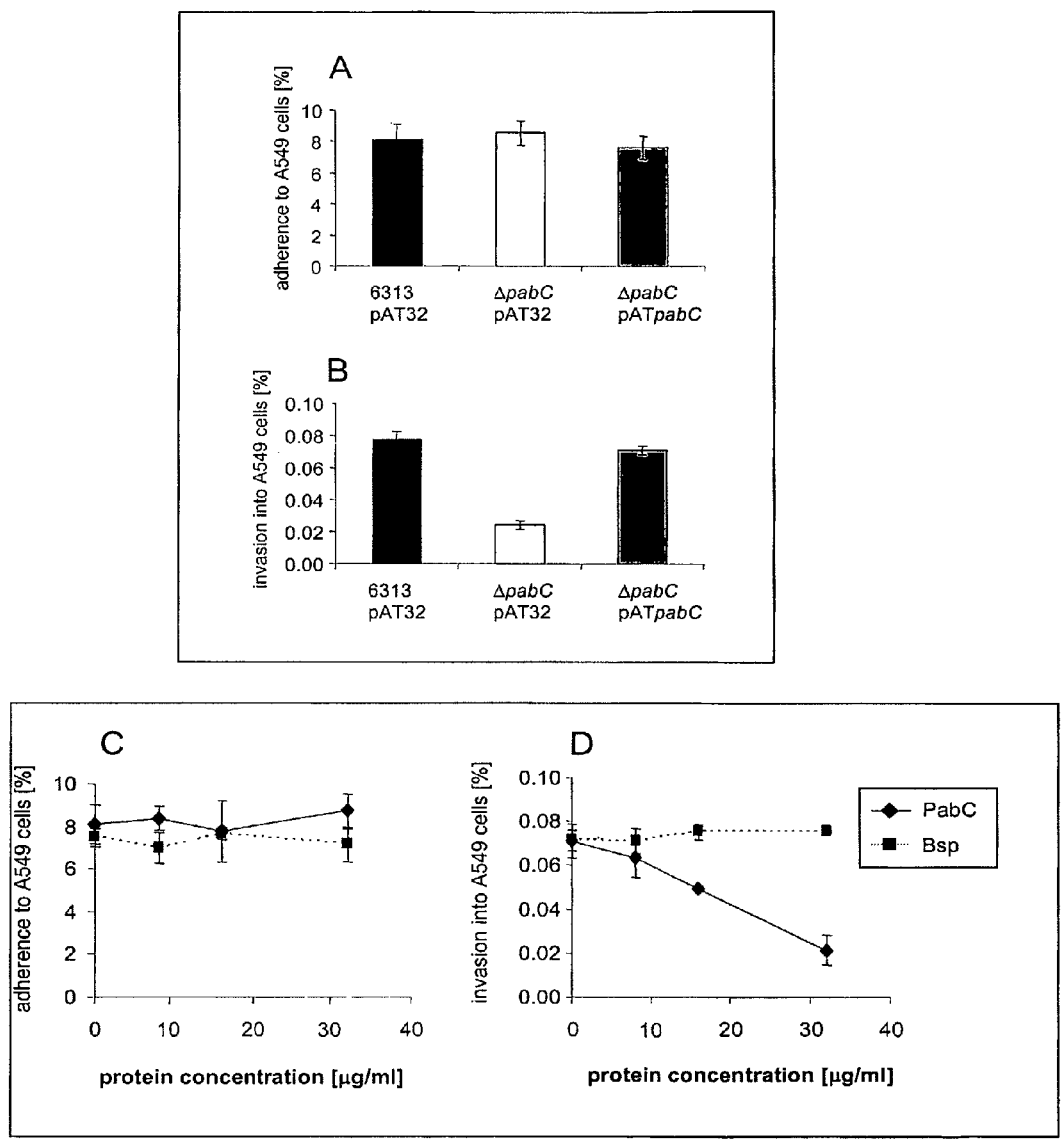

FIG. 33: shows the adherence (A) and invasion (B) of the lung epithelial cell line A549 by the *S. agalactiae* strains 6313 pAT32, ΔpabC pAT32 and ΔpabC pATpabC, respectively. Bacterial adherence and invasion were calculated as follows: Adherence=number of adherent bacteria/total number of bacteria in the assay×100. Invasion=number of internalized bacteria/total number of bacteria in the assay×100. Each experiment was performed at least three times in triplicate. (C) Eukaryotic cell adherence and invasion (D) of *S. agalactiae* 6313 in the presence of different amounts of PabC and Bsp fusion proteins. Bacterial adherence and invasion were calculated as described in the legend of FIG. 32. Each experiment was performed at least three times in triplicate.

EXAMPLES

Example 1

Experimental Procedures

It is to be noted that the following materials and methods were used throughout the examples described herein if not indicated to the contrary.

Bacterial Strains and Culture Conditions

GBS strains 6313 (serotype III) and SS1169 (serotype V) represent reference strains and have been described previously (Wibawan and Lammler, 1992). GBS strains 706 S2 (serotype Ia), 33H1A (serotype Ib), and 176 H4A (serotype II) were kindly provided by G. S. Chhatwal (GBF Braunschweig). GBS strain O90R (ATCC 12386) is a derivative of the serotype Ia strain O90. All GBS strains belonging to the serological groups Ia, Ib, II, III, and V, respectively, are clinical isolates and were isolated from infected neonates, while GBS strains from group IV were isolated from cows with mastitis (Chhatwal et al., 1984). *E. coli* DH5α (Hanahan, 1985) was used for cloning purposes and *E. coli* BL21 (Dubendorff and Studier, 1991) served as host for the production of FbsA fusion proteins. The alkaline-phosphatase-negative *E. coli* strain CC118 (Manoil and Beckwith, 1985) served as host for pHRM104-derivates and for the screening for signal-peptide encoding sequences from GBS.

GBS was cultivated at 37° C. in Todd-Hewitt yeast broth (THY) containing 1% yeast extract. *E. coli* was grown at 37° C. in Luria broth (LB) and clones carrying cosmid pTEX5236 or plasmid pET28a or pHRM104 were selected in the presence of chloramphenicol (15 µg/ml), kanamycin (50 µg/ml) or erythromycin (300 µg/ml). Screening for alkaline phosphatase secreting *E. coli* CC118 clones was performed on LB-plates containing 80 µ/ml X-phosphate (Sigma).

Antibodies, Enzymes, Peptides and Human Proteins

Affinity-purified rabbit anti-fibrinogen and peroxidase-labelled anti-rabbit antibodies were obtained from Dako-Biochemicals. Peroxidase-labelled goat anti-mouse antibodies were purchased from Dianova. Monoclonal anti-his-tag antibodies were obtained from Roche Diagnostics. Purified rabbit anti-fibronectin antibodies, trypsin, pronase, vitronectin, laminin, IgG, fibronectin, and fibrinogen were purchased from Sigma-Aldrich. Fibrinogen (Sigma) was passed through a gelatin-Sepharose column to remove residual contaminating fibronectin in the preparation. The purity of the fibrinogen preparation was confirmed by SDS-PAGE and Coomassie-staining and by Western blotting using anti-fibronectin antibodies. Synthetic peptides for spot membrane analysis and for inhibition experiments were synthesized as described previously (Frank and Overwin, 1996).

Plasmids and Cosmids Used for Cloning Purposes

A cosmid gene library from GBS 6313 (Reinscheid et al., 2001) was used for the isolation of the fbsA-gene from GBS. Low-copy cosmid pTEX5236 was also used for subcloning of the fbsA gene after partial digestion of anfbsA-carrying cosmid with Sau3A. Plasmid pET28a (Novagen) was used for the synthesis of the hexahistidyl-tagged FbsA, PabA, PabB, PabC, and PabD fusion proteins, which were constructed as follows: A truncated fbsA gene, devoid of the coding region of the signal peptide and the membrane spanning domain, was PCR amplified from chromosomal DNA of GBS 6313 using the primers 1 5'GTCCTGTATCTG CCATGGATAGTGTTGG (SEQ ID No. 223) and 2 5'CCGC GGATCCACATTTTGATCATCACCTG (SEQ ID No. 224). The repeat-encoding region of fbsA was amplified with the primers 3 5'GTCCTGTATCTGCCATGGATAGTGTTGG (SEQ ID No. 225) and 4 5'CCGC GGATCCCCTATAAGTTGACCTAC (SEQ ID No. 226). Amplification of the non-repeat region of fbsA was performed with the primers 5 5'TGCTTTG CCATGGTAGGTCAACTTATAGGG (SEQ ID No. 227) and 6 5'CCGCGGATCCACATTTTGATCATCACCTG (SEQ ID No. 228). The NcoI and BamHI restriction sites used for cloning are underlined. Amplification of the pabA, pabB, pabC and pabD genes, devoid of the coding region of the signal peptide and, if present, of the membrane spanning domain, was performed with the primers pabA1 5'GTGC-CTTGCCATGGAAAGTACCGTACCGG (SEQ ID No. 229), pabA2 5'GCGGACAG CTCGAGTTTCCCACCTGTCATCGG (SEQ ID No. 230), pabB1 5'GTGCCTTG CCATGGACGACGTAACAACTGATAC (SEQ ID No. 231), pabB2 5'GCGGACAG CTCGAGTGTACCAATACCACCTG (SEQ ID No. 232), pabC1 5'GTGCCTTGCCATGGGCCGGGATAACTAAAG (SEQ ID No. 233), pabC2 5'GCGGACAG CTCGAGCTCTTTTATACGCCATGAG (SEQ ID No. 234), pabD1 5'CCGCGGATCCGATGATAACTTTGAAATGCC (SEQ ID No. 235) and pabD2 5'TGGCAC AAGCTTACATTCTGAGCAGAAAGC (SEQ ID No. 236). The NcoI, XhoI and the BamHI, HindIII restriction sites used for cloning are underlined. The PCR products and plasmid pET28a were digested with the indicated restriction enzymes, ligated and transformed into E. coli BL21. Plasmid pETfbsA-9, carrying fbsA with nine internal repeats, was constructed by partial digestion of pETfbsA-19 with XbaI, subsequent religation and transformation into E. coli BL21.

A plasmid library of GBS chromosomal fragmens was constructed in plasmid pHRM104 essentially as described elsewhere (Pearce et al., 1993). Briefly, chromosomal DNA from GBS 6313 was fractionated by sonication for 45 sec, the obtained fragments were blunt-ended by Klenow polymerase, ligated into SmaI digested pHRM104, and the ligation mixture transformed into E. coli CC118. Transformants were plated onto erythromycin and X-phosphate containing agar plates and incubated for three days.

Southern and Blot Analysis

Chromosomal DNA from GBS was prepared as described elsewhere (Pospiech, 1995). Digoxigenin-labelled probes of the inserts in plasmid pHRM104 were obtained by PCR with the primers 7 5'AATATCGCCCTGAGC (SEQ ID No. 237) and 8 5'GGTTTTCCCAGTCACG (SEQ ID No, 238). The same primers were also used for sequencing the inserts in the pHRM104 derivates. Digoxigenin-labelled probes of the genes fbsA, pabA/B and pabC/D, respectively, were obtained by PCR with the primers fbsA1 5'GTCCTGTATCTGCTATG-GATAGTGTTGG (SEQ ID No. 239), fbsA2 5'ACATTTTGATCATCACCTG (SEQ ID No. 240), pabA 5'ACTGCTGAGCTAACAGGTG (SEQ ID No. 241), pabB 5'ACATCACCTGACAATGTCGC (SEQ ID No. 242), pabC 5'GCGATTGTGAATAGAATGAG (SEQ ID No. 243), and pabD 5'TATACAAAGCCTGAGCTTC (SEQ ID No. 244). To analyze the distribution of the genes fbsA, pabA/B and pabC/D among different clinical isolates of GBS, their chromosomal DNA was digested with HindIII, BstEII or NcoI and hybridized to the fbsA-, pabA/B- or pabB/C specific probe. Labelling, hybridization, washing and detection in Southern blots was performed using the Dig-labelling and detection kit (Roche Diagnostics) according to the instructions of the manufacturer with subsequent detection by chemiluminescence.

PCR-Amplification and Sequencing of FbsA from Different GBS Strains

The fbsA gene was amplified from the chromosome of the GBS strains 706 S2, 33H1A, 176 H4A, O90R and SS1169 by PCR using the primers 9 5'TTACCGTAGCCTGTATCACC (SEQ ID No. 245) and 10 5'CGACCTACGATAGCAACG (SEQ ID No. 246) and the PCR products were subsequently sequenced. The nucleotide sequence of the fbsA gene from strain 6313 was obtained by sequencing the 2.6 kb insert of pTEXfbsA.

Construction of fbsA Deletion Mutants

The thermosensitive plasmid pG+host6 (Appligene) was used for targeted deletion of the fbsA gene in the GBS strains 6313, 706 S2, and O90R, respectively. Two fragments flanking the fbsA gene were amplified by PCR from chromosomal DNA of GBS 6313 using the primer pairs fbsA_del5'CGCG GATCCGAATATGCTACCATCAC (SEQ ID No. 247) and fbsA_del2 5'CCCATCCACTAAACTTAAACATTCCT-GATTTCCAAGTTC (SEQ ID No. 248) as well as fbsA_del3 5'TGTTTATAGTGGATGGGGCTGCGGTTTGAGACGC (SEQ ID No. 249) and fbsA_del4 5'TGGCAC AAGCTTTACCTGCTGAGCGACTTG (SEQ ID No. 250). Complementary DNA sequences in the primers fbsA_del2 and fbsA_del3 are marked in italics and the BamHI and HindIII restriction sites in the primers fbsA_del1 and fbsA_del4 are underlined. The fbsA flanking PCR products were mixed in equal amounts with each other and subjected to crossover PCR by using primers fbsA_del1 and fbsA_del4. The resulting PCR product consisted of the fbsA flanking regions on a single DNA fragment. The crossover PCR product and plasmid pG+host6 were digested with BamHI and HindIII, ligated and transformed into E. coli DH5α. The resulting plasmid, pG+ΔfbsA was transformed into the GBS strains 6313, 706 S2, and O90R, respectively, and transformants were selected by growth on erythromycin agar at 30° C. Cells in which pG+ΔfbsA had integrated into the chromosome were selected by growth of the transformants at 39° C.

with erythromycin selection as described (Magnin et al., 1996). Four of such integrants from each strain were serially passaged for three days in liquid medium at 30° C. without erythromycin selection to facilitate the excision of plasmid pG⁺ΔfbsA, leaving the desired fbsA deletion in the chromosome. Dilutions of the serially passaged cultures were plated onto agar and single colonies were tested for erythromycin sensitivity to identify pG⁺ΔfbsA excisants. Chromosomal DNA of the parental GBS strains 6313, 706 S2, and O90R, respectively, and of 10 erythromycin sensitive GES excisants from each strain was tested by Southern blot after HindIII digestion using a digoxigenin-labelled fbsA flanking fragment obtained with the primers fbsA del3 and fbsA_del4.

Construction of pabA and pabB Deletion Mutants

Deletion mutants in the genes pabA and pabB, respectively, were constructed in GBS 6313 as described for the construction of fbsA deletion mutants. The primer pairs used to construct the pabA deletion mutant were pabA del1 5'GTTAAAGGTAACCTGCCTG (SEQ ID No. 251), pabA_del2 5'CCCATCCACTAAACTTAAACATA-CAACTCCTATTGTGCCGAAATGTCG (SEQ ID No. 252) as well as pabA_del3 5'TGTTTAAGTTTAGTG-GATGGGCACTTAGAGATTTTCCAATCC (SEQ ID No. 253) and pabA_del4 5'GACATCATAGATCCACC (SEQ ID No. 254). After cross-over PCR the resulting PCR fragment and vector pG⁺host6 were digested with HindIII and EcoRI and subsequently ligated, resulting in plasmid pG³⁰ΔpabA. The primer pairs for deleting pabB were pabB_del1 5'CCGCGGATCCGGAGCTACGTTTGAACTTC (SEQ ID No. 255), pabB_del2 5'CCCATCCACTAAACTTAAA-CAATATTACCGCAGCACCAC (SEQ ID No. 256) as well as pabB_del3 5'TGTTTAAGTTTAGTGGATGGGACAA-GAAGGCCAAGAAGG (SEQ ID No. 257) and pabB_del4 5'CACGCAACGCGTCGACGCACAGCTTTAACTGTAC (SEQ ID No. 258). The BamHI and SalI restriction sites are underlined. The fragment obtained by cross-over PCR and the vector pG⁺host6 were digested with BamHI and SalI and ligated, resulting in plasmid pG⁺ΔpabB. Plasmids pG⁺ΔpabA and pG⁺ΔpabB were subsequently transformed into GBS 6313. The procedure for the generation of pabA and pabB deletion mutants was identical to that for the construction off fbsA deletion mutants.

General DNA Techniques

Conventional techniques for DNA manipulation, such as restriction enzyme digests, PCR, ligation, transformation by electroporation and Southern blotting were performed as described by Sambrook et al. (Sambrook et al., 1989).

Binding of Soluble $^{125}$I-Labelled Fibrinogen to GBS

Purified human fibrinogen was radiolabelled with $^{125}$I, using the chloramin T method (Hunter and Greenwood, 1962). Binding of labelled fibrinogen to GBS was performed essentially as described by Chhatwal et al. (1983). Briefly, overnight cultures of GBS were pelleted by centrifugation, washed twice with phosphate-buffered saline supplemented with 0.02% Tween 20 (PBST) and adjusted photometrically to a transmission of 10% at 600 nm. A total of 0.2 ml of the bacterial suspension was added to 20 µl of $^{125}$I-labelled fibrinogen containing 23 ng of fibrinogen. After incubation for 1 h at room temperature, the streptococci were sedimented by centrifugation and washed with 1 ml of PBST. The radioactivity of the pellet was finally measured in a gamma counter (Packard Instruments). The amount of bacterial-bound fibrinogen was calculated as the percentage of total radiolabelled fibrinogen added to the bacteria. In inhibition experiments, the binding of 23 ng of radiolabelled fibrinogen to 0.2 ml of GBS (T=10%) was determined in the presence of various amounts of FbsA fusion proteins, Bsp fusion protein or synthetic peptides. Each experiment was repeated at least three times in triplicate.

Binding of FITC-Labelled GBS to Immobilized Fibrinogen

Terasaki plates were coated with human fibrinogen and the binding of FITC-labelled bacteria to the immobilized fibrinogen was measured as described by Podbielski et al. (Podbielski et al., 1999). In brief, 10 µl of a 100 µg/ml stock solution of human fibronectin, fibrinogen, laminin and collagen I and IV, respectively, was added to each well and incubated overnight at room temperature in a moist chamber. Subsequently, the microtiter plates were washed with PBS and residual buffer was carefully removed. FITC-labelling of GBS was performed with cultures in the exponential ($OD_{600}$: 0.5) and in the stationary ($OD_{600}$: 1.5) growth phase. 12 ml of bacterial culture were pelleted by centrifugation, washed with 12 ml of PBS and resuspended in 2 ml FITC-solution (1 mg/ml FITC in 50 mM sodium carbonate buffer, pH 9.2). Following a 20 min incubation in the dark, the cells were pelleted by centrifugation, washed twice with PBS and sonicated for 20 sec to disrupt bacterial chains. The bacterial suspension was adjusted to an $OD_{600}$: 1.0 with PBS, vortexed vigurously and kept in the dark until use. 10 µl of FITC-labelled GBS suspension was added to each Terasaki well coated with different human proteins. After a 60 min incubation at 37° C., unbound bacteria were removed by five washes with PBS and bound bacteria were fixed with 0.5% glutaraledhyde for 5 min. The plates were finally washed twice with PBS and the fluorescence of each well was determined in an automated Cyto Fluor II fluorescence reader (PerSeptive Biosystems) at excitation and detection wavelengths of 485 nm and 530 nm, respectively. The efficiency of FITC-labelling of the bacteria was determined by incubating 500 µl of the FITC-labelled bacteria for 60 min at 37° C., three washes of the bacteria with PBS, re-suspension of the cells in 500 µl of PBS and measuring the fluorescence of 10 µl aliquots of the suspension in uncoated Terasaki mitrotiter plates. Each assay was measured in triplicate and repeated at least four times.

Preparation and Purification of Fusion Proteins

The different FbsA fusion proteins as well as the fusion proteins PabA, PabB, PabC, PabD, and Bsp (Reinscheid et al., 2002) were synthesized in recombinant E. coli BL21 by the addition of 1 mM IPTG after the culture had reached an optical density of 1.0. The cells were disrupted using a French Press cell and purification of the fusion protein was performed according to the instructions of Qiagen using Ni$^{2+}$ affinity chromatography. Subsequently, the PabA, PabB and PabC fusion proteins were dialyzed against 20 mM Tris/HCl, pH 8.5 and loaded onto a MonoQ anion exchange column (Amersham/Pharmacia). A linear gradient from 0 M to 1.0 M NaCl in 20 mM Tris/HCl was used to elute the fusion proteins from the column. For further purification of PabD, the fusion protein was dialyzed against 20 mM Tris/HCl buffer and loaded onto a MonoS cation exchange column (Amersham/Pharmacia). A linear gradient from 0 M to 1.0 M NaCl in 20 mM Tris/HCl buffer was used for the elution of PabD. All fusion proteins were finally dialyzed against PBS and stored at −20° C.

Screening for Fibrinogen-Binding Colonies

Cosmid-carrying E. coli clones were transferred in duplicate to tetracycline containing LB plates and incubated overnight. The next day the colonies of one plate were transferred to nitrocellulose for 6 h. The cells on the filter were lysed by chloroform vapour for 20 min and subsequently incubated overnight in PBS with 1 mg/ml lysozyme and 1 mM PMSF. The membrane was blocked overnight with 10% skim milk in phosphate-buffered saline (PBS) and subsequently probed for binding of human fibrinogen as described below.

Western Blot and Spot Membrane Analysis

In Western blot experiments proteins were separated by SDS-PAGE and electroblotted onto nitrocellulose. The membrane was subsequently blocked overnight with 10% skim milk in PBS. For spot membrane experiments peptides of 16 amino acids were synthesized and equal amounts of the peptides were directly spotted onto cellulose paper as described previously (Frank and Overwin, 1996). Blocking was performed in membrane blocking solution (MBS) that consisted of 20 ml casein based blocking buffer (Genosys Biotechnologies, Cambridge, England), 80 ml Tris-buffered saline (TBS), 0.05% tween 20, and 5 g sucrose. Probing for fibrinogen-binding was performed as described below.

Detection of Fibrinogen Binding by Western Blot, Spot Membrane and Colony Blot

Membranes that had been blocked overnight were incubated for 1 h with 2 µg/ml of human fibrinogen. For Western and colony blot experiments, fibrinogen and antibodies were diluted in PBS while for spot membrane analysis they were diluted in MBS. Following three washes with PBS, the membrane was incubated with anti-fibrinogen antibodies (1:1000 in PBS or MBS) for 1 h. This incubation was followed by three washes with PBS, containing 0.05% tween 20 (PBST) and two washes with PBS. Subsequently, the membrane was incubated for 1 h with peroxidase-labelled anti-rabbit IgG (1:1000 in PBS or MBS). After three washes with PBST and two washes with PBS, bound fibrinogen was detected by chemiluminescence using the ECL-kit (Amersham/Pharmacia). In control experiments, no cross-reactivity of the used antibodies with the immobilized proteins and peptides was detected.

Opsonophagocytosis Assay

Resistance to phagocytosis was measured as described by Podbielski et al. (1996). Briefly, a growing culture of GBS was adjusted to $10^3$ colony-forming units per milliliter. 100 µl of the suspension were added to 300 µl of heparinized human blood and the reaction mixture was incubated at 37° C. with end-over-end rotation for 3 h. Pre- and postincubation aliquots were serially diluted and plated onto THY agar for overnight culture. For each strain the ratio of colony-forming units prior to, and following 3 h incubation with human blood was calculated. Each experiment was performed three times in triplicate.

Epithelial Cell Adherence and Internalization Assay

Adherence of GBS to epithelial cells and internalization into epithelial cells was assayed essentially as described previously (Caparon et al., 1991; Rubens et al., 1992). Briefly, A549 cells were transferred to 24-well tissue culture plates at approximately $4 \times 10^5$ cells per well and cultivated overnight in RPMI (Gibco BRL) tissue culture medium, supplemented with 10% of fetal calf serum. After replacement of the medium with 1 ml of fresh medium, the cells were infected with $5 \times 10^6$ streptococci per well and incubated at 37° C. for 2 h. The non-adherent bacteria were removed by washing three times with PBS. In adherence assays, the epithelial cells were subsequently detached from the well by the addition of trypsin/EDTA and lysed by adding 300 µl of distilled water. Adherent bacteria were quantitated by plating serial dilutions of the lysate onto THY agar plates. For internalization assays the epithelial cells were incubated after 2 h of infection for another 2 h in tissue culture medium supplemented with penicilling G (10 U) and streptomycin (0.01 mg) to kill extracellular bacteria. After three washes with PBS, the epithelial cells were detached by the addition of trypsin/EDTA and lysed in 300 µl of distilled water. The amount of intracellular bacteria was quantified by plating serial dilutions of the lysate onto THY agar plates. Each experiment was repeated at least three times in triplicate.

In competition studies, 1 ml of fresh tissue culture medium containing 50 µg of purified fusion protein or 1 µg of fibrinogen was added to the A549 cells and subsequently, the cells were infected with GBS 6313.

Interaction of Protein-Coated Latex Beads with A549 Cells

Approximately 108 latex beads (3 µm diameter, Sigma) were washed tree times in PBS and then coated with 300 µg of fusion protein or BSA in 500 µl PBS overnight at 4° C. Coated beads were washed once in PBS and then blocked with 200 µl of 10 mg/ml BSA in PBS for 1 h at room temperature. Beads were washed twice in PBS and once in RPMI+10% FCS and then resuspended in ml of RPMI+10% FCS. 300 µl of beads were added to approximately $4 \times 10^5$ A549 cells in 24-well plates. The cells were incubated for 1 h at 37° C. (5% $CO_2$), washed five times with PBS and fixed in a solution containing 3% glutaraldehyde and 5% formaldehyde in cacodylate bluffer for 45 min on ice. The samples were washed with cacodylate buffer, dehydrated in a graded series of acetone and subjected to critical point drying with $CO_2$. Samples were then coated with a 10 nm thick gold film and examined by scanning electron microscopy as described previously (Reinscheid et al., 2001).

Synthesis of Biotinylated Peptides

Peptides were synthesized in small scale (4 mg resin; up to 288 in parallel) using standard F-moc chemistry on a Rink amide resin (PepChem, Tubingen, Germany) using a SyroII synthesizer (Multisyntech, Witten, Germany). After the sequence was assembled, peptides were elongated with Fmoc-epsilon-aminohexanoic acid (as a linker) and biotin (Sigma, St. Louis, Mo.; activated like a normal amino acid). Peptides were cleaved off the resin with 93%TFA, 5% triethylsilane, and 2% water for one hour. Peptides were dried under vacuum and freeze dried three times from acetonitrile/water (1:1). The presence of the correct mass was verified by mass spectrometry on a Reflex III MALDI-TOF (Broker, Bremen Germany). The peptides were used without further purification.

Enzyme Linked Immune Assay (ELISA).

Biotin-labeled peptides were coating on Streptavidin ELISA plates (EXICON) at 10 µg/ml concentration according to the manufacturer's instructions. Sera were tested at two dilutions, 200× and 1,000×.

Highly specific Horse Radish Peroxidase (HRP)-conjugated anti-human IgG or anti-human IgA secondary antibodies (Southern Biotech) were used according to the manufacturers' recommendations (dilution: 1,000×). Antigen-antibody complexes were quantified by measuring the conversion of the substrate (ABTS) to colored product based on $OD_{405\ nm}$ readings in an automated ELISA reader (TECAN SUNRISE). Following manual coating, peptide plates were processed and analyzed by the Gemini 160 ELISA robot (TECAN) with a built-in reader (GEMOS, TECAN).

Example 2

Identification of a Novel *S. agalactiae* Adhesion by a Signal Peptide Tagging Screen Results GBS strain 6313, belonging to serotype III, was tested in binding experiments for its interaction with radiolabelled human vitronectin, laminin, fibronectin, fibrinogen, and IgG. Strain 6313 accumulated about 50% of the total fibrinogen on its surface. Of the other proteins tested, none interacted in significant amounts (>5%) with GBS 6313. Treatment of the bacteria with either trypsin or pronase reduced the amount of bound fibrinogen to levels below 5%, indicating a proteinacious nature of the fibrinogen-binding structures of GBS 6313.

An *Escherichia coli* cosmid gene library of GBS 6313 was screened by colony blotting for the presence of fibrinogen-binding *E. coli* clones, resulting in the identification of a clone that revealed strong interaction with human fibrinogen. Partial digestion of its cosmid with Sau3A and subcloning of fragments in the range of 2-3 kb in plasmid pTEX5236 resulted in the isolation of plasmid pTEXfbsA, carrying a 2.6 kb insert that conferred fibrinogen-binding to *E. coli* DH5α. The insert of pTEXfbsA was sequenced and the analysis of the obtained sequence identified one open reading frame of 1329 bp, designated fbsA as it encodes a fibrinogen-binding protein from *S. agalactiae* (FIG. 1). The fbsA gene is preceded by a typical ribosomal binding site (AGGAGA) and followed by a sequence resembling a transcriptional terminator ($AG°=-18$ kcal/mol). Analysis of the fbsA-encoding region revealed for the deduced FbsA protein typical features of a surface-located protein from streptococci (FIG. 1), i.e. a signal peptide sequence of 35 amino acids (Nielsen et al., 1997) at its N-terminus and a cell wall anchor motif (LPKTG) (Schneewind et al., 1993) at its C-terminus. The fbsA gene encodes a primary translation product of 442 amino acids (Mr 51319), which is putatively processed posttranslationally to yield a mature protein of 378 amino acids (Mr 44260). The most striking feature of FbsA is its highly repetitive nature: FbsA carries 19 complete repeats of 16 amino acids that are almost identical. 14 of the 19 repeats are comprised of the sequence motif 'GNVLERRQRDAENRSQ' while two repeats (3 and 10) carry an R14K substitution and three repeats (2, 9, and 19) possess both an Al 1V and an R14K substitution.

Figure 2:
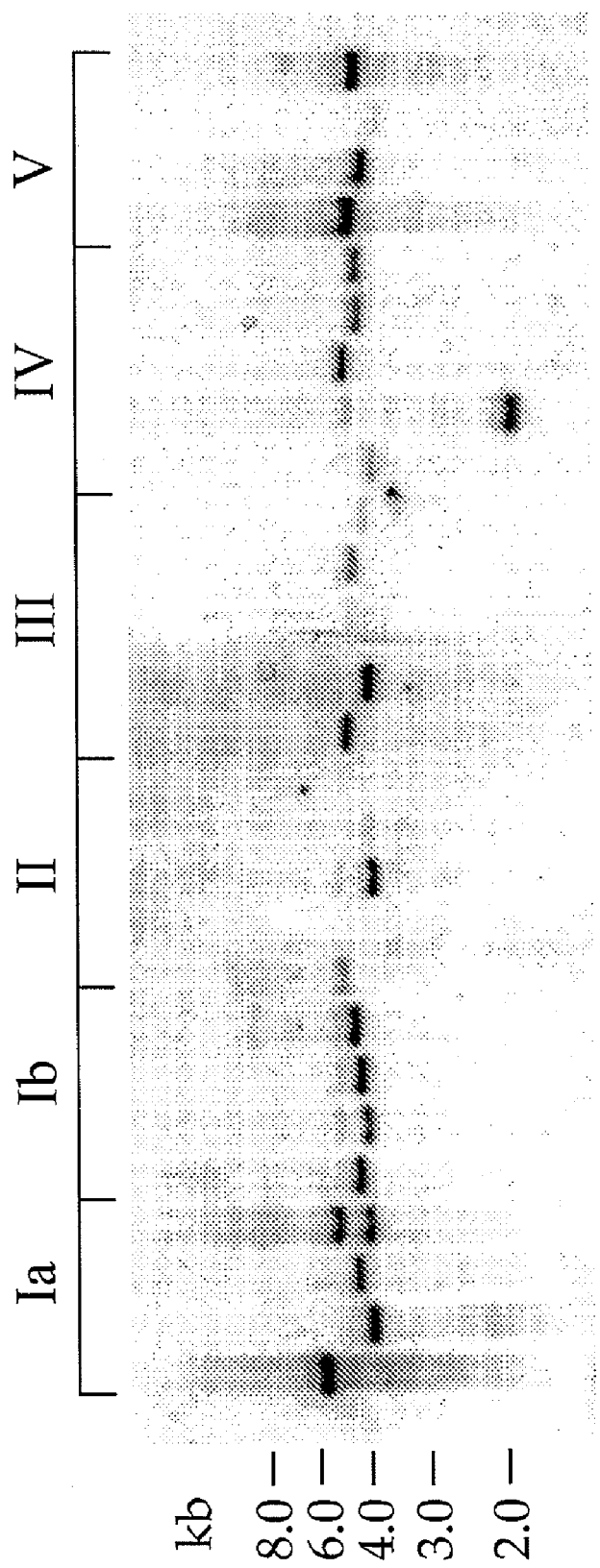
Figure 8:
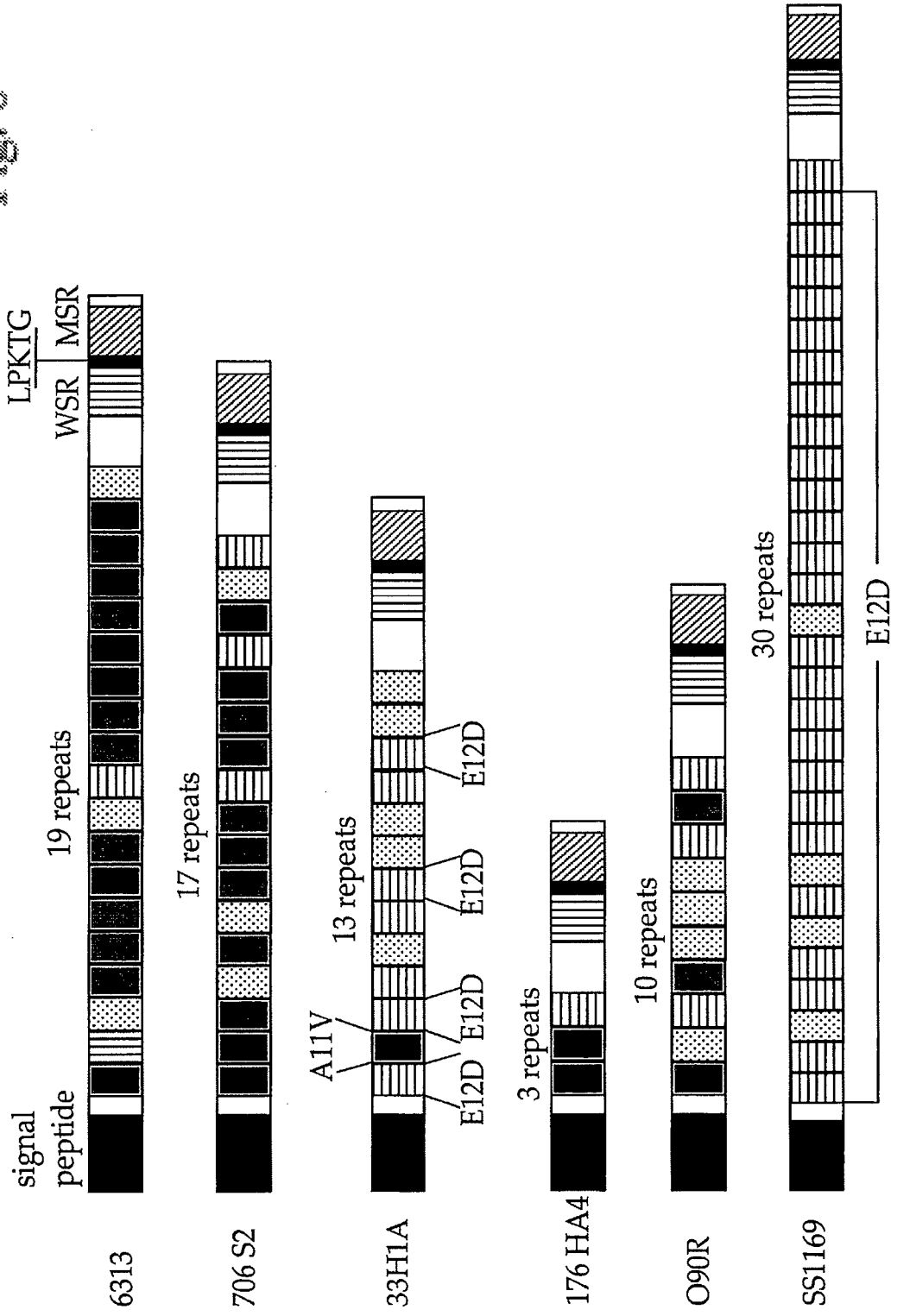

Southern blot experiments with clinical GBS isolates, belonging to the serotypes Ia, Ib, II, III, IV, and V, were performed to analyze the presence of fbsA in GBS. By Southern blot analysis, the fbsA gene was detected in 25 of 27 strains (FIG. 2), indicating a wide distribution of fbsA in different serotypes of GBS. Interestingly, the size of the fbsA gene varied significantly between the individual strains in the Southern blot analysis. To unravel the molecular basis of this size variation, the fbsA gene was amplified by PCR from the GBS strains 706 S2 (serotype Ia), 33H1A (serotype Ib), O176 H4A (serotype II), SS1169 (serotype V), and O90R (a capsule mutant derived from a serotype Ia strain) and sequenced. Analysis of the obtained sequences revealed one open reading frame in each PCR product with high identity to fbsA from GBS strain 6313 (FIGS. 3-7). Analysis of the deduced FbsA proteins identified in all of them a putative signal peptide at their N-termini and a putative cell wall anchor at their C-termini. As expected from the Southern blot experiments, the size of the single proteins is significantly different. The primary translation product of fbsA is 410 amino acids for strain 706 S2 (FIG. 3), 346 amino acids for strain 33H1A (FIG. 4), 186 amino acids for strain 176 H4A (FIG. 5), 298 amino acids for strain O90R (FIG. 6), and 618 amino acids for strain SS1169 (FIG. 7). As shown in FIG. 8, the different sizes between the single FbsA proteins are exclusively due to a different number of repeats within the individual proteins. FIG. 8 also shows, that the individual repeats of the deduced FbsA proteins reveal differences in their amino acid composition. Thus, the fbsA gene from different GBS strains appears to be highly variable in the number of and flexible in the composition of single repeat-encoding units.

Example 3

FbsA is the Fibrinogen Receptor of *Streptococcus agalactiae*

Results

Figure 9:
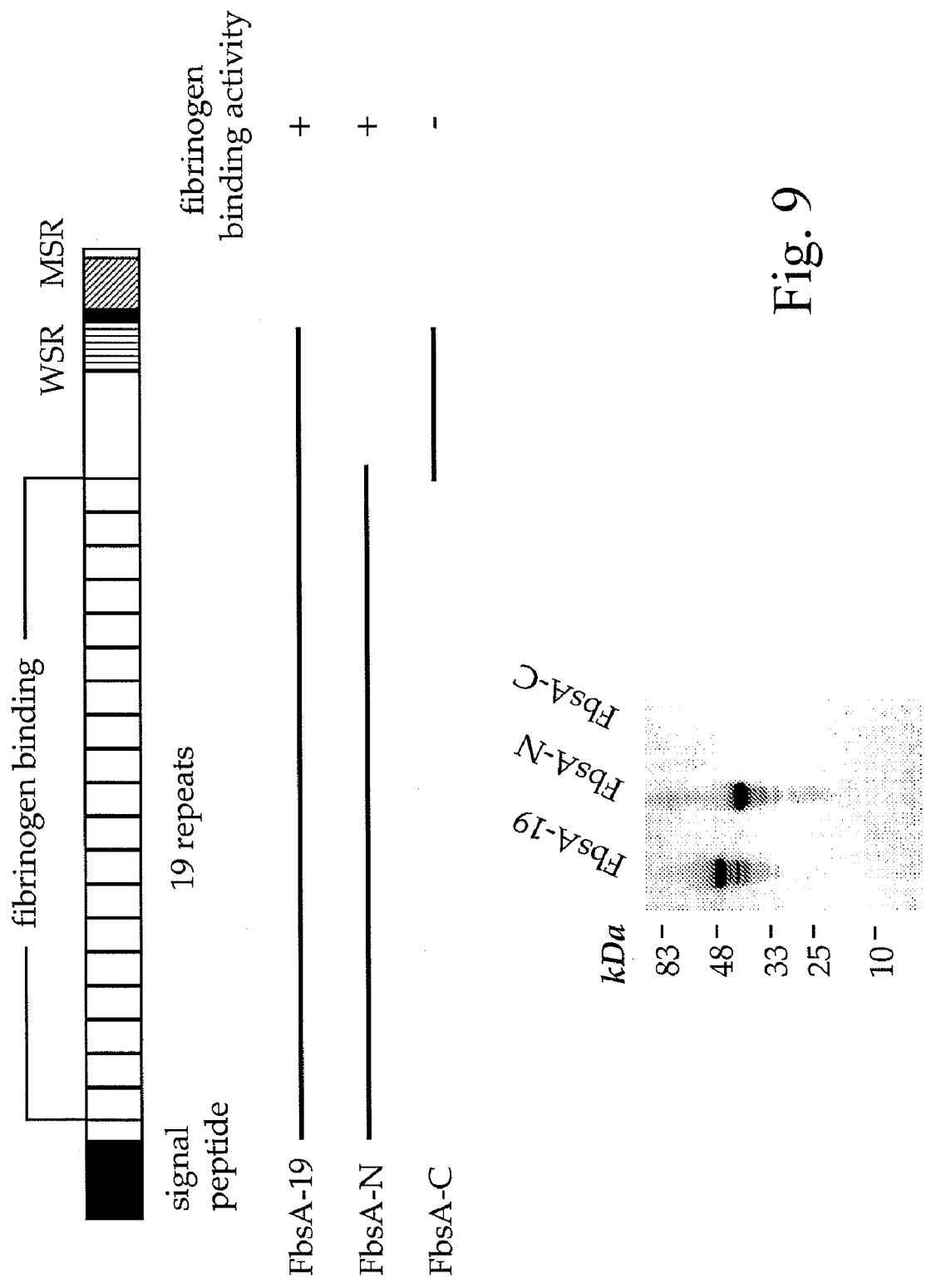

For functional analysis of FbsA, a truncated FbsA polypeptide (FbsA-19), devoid of a signal peptide and a membrane-spanning region was synthesized as a hexa-histidyl fusion protein in *E. coli* BL21 and purified by affinity chromatography. In Western blot experiments FbsA-19 revealed binding to human fibrinogen (FIG. 9), confirming FbsA as a fibrinogen receptor from GBS. To localize the fibrinogen-binding region in the FbsA protein, the N-terminal and the C-terminal regions of FbsA were synthesized as FbsA-N and FbsA-C fusion proteins and tested for fibrinogen binding. As shown in FIG. 9, fibrinogen binding was observed for FbsA-N but not for FbsA-C, indicating that the N-terminal repeats of FbsA mediates fibrinogen binding.

Figure 10:
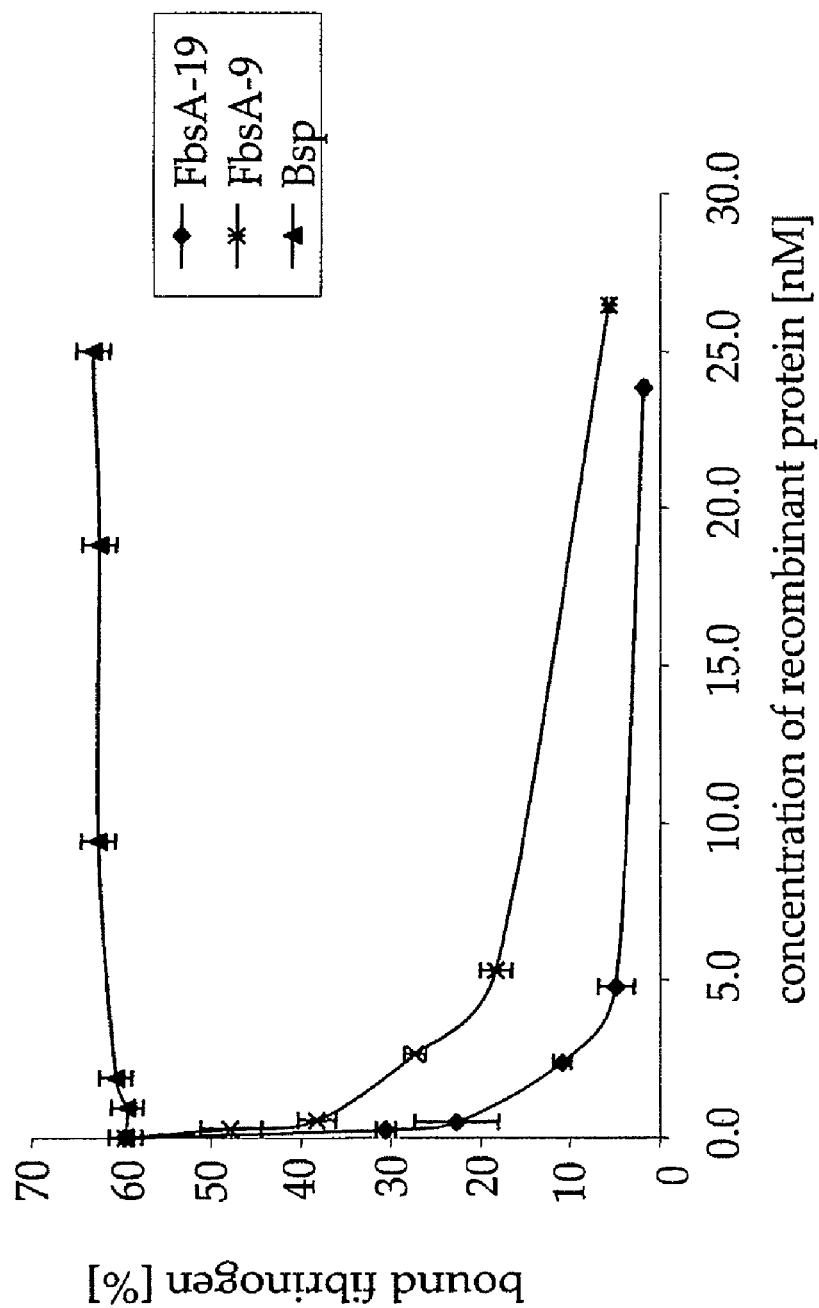

In competitive inhibition experiments with $^{125}$I-labelled fibrinogen, different proteins were tested for their capability to interfere with the binding of radiolabelled fibrinogen to GBS. As a control, the non-fibrinogen binding surface protein Bsp from GBS (Reinscheid et al., 2002) was tested for inhibiting the binding of fibrinogen to GBS. As shown in FIG. 10, the addition of increasing concentrations of Bsp had no effect on fibrinogen binding by GBS. However, increasing concentrations of purified FbsA-19 substantially inhibited the binding of $^{125}$I-labelled fibrinogen to GBS 6313 cells. To analyse, if the number of repeats of FbsA has an effect on fibrinogen binding, a derivative of FbsA with only 9 repeats (FbsA-9) was tested for its capability to inhibit fibrinogen binding by GBS. Interestingly, significantly higher concentration of FbsA-9 had to be used to obtain a comparable inhibition of fibrinogen binding as obtained with FbsA-19. This finding indicates that increasing numbers of repeats either increases the affinity of FbsA for fibrinogen and/or supports a higher amount of fibrinogen to be bound by FbsA.

To further characterize the interaction of FbsA and fibrinogen on the molecular level, FbsA-derived synthetic peptides were tested for their interaction with human fibrinogen. At first, we analysed a single repeat unit of FbsA (GNVLERRQRDAENRSQ) for its capability to interact with human fibrinogen. In Dot Blot experiments a strong interaction of this synthetic peptide with human fibrinogen was observed while a randomised peptide containing the identical amounts of amino acids but in different order, showed no binding of fibrinogen (FIG. 11). This result shows that a single repeat unit of FbsA is capable of specific binding to human fibrinogen. To identify amino acids in the repeat region that are essential for fibrinogen binding, we synthesized peptides that contained single alanine replacements at different positions. Testing of these peptides for their interaction with fibrinogen (FIG. 11) identified $N^2$, $V^3$, $L^4$, $R^6$, and $R^7$ of the repeat sequence to be essential for fibrinogen binding. Furthermore, substitution of $G^1$, $R^9$, and $R^{14}$ by alanine significantly reduced the interaction of the repeat unit with human fibrinogen.

Figure 12:
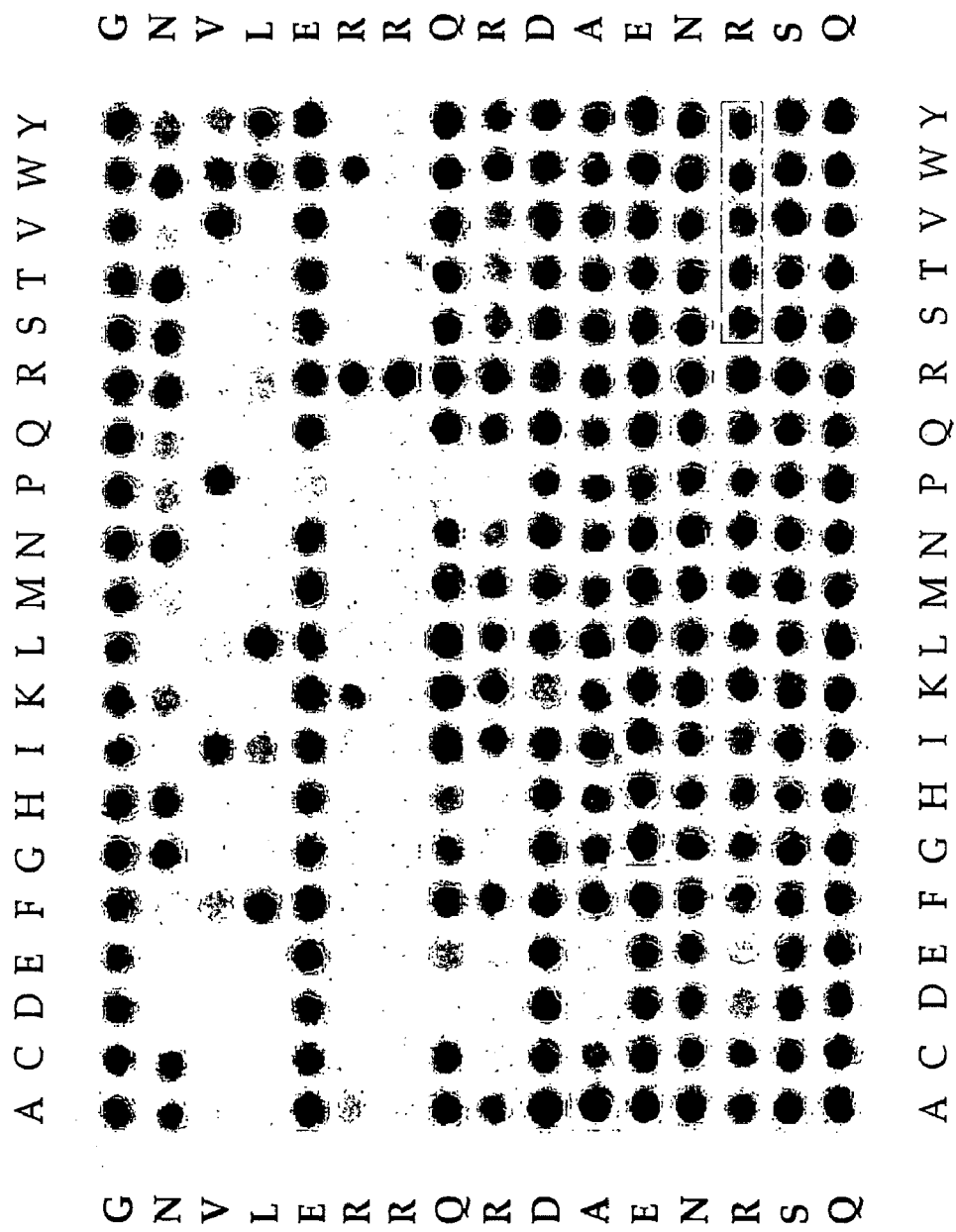

A comprehensive analysis of fibrinogen binding by the 16 amino acid sequence motif was performed to identify putative conservative substitutions within the repeat regions. Therefore, synthetic peptides, derived from the sequence motif 'GNVLERRQRDAENRSQ' were synthesized and directly spotted onto a membrane. Every peptide differed from each other by a single amino acid substitution. In this way, every amino acid within the repeat was successively replaced by one of the twenty proteinacious amino acids. Testing of the individual spots for fibrinogen binding resulted in a complex picture of the interaction between fibrinogen and the repeat unit (FIG. 12). Replacement of $G^1$ by any other amino acid reduced the fibrinogen binding of the repeat although binding was not completely abolished. N2S and N2T substitutions did not affect fibrinogen binding, although replacement of $N^2$ by any other amino acid significantly reduced fibrinogen binding. $V^3$ and $L^4$ could not be replaced by other amino acids without significant reduction of binding function. Fibrinogen binding was not affected by E5A, E5M and E5Q substitutions but any other amino acid in this position resulted in a lower binding of fibrinogen. Substitutions of $R^6$ predominantly caused a loss of fibrinogen binding while peptides with R6A, R6K and R6W substitutions retained little binding activity. However, replacement of $R^7$ by any other amino acid resulted in a loss of fibrinogen binding. $Q^8$ could be substituted by many amino acids without an effect on binding while $R^9$ could only be replaced by K or W without affecting binding. D10A, D10E, D10N, and D10Q substitutions had no effect on fibrinogen binding while the same was true for A11IF, A11I, A11L, A11V and A11Y changes. $E^{12}$ and $N^{13}$ could be replaced by a variety of amino acids without affecting binding. In contrast, only R14K substitutions retained fibrinogen binding of the peptide. Finally, $S^{15}$ and $Q^{16}$ could be replaced by many other amino acids without loss of binding function. Derived from the result of the spotting membrane experiment, the following fibrinogen binding motif can be postulated: G-N/S/T-V-L-A/E/M/Q-R-R-X-K/R/W-A/D/E/N/Q-A/F/I/L/V/Y-X-X-K/R-X-X (SEQ ID No. 222). This consensus motif could not be identified in fibrinogen binding proteins from other organisms, indicating that it represents a novel type of fibrinogen binding site.

Figure 13:
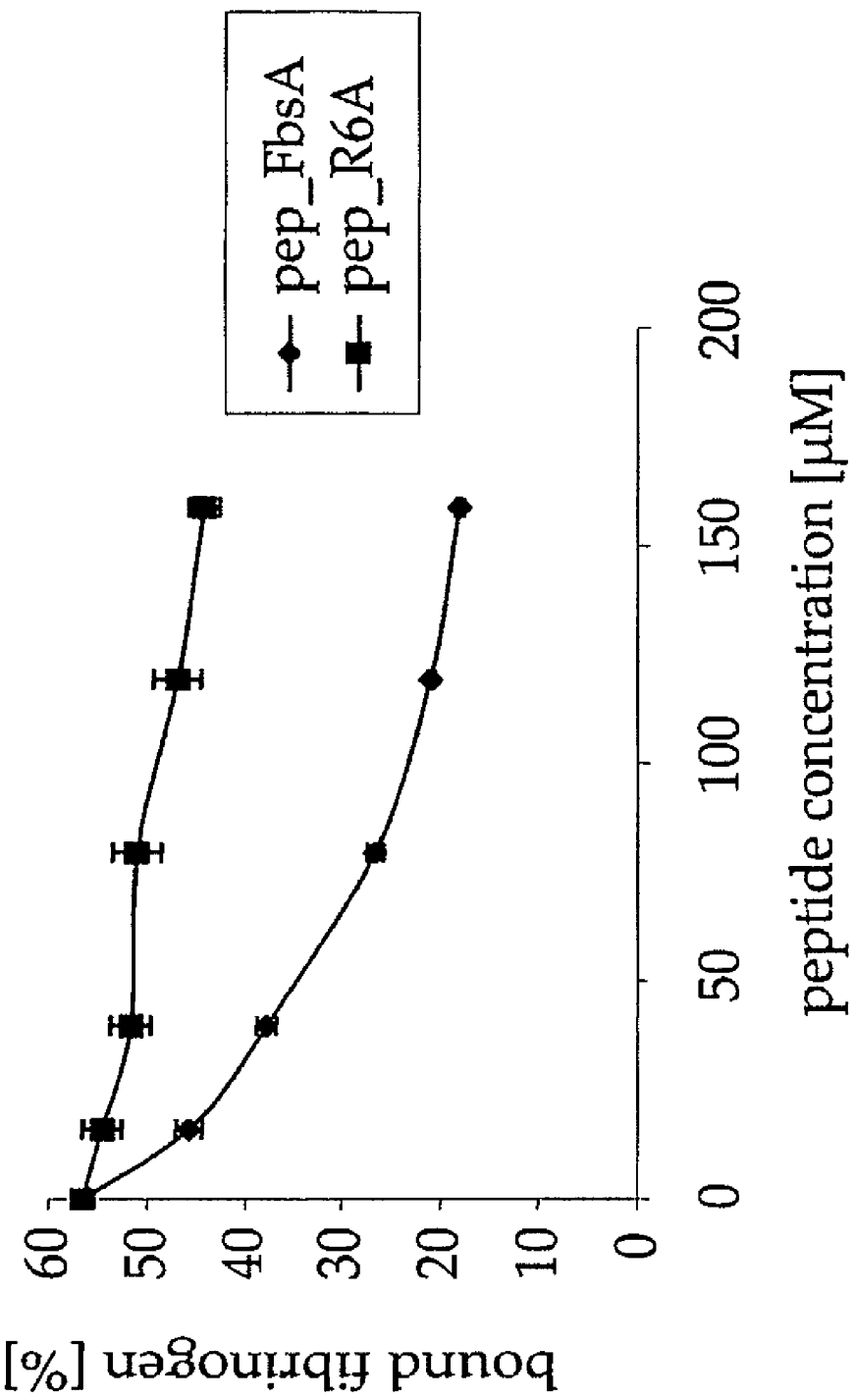

Derived from the results of the spot membrane analysis, two different synthetic peptides were tested for their capability to inhibit fibrinogen binding of GBS. One peptide (pep_FbsA) represented the original repeat unit sequence 'GNVLERRQRDAENRSQ' (SEQ ID No. 113) while the other peptide (pep_R6A) carried an R6A substitution. In spot membrane analysis, the latter peptide had revealed a significantly reduced binding to fibrinogen. In competitive inhibition experiments, both peptides were tested for inhibiting the binding of radiolabelled fibrinogen to GBS (FIG. 13). A concentration of 160 µM of pep_FbsA inhibited fibrinogen binding by 80% whereas the same concentration of pep_R6A caused only 20% inhibition of fibrinogen binding. These findings demonstrate that the soluble form of the repeat unit of FbsA is capable of fibrinogen binding. Furthermore, the difference in the inhibition of fibrinogen binding between the two peptides confirms the results of the spot membrane analysis and shows that $R^6$ plays an important role in fibrinogen binding.

To analyse the contribution of FbsA for the fibrinogen binding of GBS, fbsA deletion mutants were constructed in the GBS strains 6313, 706 S2, and O90R, respectively. Southern blot analysis revealed the successful deletion of fbsA in the respective strains (data not shown), which were termed accordingly 6313ΔfbsA, 706 S2ΔfbsA, and O90RΔfbsA. Mutants and parental strains were subsequently tested for their binding of soluble and immobilized fibrinogen. While GBS strains 6313, 706 S2 and O90R exhibited about 50%, 8%, and 12% binding of $^{125}$I-labelled soluble fibrinogen, their respective fbsA mutants bound less than 2%. Similarly, in binding experiments using FITC-labelled bacteria, about 45%, 15%, and 24% of the total bacteria from the GBS strains 6313, 706 S2, and O90R bound to immobilized fibrinogen but less than 2% of the respective fbsA mutants interacted with the immobilized fibrinogen. From these results it can be concluded that FbsA is the major fibrinogen-binding protein in the GBS strains 6313, 706 S2, and O90R, respectively, and that it mediates the binding of the bacteria both to soluble and to immobilized fibrinogen.

Example 4

FbsA Contributes to Adherence and Invasion of Epithelial Cells and Inhibits Opsonophagocytosis Results To analyse the importance of FbsA for protecting GBS from opsonophagocytosis, the GBS strains 6313 and 6313ΔfbsA were tested for survival in a classical bactericidal assay in whole human blood. After inoculation of heparinized human blood with 100±30 colony forming units (cfu) of either of the two strains, both strains revealed growth, however, after three hours of incubation, strain 6313 grew to 2500±500 cfu/assay while strain 6313ΔfbsA grew only to 800±100 cfu/assay. This finding indicates a role of FbsA in preventing opsonization.

Figure 14:
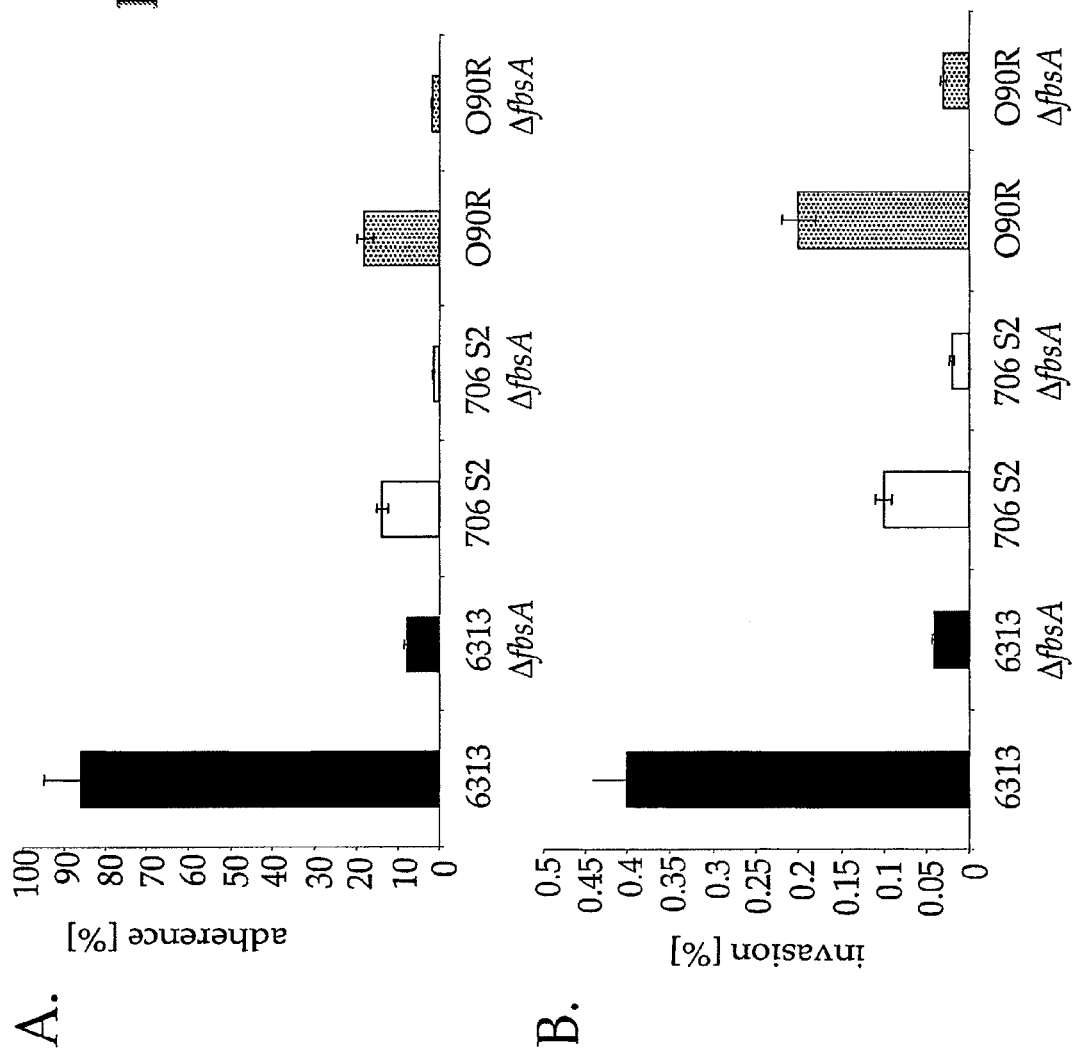

The GBS strains 6313, 706 S2 and O90R, and their respective fbsA deletion mutants were also tested for their ability to adhere to and invade the human lung epithelial cell line A549. As shown in FIG. 14A, the adhesion of the fbsA deletion mutants to A549 cells was significantly impaired compared to their parental strains. Similarly, the ability of the fbsA deletion mutants to invade A549 cells was also drastically reduced (FIG. 14B). To analyse this effect in more detail, the ability of GBS 6313 to adhere to and to invade A549 cells in the presence of 1 µg/ml of externally added fibrinogen was quantitated. The addition of fibrinogen resulted in a 90% reduction of the adherence of GBS 6313 to and invasion of A549 cells. Taken together, these findings indicate that in GBS the binding of FbsA to fibrinogen plays an important role in the bacterial adhesion to and invasion of human epithelial cells.

Example 5

FbsA is Highly Immunogenic in Humans

Results

Five sera from patients were analysed for the presence of antibodies directed against 5 peptides (wild type <1>: GNVLERRQRDAENRSQ (SEQ ID No. 113); alanine mutant peptides: <2> GAVLERRQRDAENRSQ (SEQ ID No. 207), <3> GNALERRQRDAENRSQ (SEQ ID No. 209), <4> GNVLERRQRDAENRSQ (SEQ ID No. 211), <5> GNVLERAQRDAENRSQ (SEQ ID No. 212); see FIG. 11). Besides the wild type sequence of the repeat region, 4 peptides with alanine substitutions were chosen, devoid of fibrinogen binding activity. The elimination of fibrinogen binding activity of the peptides was sought in order to evaluate whether fibrinogen may interfere with the binding antibodies. All peptides were synthesized with a N-terminal biotin-tag and used as coating reagents on Streptavidin-coated ELISA plates.

Figure 15:
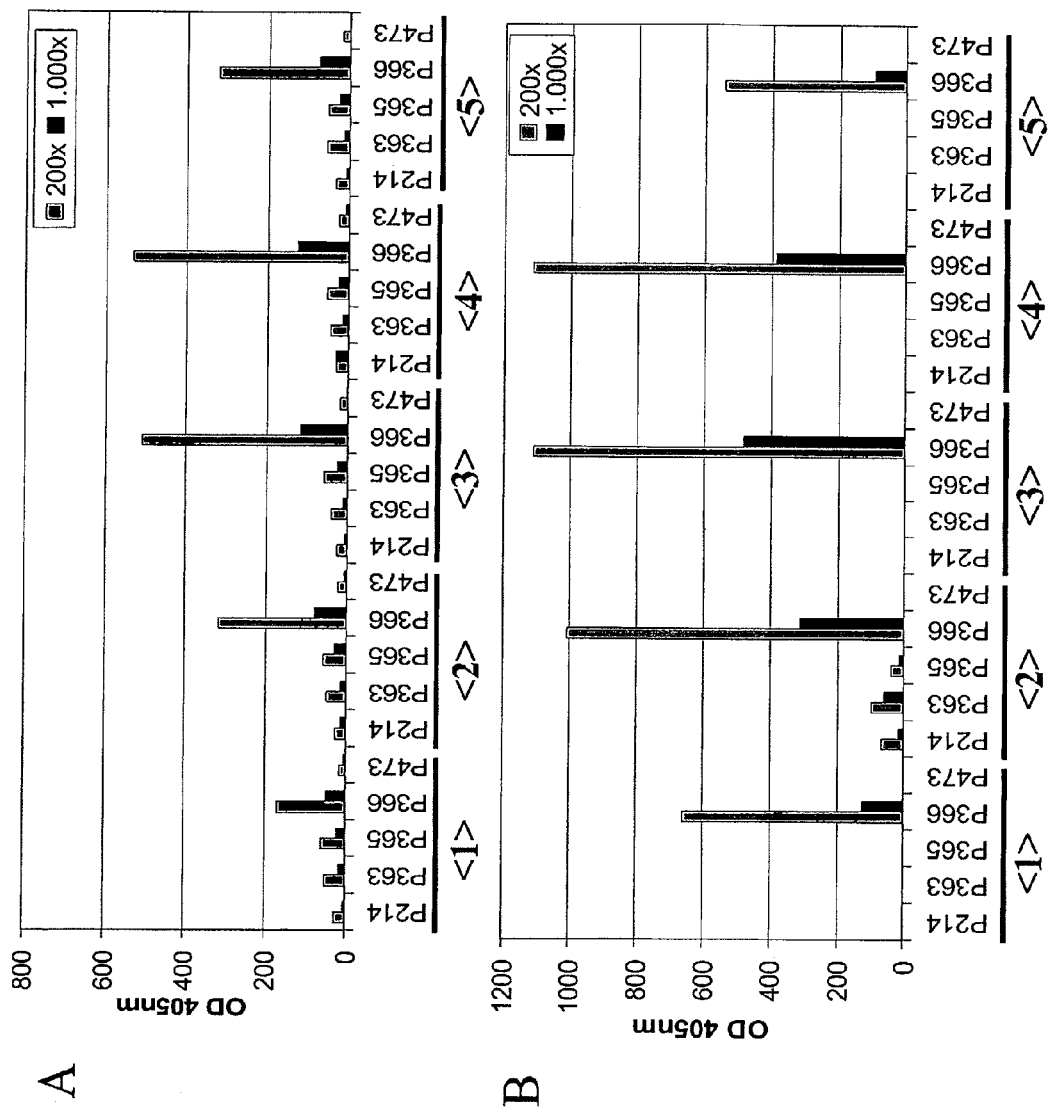

The ELISA analysis was performed with the Gemini 160 ELISA robot. IgA and IgG antibody levels are presented for the indicated sera with all five peptides (FIG. 15). Of the five sera chosen for this analysis mainly one showed a very high reactivity with the analysed peptides. Comparing the wild type and mutant peptides, the mutant peptides 2, 3 and 4 showed similar reactivities with both IgA and IgG antibodies, whereas the wild type peptide and peptide 5 were less well recognized by all sera. For the wild type peptide, this is probably explained by the presence of fibrinogen in human serum, which may compete with antibody binding to the peptide. The mutation in peptide 5 may have changed binding of the antibodies and therefore reduced reactivity. Interestingly, the reactivities of the peptides were very high with IgA antibodies and less pronounced with IgG, indicating that the antibody response in humans mainly involves the production of IgA antibodies, which are especially important for the prevention of colonization. These data are a strong indication that the FbsA protein is expressed in vivo during infection and that it is surface accessible for human antibodies.

Example 6

Identification of Additional *S. agalactiae* Adhesions by the Signal Peptide Tagging Screen Results For the identification of further adhesins and invasins from GBS, chromosomal DNA from GBS 6313 was fragmented by sonication, the obtained fragments were filled in by Klenow polymerase treatment, subsequently ligated into plasmid pHRM104 and transformed in *E. coli* CC118. After screening on X-phosphate containing LB-plates, four colonies were surrounded by a wide blue halo. The plasmids of these clones were isolated and their inserts were sequenced. Analysis of the obtained sequences identified four incomplete open reading frames, each starting with a signal-peptide-encoding sequence. As the genes represented potential adhesins from group B *streptococcus*, they were named pabA, pabB, pabC, and pabD, respectively. Digoxigenin-labelled probes were amplified from the four incomplete genes by PCR. The DNA probes were used for screening a GBS 6313 cosmid gene bank in *E. coli*, resulting in the identification of one *E. coli* clone that hybridised with both the pabA and pabB probe and one *E. coli* clone that revealed hybridisation with both the pabC and pabD probe. From these clones cosmid DNA was isolated and the complete sequence of the genes pabA-D was determined by sequencing. Analysis of the obtained sequence information revealed that the pabA gene is located in front of the pabB gene (FIG. 16), while the pabC gene is preceding the pabD gene (FIG. 17). The genes pabA, pabB, pabC, and pabD encode proteins of 901 aa, 674 aa, 643 aa, and 182 aa, respectively. By the method of Nielsen et al. (1997), a putative signal peptide of 32 aa, 29 aa, 26 aa, and 23 aa could be predicted for the proteins PabA, PabB, PabC and PabD, respectively (FIGS. 16 and 17). In addition, the proteins PabA and PabB carry at their C-terminus the sequences IPMTG and IPQTG, respectively, which reveal high identity to cell wall anchor motifs of Gram-positive bacteria. By Southern Blot analysis, the genes pabA-D were detected in 90-95% of 35 tested clinical GBS isolates, indicating a wide distribution of these genes in GBS.

Example 7

PapA-D Contribute to Adhesion and Invasion of CBS to Human Epithelial Cells

Results

Figure 18:
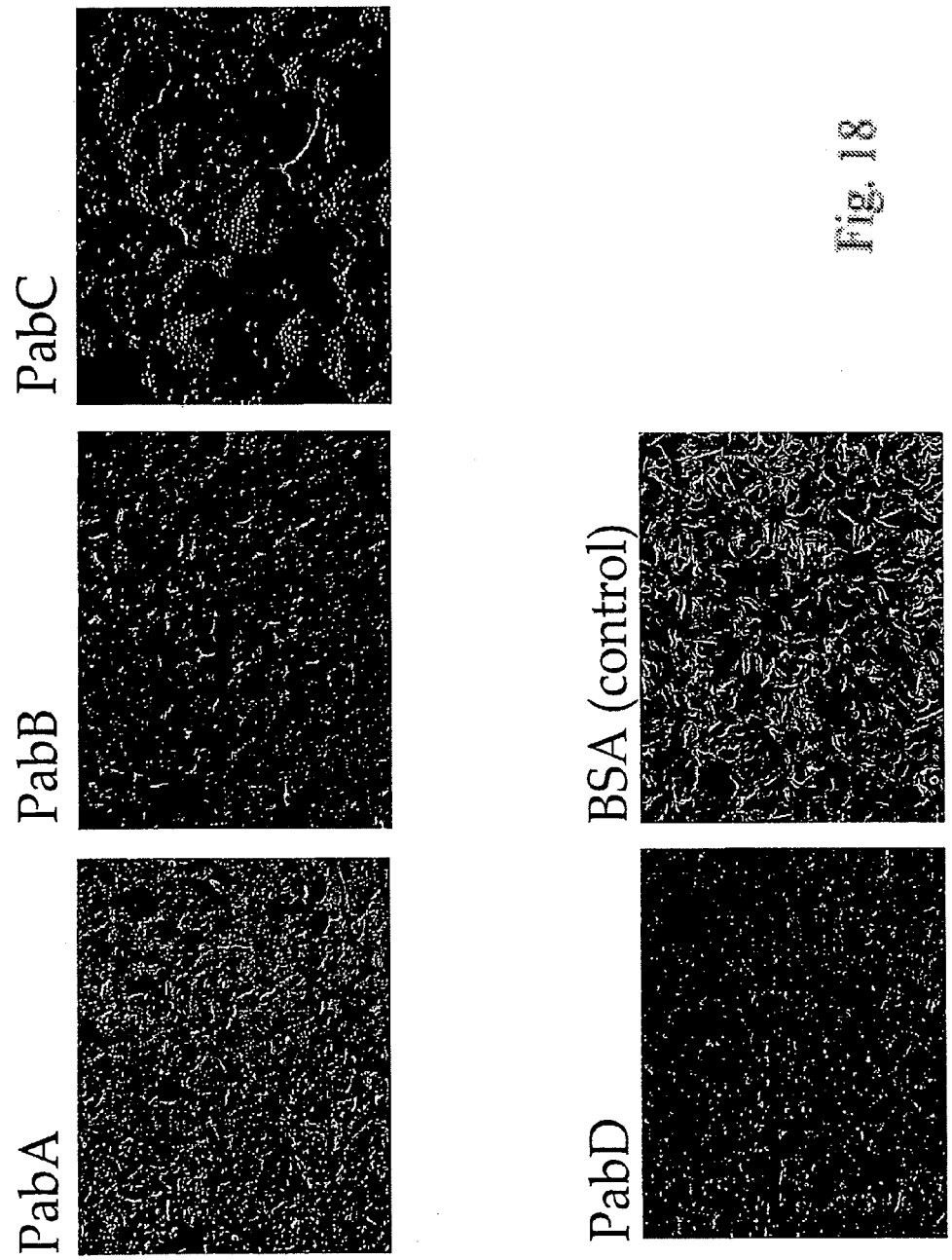
Figure 19:
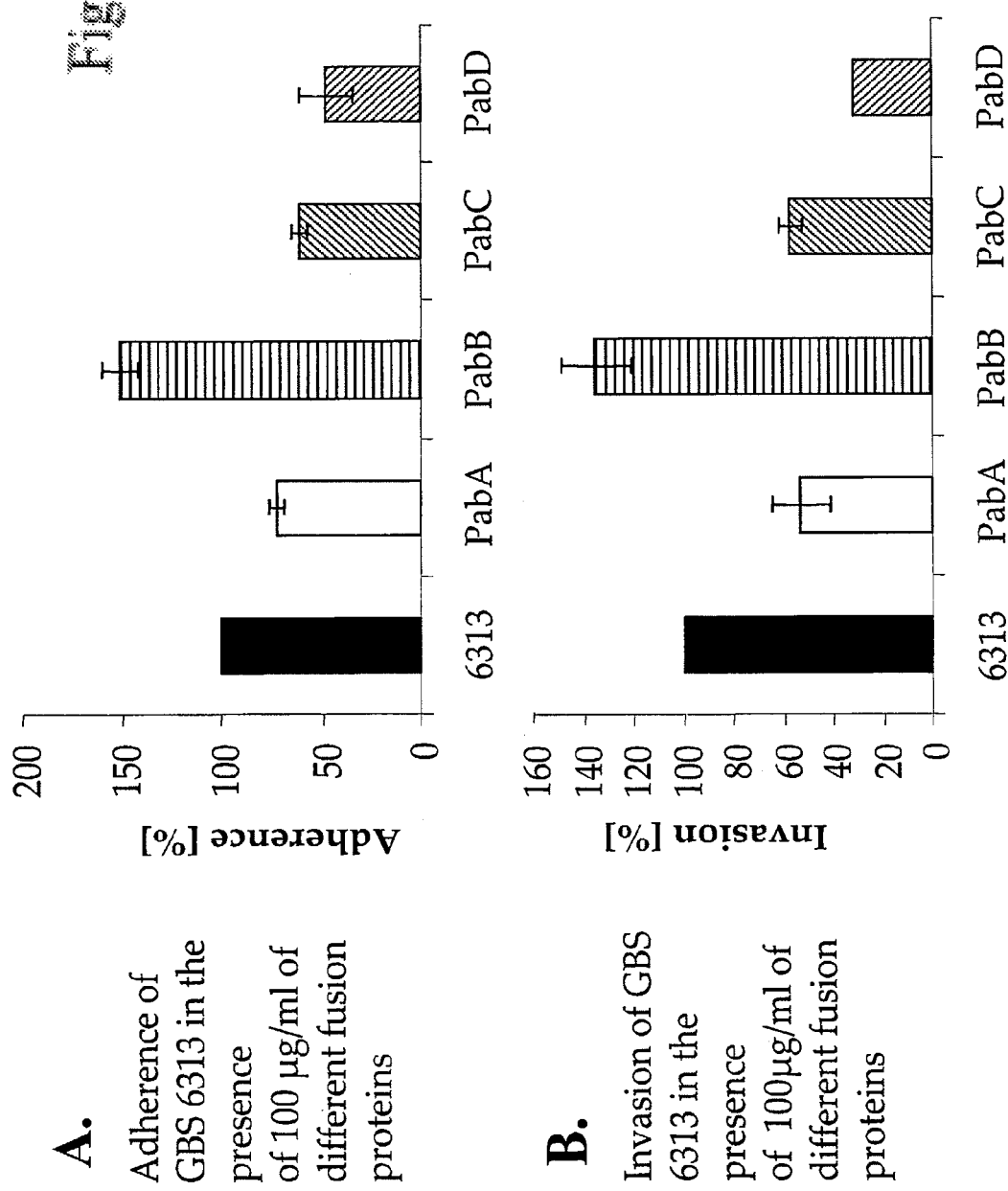

To analyse the importance of the four proteins for the adhesion of GBS to epithelial cells, the genes pabA and pabB were cloned devoid of their signal peptide encoding sequence and cell wall anchor motif in the *E. coli* expression vector pET28a, placing a hexa-histidyl tag at the C-terminus of the PabA and PabB fusion proteins. In parallel, the genes pabC and pabD were cloned devoid of their signal peptide encoding sequence in pET28a, resulting in the synthesis of the C-terminally his-tagged fusion proteins PabC and PabD. After construction of the plasmids in *E. coli* DH5α, the constructs were transformed in *E. coli* BL21 (DE) and the synthesis of the fusion proteins was induced by the addition of IPTG. The different fusion proteins were subsequently purified by $Ni^{2+}$-affinity chromatography. The proteins PabA, PabB, and PabC were further purified by cation exchange chromatography and the PabD protein was purified to homogeneity by anion exchange chromatography. The purified proteins were coated onto latex beads and the beads were allowed to interact with the human lung epithelial cell line A549. As a control, bovine serum albumin (BSA) coated beads were also allowed to bind to A549 cells. As shown in FIG. 18, BSA coated beads revealed no interaction with lung epithelial cells while beads coated with the proteins PabA, PabB, PabC or PabD revealed significant binding to A549 cells. This finding indicates that the proteins PabA, PabB, PabC and PabD mediate bacterial binding to host cells. In competition experiments, the adhesion of GBS 6313 to A549 cells and the invasion of the bacteria into this cell line were quantitated in the absence and in the presence of purified PabA, PabB, PabC or PabD fusion protein. As shown in FIG. 19, the addition of PabA, PabC and PabD significantly reduced the ability of GBS 6313 to adhere to and to invade A549 cells. Surprisingly, the addition of PabB increased the adhesion of GBS 6313 to and the invasion of A549 cells. This observation again supports the idea of PabA, PabB, PabC and PabD being adhesins of GBS.

Figure 20:
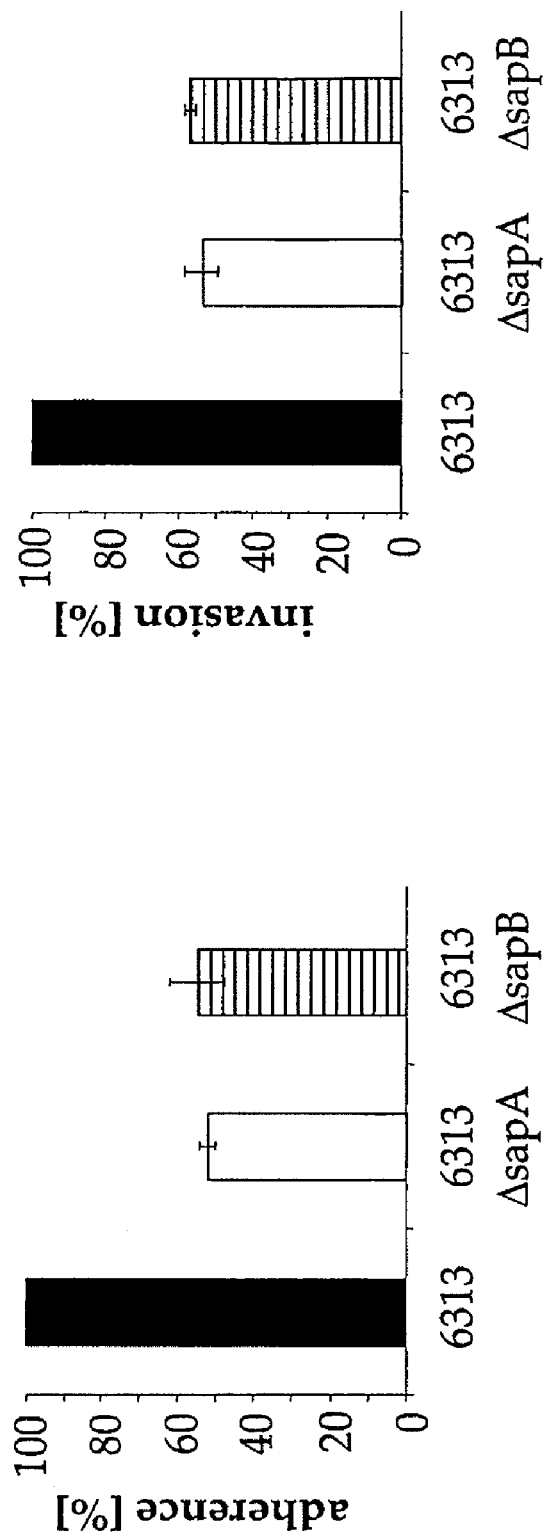

To analyse this effect further, the genes pabA and pabB, respectively, were deleted in the chromosome of GBS 6313. The resultant mutants were tested for their adhesion to and invasion of epithelial cells. Compared to the parental GBS strain 6313, both mutants revealed an about 50% reduction in their adherence to and invasion of A549 cells (FIG. 20).

Taken together, these data suggest, that the proteins PabA, PabB, PabC and PabD, respectively, play a role in the adhesion of GBS to and the invasion of epithelial cells.

Figure 21:
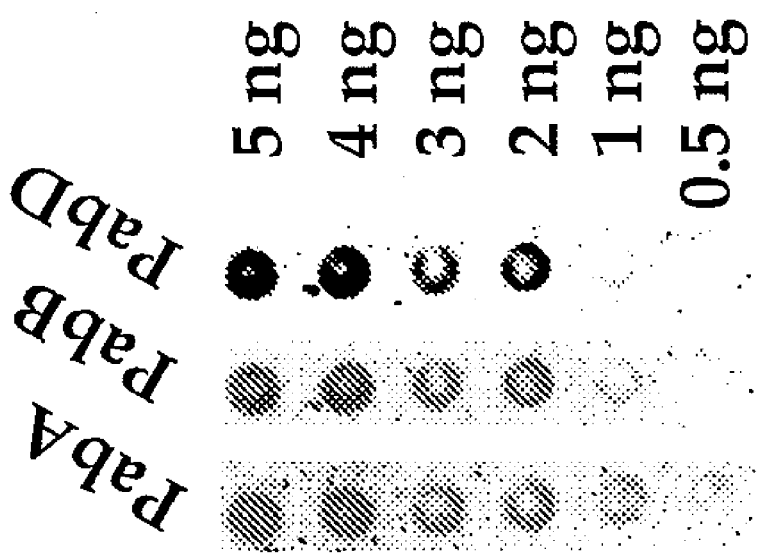

To test, if the proteins PabA, PabB and PabD elicit an immune response in mice, purified PabA, PabB and PabD fusion protein was used for the subcutaneous immunization of mice. The mice were boosted after three weeks and serum was collected six weeks after the first immunization. Serial dilutions of the PabA, PabB, and PabD fusion proteins were blotted onto nitrocellulose and probed with the mice sera against the different proteins. As depicted in FIG. 21, the fusion proteins PabA, PabB and PabD were sensitively detected by their respective antisera, indicating a high immunogenicity of the three proteins in mice.

Example 8

Experimental Procedures II

Bacterial Strains, Epithelial Cells and Growth Conditions.

The cell line A549 (ATCC CCL-185) and HEL299 (ATCC CCL-137) were obtained from the American Type Culture Collection. A549 is a human lung carcinoma cells which has many characeristics of type I alveolar pneumocytes. HEL299 is a human fibroblast cell line. A549 and HEL299 cells were propagated in RPMI or DMEM tissue culture medium (both Gibco BRL), supplemented with 10% of fetal calf serum. Tissue cultures were incubated in a humid atmosphere at 37° C. with 5% $CO_2$.

Construction of fbsA Deletion Mutants in *S. agalactiae*.

The fbsA gene was deleted in the *S. agalactiae* strains O176 H4A, and SS1169 according to the procedure described previously (Schubert et al., 2002). Briefly, the thermosensitive plasmid pG+ΔfbsA was transformed into the *S. agalactiae* strains by electroporation and transfonnants were selected by growth on erythromycin agar at 30° C. Cells in which pG+ΔfbsA had integrated into the chromosome were selected by growth of the transformants at 39° C. with erythromycin selection as described (Maguin et al., 1996). Integrant strains were serially passaged for five days in liquid medium at 30° C. without erythromycin selection to facilitate the excision of plasmid pG+ΔfbsA, leaving the desired fbsA deletion in the chromosome. Dilutions of the serially passaged cultures were plated onto agar and single colonies were tested for erythromycin sensitivity to identify pG+ΔfbsA excisants. Chromosomal DNA of erythromycin sensitive *S. agalactiae* excisants was tested by Southern blot after HindIII digestion using a digoxigenin-labelled fbsA flanking fragment as described previously {Schubert et al., 2002}.

Preparation of Hexahistidyl-Tagged Fusion Proteins.

The protein FbsA-19 represents the full-length FbsA protein from *S. agalactiae* 6313 and consists of 19 repetitive units of 16 amino acids at its N-terminus whereas protein FbsA-N contains the 19 N-terminal repeats of FbsA-19 but is truncated at its C-terminus {Schubert et al., 2002}. The Bsp protein is a surface protein of *S. agalactiae* that plays a role in the morphogenesis of the bacteria {Reinscheid et al., 2002} and served as control in the present study. The fusion proteins were synthesized in recombinant *E. coli* BL21 by the addition of 1 mM IPTG after the culture had reached an optical density of 1.0. The cells were disrupted using a French Press cell and purification of the fusion protein was performed according to the instructions of Qiagen using $Ni^{2+}$ affinity chromatography.

Adherence and Invasion Assays.

Adherence of *S. agalactiae* to A549 and HEL299 cells and internalization into these cells was assayed essentially as described in Example 1 for A549 cells: In some experiments, A549 cells were preincubated with different amounts of FbsA protein or FbsA-derived peptides in RPMI medium for 30 min with three subsequent washes with PBS:

Scanning Electron Microscopy of FbsA-Coated Latex Beads.

Approximately $1 \times 10^9$ latex beads (3 μm diameter, Sigma) were washed three times in 25 mM 2-N-morpholinoethane-sulfonic acid (MES), pH 6.8. One half was resuspended in 1.0 ml MES buffer containing 500 μg/ml FbsA fusion protein and the remaining half was resuspended in 1.0 ml MES buffer. The beads were incubated overnight at 4° C. with end-over-end rotation. After pelleting of the beads by centrifugation, the amount of remaining protein in the supernatant was determined with a Bradford protein assay kit (BioRad). The beads were washed once with MES buffer and blocked for 1 h with 10 mg/ml BSA in MES buffer at room temperature. The beads were washed twice with MES buffer, once with RPMI+10% FCS, and resuspended in RPMI+10% FCS. Confluent A549 cells in 24-well plates were inoculated with $2 \times 10^8$ beads per well in a total volume of 1.0 ml. The bead monolayer mixtures were incubated for 2 h at 37° C. in a 5% $CO_2$ atmosphere. Cells were washed five times with PBS and fixed with 3% paraformaldehyde and 4% glutaraldehyde in 0.1% cacodylate buffer for scanning electron microscopy. Scanning electron microscopy was performed with a Zeiss DSM 962 microscope.

Example 9

Figure 22:
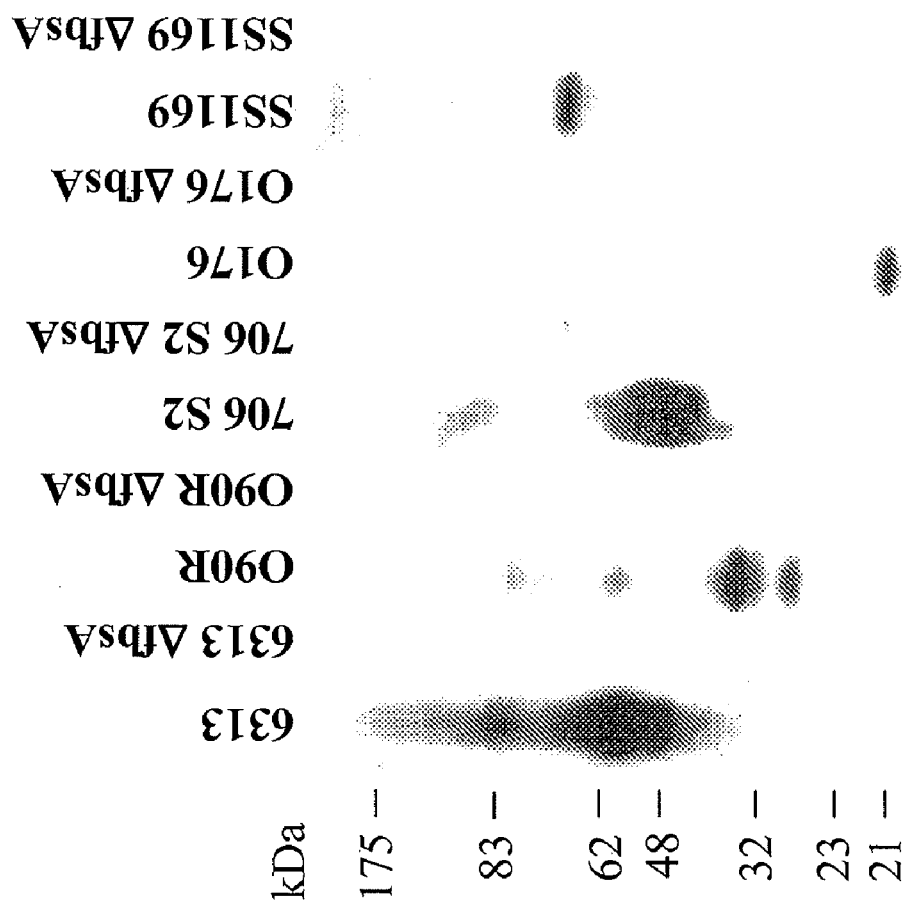

The FbsA Gene and Protein is Required in Different *S. agalactiae* Strains for Binding to Fibrinogen Results In the serotype III *S. agalactiae* strain 6313 the FbsA protein was shown to be essential for the fibrinogen binding of this strain (Example 3). The fbsA gene had been deleted in *S. agalactiae* strains 6313, 706 S2 (serotype Ia) and the capsule mutant O90R (Example 3). To further test the importance of FbsA for the fibrinogen binding of *S. agalactiae* strains from different serotypes, the fbsA gene was deleted in the genome of the *S. agalactiae* strains O176 H4A (serotype II), and SS1169 (serotype V). By Southern blot analysis the successful deletion of fbsA in the genome of the above-mentioned strains was confirmed (data not shown) and the respective mutants were named according to their original strain with the suffix ΔfbsA. The importance of the fbsA gene on the synthesis of fibrinogen binding proteins in different *S. agalactiae* was subsequently addressed by Western blot analysis. Equal amounts of culture supernatant of the *S. agalactiae* strains 6313, O90R, 706 S2, O176 H4A, and SS1169 and their respective fbsA deletion mutants were separated by SDS-PAGE, blotted onto nitrocellulose and subesquently tested for the presence of fibrinogen-binding proteins. As depicted in FIG. 22, the *S. agalactiae* stains 6313 and 706 S2 reveal the presence of significant amounts of fibrinogen proteins in their culture supernatants while the *S. agalactiae* strains O90R, O176H4A and SS1169 exhibit only small amounts of a fibrinogen-binding protein in their culture supernatants. Also the size of the fibrinogen-binding proteins differs significantly between the different strains. However, FbsA is a highly repetitive protein with different numbers of repetitive units in different *S. agalactiae* strains. The used *S. agalactiae* strains had been selected for further studies as they revealed significant differences in the number of repetitive units in their fbsA genes. According to the fbsA gene sequence from the different strains, the FbsA proteins were predicted to exhibit molecular masses of 51 kDa, 34 kDa, 47 kDa, 20 kDa, and 71 kDa for the *S. agalactiae* strains 6313, O90R, 706 S2, O176 H4A and SS1169, respectively. The observed sizes of fibrinogen-binding proteins in the culture supernatants of these strains correspond nicely to the predicted size of the FbsA protein in the different strains (FIG. 22). In the culture supernatants of the different fbsA deletion mutants, no fibrinogen binding protein could be detected. This indicates that the observed fibrinogen binding proteins in the culture supernatants from the different strains represent the FbsA protein and that FbsA is the predominant fibrinogen binding protein in the culture supernatant of all tested strains.

Figure 23:
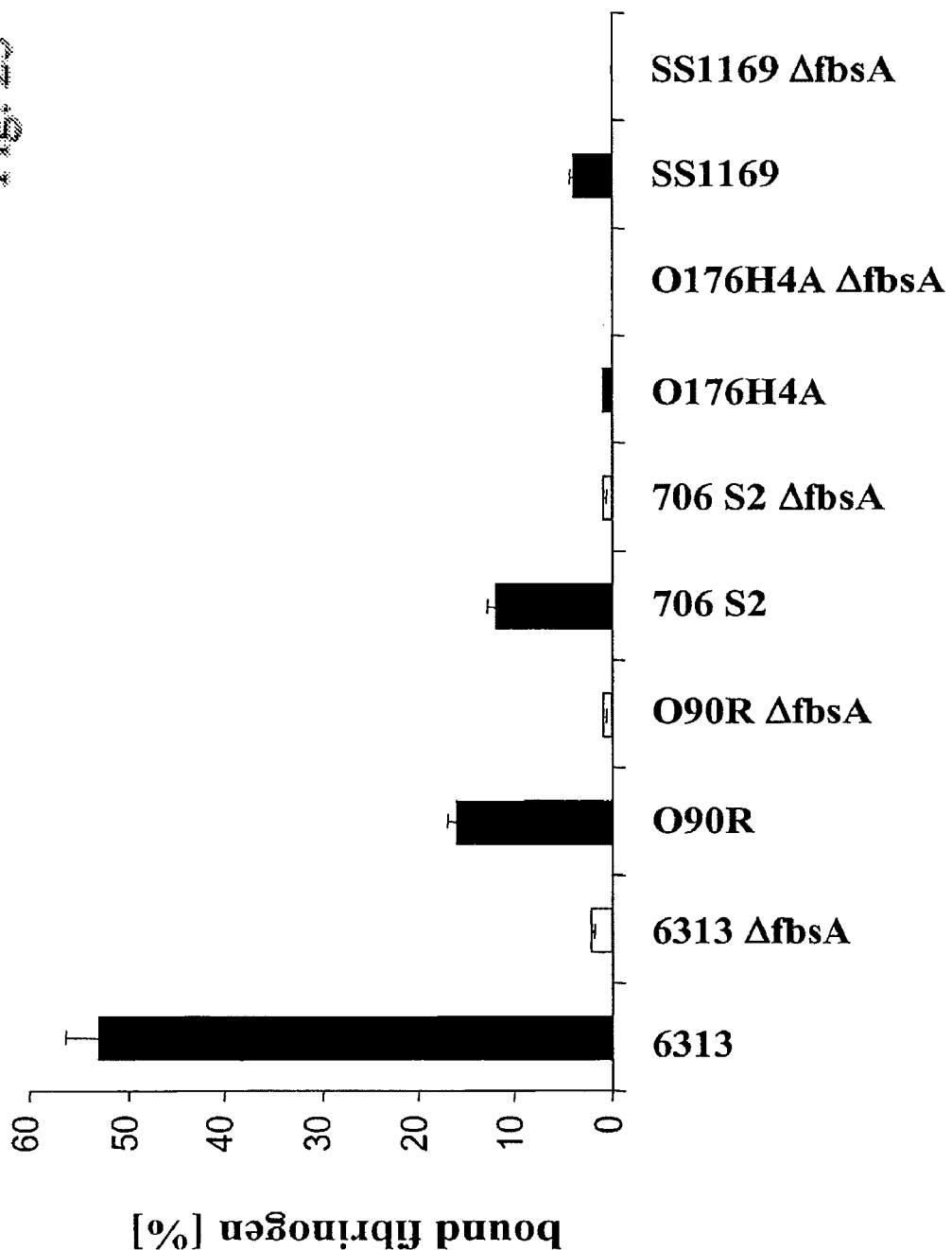

The different *S. agalactiae* strains and their fbsA mutants were tested for binding of $^{125}$I-labelled fibrinogen on their surface. *S. agalactiae* 6313 revealed significant binding of radiolabelled fibrinogen. However, the strains O90R and 706 S2 exhibited moderate and the strains O176 H4A and SS1169 weak binding of human fibrinogen. The differences in the fibrinogen binding of the different strains did not correlate with the number of fibrinogen-binding repeats in the FbsA proteins of these strains. However, in the fbsA deletion mutants, fibrinogen binding was reduced to values of 1% to 3%. Similarly, in binding experiments using FITC-labelled bacteria, about 45%, 18%, 14%, 4% and 7% of the total bacteria of the strains 6313, O90R, 706 S2, O176 H4A and SS1169 bound to immobilized fibrinogen, while less than 2% of the respective fbsA mutants bound to immobilized fibrinogen (FIG. 23). These results further show that FbsA is the major fibrinogen-binding protein in the analyzed *S. agalactiae* strains and that it mediates the binding of the bacteria both to soluble and to immobilized fibrinogen.

Example 10

Figure 24:
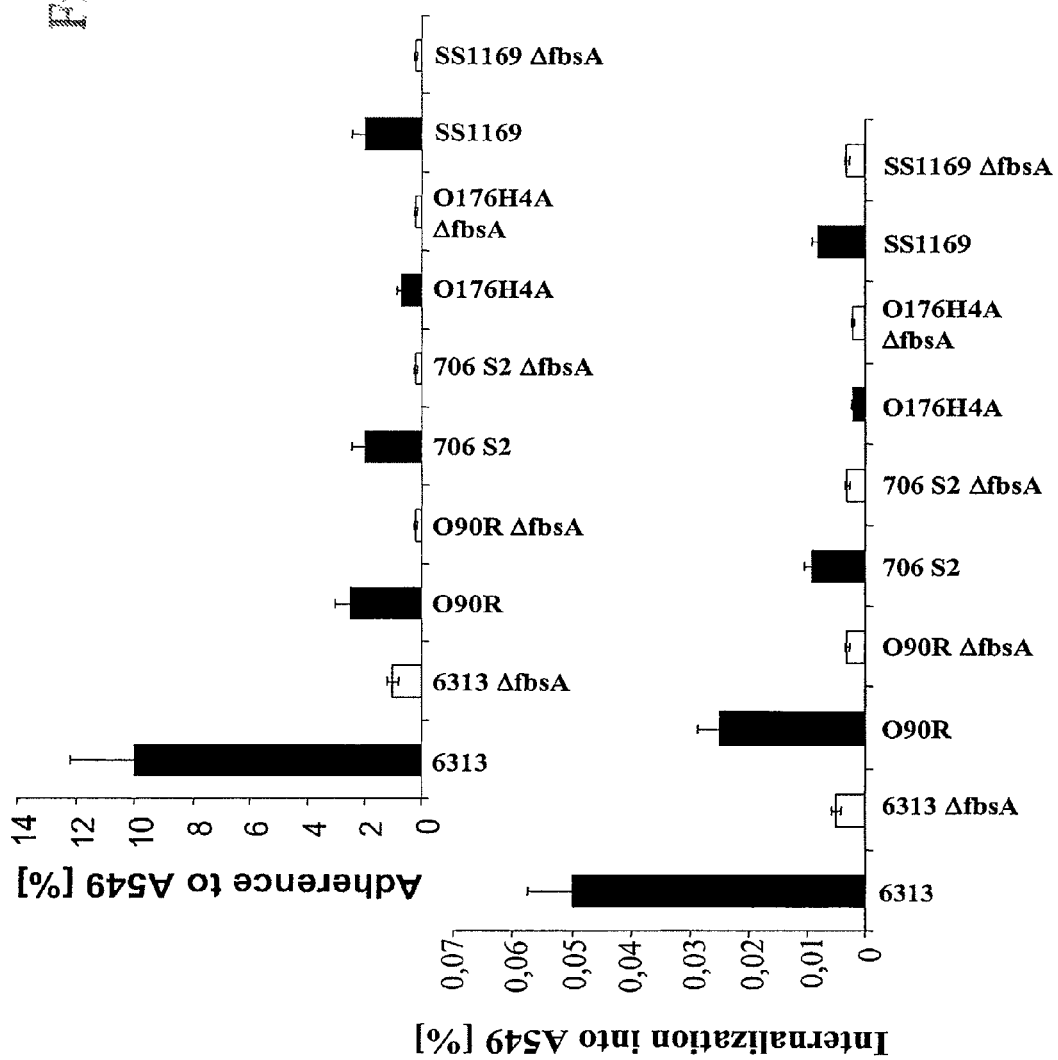
FIG. 24 shows the adherence and internalization of different *S. agalactiae* strains and their isogenic fbsA mutants into the lung epithelial cell line A549. Similar numbers of bacteria were used to infect A549 cells and the number of bacteria adherent to (A) and internalized by A549 cells (B) was related to the number of input bacteria.
Figure 25:
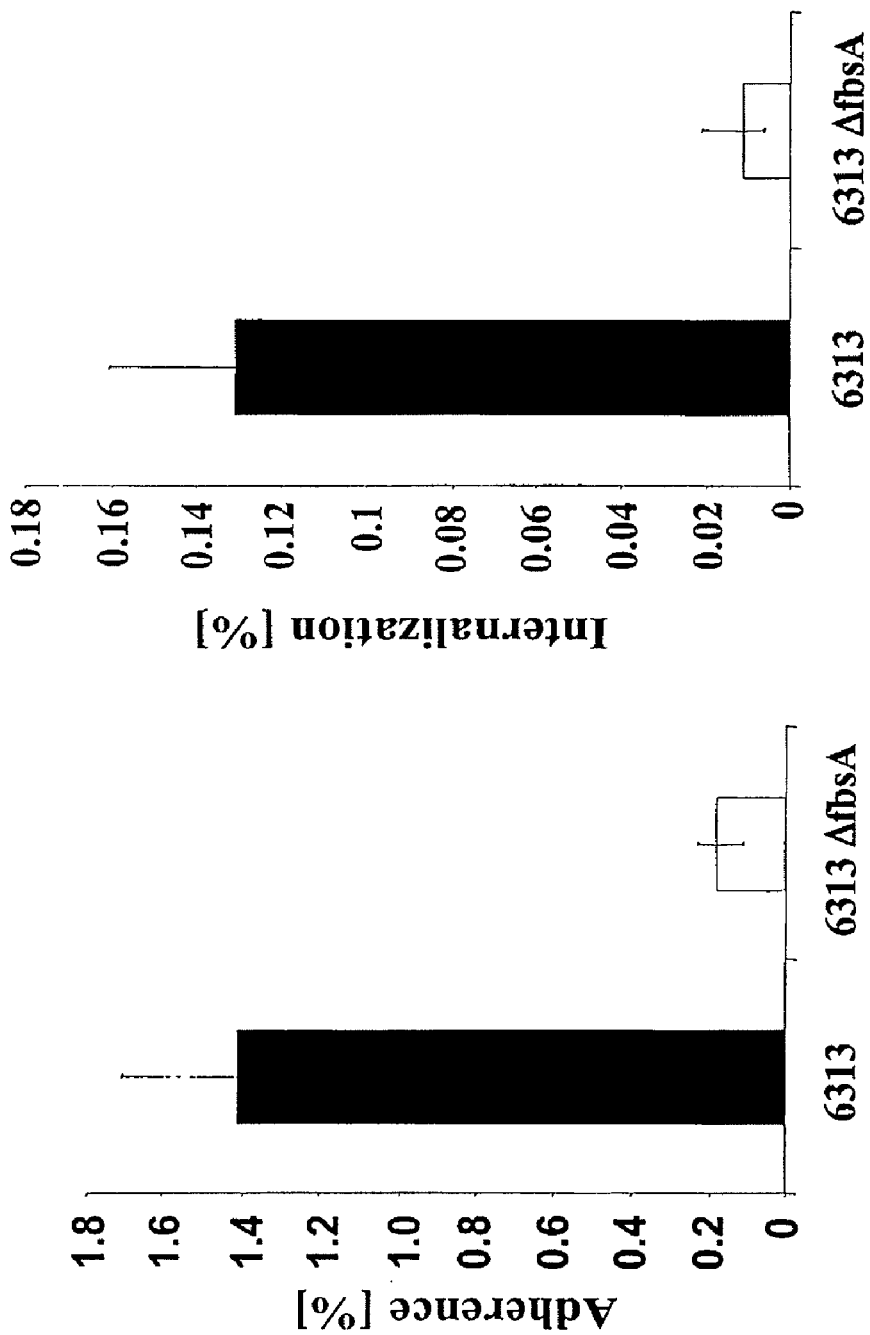
FIG. 25 shows the adherence and internalization of the *S. agalactiae* strains 6313 and 6313ΔfbsA into the fibroblast cell line HEL299. HEL299 cells were infected with *S. agalactiae* at an MOT of 10:1 and the cell adherent and internalized bacteria were related to the number of input bacteria.

The fbsA Gene and Protein is Required for Efficient Attachment of *S. agalactiae* to and Internalization into Human Cells Results The *S. agalactiae* strains 6313, O90R, 706 S2, O176 H4A and SS1169 and their isogenic fbsA mutants were tested for their capability to adhere to and to invade the human lung epithelial cell line A549. As shown in FIG. 24, *S. agalactiae* strain 6313 bound to and invaded A549 cells in high numbers whereas the strains O90R, 706 S2 and SS1169 revealed a moderate adherence to and internalization into A549 cells. In contrast, the *S. agalactiae* strain O176 H4A adhered to and invaded A549 cells in very low numbers. Irrespective from the initial differences of the various strains to adhere to and to invade A549 cells, the deletion of the fbsA gene in the different strains reduced the adherence to and the invasion into A549 cells to very low but similar values among the different strains. Only in strain O176 H4A, that already showed little internalization into A549 cells, did the deletion of the fbsA gene not reduce the internalization of the bacteria into A549 cells. These findings indicate an important role of the fbsA gene for the adhesion of *S. agalactiae* to and the internalization into human epithelial cells. To assess the role of the fbsA gene for the binding of *S. agalactiae* to a different cell line, we analyzed with the human fibroblast cell line HEL299 the adherence and internalization of *S. agalactiae* 6313 and its fbsA deletion mutant. As shown in FIG. 25, the binding of strain 6313 ΔfbsA to HEL299 cells and the internalization of the bacteria into this cell line was reduced by about 90%. These data suggest, that the fbsA gene is of general importance for the adherence and internalization of *S. agalactiae* into different human cells.

Figure 26:
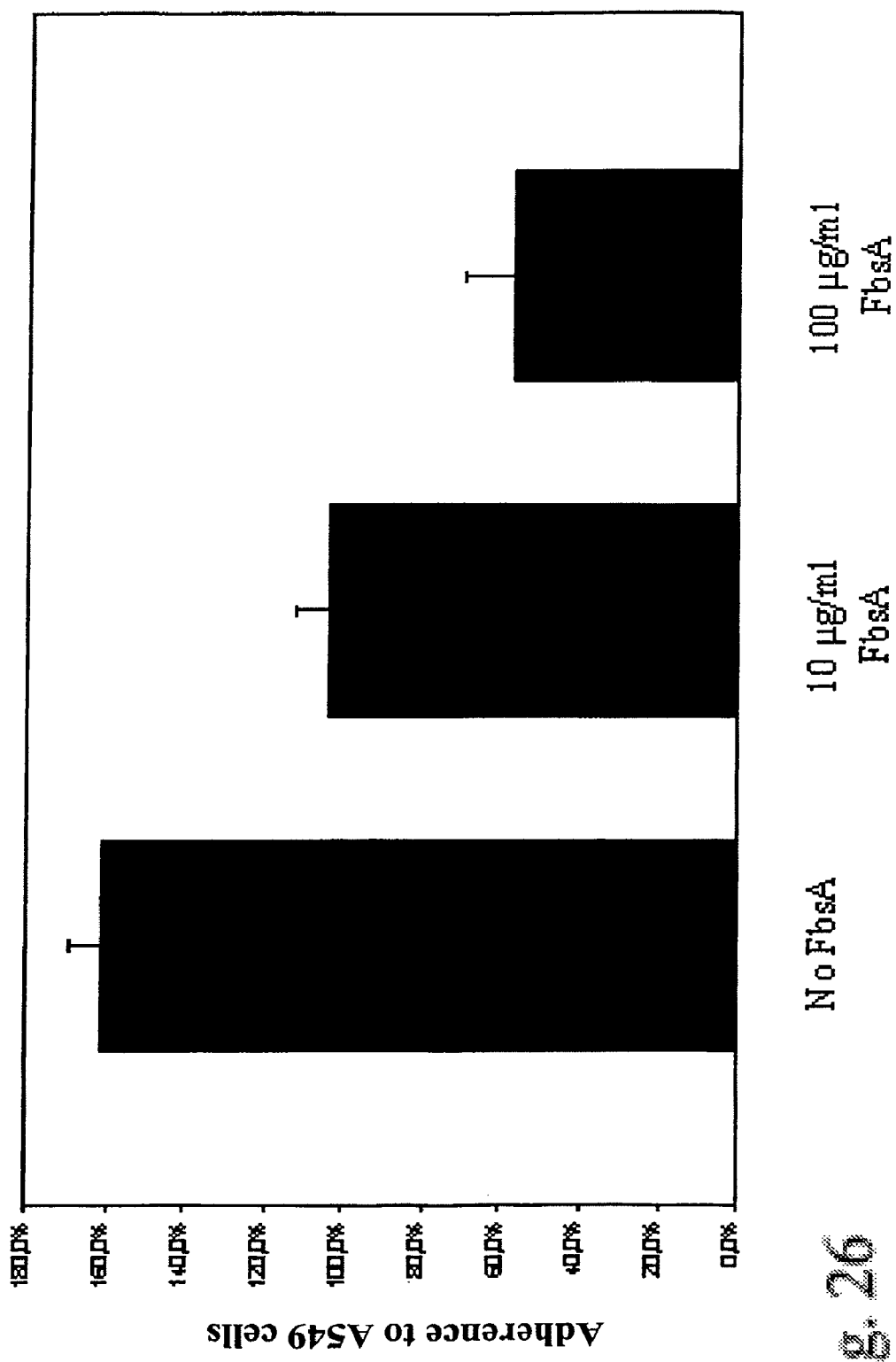
FIG. 26 shows the influence of FbsA protein on the adherence of *S. agalactiae* to A549 cells. The adherence assay was performed in the presence of different amounts of purified FbsA fusion protein and the number of cell adherent bacteria was related to the number of input bacteria.

To assess the role of the FbsA protein in the bacterial adherence and internalization, the effect of pre-treatment of eukaryotic cells with FbsA-19 fusion protein on the adherence and invasion of *S. agalactiae* 6313 was evaluated. The protein FbsA-19 represents the FbsA protein from strain 6313 and carries 19 repetitive units. As shown in FIG. 26, pre-treatment of A549 cells with increasing amounts of FbsA-19 protein substantially inhibited the adherence and invasion of this cell line by *S. agalactiae* 6313. Of note, we also found a correlation between the reduction in bacterial adherence and the invasion in HEL299 cells.

The FbsA protein was previously shown to bind to fibrinogen (Example 3). We therefore tested the effect of a pre-incubation of *S. agalactiae* 6313 with fibrinogen on the bacterial adherence and invasion of A549 cells. We observed a dose-dependent inhibition of the bacterial adherence and invasion of A549 cells by pre-incubating *S. agalactiae* 6313 with 0.1 μg/ml to 1.0 μg/ml of fibrinogen (data not shown). However, the microscopic inspection of the bacteria revealed clumping of the bacteria with increasing amounts of fibrinogen. The observed inhibition of bacterial adherence and invasion by fibrinogen may therefore be attributed to either the blocking of the FbsA protein on the surface of the bacteria or the clumping of the bacteria due to several fibrinogen binding sites in the FbsA protein. We also tested the influence of fibronectin on the adherence and invasion of *S. agalactiae* 6313, however, even 10 μg/ml fibronectin did not exert an inhibitory effect on bacterial adherence and internalization (data not shown).

Example 11

FbsA-Coated Latex Beads Adhere to A549 Cells

Results

Figure 27:
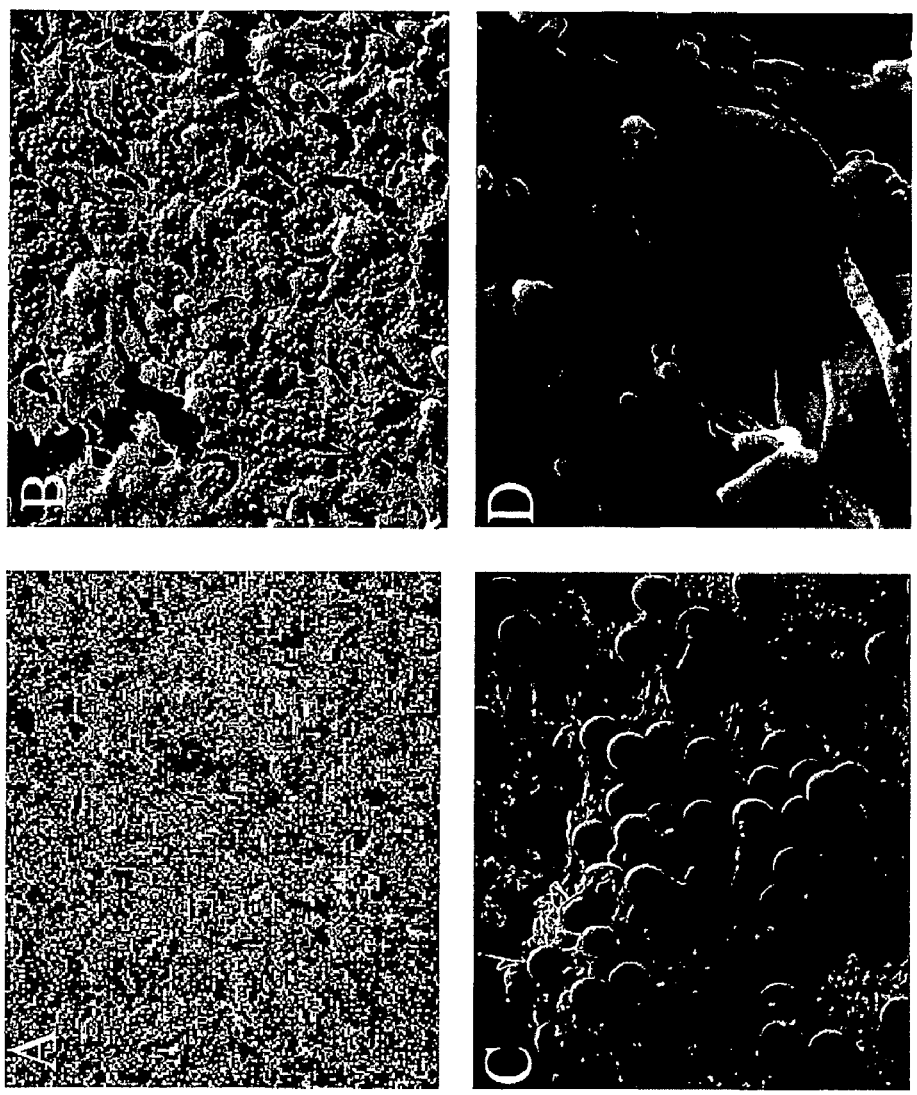
FIG. 27 shows the binding of FbA-coated latex beads to human A549 cells. Latex beads were either coated with BSA (A) or FbsA fusion protein (B-D) and the interaction of the coated beads with the lung epithelial cell line A549 was analyzed by scanning electron microscopy.

The previous experiments already indicated a role of FbsA in the interaction between *S. agalactiae* and the host cell. To investigate if the interaction of FbsA with eukaryotic cells required additional factors, latex beads were coated with FbsA-19 protein and tested for their interaction with human A549 cells. As a control, BSA coated latex beads were also analyzed for their interaction with A549 cells. By scanning electron microscopy only a few BSA coated latex beads were found to bind to A549 cells, while the FbsA-19 coated beads bound to A549 cells in high numbers (FIG. 27). Attachment of the FbsA-19 coated beads to the plasma membrane was characterized by contact with microvilli and structures that resembled early pseudopod formation (FIG. 27C). In some cases, the pseudopod appeared to surround the surface of the bead, indicating that the bead was finally internalized (FIG. 27D). However, the internalization of FbsA-19 coated beads was observed rather rarely, indicating that FbsA-19 does not usually trigger the uptake of *S. agalactiae* or FbsA-19 coated beads into eukaryotic cells.

Example 12

The Genes pabC and pabD are Co-Transcribed and Conserved in Clinical Strains of *S. agalactiae*

Results

The genomic organisation of the region encompassing the pabC gene is shown in FIG. 31. Using RT-PCR and oligonucleotides suitable to amplify overlapping regions of the respective of the four genes, it was shown that the pabC and the gbs0851 (pabD) gene is transcribed as a single transcript, whereas RNA polymerase produces independent transcripts for the metK and gbs0853 genes (FIG. 28). This result indicates that the pabC and the gbs0851 gene products may display a function required for the same or a similar process for *S. agalactiae*.

In order to determine, whether the genes encoding PabC and gbs0851 are conserved in the various serotypes and clinical isolates of GBS, chromosomal DNA of 33 different *S. agalactiae*-strains was isolated and subjected to PCR analysis with specific primers amplifying the entire gene. The two genes pabC and gbs0851 were shown to be present in all tested strains. FIG. 29 shows as an example the PCR results for the most prevalent serotypes of GBS, Ia, Ib, III and V. The gbs0851-gene was amplified from all strains with an identical length, indicative of the conservation of the sequence as well as the size of the gene. The PCR of the pabC gene resulted surprisingly in the amplification of two differently sized products dependent on the strain used for analysis, with size differences also observed in strains of the same serotype. The comparison of the amino acid sequence of the PabC protein from *S. agalactiae* 6313 (serotype III), *S. agalactiae* NEM316 (serotype III) and *S. agalactiae* 2003V_R (serotype V) is shown in FIG. 30. It shows that the PabC proteins from *S. agalactiae* 6313 and *S. agalactiae* NEM316 are identical, but clear differences are obvious in PabC from *S. agalactiae* 2003V_R. The divergence in sequence of PabC can entirely be attributed to the N-terminal part of the protein, whereas the C-terminal part is almost identical in all three serotypes. The observed difference in size is also in agreement with the PCR results in FIG. 29. Further PCR experiments confirmed that the differences in size stem from sequence variations in the 5' part of the gene rather than the 3' terminal part (data not shown).

Example 13

PabC from *S. agalactiae* Binds Human Fibrinogen and is Involved in Invasion of Eukaryotic Cells Initial experiments showed that PabC binds to the a-subunit of fibrinogen (FIG. 31A, C). III order to delineate which region of PabC is responsible for fibrinogen binding, the entire protein as well as the N-terminal and the C-terminal part of PabC were expressed as His-tagged fusion proteins. After addition of fibrinogen, binding was detected with antibodies directed against fibrinogen (FIG. 31B). This experiment showed that the conserved C-terminal part of PabC is in itself devoid of fibrinogen binding activity, while the N-terminal part is sufficient to provide this activity to a similar extent as the full-length protein.

To confirm the Western blot results, a Capture ELISA assay was performed with the same purified PabC protein derivatives (FIG. 32). For this purpose 2 µg Fibrinogen were coated per well over night at 4° C. The binding activities of increasing concentrations of PabC derivatives were quantified via a His-tag antibody based Peroxidase assay. The Capture ELISA experiments confirmed the results that the N-terminal part of the PabC protein is harbouring the fibrinogen-binding region.

It is shown in FIG. 19 that relatively large concentrations of PabC can inhibit the adherence of *S. agalactiae* to and invasion into eukaryotic A549 cells. Using lower concentrations of recombinant PabC protein, it becomes evident, that PabC is most likely facilitating invasion rather than adherence of GBS (FIG. 33C, D). A confirmative result was obtained with the pabC deletion mutant, which also showed reduced invasion into A549 cells (FIG. 33A, B). These results suggest that PabC may serve *S. agalactiae* as an invasin to colonize eukaryotic cells.

The following is a list of all of the publications and documents referred to herein. It is to be understood that the whole disclosure of these references is hereby incorporated herein by reference.

Reference List

Areschoug, T., Stalhammar-Carlemalm, M., Larsson, C., and Lindahl, G. (1999) Group B streptococcal surface proteins as targets for protective antibodies: identification of two novel proteins in strains of serotype V *Infect. Immun.* 67: 6350-6357.

Baker, C. J., Edwards, M. S. (1995) Group B streptococcal infections. In *Infectious disease of the fetus and newborn infant*. Remington, J. S., Klein, J. O. (eds). W.B. Saunders Company, pp. 980-1054.

Baker, C. J., Halsey, N. A., and Schuchat, A. (1999) 1997 AAP guidelines for prevention of early-onset group B streptococcal disease *Pediatrics* 103: 701.

Baker, C. J., Paoletti, L. C., Rench, M. A., Guttormsen, H. K., Carey, V. J., Hickman, M. E., and Kasper, D. L. (2000) Use of capsular polysaccharide-tetanus toxoid conjugate vaccine for type II group B *streptococcus* in healthy women *J. Infect. Dis.* 182: 1129-1138.

Baker, C. J., Paoletti, L. C., Wessels, M. R., Guttormsen, H. K., Rench, M. A., Hickman, M. E., and Kasper, D. L. (1999) Safety and immunogenicity of capsular polysaccharide-tetanus toxoid conjugate vaccines for group B streptococcal types Ia and Ib *J. Infect. Dis.* 179: 142-150.

Brodeur, B. R., Boyer, M., Charlebois, I., Hamel, J., Couture, F., Rioux, C. R., and Martin, D. (2000) Identification of group B streptococcal Sip protein, which elicits cross-protective immunity *Infect. Immun.* 68: 5610-5618.

Caparon, M. G., Stephens, D. S., Olsen, A., and Scott, J. R. (1991) Role of M protein in adherence of group A streptococci *Infect. Immun.* 59: 1811-1817.

Carstensen, H., Henrichsen, J., and Jepsen, O. B. (1985) A national survey of severe group B streptococcal infections in neonates and young infants in Denmark, 1978-83 *Acta Paediatr. Scand.* 74: 934-941.

Cheng, Q., Carlson, B., Pillai, S., Eby, R., Edwards, L., Olmsted, S. B., and Cleary, P. (2001) Antibody against surface-bound C5a peptidase is opsonic and initiates macrophage killing of group B streptococci *Infect. Immun.* 69: 2302-2308.

Cheung, A. L., Krishnan, M., Jaffe, E. A., and Fischetti, V. A. (1991) Fibrinogen acts as a bridging molecule in the adherence of *Staphylococcus aureus* to cultured human endothelial cells.

Chhatwal, G. S., Lammler, C., and Blobel, H. (1984) Guanidine extraction enhances the binding of human fibrinogen to group-B streptococci *Med. Microbiol. Immunol.* 173: 19-27.

Chhatwal, G. S., Muller, H. P., and Blobel, H. (1983) Characterization of binding of human alpha 2-macroglobulin to group G streptococci *Infect. Iammun.* 41: 959-964.

Courtney, H. S., Bronze, M. S., Dale, J. B., and Hasty, D. L. (1994) Analysis of the role of M24 protein in group A streptococcal adhesion and colonization by use of omega-interposon mutagenesis *Infect. Immun.* 62: 4868-4873.

Courtney, H. S., Liu, S., Dale, J. B., and Hasty, D. L. (1997) Conversion of M serotype 24 of *Streptococcus pyogenes* to M serotypes 5 and 18: effect on resistance to phagocytosis and adhesion to host cells *Infect. Immun.* 65: 2472-2474.

Dubendorff, J. W., Studier, F. W. (1991) Controlling basal expression in an inducible T7 expression system by blocking the target T7 promoter with lac repressor. *J. Mol. Biol.* 219: 45-59.

Edwards, M. S., Buffone, G. J., Fuselier, P. A., Weeks, J. L., and Baker, C. J. (1983) Deficient classical complement pathway activity in newborn sera *Pediatr. Res.* 17: 685-688.

Farley, M. M., Harvey, R. C., Stull, T., Smith, J. D., Schuchat, A., Wenger, J. D., and Stephens, D. S. (1993) A population-based assessment of invasive disease due to group B *streptococcus* in nonpregnant adults *N. Engl. J. Med.* 328: 1807-1811.

Faxelius, G., Bremme, K., Kvist-Christensen, K., Christensen, P., and Ringertz, S. (1988) Neonatal septicemia due to group B streptococci-perinatal risk factors and outcome of subsequent pregnancies *J. Perinat. Med.* 16: 423-430.

Fischetti, V. A. (1989) Streptococcal M protein: molecular design and biological behavior *Clin. Microbiol. Rev.* 2: 285-314.

Frank, R., Overwin, H. (1996) SPOT synthesis. Epitope analysis with arrays of synthetic peptides prepared on cellulose membranes *Methods Mol. Biol.* 66: 149-169.

Fuss, C., Palmaz, J. C., and Sprague, E. A. (2001) Fibrinogen: structure, function, and surface interactions *J. Vasc. Interv. Radiol.* 12: 677-682.

Gibson, R. L., Lee, M. K., Soderland, C., Chi, E. Y., and Rubens, C. E. (1993) Group B streptococci invade endothelial cells: type III capsular polysaccharide attenuates invasion *Infect. Immun.* 61: 478-485.

Hanahan, D. (1985) Studies on transformation of *Escherichia coli* with plasmids *J. Mol. Biol.* 166: 557-580.

Hunter, W. H., Greenwood, F. C. (1962) Preparation of iodine-131 labelled human growth hormone of high specific activity *Nature* 194: 495-496.

Korzeniowska-Kowal, A., Witkowska, D., and Gamian, A. (2001) Molecular mimicry of bacterial polysaccharides and their role in etiology of infectious and autoimmune. diseases *Postepy Hig. Med. Dosw.* 55: 211-232.

La Penta, D., Framson, P., Nizet, V., and Rubens, C. (1997) Epithelial cell invasion by group B streptococci is important to virulence *Adv. Exp. Med. Biol.* 418: 631-634.

Lammler, C., Chhatwal, G. S., and Blobel, H. (1983) Binding of human fibrinogen and its polypeptide chains to group B streptococci *Med. Microbiol. Immunol.* 172: 149-153.

Larsson, C., Stalhammar-Carlemalm, M., and Lindahl, G. (1997) Vaccination with highly purified cell surface proteins confers protection against experimental group B streptococcal infection *Adv. Exp. Med. Biol.* 418: 851-853.

Larsson, C., Stalhammar-Carlemalm, M., and Lindahl, G. (1999) Protection against experimental infection with group B *streptococcus* by immunization with a bivalent protein vaccine *Vaccine* 17: 454-458.

Madoff, L. C., Michel, J. L., Gong, E. W., Rodewald, A. K., and Kasper, D. L. (1992) Protection of neonatal mice from group B streptococcal infection by maternal immunization with beta C protein *Infect. Immun.* 60: 4989-4994.

Maguin, E., Prevost, H., Ehrlich, S., and Gruss, A. (1996) Efficient insertional mutagenesis in lactococci and other gram-positive bacteria *J. Bacteriol.* 178: 931-935.

Manoil, C., Beckwith, J. (1985) TnphoA: a transposon probe for protein export signals *Proc. Natl. Acad. Sci. U.S.A* 82: 8129-8133.

Meehan, M., Nowlan, P., and Owen, P. (1998) Affinity purification and characterization of a fibrinogen-binding protein complex which protects mice against lethal challenge with *Streptococcus equi* subsp. equi *Microbiology* 144: 993-1003.

Mills, E. L., Bjorksten, B., and Quie, P. G. (1979) Deficient alternative complement pathway activity in newborn sera *Pediatr. Res.* 13: 1341-1344.

Mosesson, M. W., Siebenlist, K. R., and Meh, D. A. (2001) The structure and biological features of fibrinogen and fibrin *Ann. N.Y. Acad. Sci.* 936: 11-30.

Ni, E. D., Perkins, S., Francois, P., Vaudaux, P., Hook, M., and Foster, T. J. (1998) Clumping factor B (ClfB), a new surface-located fibrinogen-binding adhesin of *Staphylococcus aureus Mol. Microbiol.* 30: 245-257.

Noel, G. J., Katz, S. L., and Edelson, P. J. (1991) The role of C3 in mediating binding and ingestion of group B *streptococcus* serotype III by murine macrophages *Pediatr. Res.* 30: 118-123.

Paoletti, L. C., Kasper, D. L. (2002) Conjugate vaccines against group B *streptococcus* types IV and VII *J. Infect. Dis.* 186: 123-126.

Paoletti, L. C., Pinel, J., Johnson, K. D., Reinap, B., Ross, R. A., and Kasper, D. L. (1999) Synthesis and preclinical evaluation of glycoconjugate vaccines against group B *streptococcus* types VI and VIII *J. Infect. Dis.* 180: 892-895.

Pearce, B. J., Yin, Y. B., and Masure, H. R. (1993) Genetic identification of exported proteins in *Streptococcus pneumoniae Mol. Microbiol.* 9: 1037-1050.

Pei, L., Flock, J. I. (2001) Functional study of antibodies against a fibrogenin-binding protein in *Staphylococcus epidermidis* adherence to polyethylene catheters.

Podbielski, A., Woischnik, M., Leonard, B. A., and Schmidt, K. H. (1999) Characterization of nra, a global negative regulator gene in group A streptococci *Mol. Microbiol.* 31: 1051-1064.

Pospiech, A., and Neumann, B. (1995) A versatile quick-prep of genomic DNA from Gram-positive bacteria. *Trends Genet* 11: 217-218.

Reinscheid, D. J., Gottschalk, B., Schubert, A., Eikmanns, B. J., and Chhatwal, G. S. (2001) Identification and molecular analysis of PcsB, a protein required for cell wall separation of group B *streptococcus J. Bacteriol.* 183: 1175-1183.

Reinscheid, D. J., Stoesser, C., Moeller, K., Ehlert, K., Jack, R. W., Eikmanns, B. E., and Chhatwal, G. S. (2002) The influence of proteins Bsp and FemH on cell shape and peptidoglycan composition in group B *streptococcus Microbiol.* 148:3245-3254.

Ringdahl, U., Svensson, H. G., Kotarsky, H., Gustafsson, M., Weineisen, M., and Sjobring, U. (2000) A role for the fibrinogen-binding regions of streptococcal M proteins in phagocytosis resistance *Mol. Microbiol.* 37: 1318-1326.

Rubens, C. E., Smith, S., Hulse, M., Chi, E. Y., and van Belle, G. (1992) Respiratory epithelial cell invasion by group B streptococci *Infect. Immun.* 60: 5157-5163.

Rubens, C. E., Wessels, M. R., Heggen, L. M., and Kasper, D. L. (1987) Transposon mutagenesis of type III group B *streptococcus*: correlation of capsule expression with virulence *Proc. Natl. Acad. Sci. U.S.A* 84: 7208-7212.

Sambrook, J., Fritsch, E. F., and Maniatis, J. (1989) *Molecular Cloning: a laboratory Manual* NY: Cold Spring Harbor.

Schneewind, O., Mihaylova-Petkov, D., and Model, P. (1993) Cell wall sorting signals in surface proteins of gam-positive bacteria *EMBO J.* 12: 4803-4811.

Schonbeck, C., Bjorck, L., and Kronvall, G. (1981) Receptors for fibrinogen and aggregated beta 2-microglobulin detected in strains of group B streptococci *Infect. Immun.* 31: 856-861.

Schubert, A., Zakikhany, K., Schreiner, M., Frank, R., Spellerberg, B., Eikmanns, B. J., and Reinscheid, D. J. (2002) A fibrinogen receptor from group B *Streptococcus* interacts with fibrinogen by repetitive units with novel ligand binding sites. *Mol. Microbiol.* 46:557-569.

Schuchat, A. (1998) Epidemiology of group B streptococcal disease in the United States: shifting paradigms *Clin. Microbiol. Rev.* 11: 497-513.

Spellerberg, B. (2000) Pathogenesis of neonatal *Streptococcus agalactiae* infections *Microbes. Infect.* 2: 1733-1742.

Spellerberg, B., Rozdzinski, E., Martin, S., Weber-Heynemann, J., and Lutticken, R. (2002) rgf encodes a novel two-component signal transduction system of *Streptococcus agalactiae Infect. Immun.* 70: 2434-2440.

Thern, A., Wastfelt, M., and Lindahl, G. (1998) Expression of two different antiphagocytic M proteins by *Streptococcus pyogenes* of the OF+ lineage *J. Immunol.* 160: 860-869.

Valentin-Weigand, P., Chhatwal, G. S. (1995) Correlation of epithelial cell invasiveness of group B streptococci with clinical source of isolation *Microb. Pathog.* 19: 83-91.

Vasi, J., Frykberg, L., Carlsson, L. E., Lindberg, M., and Guss, B. (2000) M-like proteins of *Streptococcus dysgalactiae Infect. Immun.* 68: 294-302.

Wessels, M. R. (1997) Biology of streptococcal capsular polysaccharides *Soc. Appl. Bacteriol. Symp. Ser.* 26: 20S-31S.

Whitnack, E., Beachey, E. H. (1985) Degradation products of fibrinogen and fibrin prevent opsonization of group A streptococci *Trans. Assoc. Am. Physicians* 98: 392-398.

Whitnack, E., Dale, J. B., and Beachey, E. H. (1984) Common protective antigens of group A streptococcal M proteins masked by fibrinogen *J. Exp. Med.* 159: 1201-1212.

Wibawan, I. W., Lammler, C. (1992) Relationship between group B streptococcal serotypes and cell surface hydrophobicity.

Winram, S. B., Jonas, M., Chi, E., and Rubens, C. E. (1998) Characterization of group B streptococcal invasion of human chorion and amnion epithelial cells In vitro *Infect. Immun.* 66: 4932-4941.

Zangwill, K. M., Schuchat, A., and Wenger, J. D. (1992) Group B streptococcal disease in the United States, 1990: report from a multistate active surveillance system *Mor Mortal. Wkly. Rep. CDC Surveill Summ.* 41: 25-32.

The features of the present invention disclosed in the specification, the claims and/or the drawings may both separately and in any combination thereof be material for realizing the invention in various forms thereof.

The invention claimed is:

1. An isolated antibody or an effective part thereof, which specifically binds to a *Streptococcus agalactiae* polypeptide comprising SEQ ID NO: 17.

2. The antibody of claim 1, wherein the antibody is a polyclonal antibody.

3. The antibody of claim 1, wherein the antibody is a monoclonal antibody.

4. The antibody of claim 1, wherein the antibody is a humanized antibody.

5. The antibody of claim 1, wherein the antibody is a chimeric antibody.

6. The antibody of claim 1, wherein the effective part of the antibody comprises an Fab fragment.

7. The antibody of claim 1, wherein the antibody is produced by a hybridoma cell line.

8. A pharmaceutical composition comprising the antibody of claim 1.

9. A method for treating or preventing *Streptococcus agalactiae* infection in a subject, the method comprising administering to the subject the antibody or the effective part thereof of claim 1.

* * * * *

SEQUENCE LISTING

<160> NUMBER OF SEQ ID NOS: 285

<210> SEQ ID NO 1
<211> LENGTH: 1329
<212> TYPE: DNA
<213> ORGANISM: Streptococcus agalactiae

<400> SEQUENCE: 1

```
ttgttcaata aaataggttt tagaacttgg aaatcaggaa agctttggct ttatatggga      60
gtgctaggat caactattat tttaggatca agtcctgtat ctgctatgga tagtgttgga     120
aatcaaagtc agggcaatgt tttagagcgt cgtcaacgtg atgcagaaaa cagaagccaa     180
ggcaatgttc tagagcgtcg tcaacgcgat gttgagaata gagccaagg caatgtttta      240
gagcgtcgtc aacgtgatgc ggaaaacaag agccaaggca atgttttaga gcgtcgtcaa     300
cgtgatgcag aaaacagaag ccaaggcaat gttctagagc gtcgtcaacg tgatgcagaa     360
aacagaagcc aaggcaatgt tctagagcgt cgtcaacgcg atgcagaaaa cagaagccaa     420
ggtaatgttc tagagcgtcg tcaacgtgat gcagaaaaca gaagccaagg taatgttcta     480
gagcgtcgtc aacgtgatgc agaaaacaga agccaaggta atgttctaga gcgtcgtcaa     540
cgcgatgttg agaataagag ccaaggcaat gttttagagc gtcgtcaacg tgatgcggaa     600
aacaagagcc aaggcaatgt tttagagcgt cgtcaacgtg atgcagaaaa cagaagccaa     660
ggcaatgttt tagagcgtcg tcaacgtgat gcagaaaaca gaagccaagg caatgttcta     720
gagcgtcgtc aacgtgatgc agaaaacaga agccaaggca atgttctaga gcgtcgtcaa     780
cgtgatgcag aaaacagaag ccaaggcaat gttctagagc gtcgtcaacg cgatgcagaa     840
aacagaagcc aaggtaatgt tctagagcgt cgtcaacgtg atgcagaaaa cagaagccaa     900
ggcaatgttt tagagcgtcg tcaacgtgat gcagaaaaca gaagccaagg caatgtttta     960
gagcgtcgtc aacgtgatgc agaaaacaga agccaaggca atgttttaga gcgtcgtcaa    1020
cgtgatgcgg aaaacaagag ccaagtaggt caacttatag ggaaaaatcc acttctttca    1080
aagtcaatta tatctagaga aaataatcac tcgagtcaag gtgactctaa caaacagtca    1140
ttctctaaaa aagtatctca ggttactaat gtagctaata gaccgatgtt aactaataat    1200
tctagaacaa tttcagtgat aaataaatta cctaaaacag gtgatgatca aaatgtcatt    1260
tttaaacttg taggttttgg tttaattttg ttaacaagtc gctgcggttt gagacgcaat    1320
gaaaattaa                                                            1329
```

<210> SEQ ID NO 2
<211> LENGTH: 1233
<212> TYPE: DNA
<213> ORGANISM: Streptococcus agalactiae

<400> SEQUENCE: 2

```
ttgttcaata aaataggttt tagaacttgg aaatcaggaa agctttggct ttatatggga      60
gtgctaggat caactattat tttaggatca agttctgtat ctgctatgga tagtgttgga     120
aatcaaagtc agggcaatgt tttagagcgt cgtcaacgcg atgcagaaaa cagaagccaa     180
ggcaatgttt tagagcgtcg tcaacgtgat gcagaaaaca gaagccaagg caatgtttta     240
gagcgtcgtc aacgtgatgc agaaaacaga agccaaggta atgttctaga gcgtcgtcaa     300
cgcgatgttg aaaataaaag ccaaggcaat gttttagagc gtcgtcaacg tgatgcagaa     360
aacagaagcc aaggtaatgt tctagagcgt cgtcaacgcg atgttgaaaa taaaagccaa     420
```

| | |
|---|---|
| ggcaatgttt tagagcgtcg tcaacgtgat gcagaaaaca gaagccaagg taatgttcta | 480 |
| gagcgtcgtc aacgtgatgc agaaaacaga agccaaggca atgttttaga gcgtcgtcaa | 540 |
| cgcgatgcag aaaacagaag ccaaggcaat gttctagagc gtcgtcaacg tgatgctgaa | 600 |
| aacaaaagcc aaggcaatgt tttagagcgt cgtcaacgtg atgcagaaaa cagaagccaa | 660 |
| ggcaatgttt tagagcgtcg tcaacgtgat gctgaaaaca gaagccaagg caatgtttta | 720 |
| gagcgtcgtc aacgcgatgc agaaaacaga agccaaggta tgttctaga gcgtcgtcaa | 780 |
| cgtgatgcgg aaaacaagag ccaaggcaat gttttagagc gtcgtcaacg tgatgcagaa | 840 |
| aacagaagcc aaggcaatgt tttagagcgt cgtcaacgcg atgttgagaa taagagccaa | 900 |
| ggcaatgttt tagagcgtcg tcaacgtgat gcggaaaaca agagccaagt aggtcaactt | 960 |
| atagggaaaa atccacttct ttcaaagtca attatatcta gagaaaataa tcactctagt | 1020 |
| caaggtgact ctaacaaaca gtcattctct aaaaaagtat ctcaggttac taatgtagct | 1080 |
| aatagaccga tgttaactaa taattctaga acaatttcag tgataaataa attacctaaa | 1140 |
| acaggtgatg atcaaaatgt catttttaaa cttgtaggtt ttggtttaat tttgttaaca | 1200 |
| agtcgctgcg gtttgagacg caatgaaaat taa | 1233 |

<210> SEQ ID NO 3
<211> LENGTH: 1041
<212> TYPE: DNA
<213> ORGANISM: Streptococcus agalactiae

<400> SEQUENCE: 3

| | |
|---|---|
| ttgttcaata aaataggttt tagaacttgg aaatcaggaa agctttggct ttatatggga | 60 |
| gtgctaggat caactattat tttaggatca agtcctgtat ctgctatgga tagtgttgga | 120 |
| aatcaaagtc aaggtaatgt tctagagcgt cgtcaacgtg atgcggataa caagagccaa | 180 |
| ggcaatgttc tagaacgtcg tcaacgcgat gtagaaaaca gaagccaagg caatgttcta | 240 |
| gagcgtcgtc aacgcgatgc ggataacaag agccaaggca atgttttaga gcgccgccaa | 300 |
| cgcgatgcag aaaacaaaag tcagggcaat gttctagaac gtcgtcaacg tgatgttgag | 360 |
| aataagagcc aaggcaatgt tctagagcgt cgccaacgtg atgcagaaaa caaaagtcag | 420 |
| ggtaatgttc tagagcgtcg tcaacgcgat gcagataaca agagccaagg taatgttcta | 480 |
| gaacgtcgtc aacgcgatgt ggaaaacaaa agtcagggca atgttctaga acgtcgtcaa | 540 |
| cgtgatgttg agaataagag ccaaggcaat gttctagagc gtcgccaacg tgatgcagaa | 600 |
| aacaaaagtc agggtaatgt tctagagcgt cgtcaacgcg atgcagataa caagagccaa | 660 |
| ggtaatgttc tagaacgtcg tcaacgcgat gtggaaaaca aagtcagggg caatgttcta | 720 |
| gagcgtcgcc aacgtgatgt tgagaacaag agccaagtag gtcaacttat agggaaaaat | 780 |
| ccacttcttt caaagtcaac tatatctaga gaaaataatc actctagtca aggtgactct | 840 |
| aacaaacagt cattctctaa aaagtatct caggttacta atgtagctaa tagaccaatg | 900 |
| ttaactaata attctagaac aatttcagtg ataaataaat acctaaaac aggtgatgat | 960 |
| caaaatgtca tttttaaact tgtaggtttt ggtttaattt tgttaacaag tcgctgcggt | 1020 |
| ttgagacgca atgaaaatta a | 1041 |

<210> SEQ ID NO 4
<211> LENGTH: 561
<212> TYPE: DNA
<213> ORGANISM: Streptococcus agalactiae

<400> SEQUENCE: 4

```
ttgttcaata aaataggttt tagaacttgg aaatcaggaa agctttggct ttatatggga       60
gtgctaggat caactattat tttaggatca agtcctgtat ctgctatgga tagtgttgga      120
aatcaaagtc agggcaatgt tttagagcgt cgtcaacgcg atgcagaaaa cagaagccaa      180
ggtaatgttc tagagcgtcg tcaacgcgat gcagaaaaca gaagccaagg taatgttcta      240
gagcgtcgtc aacgtgatgc ggaaaacaag agccaagtag gtcaacttat agggaaaaat      300
ccacttcttt caaagtcaat tatatctaga gaaaataatc actctagtca aggtgactct      360
aacaaacagt cattctctaa aaagtatct caggttacta atgtagctaa tagaccgatg       420
ttaactaata attctagaac aatttcagtg ataaataaat tacctaaaac aggtgatgat      480
caaaatgtca ttttttaaact tgtaggtttt ggtttaatttt tgttaacaag tcgctgcggt    540
ttgagacgca atgaaaatta a                                                561
```

<210> SEQ ID NO 5
<211> LENGTH: 897
<212> TYPE: DNA
<213> ORGANISM: Streptococcus agalactiae

<400> SEQUENCE: 5

```
ttgttcaata aaataggttt tagaacttgg aaatcaggaa agctttggct ttatatggga       60
gtgctaggat caactattat tttaggatca agtcctgtat ctgctatgga tagtgttgga      120
aatcaaagcc aaggcaatgt tctagagcgt cgtcaacgcg atgcagaaaa cagaagccaa      180
ggtaatgttt tagaacgtcg tcaacgcgat gttgagaaca agagccaagg taatgtttta      240
gagcgtcgcc aacgtgatgc ggaaaacaaa gtcagggca atgttttaga gcgtcgtcaa       300
cgtgatgcag aaaacagaag ccaaggtaat gttctagagc gtcgtcaacg cgatgttgag      360
aataagagcc aaggcaatgt tctagagcgt cgtcaacgcg atgttgagaa taagagccaa      420
ggtaatgttc tagagcgtcg tcaacgcgat gttgagaata agagccaagg taatgttcta      480
gagcgtcgtc aacgtgatgc ggaaaacaag agccaaggca atgttctaga gcgtcgtcaa      540
cgcgatgcag aaaacagaag ccaaggtaat gttttagagc gtcgccaaca tgatgttgag      600
aataagagtc aagtaggtca acttataggg aaaaatccac tttttcaaa gtcaactgta      660
tctagagaaa ataatcactc tagtcaaggt gactctaaca acagtcatt ctctaaaaaa      720
gtatctcagg ttactaatgt agctaataga ccgatgttaa ctaataattc tagaacaatt      780
tcagtgataa ataaattacc taaaacaggt gatgatcaaa atgtcatttt taaacttgta      840
ggttttggtt taattttatt aacaagtctc tgcggtttga gacgcaatga aaattaa        897
```

<210> SEQ ID NO 6
<211> LENGTH: 1857
<212> TYPE: DNA
<213> ORGANISM: Streptococcus agalactiae

<400> SEQUENCE: 6

```
ttgttcaata aaataggttt tagaacttgg aaatcaggaa agctttggct ttatatggga       60
gtgctaggat caactattat tttaggatca agtcctgtat ctgctatgga tagtgttgga      120
aatcaaagtc aaggtaatgt tctagagcgt cgccaacgtg atgcggataa caagagccaa      180
ggtaatgttt tagagcgtcg ccaacgtgat gcagataaca aaagtcaggg caatgttcta      240
gaacgtcgcc aacgtgatgt tgataacaag agccaaggta acgttctaga gcgtcgccaa      300
cgcgatgctg ataacaagag ccaaggtaat gttttagagc gccgccaacg cgatgcagat      360
aacaaaagtc aaggtaatgt tctagagcgt cgccaacgcg atgttgataa caagagccag      420
```

```
ggtaatgttt tagagcgtcg ccaacgcgat gcagataaca aaagtcaggg taatgtttta      480
gagcgtcgcc aacgcgatgt tgataacaaa agccaaggta atgttttaga gcgtcgccaa      540
cgtgatgctg ataacaaaag tcagggcaat gttctagagc gtcgccaacg tgatgcggat      600
aacaaaagcc aaggtaatgt tctagagcgt cgccaacgcg atgcggataa caaaagtcag      660
ggcaatgttt tagagcgtcg ccaacgtgat gctgataaca aaagtcaagg taatgttcta      720
gagcgtcgcc aacgcgatgc agataacaaa agccaaggta atgttctaga gcgtcgccaa      780
cgcgatgctg ataacaaaag tcaaggtaat gttctagagc gtcgccaacg tgatgctgat      840
aacaagagcc aaggcaatgt tcttgagcgt cgtcaacgcg atgtcgataa caaaagtcag      900
ggtaatgttt tagagcgtcg ccaacgtgat gcggataaca agagtcaagg taatgtttta      960
gagcgtcgcc aacgcgatgc ggataacaag agccaaggta atgttttaga gcgtcgccaa     1020
cgcgatgcgg ataacaagag tcaaggtaat gttttagagc gtcgccaacg cgatgcggat     1080
aacaagagcc aaggtaatgt tttagagcgt cgccaacgcg atgcagataa caaaagtcaa     1140
ggtaatgttt tagagcgtcg ccaacgcgat gctgataaca agagccaagg taatgtttta     1200
gagcgtcgtc aacgtgatgc agataacaaa agtcagggca atgttttaga gcgtcgtcaa     1260
cgtgatgcgg ataacaagag ccaaggtaat gttttagagc gtcgccaacg tgatgcggat     1320
aacaagagcc agggcaatgt tctagaacgt cgtcaacgtg atgcggataa caagagccaa     1380
ggtaacgttt tagagcgtcg ccaacgtgat gcggataaca agagccaggg caatgtttta     1440
gagcgccgcc aacgcgatgc agataacaaa agtcaaggta atgttctaga gcgtcgccaa     1500
cgcgatgcag ataacaagag ccagggtaat gttctagagc gtcgccaacg cgatgcggaa     1560 aacaaagtc aagtaggtca acttataggg aaaaatccac tttttcaaa gtcaactgta       1620 tctagagaaa ataatcactc tagtcaaggt gactctaaca aacagtcatt ctctaaaaaa     1680
atatctcagg ttactaatgt agctaatgga ccgatgttaa ctaataattc tagaacaatt     1740
tcagtgataa ataaattacc taaaacaggt gatgatcaaa atgtcatttt taaacttgta     1800
ggttttggtt aattttgtt aacaagtctc tgcggtttga gacgcaatga aaattaa         1857
```

<210> SEQ ID NO 7
<211> LENGTH: 2706
<212> TYPE: DNA
<213> ORGANISM: Streptococcus agalactiae

<400> SEQUENCE: 7

```
atgagaaaat accaaaaatt ttctaaaata ttgacgttaa gtcttttttg tttgtcgcaa       60
ataccgctta ataccaatgt tttaggggaa agtaccgtac cggaaaatgg tgctaaagga      120
aagttagttg ttaaaaagac agatgaccag aacaaaccac tttcaaaagc taccttttgtt     180 ttaaaaacta ctgctcatcc agaaagtaaa atagaaaaag taactgctga gctaacaggt      240
gaagctactt tgataatct catacctgga gattatactt atcagaagaa acagcgccc        300 gaaggttata aaaagactaa ccagacttgg caagttaagg ttgagagtaa tggaaaaact      360
acgatacaaa atagtggtga taaaaattcc acaattggac aaaatcacga agaactagat      420
aagcagtatc cccccacagg aatttatgaa gatacaaagg aatcttataa acttgagcat      480
gttaaaggtt cagttccaaa tggaaagtca gaggcaaaag cagttaaccc atattcaagt      540
gaaggtgagc atataagaga attccagag ggaacattat ctaaacgtat ttcagaagta      600
ggtgatttag ctcataataa atataaaatt gagttaactg tcagtggaaa aaccatagta      660
aaaccagtgg acaaacaaaa gccgttagat gttgtcttcg tactcgataa ttctaactca     720
```

| | |
|---|---|
| atgaataacg atggcccaaa ttttcaaagg cataataaag ccagaaaagc tgccgaagct | 780 |
| cttgggaccg cagtaaaaga tatttagga gcaaacagtg ataatagggt tgcattagtt | 840 |
| acctatggtt cagatatttt tgatggtagg agtgtagatg tcgtaaaagg atttaaagaa | 900 |
| gatgataaat attatggcct tcaaactaag ttcacaattc agacagagaa ttatagtcat | 960 |
| aaacaattaa caataatgc tgaagagatt ataaaaagga ttcctacaga agctcctaga | 1020 |
| gctaaatggg gatcaactac aaacggactt actccagagc aacaaaagca gtactatctt | 1080 |
| agtaaagtag gggaaacatt tactatgaaa gccttcatgg aggcagatga tattttgagt | 1140 |
| caagtagatc gaaatagtca aaaaattatt gttcatataa ctgatggtgt tccaacaaga | 1200 |
| tcatatgcta ttaataattt taaattgggt gcatcatatg aaagccaatt tgaacaaatg | 1260 |
| aaaaaaaatg gatatctaaa taaaagtaat tttctactta ctgataagcc cgaggatata | 1320 |
| aaaggaaatg gggagagtta cttttttgttt cccttagata gttatcaaac acagataatc | 1380 |
| tctggaaact acaaaaaact tcattattta gatttaaatc ttaattaccc taaaggtaca | 1440 |
| atttatcgaa atggaccagt aagagaacat ggaacaccaa ccaaacttta tataaatagt | 1500 |
| ttaaaacaga aaaattatga catctttaat tttggtatag atatatctgc ttttagacaa | 1560 |
| gtttataatg aggattataa gaaaaatcaa gatggtactt tcaaaaatt gaaagaggaa | 1620 |
| gcttttgaac tttcagatgg ggaaataaca gaactaatga agtcattctc ttctaaacct | 1680 |
| gagtattata ccccgatagt aacttcatcc gatgcatcta acaatgaaat tttatctaaa | 1740 |
| attcagcaac aatttgaaaa ggttttaaca aaagaaaact caattgttaa tggaactata | 1800 |
| gaagatccta tgggtgacaa atcaattta cagcttggca acggacaaac attgcaacca | 1860 |
| agtgattata ctttacaggg aaatgatgga agtataatga agatagcat tgcaactggt | 1920 |
| gggcctaata atgatggtgg aatacttaaa ggggttaaat tagaatacat caaaaataaa | 1980 |
| ctctacgtta gaggtttgaa cttaggggag ggacaaaaag taacactcac atatgatgtg | 2040 |
| aaactagatg acagttttat aagtaacaaa ttctatgaca ctaatggtag aacaacattg | 2100 |
| aatcctaaat cagaggatcc taatacactt agagattttc caatccctaa aattcgtgat | 2160 |
| gtgagagaat atcctacaat aacgattaaa acgagaagaa agttaggtga aattgaattt | 2220 |
| acaaaagttg ataaagataa taataagttg cttctcaaag gagctacgtt tgaacttcaa | 2280 |
| gaatttaatg aagattataa actttatttta ccaataaaaa ataataattc aaaagtagtg | 2340 |
| acgggagaaa acggcaaaat ttcttacaaa gatttgaaag atggcaaata tcagttaata | 2400 |
| gaagcagttt cgccgaagga ttatcaaaaa attactaata aaccaatttt aacttttgaa | 2460 |
| gttgttaaag gatcgataca aaatataata gctgttaata aacagatttc tgaatatcat | 2520 |
| gaggaaggtg acaagcattt aattaccaac acgcatattc caccaaaagg aattattccg | 2580 |
| atgacaggtg ggaaaggaat tctatctttc attttaatag gtggatctat gatgtctatt | 2640 |
| gcaggtggaa tttatattg gaaaagatat aagaaatcta gtgatatatc tagagaaaaa | 2700 |
| gattaa | 2706 |

<210> SEQ ID NO 8
<211> LENGTH: 2025
<212> TYPE: DNA
<213> ORGANISM: Streptococcus agalactiae

<400> SEQUENCE: 8

| | |
|---|---|
| atgaaaaaaa tcaacaaatg tcttacagtg ttctcgacac tgctattgat cttaacgtca | 60 |
| ctattctcag ttgcaccagc gtttgcggac gacgtaacaa ctgatactgt gaccttgcac | 120 |

```
aagattgtca tgccacaagc tgcatttgat aactttactg aaggtacaaa aggtaagaat      180
gatagcgatt atgttggtaa acaaattaat gaccttaaat cttatttggg ctcaaccgat      240
gctaaagaaa ttaagggtgc tttctttgtt ttcaaaaatg aaactggtac aaaattcatt      300
actgaaaatg gtaaggaagt cgatactttg gaagctaaag atgctgaagg tggtgctgtt      360
ctttcagggt taacaaaaga cactggtttt gcttttaaca ctgctaagtt aaaaggaact      420
taccaaatcg ttgaattgaa agaaaaatca aactacgata caacggttc tatcttggct      480 gattcaaaag cagttccagt taaaatcact ctgccattgg taaacaacca aggtgttgtt      540
aaagatgctc acatttatcc aaagaatact gaaacaaaac cacaagtaga taagaacttt      600
gcagataaag atcttgatta tactgacaac cgaaaagaca aaggtgttgt ctcagcgaca      660
gttggtgaca aaaagaata catagttgga acaaaaattc ttaaaggctc agactataag      720
aaactggttt ggactgatag catgactaaa ggtttgacgt tcaacaacaa cgttaaagta      780
acattggatg gtaaagattt tcctgtttta aactacaaac tcgtaacaga tgaccaaggt      840
ttccgtcttg ccttgaatgc aacaggtctt gcagcagtag cagctgctgc aaaagacaaa      900
gatgttgaaa tcaagatcac ttactcagct acggtgaacg gctccactac tgttgaagtt      960
ccagaaacca atgatgttaa attggactat ggtaataacc caacggaaga aagtgaacca     1020
caagaaggta ctccagctaa ccaagaaatt aaagtcatta agactgggc agtagatggt     1080 acaattactg atgttaatgt tgcagttaaa gctatcttta ccttgcaaga aaacaaacg      1140 gatggtacat gggtgaacgt tgcttcacac gaagcaacaa aaccatcacg ctttgaacat     1200
actttcacag gtttggataa tactaaaact taccgcgttg tcgaacgtgt tagcggctac     1260
actccagaat atgtatcatt taaaaatggt gttgtgacta tcaagaacaa caaaaactca     1320
aatgatccaa ctccaatcaa cccatcagaa ccaaaagtgg tgacttatgg acgtaaattt     1380
gtgaaaacaa atcaagctaa cactgaacgc ttggcaggag ctaccttcct tgttaagaaa     1440
gaaggaaaat acttggcacg taagcaggt gcagcaactc ctgaagcaaa ggcagctgta     1500
aaaactgcta aactagcatt ggatgaagct gttaaagctt ataacgactt gactaaagaa     1560
aaacaagaag gccaagaagg taaaacagca ttggctactg ttgatcaaaa acaaaaagct     1620
tacaatgacg cttttgttaa agctaactac tcatatgaat gggttgcaga taaaaaggct     1680
gataatgttg ttaaattgat ctctaacgcc ggtggtcaat ttgaaattac tggtttggat     1740
aaaggcactt atagcttgga agaaactcaa gcaccagcag ttatgcgac attgtcaggt     1800 gatgtaaact ttgaagtaac tgccacatca tatagcaaag gggctacaac tgacatcgca     1860
tatgataaag gatctgtaaa aaaagatgcc caacaagttc aaaacaaaaa agtaaccatc     1920
ccacaaacag gtggtattgg tacaattctt ttcacaatta ttggtttaag cattatgctt     1980
ggagcagtag ttgtcatgaa aaaacgtcaa tcagaggaag cttaa                     2025
```

<210> SEQ ID NO 9
<211> LENGTH: 1908
<212> TYPE: DNA
<213> ORGANISM: Streptococcus agalactiae

<400> SEQUENCE: 9

```
atgaaaaaac aattttttaaa atcagcagcg attctatcgc tagcagtaac agcagtatct       60
acaagtcagc cggtagccgg gataactaaa gattataata accgaaatga aaagtaaaa      120 aagtatttac aagaaaataa tttcggtcat aaaatagcgt atggatggaa aaataaagta      180
gaatttgatt ttcgttattt attggatact gctaaatatt tagtaaataa agaagaattt      240
```

-continued

| | | |
|---|---|---|
| caagatcctt tatataatga tgcgcgcgaa gaattgataa gttttatttt tccttatgag | 300 |
| aaatttttaa ttaacaatcg tgacataact aaattaacag ttaatcagta tgaagcgatt | 360 |
| gtgaatagaa tgagtgttgc tttacaaaaa ttttcaaaga atattttga gaaacagaaa | 420 |
| gtaaataaag atttaatccc tattgcgttt tggattgaga aaagttacag aactgttgga | 480 |
| acgaatgaaa tcgccgcttc tgtaggcatt caaggaggat tttatcaaaa cttccatgat | 540 |
| tattataatt attcatatct attaaattct ttatggcatg aaggaaatgt aaagaagta | 600 |
| gttaaggatt atgaaaacac tattcgtcaa atactatcta aaaagcatga gattgaaaaa | 660 |
| attcttaatc agagcacttc tgatatctct atagatgatg atgattacga aaaggaaat | 720 |
| aaagaattgc taagggaaaa attaaatatt attctaaatc tttcaaagag agattacaga | 780 |
| gtaactccat actatgaagt gaataaacta catacagggc ttattttatt ggaggatgtc | 840 |
| cctaatttaa agattgctaa ggataagttg ttctcattag agaattcttt aaggaatac | 900 |
| aaaggagaga agttaattta tgaggaacta agattcaata cggaacctt aactagttac | 960 |
| ttagaaaata agaaaaatt tttagtcccc aatattccat ataaaataa attaatttta | 1020 |
| agggaagaag ataaatatag ttttgaagat gatgaagaag agtttggaaa tgaacttcta | 1080 |
| agttacaata agcttaagaa tgaagtttta cctgttaata ttacaacttc tactatatta | 1140 |
| aaaccgtttg aacagaagaa aattgtggaa gattttaatc cttattctaa tttagacaat | 1200 |
| ttagaaataa aaaaaataag gttgaatggc tcccaaaaac aaaagtaga acaggaaaaa | 1260 |
| actaaatcgc caactcctca aaaagagact gtgaaagaac aaactgagca aaaagtatct | 1320 |
| ggaaatactc aagaggtaga aaagaaatct gaaactgtgg caacttcaca acaaagttca | 1380 |
| gttgcgcaaa cttctgtcca acagccggct ccggttcaat cagttgttca agaatccaaa | 1440 |
| gcttctcaag aggagattaa tgcagcacac gatgctattt cggcgtataa atcaacagtc | 1500 |
| aatattgcta atacagccgg tgtaacaact gcggaaatga ccacgctcat taatactcaa | 1560 |
| acttctaatc tttctgatgt tgagaaagct ttaggaaata ataaggttaa taatggtgca | 1620 |
| gtcaatgtat tgagagaaga tacagctcgt cttgagaata tgatttggaa tcgtgcttac | 1680 |
| caagctattg aagaattcaa cgtcgctcgt aatacttata ataaccaaat caagacagaa | 1740 |
| acagttccag ttgataatga tattgaagct atttttagcag gttctcaagc taaaattagc | 1800 |
| catttggaca atcgtatcgg agcgcgccac atggatcaag cttttgtagc tagtttatta | 1860 |
| gaagttactg agatgagtaa atcaatctca tcgcgtataa aagagtag | 1908 |

<210> SEQ ID NO 10
<211> LENGTH: 546
<212> TYPE: DNA
<213> ORGANISM: Streptococcus agalactiae

<400> SEQUENCE: 10

| | | |
|---|---|---|
| atgaaaaaaa taacaacttt aatcttagct agtagcttat tactagttgc aacgacatcg | 60 |
| gttaaagctg atgataactt tgaaatgcca acgcgttatg ttaaaatgag tgaaaaatca | 120 |
| aaagcatttt atcaaagact acaagaaaaa caacgtaagg cacatactac tgtgaagact | 180 |
| tttaataatt cagaaataag gcatcaacta cctcttaaac aagaaaaggc tagaaatgat | 240 |
| atctacaatt taggcattct tatttctcag gagtctaaag ggttcatcca acgtattgat | 300 |
| aatgccatt ctttggaaaa tgtctcagat attgttaatg aagctcaggc tttgtataaa | 360 |
| cgtaactatg atttatttga aaaaatcaaa tctacacgtg ataaggttca agtcttactt | 420 |
| gcatcgcatc aagataatac agacttaaaa aacttttatg ctgagttaga tgatatgtat | 480 |

```
gaacatgttt atctcaatga aagtagagtg gaggcgataa acagaaatat ccaaaaatat    540
aattag                                                               546
```

<210> SEQ ID NO 11
<211> LENGTH: 442
<212> TYPE: PRT
<213> ORGANISM: Streptococcus agalactiae

<400> SEQUENCE: 11

```
Met Phe Asn Lys Ile Gly Phe Arg Thr Trp Lys Ser Gly Lys Leu Trp
1               5                   10                  15

Leu Tyr Met Gly Val Leu Gly Ser Thr Ile Ile Leu Gly Ser Ser Pro
            20                  25                  30

Val Ser Ala Met Asp Ser Val Gly Asn Gln Ser Gln Gly Asn Val Leu
        35                  40                  45

Glu Arg Arg Gln Arg Asp Ala Glu Asn Arg Ser Gln Gly Asn Val Leu
    50                  55                  60

Glu Arg Arg Gln Arg Asp Val Glu Asn Lys Ser Gln Gly Asn Val Leu
65                  70                  75                  80

Glu Arg Arg Gln Arg Asp Ala Glu Asn Lys Ser Gln Gly Asn Val Leu
                85                  90                  95

Glu Arg Arg Gln Arg Asp Ala Glu Asn Arg Ser Gln Gly Asn Val Leu
            100                 105                 110

Glu Arg Arg Gln Arg Asp Ala Glu Asn Arg Ser Gln Gly Asn Val Leu
        115                 120                 125

Glu Arg Arg Gln Arg Asp Ala Glu Asn Arg Ser Gln Gly Asn Val Leu
    130                 135                 140

Glu Arg Arg Gln Arg Asp Ala Glu Asn Arg Ser Gln Gly Asn Val Leu
145                 150                 155                 160

Glu Arg Arg Gln Arg Asp Ala Glu Asn Arg Ser Gln Gly Asn Val Leu
                165                 170                 175

Glu Arg Arg Gln Arg Asp Val Glu Asn Lys Ser Gln Gly Asn Val Leu
            180                 185                 190

Glu Arg Arg Gln Arg Asp Ala Glu Asn Lys Ser Gln Gly Asn Val Leu
        195                 200                 205

Glu Arg Arg Gln Arg Asp Ala Glu Asn Arg Ser Gln Gly Asn Val Leu
    210                 215                 220

Glu Arg Arg Gln Arg Asp Ala Glu Asn Arg Ser Gln Gly Asn Val Leu
225                 230                 235                 240

Glu Arg Arg Gln Arg Asp Ala Glu Asn Arg Ser Gln Gly Asn Val Leu
                245                 250                 255

Glu Arg Arg Gln Arg Asp Ala Glu Asn Arg Ser Gln Gly Asn Val Leu
            260                 265                 270

Glu Arg Arg Gln Arg Asp Ala Glu Asn Arg Ser Gln Gly Asn Val Leu
        275                 280                 285

Glu Arg Arg Gln Arg Asp Ala Glu Asn Arg Ser Gln Gly Asn Val Leu
    290                 295                 300

Glu Arg Arg Gln Arg Asp Ala Glu Asn Arg Ser Gln Gly Asn Val Leu
305                 310                 315                 320

Glu Arg Arg Gln Arg Asp Ala Glu Asn Arg Ser Gln Gly Asn Val Leu
                325                 330                 335

Glu Arg Arg Gln Arg Asp Ala Glu Asn Lys Ser Gln Val Gly Gln Leu
            340                 345                 350

Ile Gly Lys Asn Pro Leu Leu Ser Lys Ser Ile Ile Ser Arg Glu Asn
        355                 360                 365
```

```
Asn His Ser Ser Gln Gly Asp Ser Asn Lys Gln Ser Phe Ser Lys Lys
    370                 375                 380

Val Ser Gln Val Thr Asn Val Ala Asn Arg Pro Met Leu Thr Asn Asn
385                 390                 395                 400

Ser Arg Thr Ile Ser Val Ile Asn Lys Leu Pro Lys Thr Gly Asp Asp
            405                 410                 415

Gln Asn Val Ile Phe Lys Leu Val Gly Phe Gly Leu Ile Leu Leu Thr
            420                 425                 430

Ser Arg Cys Gly Leu Arg Arg Asn Glu Asn
            435                 440

<210> SEQ ID NO 12
<211> LENGTH: 410
<212> TYPE: PRT
<213> ORGANISM: Streptococcus agalactiae

<400> SEQUENCE: 12

Met Phe Asn Lys Ile Gly Phe Arg Thr Trp Lys Ser Gly Lys Leu Trp
1               5                   10                  15

Leu Tyr Met Gly Val Leu Gly Ser Thr Ile Ile Leu Gly Ser Ser Ser
            20                  25                  30

Val Ser Ala Met Asp Ser Val Gly Asn Gln Ser Gln Gly Asn Val Leu
            35                  40                  45

Glu Arg Arg Gln Arg Asp Ala Glu Asn Arg Ser Gln Gly Asn Val Leu
    50                  55                  60

Glu Arg Arg Gln Arg Asp Ala Glu Asn Arg Ser Gln Gly Asn Val Leu
65                  70                  75                  80

Glu Arg Arg Gln Arg Asp Ala Glu Asn Arg Ser Gln Gly Asn Val Leu
            85                  90                  95

Glu Arg Arg Gln Arg Asp Val Glu Asn Lys Ser Gln Gly Asn Val Leu
            100                 105                 110

Glu Arg Arg Gln Arg Asp Ala Glu Asn Arg Ser Gln Gly Asn Val Leu
            115                 120                 125

Glu Arg Arg Gln Arg Asp Val Glu Asn Lys Ser Gln Gly Asn Val Leu
    130                 135                 140

Glu Arg Arg Gln Arg Asp Ala Glu Asn Arg Ser Gln Gly Asn Val Leu
145                 150                 155                 160

Glu Arg Arg Gln Arg Asp Ala Glu Asn Arg Ser Gln Gly Asn Val Leu
            165                 170                 175

Glu Arg Arg Gln Arg Asp Ala Glu Asn Arg Ser Gln Gly Asn Val Leu
            180                 185                 190

Glu Arg Arg Gln Arg Asp Ala Glu Asn Lys Ser Gln Gly Asn Val Leu
            195                 200                 205

Glu Arg Arg Gln Arg Asp Ala Glu Asn Arg Ser Gln Gly Asn Val Leu
    210                 215                 220

Glu Arg Arg Gln Arg Asp Ala Glu Asn Arg Ser Gln Gly Asn Val Leu
225                 230                 235                 240

Glu Arg Arg Gln Arg Asp Ala Glu Asn Arg Ser Gln Gly Asn Val Leu
            245                 250                 255

Glu Arg Arg Gln Arg Asp Ala Glu Asn Lys Ser Gln Gly Asn Val Leu
            260                 265                 270

Glu Arg Arg Gln Arg Asp Ala Glu Asn Arg Ser Gln Gly Asn Val Leu
            275                 280                 285

Glu Arg Arg Gln Arg Asp Val Glu Asn Lys Ser Gln Gly Asn Val Leu
    290                 295                 300
```

-continued

```
Glu Arg Arg Gln Arg Asp Ala Glu Asn Lys Ser Gln Val Gly Gln Leu
305                 310                 315                 320

Ile Gly Lys Asn Pro Leu Leu Ser Lys Ser Ile Ser Arg Glu Asn
            325                 330                 335

Asn His Ser Ser Gln Gly Asp Ser Asn Lys Gln Ser Phe Ser Lys Lys
            340                 345                 350

Val Ser Gln Val Thr Asn Val Ala Asn Arg Pro Met Leu Thr Asn Asn
        355                 360                 365

Ser Arg Thr Ile Ser Val Ile Asn Lys Leu Pro Lys Thr Gly Asp Asp
    370                 375                 380

Gln Asn Val Ile Phe Lys Leu Val Gly Phe Gly Leu Ile Leu Leu Thr
385                 390                 395                 400

Ser Arg Cys Gly Leu Arg Arg Asn Glu Asn
                405                 410

<210> SEQ ID NO 13
<211> LENGTH: 346
<212> TYPE: PRT
<213> ORGANISM: Streptococcus agalactiae

<400> SEQUENCE: 13

Met Phe Asn Lys Ile Gly Phe Arg Thr Trp Lys Ser Gly Lys Leu Trp
1               5                   10                  15

Leu Tyr Met Gly Val Leu Gly Ser Thr Ile Ile Leu Gly Ser Ser Pro
            20                  25                  30

Val Ser Ala Met Asp Ser Val Gly Asn Gln Ser Gln Gly Asn Val Leu
        35                  40                  45

Glu Arg Arg Gln Arg Asp Ala Asp Asn Lys Ser Gln Gly Asn Val Leu
50                  55                  60

Glu Arg Arg Gln Arg Asp Val Glu Asn Arg Ser Gln Gly Asn Val Leu
65                  70                  75                  80

Glu Arg Arg Gln Arg Asp Ala Asp Asn Lys Ser Gln Gly Asn Val Leu
                85                  90                  95

Glu Arg Arg Gln Arg Asp Ala Glu Asn Lys Ser Gln Gly Asn Val Leu
            100                 105                 110

Glu Arg Arg Gln Arg Asp Val Glu Asn Lys Ser Gln Gly Asn Val Leu
        115                 120                 125

Glu Arg Arg Gln Arg Asp Ala Glu Asn Lys Ser Gln Gly Asn Val Leu
    130                 135                 140

Glu Arg Arg Gln Arg Asp Ala Asp Asn Lys Ser Gln Gly Asn Val Leu
145                 150                 155                 160

Glu Arg Arg Gln Arg Asp Val Glu Asn Lys Ser Gln Gly Asn Val Leu
                165                 170                 175

Glu Arg Arg Gln Arg Asp Val Glu Asn Lys Ser Gln Gly Asn Val Leu
            180                 185                 190

Glu Arg Arg Gln Arg Asp Ala Glu Asn Lys Ser Gln Gly Asn Val Leu
        195                 200                 205

Glu Arg Arg Gln Arg Asp Ala Asp Asn Lys Ser Gln Gly Asn Val Leu
    210                 215                 220

Glu Arg Arg Gln Arg Asp Val Glu Asn Lys Ser Gln Gly Asn Val Leu
225                 230                 235                 240

Glu Arg Arg Gln Arg Asp Val Glu Asn Lys Ser Gln Val Gly Gln Leu
                245                 250                 255

Ile Gly Lys Asn Pro Leu Leu Ser Lys Ser Thr Ile Ser Arg Glu Asn
            260                 265                 270
```

```
Asn His Ser Ser Gln Gly Asp Ser Asn Lys Gln Ser Phe Ser Lys Lys
            275                 280                 285

Val Ser Gln Val Thr Asn Val Ala Asn Arg Pro Met Leu Thr Asn Asn
    290                 295                 300

Ser Arg Thr Ile Ser Val Ile Asn Lys Leu Pro Lys Thr Gly Asp Asp
305                 310                 315                 320

Gln Asn Val Ile Phe Lys Leu Val Gly Phe Gly Leu Ile Leu Leu Thr
                325                 330                 335

Ser Arg Cys Gly Leu Arg Arg Asn Glu Asn
            340                 345

<210> SEQ ID NO 14
<211> LENGTH: 186
<212> TYPE: PRT
<213> ORGANISM: Streptococcus agalactiae

<400> SEQUENCE: 14

Met Phe Asn Lys Ile Gly Phe Arg Thr Trp Lys Ser Gly Lys Leu Trp
1               5                   10                  15

Leu Tyr Met Gly Val Leu Gly Ser Thr Ile Ile Leu Gly Ser Ser Pro
            20                  25                  30

Val Ser Ala Met Asp Ser Val Gly Asn Gln Ser Gln Gly Asn Val Leu
        35                  40                  45

Glu Arg Arg Gln Arg Asp Ala Glu Asn Arg Ser Gln Gly Asn Val Leu
    50                  55                  60

Glu Arg Arg Gln Arg Asp Ala Glu Asn Arg Ser Gln Gly Asn Val Leu
65                  70                  75                  80

Glu Arg Arg Gln Arg Asp Ala Glu Asn Lys Ser Gln Val Gly Gln Leu
                85                  90                  95

Ile Gly Lys Asn Pro Leu Leu Ser Lys Ser Ile Ile Ser Arg Glu Asn
            100                 105                 110

Asn His Ser Ser Gln Gly Asp Ser Asn Lys Gln Ser Phe Ser Lys Lys
        115                 120                 125

Val Ser Gln Val Thr Asn Val Ala Asn Arg Pro Met Leu Thr Asn Asn
    130                 135                 140

Ser Arg Thr Ile Ser Val Ile Asn Lys Leu Pro Lys Thr Gly Asp Asp
145                 150                 155                 160

Gln Asn Val Ile Phe Lys Leu Val Gly Phe Gly Leu Ile Leu Leu Thr
                165                 170                 175

Ser Arg Cys Gly Leu Arg Arg Asn Glu Asn
            180                 185

<210> SEQ ID NO 15
<211> LENGTH: 298
<212> TYPE: PRT
<213> ORGANISM: Streptococcus agalactiae

<400> SEQUENCE: 15

Met Phe Asn Lys Ile Gly Phe Arg Thr Trp Lys Ser Gly Lys Leu Trp
1               5                   10                  15

Leu Tyr Met Gly Val Leu Gly Ser Thr Ile Ile Leu Gly Ser Ser Pro
            20                  25                  30

Val Ser Ala Met Asp Ser Val Gly Asn Gln Ser Gln Gly Asn Val Leu
        35                  40                  45

Glu Arg Arg Gln Arg Asp Ala Glu Asn Arg Ser Gln Gly Asn Val Leu
    50                  55                  60
```

```
Glu Arg Arg Gln Arg Asp Val Glu Asn Lys Ser Gln Gly Asn Val Leu
 65                  70                  75                  80

Glu Arg Arg Gln Arg Asp Ala Glu Asn Lys Ser Gln Gly Asn Val Leu
                 85                  90                  95

Glu Arg Arg Gln Arg Asp Ala Glu Asn Arg Ser Gln Gly Asn Val Leu
            100                 105                 110

Glu Arg Arg Gln Arg Asp Val Glu Asn Lys Ser Gln Gly Asn Val Leu
        115                 120                 125

Glu Arg Arg Gln Arg Asp Val Glu Asn Lys Ser Gln Gly Asn Val Leu
    130                 135                 140

Glu Arg Arg Gln Arg Asp Val Glu Asn Lys Ser Gln Gly Asn Val Leu
145                 150                 155                 160

Glu Arg Arg Gln Arg Asp Ala Glu Asn Lys Ser Gln Gly Asn Val Leu
                165                 170                 175

Glu Arg Arg Gln Arg Asp Ala Glu Asn Arg Ser Gln Gly Asn Val Leu
            180                 185                 190

Glu Arg Arg Gln His Asp Val Glu Asn Lys Ser Gln Val Gly Gln Leu
        195                 200                 205

Ile Gly Lys Asn Pro Leu Phe Ser Lys Ser Thr Val Ser Arg Glu Asn
    210                 215                 220

Asn His Ser Ser Gln Gly Asp Ser Asn Lys Gln Ser Phe Ser Lys Lys
225                 230                 235                 240

Val Ser Gln Val Thr Asn Val Ala Asn Arg Pro Met Leu Thr Asn Asn
                245                 250                 255

Ser Arg Thr Ile Ser Val Ile Asn Lys Leu Pro Lys Thr Gly Asp Asp
            260                 265                 270

Gln Asn Val Ile Phe Lys Leu Val Gly Phe Gly Leu Ile Leu Leu Thr
        275                 280                 285

Ser Leu Cys Gly Leu Arg Arg Asn Glu Asn
    290                 295

<210> SEQ ID NO 16
<211> LENGTH: 618
<212> TYPE: PRT
<213> ORGANISM: Streptococcus agalactiae

<400> SEQUENCE: 16

Met Phe Asn Lys Ile Gly Phe Arg Thr Trp Lys Ser Gly Lys Leu Trp
1               5                   10                  15

Leu Tyr Met Gly Val Leu Gly Ser Thr Ile Ile Leu Gly Ser Ser Pro
            20                  25                  30

Val Ser Ala Met Asp Ser Val Gly Asn Gln Ser Gln Gly Asn Val Leu
        35                  40                  45

Glu Arg Arg Gln Arg Asp Ala Asp Asn Lys Ser Gln Gly Asn Val Leu
    50                  55                  60

Glu Arg Arg Gln Arg Asp Ala Asp Asn Lys Ser Gln Gly Asn Val Leu
 65                  70                  75                  80

Glu Arg Arg Gln Arg Asp Val Asp Asn Lys Ser Gln Gly Asn Val Leu
                 85                  90                  95

Glu Arg Arg Gln Arg Asp Ala Asp Asn Lys Ser Gln Gly Asn Val Leu
            100                 105                 110

Glu Arg Arg Gln Arg Asp Ala Asp Asn Lys Ser Gln Gly Asn Val Leu
        115                 120                 125

Glu Arg Arg Gln Arg Asp Val Asp Asn Lys Ser Gln Gly Asn Val Leu
    130                 135                 140
```

```
Glu Arg Arg Gln Arg Asp Ala Asp Asn Lys Ser Gln Gly Asn Val Leu
145                 150                 155                 160

Glu Arg Arg Gln Arg Asp Val Asp Asn Lys Ser Gln Gly Asn Val Leu
                165                 170                 175

Glu Arg Arg Gln Arg Asp Ala Asp Asn Lys Ser Gln Gly Asn Val Leu
            180                 185                 190

Glu Arg Arg Gln Arg Asp Ala Asp Asn Lys Ser Gln Gly Asn Val Leu
        195                 200                 205

Glu Arg Arg Gln Arg Asp Ala Asp Asn Lys Ser Gln Gly Asn Val Leu
    210                 215                 220

Glu Arg Arg Gln Arg Asp Ala Asp Asn Lys Ser Gln Gly Asn Val Leu
225                 230                 235                 240

Glu Arg Arg Gln Arg Asp Ala Asp Asn Lys Ser Gln Gly Asn Val Leu
                245                 250                 255

Glu Arg Arg Gln Arg Asp Ala Asp Asn Lys Ser Gln Gly Asn Val Leu
            260                 265                 270

Glu Arg Arg Gln Arg Asp Ala Asp Asn Lys Ser Gln Gly Asn Val Leu
        275                 280                 285

Glu Arg Arg Gln Arg Asp Val Asp Asn Lys Ser Gln Gly Asn Val Leu
    290                 295                 300

Glu Arg Arg Gln Arg Asp Ala Asp Asn Lys Ser Gln Gly Asn Val Leu
305                 310                 315                 320

Glu Arg Arg Gln Arg Asp Ala Asp Asn Lys Ser Gln Gly Asn Val Leu
                325                 330                 335

Glu Arg Arg Gln Arg Asp Ala Asp Asn Lys Ser Gln Gly Asn Val Leu
            340                 345                 350

Glu Arg Arg Gln Arg Asp Ala Asp Asn Lys Ser Gln Gly Asn Val Leu
        355                 360                 365

Glu Arg Arg Gln Arg Asp Ala Asp Asn Lys Ser Gln Gly Asn Val Leu
    370                 375                 380

Glu Arg Arg Gln Arg Asp Ala Asp Asn Lys Ser Gln Gly Asn Val Leu
385                 390                 395                 400

Glu Arg Arg Gln Arg Asp Ala Asp Asn Lys Ser Gln Gly Asn Val Leu
                405                 410                 415

Glu Arg Arg Gln Arg Asp Ala Asp Asn Lys Ser Gln Gly Asn Val Leu
            420                 425                 430

Glu Arg Arg Gln Arg Asp Ala Asp Asn Lys Ser Gln Gly Asn Val Leu
        435                 440                 445

Glu Arg Arg Gln Arg Asp Ala Asp Asn Lys Ser Gln Gly Asn Val Leu
    450                 455                 460

Glu Arg Arg Gln Arg Asp Ala Asp Asn Lys Ser Gln Gly Asn Val Leu
465                 470                 475                 480

Glu Arg Arg Gln Arg Asp Ala Asp Asn Lys Ser Gln Gly Asn Val Leu
                485                 490                 495

Glu Arg Arg Gln Arg Asp Ala Asp Asn Lys Ser Gln Gly Asn Val Leu
            500                 505                 510

Glu Arg Arg Gln Arg Asp Ala Glu Asn Lys Ser Gln Val Gly Gln Leu
        515                 520                 525

Ile Gly Lys Asn Pro Leu Phe Ser Lys Ser Thr Val Ser Arg Glu Asn
    530                 535                 540

Asn His Ser Ser Gln Gly Asp Ser Asn Lys Gln Ser Phe Ser Lys Lys
545                 550                 555                 560

Ile Ser Gln Val Thr Asn Val Ala Asn Gly Pro Met Leu Thr Asn Asn
                565                 570                 575
```

Ser Arg Thr Ile Ser Val Ile Asn Lys Leu Pro Lys Thr Gly Asp Asp
        580                 585                 590

Gln Asn Val Ile Phe Lys Leu Val Gly Phe Gly Leu Ile Leu Leu Thr
        595                 600                 605

Ser Leu Cys Gly Leu Arg Arg Asn Glu Asn
        610                 615

<210> SEQ ID NO 17
<211> LENGTH: 901
<212> TYPE: PRT
<213> ORGANISM: Streptococcus agalactiae

<400> SEQUENCE: 17

Met Arg Lys Tyr Gln Lys Phe Ser Lys Ile Leu Thr Leu Ser Leu Phe
1               5                   10                  15

Cys Leu Ser Gln Ile Pro Leu Asn Thr Asn Val Leu Gly Glu Ser Thr
                20                  25                  30

Val Pro Glu Asn Gly Ala Lys Gly Lys Leu Val Val Lys Lys Thr Asp
            35                  40                  45

Asp Gln Asn Lys Pro Leu Ser Lys Ala Thr Phe Val Leu Lys Thr Thr
        50                  55                  60

Ala His Pro Glu Ser Lys Ile Glu Lys Val Thr Ala Glu Leu Thr Gly
65                  70                  75                  80

Glu Ala Thr Phe Asp Asn Leu Ile Pro Gly Asp Tyr Thr Leu Ser Glu
                85                  90                  95

Glu Thr Ala Pro Glu Gly Tyr Lys Lys Thr Asn Gln Thr Trp Gln Val
            100                 105                 110

Lys Val Glu Ser Asn Gly Lys Thr Thr Ile Gln Asn Ser Gly Asp Lys
        115                 120                 125

Asn Ser Thr Ile Gly Gln Asn His Glu Glu Leu Asp Lys Gln Tyr Pro
130                 135                 140

Pro Thr Gly Ile Tyr Glu Asp Thr Lys Glu Ser Tyr Lys Leu Glu His
145                 150                 155                 160

Val Lys Gly Ser Val Pro Asn Gly Lys Ser Glu Ala Lys Ala Val Asn
                165                 170                 175

Pro Tyr Ser Ser Glu Gly Glu His Ile Arg Glu Ile Pro Glu Gly Thr
            180                 185                 190

Leu Ser Lys Arg Ile Ser Glu Val Gly Asp Leu Ala His Asn Lys Tyr
        195                 200                 205

Lys Ile Glu Leu Thr Val Ser Gly Lys Thr Ile Val Lys Pro Val Asp
    210                 215                 220

Lys Gln Lys Pro Leu Asp Val Val Phe Val Leu Asp Asn Ser Asn Ser
225                 230                 235                 240

Met Asn Asn Asp Gly Pro Asn Phe Gln Arg His Asn Lys Ala Lys Lys
                245                 250                 255

Ala Ala Glu Ala Leu Gly Thr Ala Val Lys Asp Ile Leu Gly Ala Asn
            260                 265                 270

Ser Asp Asn Arg Val Ala Leu Val Thr Tyr Gly Ser Asp Ile Phe Asp
        275                 280                 285

Gly Arg Ser Val Asp Val Val Lys Gly Phe Lys Glu Asp Asp Lys Tyr
    290                 295                 300

Tyr Gly Leu Gln Thr Lys Phe Thr Ile Gln Thr Glu Asn Tyr Ser His
305                 310                 315                 320

Lys Gln Leu Thr Asn Asn Ala Glu Glu Ile Ile Lys Arg Ile Pro Thr
                325                 330                 335

-continued

Glu Ala Pro Arg Ala Lys Trp Gly Ser Thr Thr Asn Gly Leu Thr Pro
            340                 345                 350

Glu Gln Gln Lys Gln Tyr Tyr Leu Ser Lys Val Gly Glu Thr Phe Thr
            355                 360                 365

Met Lys Ala Phe Met Glu Ala Asp Asp Ile Leu Ser Gln Val Asp Arg
            370                 375                 380

Asn Ser Gln Lys Ile Ile Val His Ile Thr Asp Gly Val Pro Thr Arg
385                 390                 395                 400

Ser Tyr Ala Ile Asn Asn Phe Lys Leu Gly Ala Ser Tyr Glu Ser Gln
                405                 410                 415

Phe Glu Gln Met Lys Lys Asn Gly Tyr Leu Asn Lys Ser Asn Phe Leu
            420                 425                 430

Leu Thr Asp Lys Pro Glu Asp Ile Lys Gly Asn Gly Glu Ser Tyr Phe
            435                 440                 445

Leu Phe Pro Leu Asp Ser Tyr Gln Thr Gln Ile Ile Ser Gly Asn Leu
        450                 455                 460

Gln Lys Leu His Tyr Leu Asp Leu Asn Leu Asn Tyr Pro Lys Gly Thr
465                 470                 475                 480

Ile Tyr Arg Asn Gly Pro Val Arg Glu His Gly Thr Pro Thr Lys Leu
                485                 490                 495

Tyr Ile Asn Ser Leu Lys Gln Lys Asn Tyr Asp Ile Phe Asn Phe Gly
            500                 505                 510

Ile Asp Ile Ser Ala Phe Arg Gln Val Tyr Asn Glu Asp Tyr Lys Lys
            515                 520                 525

Asn Gln Asp Gly Thr Phe Gln Lys Leu Lys Glu Glu Ala Phe Glu Leu
        530                 535                 540

Ser Asp Gly Glu Ile Thr Glu Leu Met Lys Ser Phe Ser Ser Lys Pro
545                 550                 555                 560

Glu Tyr Tyr Thr Pro Ile Val Thr Ser Ser Asp Ala Ser Asn Asn Glu
                565                 570                 575

Ile Leu Ser Lys Ile Gln Gln Phe Glu Lys Val Leu Thr Lys Glu
            580                 585                 590

Asn Ser Ile Val Asn Gly Thr Ile Glu Asp Pro Met Gly Asp Lys Ile
            595                 600                 605

Asn Leu Gln Leu Gly Asn Gly Gln Thr Leu Gln Pro Ser Asp Tyr Thr
        610                 615                 620

Leu Gln Gly Asn Asp Gly Ser Ile Met Lys Asp Ser Ile Ala Thr Gly
625                 630                 635                 640

Gly Pro Asn Asn Asp Gly Gly Ile Leu Lys Gly Val Lys Leu Glu Tyr
                645                 650                 655

Ile Lys Asn Lys Leu Tyr Val Arg Gly Leu Asn Leu Gly Glu Gly Gln
            660                 665                 670

Lys Val Thr Leu Thr Tyr Asp Val Lys Leu Asp Ser Phe Ile Ser
            675                 680                 685

Asn Lys Phe Tyr Asp Thr Asn Gly Arg Thr Thr Leu Asn Pro Lys Ser
        690                 695                 700

Glu Asp Pro Asn Thr Leu Arg Asp Phe Pro Ile Pro Lys Ile Arg Asp
705                 710                 715                 720

Val Arg Glu Tyr Pro Thr Ile Thr Ile Lys Asn Glu Lys Lys Leu Gly
                725                 730                 735

Glu Ile Glu Phe Thr Lys Val Asp Lys Asp Asn Asn Lys Leu Leu Leu
            740                 745                 750

Lys Gly Ala Thr Phe Glu Leu Gln Glu Phe Asn Glu Asp Tyr Lys Leu 755                 760                 765
Tyr Leu Pro Ile Lys Asn Asn Ser Lys Val Thr Gly Glu Asn
770                 775                 780

Gly Lys Ile Ser Tyr Lys Asp Leu Lys Asp Gly Lys Tyr Gln Leu Ile
785                 790                 795                 800

Glu Ala Val Ser Pro Lys Asp Tyr Gln Lys Ile Thr Asn Lys Pro Ile
                805                 810                 815

Leu Thr Phe Glu Val Val Lys Gly Ser Ile Gln Asn Ile Ile Ala Val
                820                 825                 830

Asn Lys Gln Ile Ser Glu Tyr His Glu Glu Gly Asp Lys His Leu Ile
                835                 840                 845

Thr Asn Thr His Ile Pro Pro Lys Gly Ile Ile Pro Met Thr Gly Gly
                850                 855                 860

Lys Gly Ile Leu Ser Phe Ile Leu Ile Gly Gly Ser Met Met Ser Ile
865                 870                 875                 880

Ala Gly Gly Ile Tyr Ile Trp Lys Arg Tyr Lys Ser Ser Asp Ile
                885                 890                 895

Ser Arg Glu Lys Asp
            900

<210> SEQ ID NO 18
<211> LENGTH: 674
<212> TYPE: PRT
<213> ORGANISM: Streptococcus agalactiae

<400> SEQUENCE: 18

Met Lys Lys Ile Asn Lys Cys Leu Thr Val Phe Ser Thr Leu Leu Leu
1               5                   10                  15

Ile Leu Thr Ser Leu Phe Ser Val Ala Pro Ala Phe Ala Asp Asp Val
                20                  25                  30

Thr Thr Asp Thr Val Thr Leu His Lys Ile Val Met Pro Gln Ala Ala
                35                  40                  45

Phe Asp Asn Phe Thr Glu Gly Thr Lys Gly Lys Asn Asp Ser Asp Tyr
            50                  55                  60

Val Gly Lys Gln Ile Asn Asp Leu Lys Ser Tyr Phe Gly Ser Thr Asp
65              70                  75                  80

Ala Lys Glu Ile Lys Gly Ala Phe Phe Val Phe Lys Asn Glu Thr Gly
                85                  90                  95

Thr Lys Phe Ile Thr Glu Asn Gly Lys Glu Val Asp Thr Leu Glu Ala
            100                 105                 110

Lys Asp Ala Glu Gly Gly Ala Val Leu Ser Gly Leu Thr Lys Asp Thr
        115                 120                 125

Gly Phe Ala Phe Asn Thr Ala Lys Leu Lys Gly Thr Tyr Gln Ile Val
    130                 135                 140

Glu Leu Lys Glu Lys Ser Asn Tyr Asp Asn Asn Gly Ser Ile Leu Ala
145                 150                 155                 160

Asp Ser Lys Ala Val Pro Val Lys Ile Thr Leu Pro Leu Val Asn Asn
                165                 170                 175

Gln Gly Val Val Lys Asp Ala His Ile Tyr Pro Lys Asn Thr Glu Thr
            180                 185                 190

Lys Pro Gln Val Asp Lys Asn Phe Ala Asp Lys Leu Asp Tyr Thr
        195                 200                 205

Asp Asn Arg Lys Asp Lys Gly Val Val Ser Ala Thr Val Gly Asp Lys
    210                 215                 220

Lys Glu Tyr Ile Val Gly Thr Lys Ile Leu Lys Gly Ser Asp Tyr Lys

-continued

```
             225                 230                 235                 240
Lys Leu Val Trp Thr Asp Ser Met Thr Lys Gly Leu Thr Phe Asn Asn
                 245                 250                 255
Asn Val Lys Val Thr Leu Asp Gly Lys Asp Phe Pro Val Leu Asn Tyr
                 260                 265                 270
Lys Leu Val Thr Asp Asp Gln Gly Phe Arg Leu Ala Leu Asn Ala Thr
                 275                 280                 285
Gly Leu Ala Ala Val Ala Ala Ala Lys Asp Lys Asp Val Glu Ile
                 290                 295                 300
Lys Ile Thr Tyr Ser Ala Thr Val Asn Gly Ser Thr Thr Val Glu Val
305                 310                 315                 320
Pro Glu Thr Asn Asp Val Lys Leu Asp Tyr Gly Asn Asn Pro Thr Glu
                 325                 330                 335
Glu Ser Glu Pro Gln Glu Gly Thr Pro Ala Asn Gln Glu Ile Lys Val
                 340                 345                 350
Ile Lys Asp Trp Ala Val Asp Gly Thr Ile Thr Asp Val Asn Val Ala
                 355                 360                 365
Val Lys Ala Ile Phe Thr Leu Gln Glu Lys Gln Thr Asp Gly Thr Trp
370                 375                 380
Val Asn Val Ala Ser His Glu Ala Thr Lys Pro Ser Arg Phe Glu His
385                 390                 395                 400
Thr Phe Thr Gly Leu Asp Asn Thr Lys Thr Tyr Arg Val Val Glu Arg
                 405                 410                 415
Val Ser Gly Tyr Thr Pro Glu Tyr Val Ser Phe Lys Asn Gly Val Val
                 420                 425                 430
Thr Ile Lys Asn Asn Lys Asn Ser Asn Asp Pro Thr Pro Ile Asn Pro
                 435                 440                 445
Ser Glu Pro Lys Val Val Thr Tyr Gly Arg Lys Phe Val Lys Thr Asn
                 450                 455                 460
Gln Ala Asn Thr Glu Arg Leu Ala Gly Ala Thr Phe Leu Val Lys Lys
465                 470                 475                 480
Glu Gly Lys Tyr Leu Ala Arg Lys Ala Gly Ala Ala Thr Ala Glu Ala
                 485                 490                 495
Lys Ala Ala Val Lys Thr Ala Lys Leu Ala Leu Asp Glu Ala Val Lys
                 500                 505                 510
Ala Tyr Asn Asp Leu Thr Lys Glu Lys Gln Gly Glu Gln Gly Lys
                 515                 520                 525
Thr Ala Leu Ala Thr Val Asp Gln Lys Gln Lys Ala Tyr Asn Asp Ala
                 530                 535                 540
Phe Val Lys Ala Asn Tyr Ser Tyr Glu Trp Val Ala Asp Lys Lys Ala
545                 550                 555                 560
Asp Asn Val Val Lys Leu Ile Ser Asn Ala Gly Gly Gln Phe Glu Ile
                 565                 570                 575
Thr Gly Leu Asp Lys Gly Thr Tyr Ser Leu Glu Glu Thr Gln Ala Pro
                 580                 585                 590
Ala Gly Tyr Ala Thr Leu Ser Gly Asp Val Asn Phe Glu Val Thr Ala
                 595                 600                 605
Thr Ser Tyr Ser Lys Gly Ala Thr Thr Asp Ile Ala Tyr Asp Lys Gly
                 610                 615                 620
Ser Val Lys Lys Asp Ala Gln Gln Val Gln Asn Lys Lys Val Thr Ile
625                 630                 635                 640
Pro Gln Thr Gly Gly Ile Gly Thr Ile Leu Phe Thr Ile Ile Gly Leu
                 645                 650                 655
```

Ser Ile Met Leu Gly Ala Val Val Met Lys Lys Arg Gln Ser Glu
            660                 665                 670

Glu Ala

<210> SEQ ID NO 19
<211> LENGTH: 635
<212> TYPE: PRT
<213> ORGANISM: Streptococcus agalactiae

<400> SEQUENCE: 19

Met Lys Lys Gln Phe Leu Lys Ser Ala Ile Leu Ser Leu Ala Val
1               5                   10                  15

Thr Ala Val Ser Thr Ser Gln Pro Val Ala Gly Ile Thr Lys Asp Tyr
            20                  25                  30

Asn Asn Arg Asn Glu Lys Val Lys Lys Tyr Leu Gln Glu Asn Asn Phe
            35                  40                  45

Gly His Lys Ile Ala Tyr Gly Trp Lys Asn Lys Val Glu Phe Asp Phe
        50                  55                  60

Arg Tyr Leu Leu Asp Thr Ala Lys Tyr Leu Val Asn Lys Glu Glu Phe
65                  70                  75                  80

Gln Asp Pro Leu Tyr Asn Asp Ala Arg Glu Glu Leu Ile Ser Phe Ile
                85                  90                  95

Phe Pro Tyr Glu Lys Phe Leu Ile Asn Asn Arg Asp Ile Thr Lys Leu
            100                 105                 110

Thr Val Asn Gln Tyr Glu Ala Ile Val Asn Arg Met Ser Val Ala Leu
            115                 120                 125

Gln Lys Phe Ser Lys Asn Ile Phe Glu Lys Gln Lys Val Asn Lys Asp
        130                 135                 140

Leu Ile Pro Ile Ala Phe Trp Ile Glu Lys Ser Tyr Arg Thr Val Gly
145                 150                 155                 160

Thr Asn Glu Ile Ala Ala Ser Val Gly Ile Gln Gly Gly Phe Tyr Gln
                165                 170                 175

Asn Phe His Asp Tyr Tyr Asn Tyr Ser Tyr Leu Leu Asn Ser Leu Trp
            180                 185                 190

His Glu Gly Asn Val Lys Glu Val Val Lys Asp Tyr Glu Asn Thr Ile
        195                 200                 205

Arg Gln Ile Leu Ser Lys His Glu Ile Glu Lys Ile Leu Asn Gln
        210                 215                 220

Ser Thr Ser Asp Ile Ser Ile Asp Asp Asp Tyr Glu Lys Gly Asn
225                 230                 235                 240

Lys Glu Leu Leu Arg Glu Lys Leu Asn Ile Ile Leu Asn Leu Ser Lys
                245                 250                 255

Arg Asp Tyr Arg Val Thr Pro Tyr Tyr Glu Val Asn Lys Leu His Thr
            260                 265                 270

Gly Leu Ile Leu Leu Glu Asp Val Pro Asn Leu Lys Ile Ala Lys Asp
        275                 280                 285

Lys Leu Phe Ser Leu Glu Asn Ser Leu Lys Glu Tyr Lys Gly Glu Lys
    290                 295                 300

Val Asn Tyr Glu Glu Leu Arg Phe Asn Thr Glu Pro Leu Thr Ser Tyr
305                 310                 315                 320

Leu Glu Asn Lys Glu Lys Phe Leu Val Pro Asn Ile Pro Tyr Lys Asn
                325                 330                 335

Lys Leu Ile Leu Arg Glu Glu Asp Lys Tyr Ser Phe Glu Asp Asp Glu
            340                 345                 350

Glu Glu Phe Gly Asn Glu Leu Leu Ser Tyr Asn Lys Leu Lys Asn Glu

```
                    355                 360                 365
Val Leu Pro Val Asn Ile Thr Thr Ser Thr Ile Leu Lys Pro Phe Glu
370                 375                 380

Gln Lys Lys Ile Val Glu Asp Phe Asn Pro Tyr Ser Asn Leu Asp Asn
385                 390                 395                 400

Leu Glu Ile Lys Lys Ile Arg Leu Asn Gly Ser Gln Lys Gln Lys Val
            405                 410                 415

Glu Gln Glu Lys Thr Lys Ser Pro Thr Pro Gln Lys Glu Thr Val Lys
            420                 425                 430

Glu Gln Thr Glu Gln Lys Val Ser Gly Asn Thr Gln Glu Val Glu Lys
            435                 440                 445

Lys Ser Glu Thr Val Ala Thr Ser Gln Gln Ser Ser Val Ala Gln Thr
        450                 455                 460

Ser Val Gln Gln Pro Ala Pro Val Gln Ser Val Gln Glu Ser Lys
465                 470                 475                 480

Ala Ser Gln Glu Glu Ile Asn Ala Ala His Asp Ala Ile Ser Ala Tyr
            485                 490                 495

Lys Ser Thr Val Asn Ile Ala Asn Thr Ala Gly Val Thr Thr Ala Glu
            500                 505                 510

Met Thr Thr Leu Ile Asn Thr Gln Thr Ser Asn Leu Ser Asp Val Glu
        515                 520                 525

Lys Ala Leu Gly Asn Asn Lys Val Asn Asn Gly Ala Val Asn Val Leu
        530                 535                 540

Arg Glu Asp Thr Ala Arg Leu Glu Asn Met Ile Trp Asn Arg Ala Tyr
545                 550                 555                 560

Gln Ala Ile Glu Glu Phe Asn Val Ala Arg Asn Thr Tyr Asn Asn Gln
            565                 570                 575

Ile Lys Thr Glu Thr Val Pro Val Asp Asn Asp Ile Glu Ala Ile Leu
            580                 585                 590

Ala Gly Ser Gln Ala Lys Ile Ser His Leu Asp Asn Arg Ile Gly Ala
        595                 600                 605

Arg His Met Asp Gln Ala Phe Val Ala Ser Leu Leu Glu Val Thr Glu
610                 615                 620

Met Ser Lys Ser Ile Ser Ser Arg Ile Lys Glu
625                 630                 635

<210> SEQ ID NO 20
<211> LENGTH: 181
<212> TYPE: PRT
<213> ORGANISM: Streptococcus agalactiae

<400> SEQUENCE: 20

Met Lys Lys Ile Thr Thr Leu Ile Leu Ala Ser Ser Leu Leu Leu Val
1               5                   10                  15

Ala Thr Thr Ser Val Lys Ala Asp Asp Asn Phe Glu Met Pro Thr Arg
            20                  25                  30

Tyr Val Lys Met Ser Glu Lys Ser Lys Ala Phe Tyr Gln Arg Leu Gln
        35                  40                  45

Glu Lys Gln Arg Lys Ala His Thr Thr Val Lys Thr Phe Asn Asn Ser
    50                  55                  60

Glu Ile Arg His Gln Leu Pro Leu Lys Gln Glu Lys Ala Arg Asn Asp
65                  70                  75                  80

Ile Tyr Asn Leu Gly Ile Leu Ile Ser Gln Glu Ser Lys Gly Phe Ile
                85                  90                  95

Gln Arg Ile Asp Asn Ala Tyr Ser Leu Glu Asn Val Ser Asp Ile Val
```

```
                        100                 105                 110
Asn Glu Ala Gln Ala Leu Tyr Lys Arg Asn Tyr Asp Leu Phe Glu Lys
        115                 120                 125

Ile Lys Ser Thr Arg Asp Lys Val Gln Val Leu Leu Ala Ser His Gln
    130                 135                 140

Asp Asn Thr Asp Leu Lys Asn Phe Tyr Ala Glu Leu Asp Asp Met Tyr
145                 150                 155                 160

Glu His Val Tyr Leu Asn Glu Ser Arg Val Glu Ala Ile Asn Arg Asn
                165                 170                 175

Ile Gln Lys Tyr Asn
            180

<210> SEQ ID NO 21
<211> LENGTH: 48
<212> TYPE: DNA
<213> ORGANISM: Streptococcus agalactiae

<400> SEQUENCE: 21
ggcaatgttt tagagcgtcg tcaacgtgat gcagaaaaca gaagccaa                48

<210> SEQ ID NO 22
<211> LENGTH: 48
<212> TYPE: DNA
<213> ORGANISM: Streptococcus agalactiae

<400> SEQUENCE: 22
ggcaatgttc tagagcgtcg tcaacgcgat gttgagaata agagccaa                48

<210> SEQ ID NO 23
<211> LENGTH: 48
<212> TYPE: DNA
<213> ORGANISM: Streptococcus agalactiae

<400> SEQUENCE: 23
ggcaatgttt tagagcgtcg tcaacgtgat gcggaaaaca agagccaa                48

<210> SEQ ID NO 24
<211> LENGTH: 48
<212> TYPE: DNA
<213> ORGANISM: Streptococcus agalactiae

<400> SEQUENCE: 24
ggcaatgttt tagagcgtcg tcaacgtgat gcagaaaaca gaagccaa                48

<210> SEQ ID NO 25
<211> LENGTH: 48
<212> TYPE: DNA
<213> ORGANISM: Streptococcus agalactiae

<400> SEQUENCE: 25
ggcaatgttc tagagcgtcg tcaacgtgat gcagaaaaca gaagccaa                48

<210> SEQ ID NO 26
<211> LENGTH: 48
<212> TYPE: DNA
<213> ORGANISM: Streptococcus agalactiae

<400> SEQUENCE: 26
ggcaatgttc tagagcgtcg tcaacgcgat gcagaaaaca gaagccaa                48

<210> SEQ ID NO 27
<211> LENGTH: 48
```

```
<212> TYPE: DNA
<213> ORGANISM: Streptococcus agalactiae

<400> SEQUENCE: 27
ggtaatgttc tagagcgtcg tcaacgtgat gcagaaaaca gaagccaa            48

<210> SEQ ID NO 28
<211> LENGTH: 48
<212> TYPE: DNA
<213> ORGANISM: Streptococcus agalactiae

<400> SEQUENCE: 28
ggtaatgttc tagagcgtcg tcaacgtgat gcagaaaaca gaagccaa            48

<210> SEQ ID NO 29
<211> LENGTH: 48
<212> TYPE: DNA
<213> ORGANISM: Streptococcus agalactiae

<400> SEQUENCE: 29
ggtaatgttc tagagcgtcg tcaacgcgat gttgagaata agagccaa            48

<210> SEQ ID NO 30
<211> LENGTH: 48
<212> TYPE: DNA
<213> ORGANISM: Streptococcus agalactiae

<400> SEQUENCE: 30
ggcaatgttt tagagcgtcg tcaacgtgat gcggaaaaca agagccaa            48

<210> SEQ ID NO 31
<211> LENGTH: 48
<212> TYPE: DNA
<213> ORGANISM: Streptococcus agalactiae

<400> SEQUENCE: 31
ggcaatgttt tagagcgtcg tcaacgtgat gcagaaaaca gaagccaa            48

<210> SEQ ID NO 32
<211> LENGTH: 48
<212> TYPE: DNA
<213> ORGANISM: Streptococcus agalactiae

<400> SEQUENCE: 32
ggcaatgttt tagagcgtcg tcaacgtgat gcagaaaaca gaagccaa            48

<210> SEQ ID NO 33
<211> LENGTH: 48
<212> TYPE: DNA
<213> ORGANISM: Streptococcus agalactiae

<400> SEQUENCE: 33
ggcaatgttc tagagcgtcg tcaacgtgat gcagaaaaca gaagccaa            48

<210> SEQ ID NO 34
<211> LENGTH: 48
<212> TYPE: DNA
<213> ORGANISM: Streptococcus agalactiae

<400> SEQUENCE: 34
ggcaatgttc tagagcgtcg tcaacgtgat gcagaaaaca gaagccaa            48

<210> SEQ ID NO 35
<211> LENGTH: 48
```

```
<212> TYPE: DNA
<213> ORGANISM: Streptococcus agalactiae

<400> SEQUENCE: 35
ggcaatgttc tagagcgtcg tcaacgcgat gcagaaaaca gaagccaa          48

<210> SEQ ID NO 36
<211> LENGTH: 48
<212> TYPE: DNA
<213> ORGANISM: Streptococcus agalactiae

<400> SEQUENCE: 36
ggtaatgttc tagagcgtcg tcaacgtgat gcagaaaaca gaagccaa          48

<210> SEQ ID NO 37
<211> LENGTH: 48
<212> TYPE: DNA
<213> ORGANISM: Streptococcus agalactiae

<400> SEQUENCE: 37
ggcaatgttt tagagcgtcg tcaacgtgat gcagaaaaca gaagccaa          48

<210> SEQ ID NO 38
<211> LENGTH: 48
<212> TYPE: DNA
<213> ORGANISM: Streptococcus agalactiae

<400> SEQUENCE: 38
ggcaatgttt tagagcgtcg tcaacgtgat gcagaaaaca gaagccaa          48

<210> SEQ ID NO 39
<211> LENGTH: 48
<212> TYPE: DNA
<213> ORGANISM: Streptococcus agalactiae

<400> SEQUENCE: 39
ggcaatgttt tagagcgtcg tcaacgtgat gcggaaaaca agagccaa          48

<210> SEQ ID NO 40
<211> LENGTH: 48
<212> TYPE: DNA
<213> ORGANISM: Streptococcus agalactiae

<400> SEQUENCE: 40
ggcaatgttt tagagcgtcg tcaacgcgat gcagaaaaca gaagccaa          48

<210> SEQ ID NO 41
<211> LENGTH: 48
<212> TYPE: DNA
<213> ORGANISM: Streptococcus agalactiae

<400> SEQUENCE: 41
ggcaatgttt tagagcgtcg tcaacgtgat gcagaaaaca gaagccaa          48

<210> SEQ ID NO 42
<211> LENGTH: 48
<212> TYPE: DNA
<213> ORGANISM: Streptococcus agalactiae

<400> SEQUENCE: 42
ggcaatgttt tagagcgtcg tcaacgtgat gcagaaaaca gaagccaa          48

<210> SEQ ID NO 43
<211> LENGTH: 48
```

```
<212> TYPE: DNA
<213> ORGANISM: Streptococcus agalactiae

<400> SEQUENCE: 43
ggtaatgttc tagagcgtcg tcaacgcgat gttgaaaata aaagccaa         48

<210> SEQ ID NO 44
<211> LENGTH: 48
<212> TYPE: DNA
<213> ORGANISM: Streptococcus agalactiae

<400> SEQUENCE: 44
ggcaatgttt tagagcgtcg tcaacgtgat gcagaaaaca gaagccaa         48

<210> SEQ ID NO 45
<211> LENGTH: 48
<212> TYPE: DNA
<213> ORGANISM: Streptococcus agalactiae

<400> SEQUENCE: 45
ggtaatgttc tagagcgtcg tcaacgcgat gttgaaaata aaagccaa         48

<210> SEQ ID NO 46
<211> LENGTH: 48
<212> TYPE: DNA
<213> ORGANISM: Streptococcus agalactiae

<400> SEQUENCE: 46
ggcaatgttt tagagcgtcg tcaacgtgat gcagaaaaca gaagccaa         48

<210> SEQ ID NO 47
<211> LENGTH: 48
<212> TYPE: DNA
<213> ORGANISM: Streptococcus agalactiae

<400> SEQUENCE: 47
ggtaatgttc tagagcgtcg tcaacgtgat gcagaaaaca gaagccaa         48

<210> SEQ ID NO 48
<211> LENGTH: 48
<212> TYPE: DNA
<213> ORGANISM: Streptococcus agalactiae

<400> SEQUENCE: 48
ggcaatgttt tagagcgtcg tcaacgcgat gcagaaaaca gaagccaa         48

<210> SEQ ID NO 49
<211> LENGTH: 48
<212> TYPE: DNA
<213> ORGANISM: Streptococcus agalactiae

<400> SEQUENCE: 49
ggcaatgttc tagagcgtcg tcaacgtgat gctgaaaaca aaagccaa         48

<210> SEQ ID NO 50
<211> LENGTH: 48
<212> TYPE: DNA
<213> ORGANISM: Streptococcus agalactiae

<400> SEQUENCE: 50
ggcaatgttt tagagcgtcg tcaacgtgat gcagaaaaca gaagccaa         48

<210> SEQ ID NO 51
<211> LENGTH: 48
```

<212> TYPE: DNA
<213> ORGANISM: Streptococcus agalactiae

<400> SEQUENCE: 51
ggcaatgttt tagagcgtcg tcaacgtgat gctgaaaaca gaagccaa            48

<210> SEQ ID NO 52
<211> LENGTH: 48
<212> TYPE: DNA
<213> ORGANISM: Streptococcus agalactiae

<400> SEQUENCE: 52
ggcaatgttt tagagcgtcg tcaacgcgat gcagaaaaca gaagccaa            48

<210> SEQ ID NO 53
<211> LENGTH: 48
<212> TYPE: DNA
<213> ORGANISM: Streptococcus agalactiae

<400> SEQUENCE: 53
ggtaatgttc tagagcgtcg tcaacgtgat gcggaaaaca agagccaa            48

<210> SEQ ID NO 54
<211> LENGTH: 48
<212> TYPE: DNA
<213> ORGANISM: Streptococcus agalactiae

<400> SEQUENCE: 54
ggcaatgttt tagagcgtcg tcaacgtgat gcagaaaaca gaagccaa            48

<210> SEQ ID NO 55
<211> LENGTH: 48
<212> TYPE: DNA
<213> ORGANISM: Streptococcus agalactiae

<400> SEQUENCE: 55
ggcaatgttt tagagcgtcg tcaacgcgat gttgagaata agagccaa            48

<210> SEQ ID NO 56
<211> LENGTH: 48
<212> TYPE: DNA
<213> ORGANISM: Streptococcus agalactiae

<400> SEQUENCE: 56
ggcaatgttt tagagcgtcg tcaacgtgat gcggaaaaca agagccaa            48

<210> SEQ ID NO 57
<211> LENGTH: 48
<212> TYPE: DNA
<213> ORGANISM: Streptococcus agalactiae

<400> SEQUENCE: 57
ggtaatgttc tagagcgtcg tcaacgtgat gcggataaca agagccaa            48

<210> SEQ ID NO 58
<211> LENGTH: 48
<212> TYPE: DNA
<213> ORGANISM: Streptococcus agalactiae

<400> SEQUENCE: 58
ggcaatgttc tagaacgtcg tcaacgcgat gtagaaaaca gaagccaa            48

<210> SEQ ID NO 59
<211> LENGTH: 48

```
<212> TYPE: DNA
<213> ORGANISM: Streptococcus agalactiae

<400> SEQUENCE: 59
ggcaatgttc tagagcgtcg tcaacgcgat gcggataaca agagccaa        48

<210> SEQ ID NO 60
<211> LENGTH: 48
<212> TYPE: DNA
<213> ORGANISM: Streptococcus agalactiae

<400> SEQUENCE: 60
ggcaatgttt tagagcgccg ccaacgcgat gcagaaaaca aaagtcag        48

<210> SEQ ID NO 61
<211> LENGTH: 48
<212> TYPE: DNA
<213> ORGANISM: Streptococcus agalactiae

<400> SEQUENCE: 61
ggcaatgttc tagaacgtcg tcaacgtgat gttgagaata agagccaa        48

<210> SEQ ID NO 62
<211> LENGTH: 48
<212> TYPE: DNA
<213> ORGANISM: Streptococcus agalactiae

<400> SEQUENCE: 62
ggcaatgttc tagagcgtcg ccaacgtgat gcagaaaaca aaagtcag        48

<210> SEQ ID NO 63
<211> LENGTH: 48
<212> TYPE: DNA
<213> ORGANISM: Streptococcus agalactiae

<400> SEQUENCE: 63
ggtaatgttc tagagcgtcg tcaacgcgat gcagataaca agagccaa        48

<210> SEQ ID NO 64
<211> LENGTH: 48
<212> TYPE: DNA
<213> ORGANISM: Streptococcus agalactiae

<400> SEQUENCE: 64
ggcaatgttc tagaacgtcg tcaacgtgat gttgagaata agagccaa        48

<210> SEQ ID NO 65
<211> LENGTH: 48
<212> TYPE: DNA
<213> ORGANISM: Streptococcus agalactiae

<400> SEQUENCE: 65
ggcaatgttc tagaacgtcg tcaacgtgat gttgagaata agagccaa        48

<210> SEQ ID NO 66
<211> LENGTH: 48
<212> TYPE: DNA
<213> ORGANISM: Streptococcus agalactiae

<400> SEQUENCE: 66
ggcaatgttc tagagcgtcg ccaacgtgat gcagaaaaca aaagtcag        48

<210> SEQ ID NO 67
<211> LENGTH: 48
```

<210> SEQ ID NO 67
<211> LENGTH: 48
<212> TYPE: DNA
<213> ORGANISM: Streptococcus agalactiae

<400> SEQUENCE: 67
ggtaatgttc tagagcgtcg tcaacgcgat gcagataaca agagccaa      48

<210> SEQ ID NO 68
<211> LENGTH: 48
<212> TYPE: DNA
<213> ORGANISM: Streptococcus agalactiae

<400> SEQUENCE: 68
ggtaatgttc tagaacgtcg tcaacgcgat gtggaaaaca aaagtcag      48

<210> SEQ ID NO 69
<211> LENGTH: 48
<212> TYPE: DNA
<213> ORGANISM: Streptococcus agalactiae

<400> SEQUENCE: 69
ggcaatgttc tagagcgtcg ccaacgtgat gttgagaaca agagccaa      48

<210> SEQ ID NO 70
<211> LENGTH: 48
<212> TYPE: DNA
<213> ORGANISM: Streptococcus agalactiae

<400> SEQUENCE: 70
ggcaatgttt tagagcgtcg tcaacgcgat gcagaaaaca gaagccaa      48

<210> SEQ ID NO 71
<211> LENGTH: 48
<212> TYPE: DNA
<213> ORGANISM: Streptococcus agalactiae

<400> SEQUENCE: 71
ggtaatgttc tagagcgtcg tcaacgcgat gcagaaaaca gaagccaa      48

<210> SEQ ID NO 72
<211> LENGTH: 48
<212> TYPE: DNA
<213> ORGANISM: Streptococcus agalactiae

<400> SEQUENCE: 72
ggtaatgttc tagagcgtcg tcaacgtgat gcggaaaaca agagccaa      48

<210> SEQ ID NO 73
<211> LENGTH: 48
<212> TYPE: DNA
<213> ORGANISM: Streptococcus agalactiae

<400> SEQUENCE: 73
ggcaatgttc tagagcgtcg tcaacgcgat gcagaaaaca gaagccaa      48

<210> SEQ ID NO 74
<211> LENGTH: 48
<212> TYPE: DNA
<213> ORGANISM: Streptococcus agalactiae

<400> SEQUENCE: 74
ggtaatgttt tagaacgtcg tcaacgcgat gttgagaaca agagccaa      48

<210> SEQ ID NO 75
<211> LENGTH: 48

```
<212> TYPE: DNA
<213> ORGANISM: Streptococcus agalactiae

<400> SEQUENCE: 75
ggtaatgttt tagagcgtcg ccaacgtgat gcggaaaaca aaagtcag            48

<210> SEQ ID NO 76
<211> LENGTH: 48
<212> TYPE: DNA
<213> ORGANISM: Streptococcus agalactiae

<400> SEQUENCE: 76
ggcaatgttt tagagcgtcg tcaacgtgat gcagaaaaca gaagccaa            48

<210> SEQ ID NO 77
<211> LENGTH: 48
<212> TYPE: DNA
<213> ORGANISM: Streptococcus agalactiae

<400> SEQUENCE: 77
ggtaatgttc tagagcgtcg tcaacgcgat gttgagaata agagccaa            48

<210> SEQ ID NO 78
<211> LENGTH: 48
<212> TYPE: DNA
<213> ORGANISM: Streptococcus agalactiae

<400> SEQUENCE: 78
ggcaatgttc tagagcgtcg tcaacgcgat gttgagaata agagccaa            48

<210> SEQ ID NO 79
<211> LENGTH: 48
<212> TYPE: DNA
<213> ORGANISM: Streptococcus agalactiae

<400> SEQUENCE: 79
ggtaatgttc tagagcgtcg tcaacgcgat gttgagaata agagccaa            48

<210> SEQ ID NO 80
<211> LENGTH: 48
<212> TYPE: DNA
<213> ORGANISM: Streptococcus agalactiae

<400> SEQUENCE: 80
ggtaatgttc tagagcgtcg tcaacgtgat gcggaaaaca agagccaa            48

<210> SEQ ID NO 81
<211> LENGTH: 48
<212> TYPE: DNA
<213> ORGANISM: Streptococcus agalactiae

<400> SEQUENCE: 81
ggcaatgttc tagagcgtcg tcaacgcgat gcagaaaaca gaagccaa            48

<210> SEQ ID NO 82
<211> LENGTH: 48
<212> TYPE: DNA
<213> ORGANISM: Streptococcus agalactiae

<400> SEQUENCE: 82
ggtaatgttt tagagcgtcg ccaacatgat gttgagaata agagtcaa            48

<210> SEQ ID NO 83
<211> LENGTH: 48
```

<212> TYPE: DNA
<213> ORGANISM: Streptococcus agalactiae

<400> SEQUENCE: 83
ggtaatgttc tagagcgtcg ccaacgtgat gcggataaca agagccaa        48

<210> SEQ ID NO 84
<211> LENGTH: 48
<212> TYPE: DNA
<213> ORGANISM: Streptococcus agalactiae

<400> SEQUENCE: 84
ggtaatgttt tagagcgtcg ccaacgtgat gcagataaca aaagtcag        48

<210> SEQ ID NO 85
<211> LENGTH: 48
<212> TYPE: DNA
<213> ORGANISM: Streptococcus agalactiae

<400> SEQUENCE: 85
ggcaatgttc tagaacgtcg ccaacgtgat gttgataaca agagccaa        48

<210> SEQ ID NO 86
<211> LENGTH: 48
<212> TYPE: DNA
<213> ORGANISM: Streptococcus agalactiae

<400> SEQUENCE: 86
ggtaacgttc tagagcgtcg ccaacgcgat gctgataaca agagccaa        48

<210> SEQ ID NO 87
<211> LENGTH: 48
<212> TYPE: DNA
<213> ORGANISM: Streptococcus agalactiae

<400> SEQUENCE: 87
ggtaatgttt tagagcgccg ccaacgcgat gcagataaca aaagtcaa        48

<210> SEQ ID NO 88
<211> LENGTH: 48
<212> TYPE: DNA
<213> ORGANISM: Streptococcus agalactiae

<400> SEQUENCE: 88
ggtaatgttc tagagcgtcg ccaacgcgat gttgataaca agagccag        48

<210> SEQ ID NO 89
<211> LENGTH: 48
<212> TYPE: DNA
<213> ORGANISM: Streptococcus agalactiae

<400> SEQUENCE: 89
ggtaatgttt tagagcgtcg ccaacgcgat gcagataaca aaagtcag        48

<210> SEQ ID NO 90
<211> LENGTH: 48
<212> TYPE: DNA
<213> ORGANISM: Streptococcus agalactiae

<400> SEQUENCE: 90
ggtaatgttt tagagcgtcg ccaacgcgat gttgataaca aaagccaa        48

<210> SEQ ID NO 91
<211> LENGTH: 48

```
<212> TYPE: DNA
<213> ORGANISM: Streptococcus agalactiae

<400> SEQUENCE: 91
ggtaatgttt tagagcgtcg ccaacgtgat gctgataaca aaagtcag          48

<210> SEQ ID NO 92
<211> LENGTH: 48
<212> TYPE: DNA
<213> ORGANISM: Streptococcus agalactiae

<400> SEQUENCE: 92
ggcaatgttc tagagcgtcg ccaacgtgat gcggataaca aaagccaa          48

<210> SEQ ID NO 93
<211> LENGTH: 48
<212> TYPE: DNA
<213> ORGANISM: Streptococcus agalactiae

<400> SEQUENCE: 93
ggtaatgttc tagagcgtcg ccaacgcgat gcggataaca aaagtcag          48

<210> SEQ ID NO 94
<211> LENGTH: 48
<212> TYPE: DNA
<213> ORGANISM: Streptococcus agalactiae

<400> SEQUENCE: 94
ggcaatgttt tagagcgtcg ccaacgtgat gctgataaca aaagtcaa          48

<210> SEQ ID NO 95
<211> LENGTH: 48
<212> TYPE: DNA
<213> ORGANISM: Streptococcus agalactiae

<400> SEQUENCE: 95
ggtaatgttc tagagcgtcg ccaacgcgat gcagataaca aaagccaa          48

<210> SEQ ID NO 96
<211> LENGTH: 48
<212> TYPE: DNA
<213> ORGANISM: Streptococcus agalactiae

<400> SEQUENCE: 96
ggtaatgttc tagagcgtcg ccaacgcgat gctgataaca aaagtcaa          48

<210> SEQ ID NO 97
<211> LENGTH: 48
<212> TYPE: DNA
<213> ORGANISM: Streptococcus agalactiae

<400> SEQUENCE: 97
ggtaatgttc tagagcgtcg ccaacgtgat gctgataaca agagccaa          48

<210> SEQ ID NO 98
<211> LENGTH: 48
<212> TYPE: DNA
<213> ORGANISM: Streptococcus agalactiae

<400> SEQUENCE: 98
ggcaatgttc ttgagcgtcg tcaacgcgat gtcgataaca aaagtcag          48

<210> SEQ ID NO 99
<211> LENGTH: 48
```

```
<212> TYPE: DNA
<213> ORGANISM: Streptococcus agalactiae

<400> SEQUENCE: 99
ggtaatgttt tagagcgtcg ccaacgtgat gcggataaca agagtcaa          48

<210> SEQ ID NO 100
<211> LENGTH: 48
<212> TYPE: DNA
<213> ORGANISM: Streptococcus agalactiae

<400> SEQUENCE: 100
ggtaatgttt tagagcgtcg ccaacgcgat gcggataaca agagccaa          48

<210> SEQ ID NO 101
<211> LENGTH: 48
<212> TYPE: DNA
<213> ORGANISM: Streptococcus agalactiae

<400> SEQUENCE: 101
ggtaatgttt tagagcgtcg ccaacgcgat gcggataaca agagtcaa          48

<210> SEQ ID NO 102
<211> LENGTH: 48
<212> TYPE: DNA
<213> ORGANISM: Streptococcus agalactiae

<400> SEQUENCE: 102
ggtaatgttt tagagcgtcg ccaacgcgat gcggataaca agagccaa          48

<210> SEQ ID NO 103
<211> LENGTH: 48
<212> TYPE: DNA
<213> ORGANISM: Streptococcus agalactiae

<400> SEQUENCE: 103
ggtaatgttt tagagcgtcg ccaacgcgat gcagataaca aaagtcaa          48

<210> SEQ ID NO 104
<211> LENGTH: 48
<212> TYPE: DNA
<213> ORGANISM: Streptococcus agalactiae

<400> SEQUENCE: 104
ggtaatgttt tagagcgtcg ccaacgcgat gctgataaca agagccaa          48

<210> SEQ ID NO 105
<211> LENGTH: 48
<212> TYPE: DNA
<213> ORGANISM: Streptococcus agalactiae

<400> SEQUENCE: 105
ggtaatgttt tagagcgtcg tcaacgtgat gcagataaca aaagtcag          48

<210> SEQ ID NO 106
<211> LENGTH: 48
<212> TYPE: DNA
<213> ORGANISM: Streptococcus agalactiae

<400> SEQUENCE: 106
ggcaatgttt tagagcgtcg tcaacgtgat gcggataaca agagccaa          48

<210> SEQ ID NO 107
<211> LENGTH: 48
```

```
<212> TYPE: DNA
<213> ORGANISM: Streptococcus agalactiae

<400> SEQUENCE: 107
ggtaatgttt tagagcgtcg ccaacgtgat gcggataaca agagccag          48

<210> SEQ ID NO 108
<211> LENGTH: 48
<212> TYPE: DNA
<213> ORGANISM: Streptococcus agalactiae

<400> SEQUENCE: 108
ggcaatgttc tagaacgtcg tcaacgtgat gcggataaca agagccaa          48

<210> SEQ ID NO 109
<211> LENGTH: 48
<212> TYPE: DNA
<213> ORGANISM: Streptococcus agalactiae

<400> SEQUENCE: 109
ggtaacgttt tagagcgtcg ccaacgtgat gcggataaca agagccag          48

<210> SEQ ID NO 110
<211> LENGTH: 48
<212> TYPE: DNA
<213> ORGANISM: Streptococcus agalactiae

<400> SEQUENCE: 110
ggcaatgttt tagagcgccg ccaacgcgat gcagataaca aaagtcaa          48

<210> SEQ ID NO 111
<211> LENGTH: 48
<212> TYPE: DNA
<213> ORGANISM: Streptococcus agalactiae

<400> SEQUENCE: 111
ggtaatgttc tagagcgtcg ccaacgcgat gcagataaca agagccag          48

<210> SEQ ID NO 112
<211> LENGTH: 48
<212> TYPE: DNA
<213> ORGANISM: Streptococcus agalactiae

<400> SEQUENCE: 112
ggtaatgttc tagagcgtcg ccaacgcgat gcggaaaaca aaagtcaa          48

<210> SEQ ID NO 113
<211> LENGTH: 16
<212> TYPE: PRT
<213> ORGANISM: Streptococcus agalactiae

<400> SEQUENCE: 113

Gly Asn Val Leu Glu Arg Arg Gln Arg Asp Ala Glu Asn Arg Ser Gln
1               5                   10                  15

<210> SEQ ID NO 114
<211> LENGTH: 16
<212> TYPE: PRT
<213> ORGANISM: Streptococcus agalactiae

<400> SEQUENCE: 114

Gly Asn Val Leu Glu Arg Arg Gln Arg Asp Val Glu Asn Lys Ser Gln
1               5                   10                  15
```

```
<210> SEQ ID NO 115
<211> LENGTH: 16
<212> TYPE: PRT
<213> ORGANISM: Streptococcus agalactiae

<400> SEQUENCE: 115

Gly Asn Val Leu Glu Arg Arg Gln Arg Asp Ala Glu Asn Lys Ser Gln
1               5                   10                  15

<210> SEQ ID NO 116
<211> LENGTH: 16
<212> TYPE: PRT
<213> ORGANISM: Streptococcus agalactiae

<400> SEQUENCE: 116

Gly Asn Val Leu Glu Arg Arg Gln Arg Asp Ala Glu Asn Arg Ser Gln
1               5                   10                  15

<210> SEQ ID NO 117
<211> LENGTH: 16
<212> TYPE: PRT
<213> ORGANISM: Streptococcus agalactiae

<400> SEQUENCE: 117

Gly Asn Val Leu Glu Arg Arg Gln Arg Asp Ala Glu Asn Arg Ser Gln
1               5                   10                  15

<210> SEQ ID NO 118
<211> LENGTH: 16
<212> TYPE: PRT
<213> ORGANISM: Streptococcus agalactiae

<400> SEQUENCE: 118

Gly Asn Val Leu Glu Arg Arg Gln Arg Asp Ala Glu Asn Arg Ser Gln
1               5                   10                  15

<210> SEQ ID NO 119
<211> LENGTH: 16
<212> TYPE: PRT
<213> ORGANISM: Streptococcus agalactiae

<400> SEQUENCE: 119

Gly Asn Val Leu Glu Arg Arg Gln Arg Asp Ala Glu Asn Arg Ser Gln
1               5                   10                  15

<210> SEQ ID NO 120
<211> LENGTH: 16
<212> TYPE: PRT
<213> ORGANISM: Streptococcus agalactiae

<400> SEQUENCE: 120

Gly Asn Val Leu Glu Arg Arg Gln Arg Asp Ala Glu Asn Arg Ser Gln
1               5                   10                  15

<210> SEQ ID NO 121
<211> LENGTH: 16
<212> TYPE: PRT
<213> ORGANISM: Streptococcus agalactiae

<400> SEQUENCE: 121

Gly Asn Val Leu Glu Arg Arg Gln Arg Asp Val Glu Asn Lys Ser Gln
1               5                   10                  15

<210> SEQ ID NO 122
<211> LENGTH: 16
<212> TYPE: PRT
```

<213> ORGANISM: Streptococcus agalactiae

<400> SEQUENCE: 122

Gly Asn Val Leu Glu Arg Arg Gln Arg Asp Ala Glu Asn Lys Ser Gln
1               5                   10                  15

<210> SEQ ID NO 123
<211> LENGTH: 16
<212> TYPE: PRT
<213> ORGANISM: Streptococcus agalactiae

<400> SEQUENCE: 123

Gly Asn Val Leu Glu Arg Arg Gln Arg Asp Ala Glu Asn Arg Ser Gln
1               5                   10                  15

<210> SEQ ID NO 124
<211> LENGTH: 16
<212> TYPE: PRT
<213> ORGANISM: Streptococcus agalactiae

<400> SEQUENCE: 124

Gly Asn Val Leu Glu Arg Arg Gln Arg Asp Ala Glu Asn Arg Ser Gln
1               5                   10                  15

<210> SEQ ID NO 125
<211> LENGTH: 16
<212> TYPE: PRT
<213> ORGANISM: Streptococcus agalactiae

<400> SEQUENCE: 125

Gly Asn Val Leu Glu Arg Arg Gln Arg Asp Ala Glu Asn Arg Ser Gln
1               5                   10                  15

<210> SEQ ID NO 126
<211> LENGTH: 16
<212> TYPE: PRT
<213> ORGANISM: Streptococcus agalactiae

<400> SEQUENCE: 126

Gly Asn Val Leu Glu Arg Arg Gln Arg Asp Ala Glu Asn Arg Ser Gln
1               5                   10                  15

<210> SEQ ID NO 127
<211> LENGTH: 16
<212> TYPE: PRT
<213> ORGANISM: Streptococcus agalactiae

<400> SEQUENCE: 127

Gly Asn Val Leu Glu Arg Arg Gln Arg Asp Ala Glu Asn Arg Ser Gln
1               5                   10                  15

<210> SEQ ID NO 128
<211> LENGTH: 16
<212> TYPE: PRT
<213> ORGANISM: Streptococcus agalactiae

<400> SEQUENCE: 128

Gly Asn Val Leu Glu Arg Arg Gln Arg Asp Ala Glu Asn Arg Ser Gln
1               5                   10                  15

<210> SEQ ID NO 129
<211> LENGTH: 16
<212> TYPE: PRT
<213> ORGANISM: Streptococcus agalactiae

<400> SEQUENCE: 129

Gly Asn Val Leu Glu Arg Arg Gln Arg Asp Ala Glu Asn Arg Ser Gln
1               5                   10                  15

<210> SEQ ID NO 130
<211> LENGTH: 16
<212> TYPE: PRT
<213> ORGANISM: Streptococcus agalactiae

<400> SEQUENCE: 130

Gly Asn Val Leu Glu Arg Arg Gln Arg Asp Ala Glu Asn Arg Ser Gln
1               5                   10                  15

<210> SEQ ID NO 131
<211> LENGTH: 16
<212> TYPE: PRT
<213> ORGANISM: Streptococcus agalactiae

<400> SEQUENCE: 131

Gly Asn Val Leu Glu Arg Arg Gln Arg Asp Ala Glu Asn Lys Ser Gln
1               5                   10                  15

<210> SEQ ID NO 132
<211> LENGTH: 16
<212> TYPE: PRT
<213> ORGANISM: Streptococcus agalactiae

<400> SEQUENCE: 132

Gly Asn Val Leu Glu Arg Arg Gln Arg Asp Ala Glu Asn Arg Ser Gln
1               5                   10                  15

<210> SEQ ID NO 133
<211> LENGTH: 16
<212> TYPE: PRT
<213> ORGANISM: Streptococcus agalactiae

<400> SEQUENCE: 133

Gly Asn Val Leu Glu Arg Arg Gln Arg Asp Ala Glu Asn Arg Ser Gln
1               5                   10                  15

<210> SEQ ID NO 134
<211> LENGTH: 16
<212> TYPE: PRT
<213> ORGANISM: Streptococcus agalactiae

<400> SEQUENCE: 134

Gly Asn Val Leu Glu Arg Arg Gln Arg Asp Ala Glu Asn Arg Ser Gln
1               5                   10                  15

<210> SEQ ID NO 135
<211> LENGTH: 16
<212> TYPE: PRT
<213> ORGANISM: Streptococcus agalactiae

<400> SEQUENCE: 135

Gly Asn Val Leu Glu Arg Arg Gln Arg Asp Val Glu Asn Lys Ser Gln
1               5                   10                  15

<210> SEQ ID NO 136
<211> LENGTH: 16
<212> TYPE: PRT
<213> ORGANISM: Streptococcus agalactiae

<400> SEQUENCE: 136

Gly Asn Val Leu Glu Arg Arg Gln Arg Asp Ala Glu Asn Arg Ser Gln
1               5                   10                  15

<210> SEQ ID NO 137
<211> LENGTH: 16
<212> TYPE: PRT
<213> ORGANISM: Streptococcus agalactiae

<400> SEQUENCE: 137

Gly Asn Val Leu Glu Arg Arg Gln Arg Asp Val Glu Asn Lys Ser Gln
1               5                   10                  15

<210> SEQ ID NO 138
<211> LENGTH: 16
<212> TYPE: PRT
<213> ORGANISM: Streptococcus agalactiae

<400> SEQUENCE: 138

Gly Asn Val Leu Glu Arg Arg Gln Arg Asp Ala Glu Asn Arg Ser Gln
1               5                   10                  15

<210> SEQ ID NO 139
<211> LENGTH: 16
<212> TYPE: PRT
<213> ORGANISM: Streptococcus agalactiae

<400> SEQUENCE: 139

Gly Asn Val Leu Glu Arg Arg Gln Arg Asp Ala Glu Asn Arg Ser Gln
1               5                   10                  15

<210> SEQ ID NO 140
<211> LENGTH: 16
<212> TYPE: PRT
<213> ORGANISM: Streptococcus agalactiae

<400> SEQUENCE: 140

Gly Asn Val Leu Glu Arg Arg Gln Arg Asp Ala Glu Asn Arg Ser Gln
1               5                   10                  15

<210> SEQ ID NO 141
<211> LENGTH: 16
<212> TYPE: PRT
<213> ORGANISM: Streptococcus agalactiae

<400> SEQUENCE: 141

Gly Asn Val Leu Glu Arg Arg Gln Arg Asp Ala Glu Asn Lys Ser Gln
1               5                   10                  15

<210> SEQ ID NO 142
<211> LENGTH: 16
<212> TYPE: PRT
<213> ORGANISM: Streptococcus agalactiae

<400> SEQUENCE: 142

Gly Asn Val Leu Glu Arg Arg Gln Arg Asp Ala Glu Asn Arg Ser Gln
1               5                   10                  15

<210> SEQ ID NO 143
<211> LENGTH: 16
<212> TYPE: PRT
<213> ORGANISM: Streptococcus agalactiae

<400> SEQUENCE: 143

Gly Asn Val Leu Glu Arg Arg Gln Arg Asp Ala Glu Asn Arg Ser Gln
1               5                   10                  15

<210> SEQ ID NO 144

```
<211> LENGTH: 16
<212> TYPE: PRT
<213> ORGANISM: Streptococcus agalactiae

<400> SEQUENCE: 144

Gly Asn Val Leu Glu Arg Arg Gln Arg Asp Ala Glu Asn Arg Ser Gln
1               5                   10                  15

<210> SEQ ID NO 145
<211> LENGTH: 16
<212> TYPE: PRT
<213> ORGANISM: Streptococcus agalactiae

<400> SEQUENCE: 145

Gly Asn Val Leu Glu Arg Arg Gln Arg Asp Ala Glu Asn Lys Ser Gln
1               5                   10                  15

<210> SEQ ID NO 146
<211> LENGTH: 16
<212> TYPE: PRT
<213> ORGANISM: Streptococcus agalactiae

<400> SEQUENCE: 146

Gly Asn Val Leu Glu Arg Arg Gln Arg Asp Ala Glu Asn Arg Ser Gln
1               5                   10                  15

<210> SEQ ID NO 147
<211> LENGTH: 16
<212> TYPE: PRT
<213> ORGANISM: Streptococcus agalactiae

<400> SEQUENCE: 147

Gly Asn Val Leu Glu Arg Arg Gln Arg Asp Val Glu Asn Lys Ser Gln
1               5                   10                  15

<210> SEQ ID NO 148
<211> LENGTH: 16
<212> TYPE: PRT
<213> ORGANISM: Streptococcus agalactiae

<400> SEQUENCE: 148

Gly Asn Val Leu Glu Arg Arg Gln Arg Asp Ala Glu Asn Lys Ser Gln
1               5                   10                  15

<210> SEQ ID NO 149
<211> LENGTH: 16
<212> TYPE: PRT
<213> ORGANISM: Streptococcus agalactiae

<400> SEQUENCE: 149

Gly Asn Val Leu Glu Arg Arg Gln Arg Asp Ala Asp Asn Lys Ser Gln
1               5                   10                  15

<210> SEQ ID NO 150
<211> LENGTH: 16
<212> TYPE: PRT
<213> ORGANISM: Streptococcus agalactiae

<400> SEQUENCE: 150

Gly Asn Val Leu Glu Arg Arg Gln Arg Asp Val Glu Asn Arg Ser Gln
1               5                   10                  15

<210> SEQ ID NO 151
<211> LENGTH: 16
<212> TYPE: PRT
<213> ORGANISM: Streptococcus agalactiae
```

<400> SEQUENCE: 151

Gly Asn Val Leu Glu Arg Arg Gln Arg Asp Ala Asp Asn Lys Ser Gln
1               5                   10                  15

<210> SEQ ID NO 152
<211> LENGTH: 16
<212> TYPE: PRT
<213> ORGANISM: Streptococcus agalactiae

<400> SEQUENCE: 152

Gly Asn Val Leu Glu Arg Arg Gln Arg Asp Ala Glu Asn Lys Ser Gln
1               5                   10                  15

<210> SEQ ID NO 153
<211> LENGTH: 16
<212> TYPE: PRT
<213> ORGANISM: Streptococcus agalactiae

<400> SEQUENCE: 153

Gly Asn Val Leu Glu Arg Arg Gln Arg Asp Val Glu Asn Lys Ser Gln
1               5                   10                  15

<210> SEQ ID NO 154
<211> LENGTH: 16
<212> TYPE: PRT
<213> ORGANISM: Streptococcus agalactiae

<400> SEQUENCE: 154

Gly Asn Val Leu Glu Arg Arg Gln Arg Asp Ala Glu Asn Lys Ser Gln
1               5                   10                  15

<210> SEQ ID NO 155
<211> LENGTH: 16
<212> TYPE: PRT
<213> ORGANISM: Streptococcus agalactiae

<400> SEQUENCE: 155

Gly Asn Val Leu Glu Arg Arg Gln Arg Asp Ala Asp Asn Lys Ser Gln
1               5                   10                  15

<210> SEQ ID NO 156
<211> LENGTH: 16
<212> TYPE: PRT
<213> ORGANISM: Streptococcus agalactiae

<400> SEQUENCE: 156

Gly Asn Val Leu Glu Arg Arg Gln Arg Asp Val Glu Asn Lys Ser Gln
1               5                   10                  15

<210> SEQ ID NO 157
<211> LENGTH: 16
<212> TYPE: PRT
<213> ORGANISM: Streptococcus agalactiae

<400> SEQUENCE: 157

Gly Asn Val Leu Glu Arg Arg Gln Arg Asp Val Glu Asn Lys Ser Gln
1               5                   10                  15

<210> SEQ ID NO 158
<211> LENGTH: 16
<212> TYPE: PRT
<213> ORGANISM: Streptococcus agalactiae

<400> SEQUENCE: 158

Gly Asn Val Leu Glu Arg Arg Gln Arg Asp Ala Glu Asn Lys Ser Gln
1               5                   10                  15

<210> SEQ ID NO 159
<211> LENGTH: 16
<212> TYPE: PRT
<213> ORGANISM: Streptococcus agalactiae

<400> SEQUENCE: 159

Gly Asn Val Leu Glu Arg Arg Gln Arg Asp Ala Asp Asn Lys Ser Gln
1               5                   10                  15

<210> SEQ ID NO 160
<211> LENGTH: 16
<212> TYPE: PRT
<213> ORGANISM: Streptococcus agalactiae

<400> SEQUENCE: 160

Gly Asn Val Leu Glu Arg Arg Gln Arg Asp Val Glu Asn Lys Ser Gln
1               5                   10                  15

<210> SEQ ID NO 161
<211> LENGTH: 16
<212> TYPE: PRT
<213> ORGANISM: Streptococcus agalactiae

<400> SEQUENCE: 161

Gly Asn Val Leu Glu Arg Arg Gln Arg Asp Val Glu Asn Lys Ser Gln
1               5                   10                  15

<210> SEQ ID NO 162
<211> LENGTH: 16
<212> TYPE: PRT
<213> ORGANISM: Streptococcus agalactiae

<400> SEQUENCE: 162

Gly Asn Val Leu Glu Arg Arg Gln Arg Asp Ala Glu Asn Arg Ser Gln
1               5                   10                  15

<210> SEQ ID NO 163
<211> LENGTH: 16
<212> TYPE: PRT
<213> ORGANISM: Streptococcus agalactiae

<400> SEQUENCE: 163

Gly Asn Val Leu Glu Arg Arg Gln Arg Asp Ala Glu Asn Arg Ser Gln
1               5                   10                  15

<210> SEQ ID NO 164
<211> LENGTH: 16
<212> TYPE: PRT
<213> ORGANISM: Streptococcus agalactiae

<400> SEQUENCE: 164

Gly Asn Val Leu Glu Arg Arg Gln Arg Asp Ala Glu Asn Lys Ser Gln
1               5                   10                  15

<210> SEQ ID NO 165
<211> LENGTH: 16
<212> TYPE: PRT
<213> ORGANISM: Streptococcus agalactiae

<400> SEQUENCE: 165

Gly Asn Val Leu Glu Arg Arg Gln Arg Asp Ala Glu Asn Arg Ser Gln
1               5                   10                  15

```
<210> SEQ ID NO 166
<211> LENGTH: 16
<212> TYPE: PRT
<213> ORGANISM: Streptococcus agalactiae

<400> SEQUENCE: 166

Gly Asn Val Leu Glu Arg Arg Gln Arg Asp Val Glu Asn Lys Ser Gln
1               5                   10                  15

<210> SEQ ID NO 167
<211> LENGTH: 16
<212> TYPE: PRT
<213> ORGANISM: Streptococcus agalactiae

<400> SEQUENCE: 167

Gly Asn Val Leu Glu Arg Arg Gln Arg Asp Ala Glu Asn Lys Ser Gln
1               5                   10                  15

<210> SEQ ID NO 168
<211> LENGTH: 16
<212> TYPE: PRT
<213> ORGANISM: Streptococcus agalactiae

<400> SEQUENCE: 168

Gly Asn Val Leu Glu Arg Arg Gln Arg Asp Ala Glu Asn Arg Ser Gln
1               5                   10                  15

<210> SEQ ID NO 169
<211> LENGTH: 16
<212> TYPE: PRT
<213> ORGANISM: Streptococcus agalactiae

<400> SEQUENCE: 169

Gly Asn Val Leu Glu Arg Arg Gln Arg Asp Val Glu Asn Lys Ser Gln
1               5                   10                  15

<210> SEQ ID NO 170
<211> LENGTH: 16
<212> TYPE: PRT
<213> ORGANISM: Streptococcus agalactiae

<400> SEQUENCE: 170

Gly Asn Val Leu Glu Arg Arg Gln Arg Asp Val Glu Asn Lys Ser Gln
1               5                   10                  15

<210> SEQ ID NO 171
<211> LENGTH: 16
<212> TYPE: PRT
<213> ORGANISM: Streptococcus agalactiae

<400> SEQUENCE: 171

Gly Asn Val Leu Glu Arg Arg Gln Arg Asp Val Glu Asn Lys Ser Gln
1               5                   10                  15

<210> SEQ ID NO 172
<211> LENGTH: 16
<212> TYPE: PRT
<213> ORGANISM: Streptococcus agalactiae

<400> SEQUENCE: 172

Gly Asn Val Leu Glu Arg Arg Gln Arg Asp Ala Glu Asn Lys Ser Gln
1               5                   10                  15

<210> SEQ ID NO 173
<211> LENGTH: 16
```

```
<212> TYPE: PRT
<213> ORGANISM: Streptococcus agalactiae

<400> SEQUENCE: 173

Gly Asn Val Leu Glu Arg Arg Gln Arg Asp Ala Glu Asn Arg Ser Gln
1               5                   10                  15

<210> SEQ ID NO 174
<211> LENGTH: 16
<212> TYPE: PRT
<213> ORGANISM: Streptococcus agalactiae

<400> SEQUENCE: 174

Gly Asn Val Leu Glu Arg Arg Gln His Asp Val Glu Asn Lys Ser Gln
1               5                   10                  15

<210> SEQ ID NO 175
<211> LENGTH: 16
<212> TYPE: PRT
<213> ORGANISM: Streptococcus agalactiae

<400> SEQUENCE: 175

Gly Asn Val Leu Glu Arg Arg Gln Arg Asp Ala Asp Asn Lys Ser Gln
1               5                   10                  15

<210> SEQ ID NO 176
<211> LENGTH: 16
<212> TYPE: PRT
<213> ORGANISM: Streptococcus agalactiae

<400> SEQUENCE: 176

Gly Asn Val Leu Glu Arg Arg Gln Arg Asp Ala Asp Asn Lys Ser Gln
1               5                   10                  15

<210> SEQ ID NO 177
<211> LENGTH: 16
<212> TYPE: PRT
<213> ORGANISM: Streptococcus agalactiae

<400> SEQUENCE: 177

Gly Asn Val Leu Glu Arg Arg Gln Arg Asp Val Asp Asn Lys Ser Gln
1               5                   10                  15

<210> SEQ ID NO 178
<211> LENGTH: 16
<212> TYPE: PRT
<213> ORGANISM: Streptococcus agalactiae

<400> SEQUENCE: 178

Gly Asn Val Leu Glu Arg Arg Gln Arg Asp Ala Asp Asn Lys Ser Gln
1               5                   10                  15

<210> SEQ ID NO 179
<211> LENGTH: 16
<212> TYPE: PRT
<213> ORGANISM: Streptococcus agalactiae

<400> SEQUENCE: 179

Gly Asn Val Leu Glu Arg Arg Gln Arg Asp Ala Asp Asn Lys Ser Gln
1               5                   10                  15

<210> SEQ ID NO 180
<211> LENGTH: 16
<212> TYPE: PRT
<213> ORGANISM: Streptococcus agalactiae
```

```
<400> SEQUENCE: 180

Gly Asn Val Leu Glu Arg Arg Gln Arg Asp Val Asp Asn Lys Ser Gln
1               5                   10                  15

<210> SEQ ID NO 181
<211> LENGTH: 16
<212> TYPE: PRT
<213> ORGANISM: Streptococcus agalactiae

<400> SEQUENCE: 181

Gly Asn Val Leu Glu Arg Arg Gln Arg Asp Ala Asp Asn Lys Ser Gln
1               5                   10                  15

<210> SEQ ID NO 182
<211> LENGTH: 16
<212> TYPE: PRT
<213> ORGANISM: Streptococcus agalactiae

<400> SEQUENCE: 182

Gly Asn Val Leu Glu Arg Arg Gln Arg Asp Val Asp Asn Lys Ser Gln
1               5                   10                  15

<210> SEQ ID NO 183
<211> LENGTH: 16
<212> TYPE: PRT
<213> ORGANISM: Streptococcus agalactiae

<400> SEQUENCE: 183

Gly Asn Val Leu Glu Arg Arg Gln Arg Asp Ala Asp Asn Lys Ser Gln
1               5                   10                  15

<210> SEQ ID NO 184
<211> LENGTH: 16
<212> TYPE: PRT
<213> ORGANISM: Streptococcus agalactiae

<400> SEQUENCE: 184

Gly Asn Val Leu Glu Arg Arg Gln Arg Asp Ala Asp Asn Lys Ser Gln
1               5                   10                  15

<210> SEQ ID NO 185
<211> LENGTH: 16
<212> TYPE: PRT
<213> ORGANISM: Streptococcus agalactiae

<400> SEQUENCE: 185

Gly Asn Val Leu Glu Arg Arg Gln Arg Asp Ala Asp Asn Lys Ser Gln
1               5                   10                  15

<210> SEQ ID NO 186
<211> LENGTH: 16
<212> TYPE: PRT
<213> ORGANISM: Streptococcus agalactiae

<400> SEQUENCE: 186

Gly Asn Val Leu Glu Arg Arg Gln Arg Asp Ala Asp Asn Lys Ser Gln
1               5                   10                  15

<210> SEQ ID NO 187
<211> LENGTH: 16
<212> TYPE: PRT
<213> ORGANISM: Streptococcus agalactiae

<400> SEQUENCE: 187

Gly Asn Val Leu Glu Arg Arg Gln Arg Asp Ala Asp Asn Lys Ser Gln
```

<210> SEQ ID NO 188
<211> LENGTH: 16
<212> TYPE: PRT
<213> ORGANISM: Streptococcus agalactiae

<400> SEQUENCE: 188

Gly Asn Val Leu Glu Arg Arg Gln Arg Asp Ala Asp Asn Lys Ser Gln
1               5                   10                  15

<210> SEQ ID NO 189
<211> LENGTH: 16
<212> TYPE: PRT
<213> ORGANISM: Streptococcus agalactiae

<400> SEQUENCE: 189

Gly Asn Val Leu Glu Arg Arg Gln Arg Asp Ala Asp Asn Lys Ser Gln
1               5                   10                  15

<210> SEQ ID NO 190
<211> LENGTH: 16
<212> TYPE: PRT
<213> ORGANISM: Streptococcus agalactiae

<400> SEQUENCE: 190

Gly Asn Val Leu Glu Arg Arg Gln Arg Asp Val Asp Asn Lys Ser Gln
1               5                   10                  15

<210> SEQ ID NO 191
<211> LENGTH: 16
<212> TYPE: PRT
<213> ORGANISM: Streptococcus agalactiae

<400> SEQUENCE: 191

Gly Asn Val Leu Glu Arg Arg Gln Arg Asp Ala Asp Asn Lys Ser Gln
1               5                   10                  15

<210> SEQ ID NO 192
<211> LENGTH: 16
<212> TYPE: PRT
<213> ORGANISM: Streptococcus agalactiae

<400> SEQUENCE: 192

Gly Asn Val Leu Glu Arg Arg Gln Arg Asp Ala Asp Asn Lys Ser Gln
1               5                   10                  15

<210> SEQ ID NO 193
<211> LENGTH: 16
<212> TYPE: PRT
<213> ORGANISM: Streptococcus agalactiae

<400> SEQUENCE: 193

Gly Asn Val Leu Glu Arg Arg Gln Arg Asp Ala Asp Asn Lys Ser Gln
1               5                   10                  15

<210> SEQ ID NO 194
<211> LENGTH: 16
<212> TYPE: PRT
<213> ORGANISM: Streptococcus agalactiae

<400> SEQUENCE: 194

Gly Asn Val Leu Glu Arg Arg Gln Arg Asp Ala Asp Asn Lys Ser Gln
1               5                   10                  15

```
<210> SEQ ID NO 195
<211> LENGTH: 16
<212> TYPE: PRT
<213> ORGANISM: Streptococcus agalactiae

<400> SEQUENCE: 195

Gly Asn Val Leu Glu Arg Arg Gln Arg Asp Ala Asp Asn Lys Ser Gln
1               5                   10                  15

<210> SEQ ID NO 196
<211> LENGTH: 16
<212> TYPE: PRT
<213> ORGANISM: Streptococcus agalactiae

<400> SEQUENCE: 196

Gly Asn Val Leu Glu Arg Arg Gln Arg Asp Ala Asp Asn Lys Ser Gln
1               5                   10                  15

<210> SEQ ID NO 197
<211> LENGTH: 16
<212> TYPE: PRT
<213> ORGANISM: Streptococcus agalactiae

<400> SEQUENCE: 197

Gly Asn Val Leu Glu Arg Arg Gln Arg Asp Ala Asp Asn Lys Ser Gln
1               5                   10                  15

<210> SEQ ID NO 198
<211> LENGTH: 16
<212> TYPE: PRT
<213> ORGANISM: Streptococcus agalactiae

<400> SEQUENCE: 198

Gly Asn Val Leu Glu Arg Arg Gln Arg Asp Ala Asp Asn Lys Ser Gln
1               5                   10                  15

<210> SEQ ID NO 199
<211> LENGTH: 16
<212> TYPE: PRT
<213> ORGANISM: Streptococcus agalactiae

<400> SEQUENCE: 199

Gly Asn Val Leu Glu Arg Arg Gln Arg Asp Ala Asp Asn Lys Ser Gln
1               5                   10                  15

<210> SEQ ID NO 200
<211> LENGTH: 16
<212> TYPE: PRT
<213> ORGANISM: Streptococcus agalactiae

<400> SEQUENCE: 200

Gly Asn Val Leu Glu Arg Arg Gln Arg Asp Ala Asp Asn Lys Ser Gln
1               5                   10                  15

<210> SEQ ID NO 201
<211> LENGTH: 16
<212> TYPE: PRT
<213> ORGANISM: Streptococcus agalactiae

<400> SEQUENCE: 201

Gly Asn Val Leu Glu Arg Arg Gln Arg Asp Ala Asp Asn Lys Ser Gln
1               5                   10                  15

<210> SEQ ID NO 202
<211> LENGTH: 16
<212> TYPE: PRT
```

```
<213> ORGANISM: Streptococcus agalactiae

<400> SEQUENCE: 202

Gly Asn Val Leu Glu Arg Arg Gln Arg Asp Ala Asp Asn Lys Ser Gln
1               5                   10                  15

<210> SEQ ID NO 203
<211> LENGTH: 16
<212> TYPE: PRT
<213> ORGANISM: Streptococcus agalactiae

<400> SEQUENCE: 203

Gly Asn Val Leu Glu Arg Arg Gln Arg Asp Ala Asp Asn Lys Ser Gln
1               5                   10                  15

<210> SEQ ID NO 204
<211> LENGTH: 16
<212> TYPE: PRT
<213> ORGANISM: Streptococcus agalactiae

<400> SEQUENCE: 204

Gly Asn Val Leu Glu Arg Arg Gln Arg Asp Ala Glu Asn Lys Ser Gln
1               5                   10                  15

<210> SEQ ID NO 205
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 205

Gly Leu Ser Gln Asn Arg Asp Val Arg Glu Asn Gln Arg Ala Arg Glu
1               5                   10                  15

<210> SEQ ID NO 206
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 206

Ala Asn Val Leu Glu Arg Arg Gln Arg Asp Ala Glu Asn Arg Ser Gln
1               5                   10                  15

<210> SEQ ID NO 207
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 207

Gly Ala Val Leu Glu Arg Arg Gln Arg Asp Ala Glu Asn Arg Ser Gln
1               5                   10                  15

<210> SEQ ID NO 208
<211> LENGTH: 16
<212> TYPE: PRT
<213> ORGANISM: Artificial sequence
<220> FEATURE:
<223> OTHER INFORMATION: Description of Artificial sequence: Synthetic
      peptide
```

-continued

```
<400> SEQUENCE: 208

Gly Asn Ala Leu Glu Arg Arg Gln Arg Asp Ala Glu Asn Arg Ser Gln
1               5                   10                  15

<210> SEQ ID NO 209
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 209

Gly Asn Val Ala Glu Arg Arg Gln Arg Asp Ala Glu Asn Arg Ser Gln
1               5                   10                  15

<210> SEQ ID NO 210
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 210

Gly Asn Val Leu Ala Arg Arg Gln Arg Asp Ala Glu Asn Arg Ser Gln
1               5                   10                  15

<210> SEQ ID NO 211
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 211

Gly Asn Val Leu Glu Ala Arg Gln Arg Asp Ala Glu Asn Arg Ser Gln
1               5                   10                  15

<210> SEQ ID NO 212
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 212

Gly Asn Val Leu Glu Arg Ala Gln Arg Asp Ala Glu Asn Arg Ser Gln
1               5                   10                  15

<210> SEQ ID NO 213
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 213

Gly Asn Val Leu Glu Arg Arg Ala Arg Asp Ala Glu Asn Arg Ser Gln
1               5                   10                  15

<210> SEQ ID NO 214
<211> LENGTH: 16
<212> TYPE: PRT
<213> ORGANISM: Artificial sequence
```

```
<220> FEATURE:
<223> OTHER INFORMATION: Description of Artificial sequence: Synthetic
      peptide

<400> SEQUENCE: 214

Gly Asn Val Leu Glu Arg Arg Gln Ala Asp Ala Glu Asn Arg Ser Gln
1               5                   10                  15

<210> SEQ ID NO 215
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 215

Gly Asn Val Leu Glu Arg Arg Gln Arg Ala Ala Glu Asn Arg Ser Gln
1               5                   10                  15

<210> SEQ ID NO 216
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 216

Gly Asn Val Leu Glu Arg Arg Gln Arg Asp Ala Glu Asn Arg Ser Gln
1               5                   10                  15

<210> SEQ ID NO 217
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 217

Gly Asn Val Leu Glu Arg Arg Gln Arg Asp Ala Ala Asn Arg Ser Gln
1               5                   10                  15

<210> SEQ ID NO 218
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 218

Gly Asn Val Leu Glu Arg Arg Gln Arg Asp Ala Glu Ala Arg Ser Gln
1               5                   10                  15

<210> SEQ ID NO 219
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 219

Gly Asn Val Leu Glu Arg Arg Gln Arg Asp Ala Glu Asn Ala Ser Gln
1               5                   10                  15
```

```
<210> SEQ ID NO 220
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 220

Gly Asn Val Leu Glu Arg Arg Gln Arg Asp Ala Glu Asn Arg Ala Gln
1               5                   10                  15

<210> SEQ ID NO 221
<211> LENGTH: 16
<212> TYPE: PRT
<213> ORGANISM: Artificial sequence
<220> FEATURE:
<223> OTHER INFORMATION: Description of Artificial sequence: Synthetic
      peptide

<400> SEQUENCE: 221

Gly Asn Val Leu Glu Arg Arg Gln Arg Asp Ala Glu Asn Arg Ser Ala
1               5                   10                  15

<210> SEQ ID NO 222
<211> LENGTH: 16
<212> TYPE: PRT
<213> ORGANISM: Artificial sequence
<220> FEATURE:
<223> OTHER INFORMATION: Description of Artificial sequence: Synthetic
      peptide
<220> FEATURE:
<221> NAME/KEY: MOD_RES
<222> LOCATION: (2)..(2)
<223> OTHER INFORMATION: Asn, Ser or Thr
<220> FEATURE:
<221> NAME/KEY: MOD_RES
<222> LOCATION: (5)..(5)
<223> OTHER INFORMATION: Ala, Glu, Met or Gln
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Lys, Arg or Trp
<220> FEATURE:
<221> NAME/KEY: MOD_RES
<222> LOCATION: (10)..(10)
<223> OTHER INFORMATION: Ala, Asp, Glu, Asn or Gln
<220> FEATURE:
<221> NAME/KEY: MOD_RES
<222> LOCATION: (11)..(11)
<223> OTHER INFORMATION: Ala, Phe, Ile, Leu, Val or Tyr
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (14)..(14)
<223> OTHER INFORMATION: Lys or Arg
<220> FEATURE:
<221> NAME/KEY: MOD_RES
<222> LOCATION: (15)..(16)
<223> OTHER INFORMATION: Any amino acid

<400> SEQUENCE: 222

Gly Xaa Val Leu Xaa Arg Arg Xaa Xaa Xaa Xaa Xaa Xaa Xaa Xaa Xaa
1               5                   10                  15

<210> SEQ ID NO 223
<211> LENGTH: 28
```

```
<212> TYPE: DNA
<213> ORGANISM: Artificial sequence
<220> FEATURE:
<223> OTHER INFORMATION: Description of Artificial sequence: Synthetic
      primer

<400> SEQUENCE: 223
gtcctgtatc tgccatggat agtgttgg                                              28

<210> SEQ ID NO 224
<211> LENGTH: 29
<212> TYPE: DNA
<213> ORGANISM: Artificial sequence
<220> FEATURE:
<223> OTHER INFORMATION: Description of Artificial sequence: Synthetic
      primer

<400> SEQUENCE: 224
ccgcggatcc acattttgat catcacctg                                             29

<210> SEQ ID NO 225
<211> LENGTH: 28
<212> TYPE: DNA
<213> ORGANISM: Artificial sequence
<220> FEATURE:
<223> OTHER INFORMATION: Description of Artificial sequence: Synthetic
      primer

<400> SEQUENCE: 225
gtcctgtatc tgccatggat agtgttgg                                              28

<210> SEQ ID NO 226
<211> LENGTH: 27
<212> TYPE: DNA
<213> ORGANISM: Artificial sequence
<220> FEATURE:
<223> OTHER INFORMATION: Description of Artificial sequence: Synthetic
      primer

<400> SEQUENCE: 226
ccgcggatcc cctataagtt gacctac                                               27

<210> SEQ ID NO 227
<211> LENGTH: 30
<212> TYPE: DNA
<213> ORGANISM: Artificial sequence
<220> FEATURE:
<223> OTHER INFORMATION: Description of Artificial sequence: Synthetic
      primer

<400> SEQUENCE: 227
tgctttgcca tggtaggtca acttataggg                                            30

<210> SEQ ID NO 228
<211> LENGTH: 29
<212> TYPE: DNA
<213> ORGANISM: Artificial sequence
<220> FEATURE:
<223> OTHER INFORMATION: Description of Artificial sequence: Synthetic
      primer

<400> SEQUENCE: 228
ccgcggatcc acattttgat catcacctg                                             29

<210> SEQ ID NO 229
<211> LENGTH: 29
<212> TYPE: DNA
<213> ORGANISM: Artificial sequence
```

```
<220> FEATURE:
<223> OTHER INFORMATION: Description of Artificial sequence: Synthetic
      primer

<400> SEQUENCE: 229
gtgccttgcc atggaaagta ccgtaccgg                                        29

<210> SEQ ID NO 230
<211> LENGTH: 32
<212> TYPE: DNA
<213> ORGANISM: Artificial sequence
<220> FEATURE:
<223> OTHER INFORMATION: Description of Artificial sequence: Synthetic
      primer

<400> SEQUENCE: 230
gcggacagct cgagtttccc acctgtcatc gg                                    32

<210> SEQ ID NO 231
<211> LENGTH: 33
<212> TYPE: DNA
<213> ORGANISM: Artificial sequence
<220> FEATURE:
<223> OTHER INFORMATION: Description of Artificial sequence: Synthetic
      primer

<400> SEQUENCE: 231
gtgccttgcc atggacgacg taacaactga tac                                   33

<210> SEQ ID NO 232
<211> LENGTH: 31
<212> TYPE: DNA
<213> ORGANISM: Artificial sequence
<220> FEATURE:
<223> OTHER INFORMATION: Description of Artificial sequence: Synthetic
      primer

<400> SEQUENCE: 232
gcggacagct cgagtgtacc aataccacct g                                     31

<210> SEQ ID NO 233
<211> LENGTH: 30
<212> TYPE: DNA
<213> ORGANISM: Artificial sequence
<220> FEATURE:
<223> OTHER INFORMATION: Description of Artificial sequence: Synthetic
      primer

<400> SEQUENCE: 233
gtgccttgcc atgggccggg ataactaaag                                       30

<210> SEQ ID NO 234
<211> LENGTH: 33
<212> TYPE: DNA
<213> ORGANISM: Artificial sequence
<220> FEATURE:
<223> OTHER INFORMATION: Description of Artificial sequence: Synthetic
      primer

<400> SEQUENCE: 234
gcggacagct cgagctcttt tatacgccat gag                                   33

<210> SEQ ID NO 235
<211> LENGTH: 30
<212> TYPE: DNA
<213> ORGANISM: Artificial sequence
<220> FEATURE:
<223> OTHER INFORMATION: Description of Artificial sequence: Synthetic
```

```
                              primer

<400> SEQUENCE: 235
ccgcggatcc gatgataact ttgaaatgcc                                       30

<210> SEQ ID NO 236
<211> LENGTH: 30
<212> TYPE: DNA
<213> ORGANISM: Artificial sequence
<220> FEATURE:
<223> OTHER INFORMATION: Description of Artificial sequence: Synthetic
      primer

<400> SEQUENCE: 236
tggcacaagc ttacattctg agcagaaagc                                       30

<210> SEQ ID NO 237
<211> LENGTH: 15
<212> TYPE: DNA
<213> ORGANISM: Artificial sequence
<220> FEATURE:
<223> OTHER INFORMATION: Description of Artificial sequence: Synthetic
      primer

<400> SEQUENCE: 237
aatatcgccc tgagc                                                       15

<210> SEQ ID NO 238
<211> LENGTH: 16
<212> TYPE: DNA
<213> ORGANISM: Artificial sequence
<220> FEATURE:
<223> OTHER INFORMATION: Description of Artificial sequence: Synthetic
      primer

<400> SEQUENCE: 238
ggttttccca gtcacg                                                      16

<210> SEQ ID NO 239
<211> LENGTH: 28
<212> TYPE: DNA
<213> ORGANISM: Artificial sequence
<220> FEATURE:
<223> OTHER INFORMATION: Description of Artificial sequence: Synthetic
      primer

<400> SEQUENCE: 239
gtcctgtatc tgctatggat agtgttgg                                         28

<210> SEQ ID NO 240
<211> LENGTH: 19
<212> TYPE: DNA
<213> ORGANISM: Artificial sequence
<220> FEATURE:
<223> OTHER INFORMATION: Description of Artificial sequence: Synthetic
      primer

<400> SEQUENCE: 240
acattttgat catcacctg                                                   19

<210> SEQ ID NO 241
<211> LENGTH: 19
<212> TYPE: DNA
<213> ORGANISM: Artificial sequence
<220> FEATURE:
<223> OTHER INFORMATION: Description of Artificial sequence: Synthetic
      primer
```

<400> SEQUENCE: 241
actgctgagc taacaggtg                                                                19

<210> SEQ ID NO 242
<211> LENGTH: 20
<212> TYPE: DNA
<213> ORGANISM: Artificial sequence
<220> FEATURE:
<223> OTHER INFORMATION: Description of Artificial sequence: Synthetic
      primer

<400> SEQUENCE: 242
acatcacctg acaatgtcgc                                                               20

<210> SEQ ID NO 243
<211> LENGTH: 20
<212> TYPE: DNA
<213> ORGANISM: Artificial sequence
<220> FEATURE:
<223> OTHER INFORMATION: Description of Artificial sequence: Synthetic
      primer

<400> SEQUENCE: 243
gcgattgtga atagaatgag                                                               20

<210> SEQ ID NO 244
<211> LENGTH: 19
<212> TYPE: DNA
<213> ORGANISM: Artificial sequence
<220> FEATURE:
<223> OTHER INFORMATION: Description of Artificial sequence: Synthetic
      primer

<400> SEQUENCE: 244
tatacaaagc ctgagcttc                                                                19

<210> SEQ ID NO 245
<211> LENGTH: 20
<212> TYPE: DNA
<213> ORGANISM: Artificial sequence
<220> FEATURE:
<223> OTHER INFORMATION: Description of Artificial sequence: Synthetic
      primer

<400> SEQUENCE: 245
ttaccgtagc ctgtatcacc                                                               20

<210> SEQ ID NO 246
<211> LENGTH: 18
<212> TYPE: DNA
<213> ORGANISM: Artificial sequence
<220> FEATURE:
<223> OTHER INFORMATION: Description of Artificial sequence: Synthetic
      primer

<400> SEQUENCE: 246
cgacctacga tagcaacg                                                                 18

<210> SEQ ID NO 247
<211> LENGTH: 27
<212> TYPE: DNA
<213> ORGANISM: Artificial sequence
<220> FEATURE:
<223> OTHER INFORMATION: Description of Artificial sequence: Synthetic
      primer

<400> SEQUENCE: 247
ccgcggatcc gaatatgcta ccatcac                                                    27

<210> SEQ ID NO 248
<211> LENGTH: 39
<212> TYPE: DNA
<213> ORGANISM: Artificial sequence
<220> FEATURE:
<223> OTHER INFORMATION: Description of Artificial sequence: Synthetic primer

<400> SEQUENCE: 248
cccatccact aaacttaaac attcctgatt tccaagttc                                       39

<210> SEQ ID NO 249
<211> LENGTH: 38
<212> TYPE: DNA
<213> ORGANISM: Artificial sequence
<220> FEATURE:
<223> OTHER INFORMATION: Description of Artificial sequence: Synthetic primer

<400> SEQUENCE: 249
tgtttaagtt tagtggatgg ggctgcggtt tgagacgc                                        38

<210> SEQ ID NO 250
<211> LENGTH: 30
<212> TYPE: DNA
<213> ORGANISM: Artificial sequence
<220> FEATURE:
<223> OTHER INFORMATION: Description of Artificial sequence: Synthetic primer

<400> SEQUENCE: 250
tggcacaagc tttacctgct gagcgacttg                                                 30

<210> SEQ ID NO 251
<211> LENGTH: 19
<212> TYPE: DNA
<213> ORGANISM: Artificial sequence
<220> FEATURE:
<223> OTHER INFORMATION: Description of Artificial sequence: Synthetic primer

<400> SEQUENCE: 251
gttaaaggta acctgcctg                                                             19

<210> SEQ ID NO 252
<211> LENGTH: 48
<212> TYPE: DNA
<213> ORGANISM: Artificial sequence
<220> FEATURE:
<223> OTHER INFORMATION: Description of Artificial sequence: Synthetic primer

<400> SEQUENCE: 252
cccatccact aaacttaaac atacaactcc tattgtgccg aaatgtcg                             48

<210> SEQ ID NO 253
<211> LENGTH: 42
<212> TYPE: DNA
<213> ORGANISM: Artificial sequence
<220> FEATURE:
<223> OTHER INFORMATION: Description of Artificial sequence: Synthetic primer

<400> SEQUENCE: 253
tgtttaagtt tagtggatgg gcacttagag attttccaat cc                                   42

-continued

<210> SEQ ID NO 254
<211> LENGTH: 17
<212> TYPE: DNA
<213> ORGANISM: Artificial sequence
<220> FEATURE:
<223> OTHER INFORMATION: Description of Artificial sequence: Synthetic
      primer

<400> SEQUENCE: 254
gacatcatag atccacc                                                  17

<210> SEQ ID NO 255
<211> LENGTH: 29
<212> TYPE: DNA
<213> ORGANISM: Artificial sequence
<220> FEATURE:
<223> OTHER INFORMATION: Description of Artificial sequence: Synthetic
      primer

<400> SEQUENCE: 255
ccgcggatcc ggagctacgt ttgaacttc                                     29

<210> SEQ ID NO 256
<211> LENGTH: 39
<212> TYPE: DNA
<213> ORGANISM: Artificial sequence
<220> FEATURE:
<223> OTHER INFORMATION: Description of Artificial sequence: Synthetic
      primer

<400> SEQUENCE: 256
cccatccact aaacttaaac aatattaccg cagcaccac                          39

<210> SEQ ID NO 257
<211> LENGTH: 39
<212> TYPE: DNA
<213> ORGANISM: Artificial sequence
<220> FEATURE:
<223> OTHER INFORMATION: Description of Artificial sequence: Synthetic
      primer

<400> SEQUENCE: 257
tgtttaagtt tagtggatgg gacaagaagg ccaagaagg                          39

<210> SEQ ID NO 258
<211> LENGTH: 34
<212> TYPE: DNA
<213> ORGANISM: Artificial sequence
<220> FEATURE:
<223> OTHER INFORMATION: Description of Artificial sequence: Synthetic
      primer

<400> SEQUENCE: 258
cacgcaacgc gtcgacgcac agctttaact gtac                               34

<210> SEQ ID NO 259
<211> LENGTH: 5
<212> TYPE: PRT
<213> ORGANISM: Artificial sequence
<220> FEATURE:
<223> OTHER INFORMATION: Description of Artificial sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 259

```
Leu Pro Xaa Thr Gly
1               5

<210> SEQ ID NO 260
<211> LENGTH: 6
<212> TYPE: PRT
<213> ORGANISM: Artificial sequence
<220> FEATURE:
<223> OTHER INFORMATION: Description of Artificial sequence: Synthetic
      6xHis tag

<400> SEQUENCE: 260

His His His His His His
1               5

<210> SEQ ID NO 261
<211> LENGTH: 36
<212> TYPE: PRT
<213> ORGANISM: Mus sp.

<400> SEQUENCE: 261

Arg Leu Ala Gly Leu Leu Arg Lys Gly Gly Glu Lys Ile Gly Glu Lys
1               5                   10                  15

Leu Lys Lys Ile Gly Gln Lys Ile Lys Asn Phe Phe Gln Lys Leu Val
            20                  25                  30

Pro Gln Pro Glu
        35

<210> SEQ ID NO 262
<211> LENGTH: 5
<212> TYPE: PRT
<213> ORGANISM: Artificial sequence
<220> FEATURE:
<223> OTHER INFORMATION: Description of Artificial sequence: Synthetic
      peptide

<400> SEQUENCE: 262

Leu Pro Lys Thr Gly
1               5

<210> SEQ ID NO 263
<211> LENGTH: 5
<212> TYPE: PRT
<213> ORGANISM: Artificial sequence
<220> FEATURE:
<223> OTHER INFORMATION: Description of Artificial sequence: Synthetic
      peptide

<400> SEQUENCE: 263

Ile Pro Met Thr Gly
1               5

<210> SEQ ID NO 264
<211> LENGTH: 5
<212> TYPE: PRT
<213> ORGANISM: Artificial sequence
<220> FEATURE:
<223> OTHER INFORMATION: Description of Artificial sequence: Synthetic
      primer

<400> SEQUENCE: 264

Ile Pro Gln Thr Gly
1               5

<210> SEQ ID NO 265
<211> LENGTH: 2552
<212> TYPE: DNA
```

<213> ORGANISM: Streptococcus agalactiae
<220> FEATURE:
<221> NAME/KEY: CDS
<222> LOCATION: (791)..(2116)

<400> SEQUENCE: 265

```
gatcattaaa taaatcaagg ttagttagct tgaaagatat aaatatattc caaaattcca      60
aaaagtaatt ggcatagtga caaaaactat tgctcccctg ctttagaaat aatttatttt     120
taatttaata ttaaaagtaa actgaagaat ctagttatat ttaaaaagta aaggttgcat     180
tttaactaaa ttatgttaaa ctactgttat gcgatgagtc gatatgtggt tttaccacta     240
ttgcgcaggg agattataaa cgcaggagcg gatcttgata agttgtgtga accttcttgt     300
cacacttgaa aaggtgccct tagcttacta ctacttgtaa tttcttacaa attgtggtaa     360
gtagctgaaa agcaaaaaag aaagaaccag tttggttctt tcttttttgc ataaataagt     420
cacaatttcc ttcttaaaat tatgtcttta cttaactttta attgaatatg ctaccatcac     480
attctttgta aaatttttaa ataatctagt ttctgatggt ttagatgaag tattaaaaat     540
atactattac ctcattgtaa atcttaatgt tagtatgact atctatcatg ctttataata     600
ttaaaggaaa atttaaaaat atcatgtttt agatatcaac tatttaattt taaacataca     660
aattaataat aaattgcaac taaataataa attatcttga cataacttat aaaatgtttt     720
aatatataat ctaaataaaa gtaataataa aatgactttt aaaatttaaa aaaagtaagg     780
agaaaattaa ttg ttc aat aaa ata ggt ttt aga act tgg aaa tca gga         829
           Met Phe Asn Lys Ile Gly Phe Arg Thr Trp Lys Ser Gly
            1               5                   10 aag ctt tgg ctt tat atg gga gtg cta gga tca act att att tta gga       877
Lys Leu Trp Leu Tyr Met Gly Val Leu Gly Ser Thr Ile Ile Leu Gly
 15                  20                  25 tca agt cct gta tct gct atg gat agt gtt gga aat caa agt cag ggc       925
Ser Ser Pro Val Ser Ala Met Asp Ser Val Gly Asn Gln Ser Gln Gly
 30              35                  40                  45 aat gtt tta gag cgt cgt caa cgt gat gca gaa aac aga agc caa ggc       973
Asn Val Leu Glu Arg Arg Gln Arg Asp Ala Glu Asn Arg Ser Gln Gly
             50                  55                  60 aat gtt cta gag cgt cgt caa cgc gat gtt gag aat aag agc caa ggc      1021
Asn Val Leu Glu Arg Arg Gln Arg Asp Val Glu Asn Lys Ser Gln Gly
         65                  70                  75 aat gtt tta gag cgt cgt caa cgt gat gcg gaa aac aag agc caa ggc      1069
Asn Val Leu Glu Arg Arg Gln Arg Asp Ala Glu Asn Lys Ser Gln Gly
     80                  85                  90 aat gtt tta gag cgt cgt caa cgt gat gca gaa aac aga agc caa ggc      1117
Asn Val Leu Glu Arg Arg Gln Arg Asp Ala Glu Asn Arg Ser Gln Gly
 95                 100                 105 aat gtt cta gag cgt cgt caa cgt gat gca gaa aac aga agc caa ggc      1165
Asn Val Leu Glu Arg Arg Gln Arg Asp Ala Glu Asn Arg Ser Gln Gly
110                 115                 120                 125 aat gtt cta gag cgt cgt caa cgc gat gca gaa aac aga agc caa ggt      1213
Asn Val Leu Glu Arg Arg Gln Arg Asp Ala Glu Asn Arg Ser Gln Gly
            130                 135                 140 aat gtt cta gag cgt cgt caa cgt gat gca gaa aac aga agc caa ggt      1261
Asn Val Leu Glu Arg Arg Gln Arg Asp Ala Glu Asn Arg Ser Gln Gly
        145                 150                 155 aat gtt cta gag cgt cgt caa cgt gat gca gaa aac aga agc caa ggt      1309
Asn Val Leu Glu Arg Arg Gln Arg Asp Ala Glu Asn Arg Ser Gln Gly
    160                 165                 170 aat gtt cta gag cgt cgt caa cgc gat gtt gag aat aag agc caa ggc      1357
Asn Val Leu Glu Arg Arg Gln Arg Asp Val Glu Asn Lys Ser Gln Gly
175                 180                 185
```

```
aat gtt tta gag cgt cgt caa cgt gat gcg gaa aac aag agc caa ggc     1405
Asn Val Leu Glu Arg Arg Gln Arg Asp Ala Glu Asn Lys Ser Gln Gly
190                 195                 200                 205 aat gtt tta gag cgt cgt caa cgt gat gca gaa aac aga agc caa ggc     1453
Asn Val Leu Glu Arg Arg Gln Arg Asp Ala Glu Asn Arg Ser Gln Gly
            210                 215                 220 aat gtt tta gag cgt cgt caa cgt gat gca gaa aac aga agc caa ggc     1501
Asn Val Leu Glu Arg Arg Gln Arg Asp Ala Glu Asn Arg Ser Gln Gly
                225                 230                 235 aat gtt cta gag cgt cgt caa cgt gat gca gaa aac aga agc caa ggc     1549
Asn Val Leu Glu Arg Arg Gln Arg Asp Ala Glu Asn Arg Ser Gln Gly
            240                 245                 250 aat gtt cta gag cgt cgt caa cgt gat gca gaa aac aga agc caa ggc     1597
Asn Val Leu Glu Arg Arg Gln Arg Asp Ala Glu Asn Arg Ser Gln Gly
                255                 260                 265 aat gtt cta gag cgt cgt caa cgc gat gca gaa aac aga agc caa ggt     1645
Asn Val Leu Glu Arg Arg Gln Arg Asp Ala Glu Asn Arg Ser Gln Gly
270                 275                 280                 285 aat gtt cta gag cgt cgt caa cgt gat gca gaa aac aga agc caa ggc     1693
Asn Val Leu Glu Arg Arg Gln Arg Asp Ala Glu Asn Arg Ser Gln Gly
            290                 295                 300 aat gtt tta gag cgt cgt caa cgt gat gca gaa aac aga agc caa ggc     1741
Asn Val Leu Glu Arg Arg Gln Arg Asp Ala Glu Asn Arg Ser Gln Gly
                305                 310                 315 aat gtt tta gag cgt cgt caa cgt gat gca gaa aac aga agc caa ggc     1789
Asn Val Leu Glu Arg Arg Gln Arg Asp Ala Glu Asn Arg Ser Gln Gly
            320                 325                 330 aat gtt tta gag cgt cgt caa cgt gat gcg gaa aac aag agc caa gta     1837
Asn Val Leu Glu Arg Arg Gln Arg Asp Ala Glu Asn Lys Ser Gln Val
                335                 340                 345 ggt caa ctt ata ggg aaa aat cca ctt ctt tca aag tca att ata tct     1885
Gly Gln Leu Ile Gly Lys Asn Pro Leu Leu Ser Lys Ser Ile Ile Ser
350                 355                 360                 365 aga gaa aat aat cac tcg agt caa ggt gac tct aac aaa cag tca ttc     1933
Arg Glu Asn Asn His Ser Ser Gln Gly Asp Ser Asn Lys Gln Ser Phe
            370                 375                 380 tct aaa aaa gta tct cag gtt act aat gta gct aat aga ccg atg tta     1981
Ser Lys Lys Val Ser Gln Val Thr Asn Val Ala Asn Arg Pro Met Leu
                385                 390                 395 act aat aat tct aga aca att tca gtg ata aat aaa tta cct aaa aca     2029
Thr Asn Asn Ser Arg Thr Ile Ser Val Ile Asn Lys Leu Pro Lys Thr
            400                 405                 410 ggt gat gat caa aat gtc att ttt aaa ctt gta ggt ttt ggt tta att     2077
Gly Asp Asp Gln Asn Val Ile Phe Lys Leu Val Gly Phe Gly Leu Ile
                415                 420                 425 ttg tta aca agt cgc tgc ggt ttg aga cgc aat gaa aat taagtataat     2126
Leu Leu Thr Ser Arg Cys Gly Leu Arg Arg Asn Glu Asn
430                 435                 440 caatcattta gtaactatat ataatgatat atgcaatcaa taaaaaggaa tcggatacga   2186
gattcctttt tataattagg ttggttaggg tgactttttt catttggcta ttcttgaaag   2246
tttataaaaa tgtagttata atagtcacat taaaatgttt tgaaaatatt gatgaacaac   2306
atcaacaaat agaggtcatt atatgggata taccgttgct atcgtaggtg ctacaggtgc   2366
cgtaggaaca caaatgattc gtcaattaga acaatcgaat ttaccaatag aacaagtgaa   2426
acttttatca tcaagtcgct cagcaggtaa aattttacat tttaaagatg aggctatacg   2486
tgttgaagag acaacaaaag aatcatttta cgatgttgat attgccttgt tttcagctgg   2546
tggatc                                                             2552
```

<210> SEQ ID NO 266
<211> LENGTH: 442
<212> TYPE: PRT
<213> ORGANISM: Streptococcus agalactiae

<400> SEQUENCE: 266

```
Met Phe Asn Lys Ile Gly Phe Arg Thr Trp Lys Ser Gly Lys Leu Trp
1               5                   10                  15

Leu Tyr Met Gly Val Leu Gly Ser Thr Ile Ile Leu Gly Ser Ser Pro
            20                  25                  30

Val Ser Ala Met Asp Ser Val Gly Asn Gln Ser Gln Gly Asn Val Leu
        35                  40                  45

Glu Arg Arg Gln Arg Asp Ala Glu Asn Arg Ser Gln Gly Asn Val Leu
    50                  55                  60

Glu Arg Arg Gln Arg Asp Val Glu Asn Lys Ser Gln Gly Asn Val Leu
65                  70                  75                  80

Glu Arg Arg Gln Arg Asp Ala Glu Asn Lys Ser Gln Gly Asn Val Leu
                85                  90                  95

Glu Arg Arg Gln Arg Asp Ala Glu Asn Arg Ser Gln Gly Asn Val Leu
            100                 105                 110

Glu Arg Arg Gln Arg Asp Ala Glu Asn Arg Ser Gln Gly Asn Val Leu
        115                 120                 125

Glu Arg Arg Gln Arg Asp Ala Glu Asn Arg Ser Gln Gly Asn Val Leu
    130                 135                 140

Glu Arg Arg Gln Arg Asp Ala Glu Asn Arg Ser Gln Gly Asn Val Leu
145                 150                 155                 160

Glu Arg Arg Gln Arg Asp Ala Glu Asn Arg Ser Gln Gly Asn Val Leu
                165                 170                 175

Glu Arg Arg Gln Arg Asp Val Glu Asn Lys Ser Gln Gly Asn Val Leu
            180                 185                 190

Glu Arg Arg Gln Arg Asp Ala Glu Asn Lys Ser Gln Gly Asn Val Leu
        195                 200                 205

Glu Arg Arg Gln Arg Asp Ala Glu Asn Arg Ser Gln Gly Asn Val Leu
    210                 215                 220

Glu Arg Arg Gln Arg Asp Ala Glu Asn Arg Ser Gln Gly Asn Val Leu
225                 230                 235                 240

Glu Arg Arg Gln Arg Asp Ala Glu Asn Arg Ser Gln Gly Asn Val Leu
                245                 250                 255

Glu Arg Arg Gln Arg Asp Ala Glu Asn Arg Ser Gln Gly Asn Val Leu
            260                 265                 270

Glu Arg Arg Gln Arg Asp Ala Glu Asn Arg Ser Gln Gly Asn Val Leu
        275                 280                 285

Glu Arg Arg Gln Arg Asp Ala Glu Asn Arg Ser Gln Gly Asn Val Leu
    290                 295                 300

Glu Arg Arg Gln Arg Asp Ala Glu Asn Arg Ser Gln Gly Asn Val Leu
305                 310                 315                 320

Glu Arg Arg Gln Arg Asp Ala Glu Asn Arg Ser Gln Gly Asn Val Leu
                325                 330                 335

Glu Arg Arg Gln Arg Asp Ala Glu Asn Lys Ser Gln Val Gly Gln Leu
            340                 345                 350

Ile Gly Lys Asn Pro Leu Leu Ser Lys Ser Ile Ile Ser Arg Glu Asn
        355                 360                 365

Asn His Ser Ser Gln Gly Asp Ser Asn Lys Gln Ser Phe Ser Lys Lys
    370                 375                 380
```

```
Val Ser Gln Val Thr Asn Val Ala Asn Arg Pro Met Leu Thr Asn Asn
385                 390                 395                 400

Ser Arg Thr Ile Ser Val Ile Asn Lys Leu Pro Lys Thr Gly Asp Asp
            405                 410                 415

Gln Asn Val Ile Phe Lys Leu Val Gly Phe Gly Leu Ile Leu Leu Thr
            420                 425                 430

Ser Arg Cys Gly Leu Arg Arg Asn Glu Asn
        435                 440

<210> SEQ ID NO 267
<211> LENGTH: 1820
<212> TYPE: DNA
<213> ORGANISM: Streptococcus agalactiae
<220> FEATURE:
<221> NAME/KEY: CDS
<222> LOCATION: (383)..(1612)

<400> SEQUENCE: 267
gcataaataa gtcacaattt ccttcttaaa attatgtctt tacttaactt taattgaata      60
tgctaccatc acattctttg taaaatttt  aaataatcta gtttctgatg gtttagatga     120
agtattaaaa atatactatt acctcattgt aaatcttaat gttagtatga ctatctatca    180
tgctttataa tattaaagga aaatttaaaa atatcatgtt ttagatatca actatttaat    240
tttaaacata caaattaata ataaattgca actaaataat aaattatctt gacataactt    300
ataaaatgtt ttaatatata atctaaataa aagtaataat aaaatgactt ttaaaatta    360 aaaaaagtaa ggagaaaatt aa ttg ttc aat aaa ata ggt ttt aga act tgg    412
                        Met Phe Asn Lys Ile Gly Phe Arg Thr Trp
                         1               5                  10 aaa tca gga aag ctt tgg ctt tat atg gga gtg cta gga tca act att     460
Lys Ser Gly Lys Leu Trp Leu Tyr Met Gly Val Leu Gly Ser Thr Ile
            15                  20                  25 att tta gga tca agt tct gta tct gct atg gat agt gtt gga aat caa    508
Ile Leu Gly Ser Ser Ser Val Ser Ala Met Asp Ser Val Gly Asn Gln
        30                  35                  40 agt cag ggc aat gtt tta gag cgt cgt caa cgc gat gca gaa aac aga    556
Ser Gln Gly Asn Val Leu Glu Arg Arg Gln Arg Asp Ala Glu Asn Arg
    45                  50                  55 agc caa ggc aat gtt tta gag cgt cgt caa cgt gat gca gaa aac aga    604
Ser Gln Gly Asn Val Leu Glu Arg Arg Gln Arg Asp Ala Glu Asn Arg
60                  65                  70 agc caa ggc aat gtt tta gag cgt cgt caa cgt gat gca gaa aac aga    652
Ser Gln Gly Asn Val Leu Glu Arg Arg Gln Arg Asp Ala Glu Asn Arg
75                  80                  85                  90 agc caa ggt aat gtt cta gag cgt cgt caa cgc gat gtt gaa aat aaa    700
Ser Gln Gly Asn Val Leu Glu Arg Arg Gln Arg Asp Val Glu Asn Lys
                95                  100                 105 agc caa ggc aat gtt tta gag cgt cgt caa cgt gat gca gaa aac aga    748
Ser Gln Gly Asn Val Leu Glu Arg Arg Gln Arg Asp Ala Glu Asn Arg
            110                 115                 120 agc caa ggt aat gtt cta gag cgt cgt caa cgc gat gtt gaa aat aaa    796
Ser Gln Gly Asn Val Leu Glu Arg Arg Gln Arg Asp Val Glu Asn Lys
        125                 130                 135 agc caa ggc aat gtt tta gag cgt cgt caa cgt gat gca gaa aac aga    844
Ser Gln Gly Asn Val Leu Glu Arg Arg Gln Arg Asp Ala Glu Asn Arg
    140                 145                 150 agc caa ggt aat gtt cta gag cgt cgt caa cgt gat gca gaa aac aga    892
Ser Gln Gly Asn Val Leu Glu Arg Arg Gln Arg Asp Ala Glu Asn Arg
155                 160                 165                 170
```

```
                                     -continued
agc caa ggc aat gtt tta gag cgt cgt caa cgc gat gca gaa aac aga      940
Ser Gln Gly Asn Val Leu Glu Arg Arg Gln Arg Asp Ala Glu Asn Arg
            175                 180                 185 agc caa ggc aat gtt cta gag cgt cgt caa cgt gat gct gaa aac aaa      988
Ser Gln Gly Asn Val Leu Glu Arg Arg Gln Arg Asp Ala Glu Asn Lys
            190                 195                 200 agc caa ggc aat gtt tta gag cgt cgt caa cgt gat gca gaa aac aga     1036
Ser Gln Gly Asn Val Leu Glu Arg Arg Gln Arg Asp Ala Glu Asn Arg
            205                 210                 215 agc caa ggc aat gtt tta gag cgt cgt caa cgt gat gct gaa aac aga     1084
Ser Gln Gly Asn Val Leu Glu Arg Arg Gln Arg Asp Ala Glu Asn Arg
            220                 225                 230 agc caa ggc aat gtt tta gag cgt cgt caa cgc gat gca gaa aac aga     1132
Ser Gln Gly Asn Val Leu Glu Arg Arg Gln Arg Asp Ala Glu Asn Arg
235                 240                 245                 250 agc caa ggt aat gtt cta gag cgt cgt caa cgt gat gcg gaa aac aag     1180
Ser Gln Gly Asn Val Leu Glu Arg Arg Gln Arg Asp Ala Glu Asn Lys
            255                 260                 265 agc caa ggc aat gtt tta gag cgt cgt caa cgt gat gca gaa aac aga     1228
Ser Gln Gly Asn Val Leu Glu Arg Arg Gln Arg Asp Ala Glu Asn Arg
            270                 275                 280 agc caa ggc aat gtt tta gag cgt cgt caa cgc gat gtt gag aat aag     1276
Ser Gln Gly Asn Val Leu Glu Arg Arg Gln Arg Asp Val Glu Asn Lys
            285                 290                 295 agc caa ggc aat gtt tta gag cgt cgt caa cgt gat gcg gaa aac aag     1324
Ser Gln Gly Asn Val Leu Glu Arg Arg Gln Arg Asp Ala Glu Asn Lys
            300                 305                 310 agc caa gta ggt caa ctt ata ggg aaa aat cca ctt ctt tca aag tca     1372
Ser Gln Val Gly Gln Leu Ile Gly Lys Asn Pro Leu Leu Ser Lys Ser
315                 320                 325                 330 att ata tct aga gaa aat aat cac tct agt caa ggt gac tct aac aaa     1420
Ile Ile Ser Arg Glu Asn Asn His Ser Ser Gln Gly Asp Ser Asn Lys
            335                 340                 345 cag tca ttc tct aaa aaa gta tct cag gtt act aat gta gct aat aga     1468
Gln Ser Phe Ser Lys Lys Val Ser Gln Val Thr Asn Val Ala Asn Arg
            350                 355                 360 ccg atg tta act aat aat tct aga aca att tca gtg ata aat aaa tta     1516
Pro Met Leu Thr Asn Asn Ser Arg Thr Ile Ser Val Ile Asn Lys Leu
            365                 370                 375 cct aaa aca ggt gat gat caa aat gtc att ttt aaa ctt gta ggt ttt     1564
Pro Lys Thr Gly Asp Asp Gln Asn Val Ile Phe Lys Leu Val Gly Phe
            380                 385                 390 ggt tta att ttg tta aca agt cgc tgc ggt ttg aga cgc aat gaa aat     1612
Gly Leu Ile Leu Leu Thr Ser Arg Cys Gly Leu Arg Arg Asn Glu Asn
395                 400                 405                 410 taagtataat caatcattta gtaactatat ataatgatat atgcaatcaa taaaaggaa    1672 tcggatacga gattcctttt tataattagg ttggttaggg tgactttttt catttggcta   1732
ttcttgaaag tttataaaaa tgtagtataa tagtcacatt aaaatgtttt gaaaatattg   1792
atgaacaaca tcaacaaata gaggtcat                                      1820

<210> SEQ ID NO 268
<211> LENGTH: 410
<212> TYPE: PRT
<213> ORGANISM: Streptococcus agalactiae

<400> SEQUENCE: 268

Met Phe Asn Lys Ile Gly Phe Arg Thr Trp Lys Ser Gly Lys Leu Trp
1               5                   10                  15

Leu Tyr Met Gly Val Leu Gly Ser Thr Ile Ile Leu Gly Ser Ser Ser
```

```
                     20                  25                  30
Val Ser Ala Met Asp Ser Val Gly Asn Gln Ser Gln Gly Asn Val Leu
             35                  40                  45

Glu Arg Arg Gln Arg Asp Ala Glu Asn Arg Ser Gln Gly Asn Val Leu
         50                  55                  60

Glu Arg Arg Gln Arg Asp Ala Glu Asn Arg Ser Gln Gly Asn Val Leu
 65                  70                  75                  80

Glu Arg Arg Gln Arg Asp Ala Glu Asn Arg Ser Gln Gly Asn Val Leu
                 85                  90                  95

Glu Arg Arg Gln Arg Asp Val Glu Asn Lys Ser Gln Gly Asn Val Leu
            100                 105                 110

Glu Arg Arg Gln Arg Asp Ala Glu Asn Arg Ser Gln Gly Asn Val Leu
            115                 120                 125

Glu Arg Arg Gln Arg Asp Val Glu Asn Lys Ser Gln Gly Asn Val Leu
            130                 135                 140

Glu Arg Arg Gln Arg Asp Ala Glu Asn Arg Ser Gln Gly Asn Val Leu
145                 150                 155                 160

Glu Arg Arg Gln Arg Asp Ala Glu Asn Arg Ser Gln Gly Asn Val Leu
                165                 170                 175

Glu Arg Arg Gln Arg Asp Ala Glu Asn Arg Ser Gln Gly Asn Val Leu
            180                 185                 190

Glu Arg Arg Gln Arg Asp Ala Glu Asn Lys Ser Gln Gly Asn Val Leu
            195                 200                 205

Glu Arg Arg Gln Arg Asp Ala Glu Asn Arg Ser Gln Gly Asn Val Leu
            210                 215                 220

Glu Arg Arg Gln Arg Asp Ala Glu Asn Arg Ser Gln Gly Asn Val Leu
225                 230                 235                 240

Glu Arg Arg Gln Arg Asp Ala Glu Asn Arg Ser Gln Gly Asn Val Leu
                245                 250                 255

Glu Arg Arg Gln Arg Asp Ala Glu Asn Lys Ser Gln Gly Asn Val Leu
            260                 265                 270

Glu Arg Arg Gln Arg Asp Ala Glu Asn Arg Ser Gln Gly Asn Val Leu
            275                 280                 285

Glu Arg Arg Gln Arg Asp Val Glu Asn Lys Ser Gln Gly Asn Val Leu
            290                 295                 300

Glu Arg Arg Gln Arg Asp Ala Glu Asn Lys Ser Gln Val Gly Gln Leu
305                 310                 315                 320

Ile Gly Lys Asn Pro Leu Leu Ser Lys Ser Ile Ile Ser Arg Glu Asn
                325                 330                 335

Asn His Ser Ser Gln Gly Asp Ser Asn Lys Gln Ser Phe Ser Lys Lys
            340                 345                 350

Val Ser Gln Val Thr Asn Val Ala Asn Arg Pro Met Leu Thr Asn Asn
            355                 360                 365

Ser Arg Thr Ile Ser Val Ile Asn Lys Leu Pro Lys Thr Gly Asp Asp
            370                 375                 380

Gln Asn Val Ile Phe Lys Leu Val Gly Phe Gly Leu Ile Leu Leu Thr
385                 390                 395                 400

Ser Arg Cys Gly Leu Arg Arg Asn Glu Asn
                405                 410

<210> SEQ ID NO 269
<211> LENGTH: 1628
<212> TYPE: DNA
<213> ORGANISM: Streptococcus agalactiae
<220> FEATURE:
```

```
<221> NAME/KEY: CDS
<222> LOCATION: (385)..(1422)

<400> SEQUENCE: 269
```

| | |
|---|---:|
| gcataaataa gtcacaattt ccttctaaaa attatgtctt tacttaactt taattgaata | 60 |
| tgctaccatc acattctttg taaaatttt aataatcta gtttctgatg gtttagatga | 120 |
| agtattaaaa atatactatt atctcattgt aaatcctaat gttagtatga ctatctatca | 180 |
| tgttttataa tattgaagga aaatttaaaa atatcatgtt ttagatatca actatttaat | 240 |
| tttaaacata caaattaata ataaattgca attaaataac aaattacctt gacataaatt | 300 |
| ataaaatgtt ttaatatata taatctaaat aaaaataata ataaaatgac ttttaaaatt | 360 |

```
taaaaaagt aaggagaaaa ttaa ttg ttc aat aaa ata ggt ttt aga act       411
                         Met Phe Asn Lys Ile Gly Phe Arg Thr
                           1               5 tgg aaa tca gga aag ctt tgg ctt tat atg gga gtg cta gga tca act     459
Trp Lys Ser Gly Lys Leu Trp Leu Tyr Met Gly Val Leu Gly Ser Thr
 10              15                  20                  25 att att tta gga tca agt cct gta tct gct atg gat agt gtt gga aat    507
Ile Ile Leu Gly Ser Ser Pro Val Ser Ala Met Asp Ser Val Gly Asn
             30                  35                  40 caa agt caa ggt aat gtt cta gag cgt cgt caa cgt gat gcg gat aac    555
Gln Ser Gln Gly Asn Val Leu Glu Arg Arg Gln Arg Asp Ala Asp Asn
         45                  50                  55 aag agc caa ggc aat gtt cta gaa cgt cgt caa cgc gat gta gaa aac    603
Lys Ser Gln Gly Asn Val Leu Glu Arg Arg Gln Arg Asp Val Glu Asn
     60                  65                  70 aga agc caa ggc aat gtt cta gag cgt cgt caa cgc gat gcg gat aac    651
Arg Ser Gln Gly Asn Val Leu Glu Arg Arg Gln Arg Asp Ala Asp Asn
 75                  80                  85 aag agc caa ggc aat gtt tta gag cgc cgc caa cgc gat gca gaa aac    699
Lys Ser Gln Gly Asn Val Leu Glu Arg Arg Gln Arg Asp Ala Glu Asn
 90                  95                 100                 105 aaa agt cag ggc aat gtt cta gaa cgt cgt caa cgt gat gtt gag aat    747
Lys Ser Gln Gly Asn Val Leu Glu Arg Arg Gln Arg Asp Val Glu Asn
            110                 115                 120 aag agc caa ggc aat gtt cta gag cgt cgc caa cgt gat gca gaa aac    795
Lys Ser Gln Gly Asn Val Leu Glu Arg Arg Gln Arg Asp Ala Glu Asn
        125                 130                 135 aaa agt cag ggt aat gtt cta gag cgt cgt caa cgc gat gca gat aac    843
Lys Ser Gln Gly Asn Val Leu Glu Arg Arg Gln Arg Asp Ala Asp Asn
    140                 145                 150 aag agc caa ggt aat gtt cta gaa cgt cgt caa cgc gat gtg gaa aac    891
Lys Ser Gln Gly Asn Val Leu Glu Arg Arg Gln Arg Asp Val Glu Asn
155                 160                 165 aaa agt cag ggc aat gtt cta gaa cgt cgt caa cgt gat gtt gag aat    939
Lys Ser Gln Gly Asn Val Leu Glu Arg Arg Gln Arg Asp Val Glu Asn
170                 175                 180                 185 aag agc caa ggc aat gtt cta gag cgt cgc caa cgt gat gca gaa aac    987
Lys Ser Gln Gly Asn Val Leu Glu Arg Arg Gln Arg Asp Ala Glu Asn
                190                 195                 200 aaa agt cag ggt aat gtt cta gag cgt cgt caa cgc gat gca gat aac   1035
Lys Ser Gln Gly Asn Val Leu Glu Arg Arg Gln Arg Asp Ala Asp Asn
            205                 210                 215 aag agc caa ggt aat gtt cta gaa cgt cgt caa cgc gat gtg gaa aac   1083
Lys Ser Gln Gly Asn Val Leu Glu Arg Arg Gln Arg Asp Val Glu Asn
        220                 225                 230 aaa agt cag ggc aat gtt cta gag cgt cgc caa cgt gat gtt gag aac   1131
Lys Ser Gln Gly Asn Val Leu Glu Arg Arg Gln Arg Asp Val Glu Asn
    235                 240                 245
```

```
aag agc caa gta ggt caa ctt ata ggg aaa aat cca ctt ctt tca aag    1179
Lys Ser Gln Val Gly Gln Leu Ile Gly Lys Asn Pro Leu Leu Ser Lys
250             255                 260                 265 tca act ata tct aga gaa aat aat cac tct agt caa ggt gac tct aac    1227
Ser Thr Ile Ser Arg Glu Asn Asn His Ser Ser Gln Gly Asp Ser Asn
        270                 275                 280 aaa cag tca ttc tct aaa aaa gta tct cag gtt act aat gta gct aat    1275
Lys Gln Ser Phe Ser Lys Lys Val Ser Gln Val Thr Asn Val Ala Asn
    285                 290                 295 aga cca atg tta act aat aat tct aga aca att tca gtg ata aat aaa    1323
Arg Pro Met Leu Thr Asn Asn Ser Arg Thr Ile Ser Val Ile Asn Lys
300                 305                 310 tta cct aaa aca ggt gat gat caa aat gtc att ttt aaa ctt gta ggt    1371
Leu Pro Lys Thr Gly Asp Asp Gln Asn Val Ile Phe Lys Leu Val Gly
315                 320                 325 ttt ggt tta att ttg tta aca agt cgc tgc ggt ttg aga cgc aat gaa    1419
Phe Gly Leu Ile Leu Leu Thr Ser Arg Cys Gly Leu Arg Arg Asn Glu
330             335                 340                 345 aat taagtataat caatcattta gtaactatta taatgatata tgcaatcaat         1472
Asn aaaaaggaat cggatacaag attcctttt ataattaggt tggttagggt gactttttca   1532
tttggctatt cttgaaagtt tataaaaatg tagtataata gtcacattaa aatgttttga  1592
aaatattgat gaacaacatc aacaaataga ggtcat                            1628

<210> SEQ ID NO 270
<211> LENGTH: 346
<212> TYPE: PRT
<213> ORGANISM: Streptococcus agalactiae

<400> SEQUENCE: 270

Met Phe Asn Lys Ile Gly Phe Arg Thr Trp Lys Ser Gly Lys Leu Trp
1               5                   10                  15

Leu Tyr Met Gly Val Leu Gly Ser Thr Ile Ile Leu Gly Ser Ser Pro
            20                  25                  30

Val Ser Ala Met Asp Ser Val Gly Asn Gln Ser Gln Gly Asn Val Leu
        35                  40                  45

Glu Arg Arg Gln Arg Asp Ala Asp Asn Lys Ser Gln Gly Asn Val Leu
    50                  55                  60

Glu Arg Arg Gln Arg Asp Val Glu Asn Arg Ser Gln Gly Asn Val Leu
65                  70                  75                  80

Glu Arg Arg Gln Arg Asp Ala Asp Asn Lys Ser Gln Gly Asn Val Leu
                85                  90                  95

Glu Arg Arg Gln Arg Asp Ala Glu Asn Lys Ser Gln Gly Asn Val Leu
            100                 105                 110

Glu Arg Arg Gln Arg Asp Val Glu Asn Lys Ser Gln Gly Asn Val Leu
        115                 120                 125

Glu Arg Arg Gln Arg Asp Ala Glu Asn Lys Ser Gln Gly Asn Val Leu
    130                 135                 140

Glu Arg Arg Gln Arg Asp Ala Asp Asn Lys Ser Gln Gly Asn Val Leu
145                 150                 155                 160

Glu Arg Arg Gln Arg Asp Val Glu Asn Lys Ser Gln Gly Asn Val Leu
                165                 170                 175

Glu Arg Arg Gln Arg Asp Val Glu Asn Lys Ser Gln Gly Asn Val Leu
            180                 185                 190

Glu Arg Arg Gln Arg Asp Ala Glu Asn Lys Ser Gln Gly Asn Val Leu
        195                 200                 205
```

```
Glu Arg Arg Gln Arg Asp Ala Asp Asn Lys Ser Gln Gly Asn Val Leu
    210                 215                 220
Glu Arg Arg Gln Arg Asp Val Glu Asn Lys Ser Gln Gly Asn Val Leu
225                 230                 235                 240
Glu Arg Arg Gln Arg Asp Val Glu Asn Lys Ser Gln Val Gly Gln Leu
                245                 250                 255
Ile Gly Lys Asn Pro Leu Leu Ser Lys Ser Thr Ile Ser Arg Glu Asn
            260                 265                 270
Asn His Ser Ser Gln Gly Asp Ser Asn Lys Gln Ser Phe Ser Lys Lys
        275                 280                 285
Val Ser Gln Val Thr Asn Val Ala Asn Arg Pro Met Leu Thr Asn Asn
    290                 295                 300
Ser Arg Thr Ile Ser Val Ile Asn Lys Leu Pro Lys Thr Gly Asp Asp
305                 310                 315                 320
Gln Asn Val Ile Phe Lys Leu Val Gly Phe Gly Leu Ile Leu Leu Thr
                325                 330                 335
Ser Arg Cys Gly Leu Arg Arg Asn Glu Asn
            340                 345

<210> SEQ ID NO 271
<211> LENGTH: 1150
<212> TYPE: DNA
<213> ORGANISM: Streptococcus agalactiae
<220> FEATURE:
<221> NAME/KEY: CDS
<222> LOCATION: (385)..(942)

<400> SEQUENCE: 271
```

| | |
|---|---|
| gcataaataa gtcaccaatt tcccttctta aaattatgtc tttacttaac tttaattgaa | 60 |
| tatgctacca tcacattctt tgtaaaattt ttaaataatc tagtttctga tggtttagat | 120 |
| gaagtattaa aaatatacta ttacctcatt gtaaatctta atgttagtat gactatctat | 180 |
| catgctttat aatattaaag gaaaatttaa aaatatcatg ttttagatat caactattta | 240 |
| attttaaaca tacaaattaa taataaattg caactaaata ataaattatc ttgacataac | 300 |
| ttataaaatg ttttaatata taatctaaat aaaagtaata ataaaatgac ttttaaaatt | 360 |

```
taaaaaagt aaggagaaaa ttaa ttg ttc aat aaa ata ggt ttt aga act       411
                         Met Phe Asn Lys Ile Gly Phe Arg Thr
                         1               5 tgg aaa tca gga aag ctt tgg ctt tat atg gga gtg cta gga tca act     459
Trp Lys Ser Gly Lys Leu Trp Leu Tyr Met Gly Val Leu Gly Ser Thr
10              15                  20                  25 att att tta gga tca agt cct gta tct gct atg gat agt gtt gga aat    507
Ile Ile Leu Gly Ser Ser Pro Val Ser Ala Met Asp Ser Val Gly Asn
                30                  35                  40 caa agt cag ggc aat gtt tta gag cgt cgt caa cgc gat gca gaa aac    555
Gln Ser Gln Gly Asn Val Leu Glu Arg Arg Gln Arg Asp Ala Glu Asn
            45                  50                  55 aga agc caa ggt aat gtt cta gag cgt cgt caa cgc gat gca gaa aac    603
Arg Ser Gln Gly Asn Val Leu Glu Arg Arg Gln Arg Asp Ala Glu Asn
        60                  65                  70 aga agc caa ggt aat gtt cta gag cgt cgt caa cgt gat gcg gaa aac    651
Arg Ser Gln Gly Asn Val Leu Glu Arg Arg Gln Arg Asp Ala Glu Asn
    75                  80                  85 aag agc caa gta ggt caa ctt ata ggg aaa aat cca ctt ctt tca aag    699
Lys Ser Gln Val Gly Gln Leu Ile Gly Lys Asn Pro Leu Leu Ser Lys
90                  95                  100                 105 tca att ata tct aga gaa aat aat cac tct agt caa ggt gac tct aac    747
Ser Ile Ile Ser Arg Glu Asn Asn His Ser Ser Gln Gly Asp Ser Asn
```

```
                Ser Ile Ile Ser Arg Glu Asn Asn His Ser Ser Gln Gly Asp Ser Asn
                            110                 115                 120 aaa cag tca ttc tct aaa aaa gta tct cag gtt act aat gta gct aat        795
Lys Gln Ser Phe Ser Lys Lys Val Ser Gln Val Thr Asn Val Ala Asn
            125                 130                 135 aga ccg atg tta act aat aat tct aga aca att tca gtg ata aat aaa        843
Arg Pro Met Leu Thr Asn Asn Ser Arg Thr Ile Ser Val Ile Asn Lys
            140                 145                 150 tta cct aaa aca ggt gat gat caa aat gtc att ttt aaa ctt gta ggt        891
Leu Pro Lys Thr Gly Asp Asp Gln Asn Val Ile Phe Lys Leu Val Gly
        155                 160                 165 ttt ggt tta att ttg tta aca agt cgc tgc ggt ttg aga cgc aat gaa        939
Phe Gly Leu Ile Leu Leu Thr Ser Arg Cys Gly Leu Arg Arg Asn Glu
170                 175                 180                 185 aat taagtataat caatcattta gtaactatat ataatgatat atgcaatcaa             992
Asn taaaaaggaa tcggatacga gattcctttt tataattagg ttggttaggg tgactttttt     1052
catttggcta ttcttgaaag tttataaaaa tgtagtataa tagtcacatt aaaatgtttt     1112 gaaatattg atgaacaaca tcaacaaata gaggtcat                              1150
```

<210> SEQ ID NO 272
<211> LENGTH: 186
<212> TYPE: PRT
<213> ORGANISM: Streptococcus agalactiae

<400> SEQUENCE: 272

```
Met Phe Asn Lys Ile Gly Phe Arg Thr Trp Lys Ser Gly Lys Leu Trp
1               5                   10                  15

Leu Tyr Met Gly Val Leu Gly Ser Thr Ile Ile Leu Gly Ser Ser Pro
            20                  25                  30

Val Ser Ala Met Asp Ser Val Gly Asn Gln Ser Gln Gly Asn Val Leu
        35                  40                  45

Glu Arg Arg Gln Arg Asp Ala Glu Asn Arg Ser Gln Gly Asn Val Leu
    50                  55                  60

Glu Arg Arg Gln Arg Asp Ala Glu Asn Arg Ser Gln Gly Asn Val Leu
65                  70                  75                  80

Glu Arg Arg Gln Arg Asp Ala Glu Asn Lys Ser Gln Val Gly Gln Leu
                85                  90                  95

Ile Gly Lys Asn Pro Leu Leu Ser Lys Ser Ile Ile Ser Arg Glu Asn
            100                 105                 110

Asn His Ser Ser Gln Gly Asp Ser Asn Lys Gln Ser Phe Ser Lys Lys
        115                 120                 125

Val Ser Gln Val Thr Asn Val Ala Asn Arg Pro Met Leu Thr Asn Asn
    130                 135                 140

Ser Arg Thr Ile Ser Val Ile Asn Lys Leu Pro Lys Thr Gly Asp Asp
145                 150                 155                 160

Gln Asn Val Ile Phe Lys Leu Val Gly Phe Gly Leu Ile Leu Leu Thr
                165                 170                 175

Ser Arg Cys Gly Leu Arg Arg Asn Glu Asn
            180                 185
```

<210> SEQ ID NO 273
<211> LENGTH: 1484
<212> TYPE: DNA
<213> ORGANISM: Streptococcus agalactiae
<220> FEATURE:
<221> NAME/KEY: CDS
<222> LOCATION: (383)..(1276)

-continued

```
<400> SEQUENCE: 273
gcataaataa gtcacaattt ccttcttaaa attatgtctt tacttaactt taattgaata      60
tgctaccatc acattctttg taaaatttt aaataatcta gtttctgatg gtttagatga      120
agtattaaaa atatactatt acctcattgt aaatcttaat gttagtatga ctatctatca     180
tgctttataa tattaaagga aaatttaaaa atatcatgtt ttagatatca actatttaat     240
tttaaacata caaattaata ataaattgca actaaataat aaattatctt gacataactt     300
ataaaatgtt ttaatatata atctaaataa aagtaatataa aaaatgactt ttaaaattta    360
aaaaaagtaa ggagaaaatt aa ttg ttc aat aaa ata ggt ttt aga act tgg     412
                        Met Phe Asn Lys Ile Gly Phe Arg Thr Trp
                         1               5                   10 aaa tca gga aag ctt tgg ctt tat atg gga gtg cta gga tca act att      460
Lys Ser Gly Lys Leu Trp Leu Tyr Met Gly Val Leu Gly Ser Thr Ile
             15                  20                  25 att tta gga tca agt cct gta tct gct atg gat agt gtt gga aat caa     508
Ile Leu Gly Ser Ser Pro Val Ser Ala Met Asp Ser Val Gly Asn Gln
         30                  35                  40 agc caa ggc aat gtt cta gag cgt cgt caa cgc gat gca gaa aac aga     556
Ser Gln Gly Asn Val Leu Glu Arg Arg Gln Arg Asp Ala Glu Asn Arg
     45                  50                  55 agc caa ggt aat gtt tta gaa cgt cgt caa cgc gat gtt gag aac aag     604
Ser Gln Gly Asn Val Leu Glu Arg Arg Gln Arg Asp Val Glu Asn Lys
 60                  65                  70 agc caa ggt aat gtt tta gag cgt cgc caa cgt gat gcg gaa aac aaa     652
Ser Gln Gly Asn Val Leu Glu Arg Arg Gln Arg Asp Ala Glu Asn Lys
75                  80                  85                  90 agt cag ggc aat gtt tta gag cgt cgt caa cgt gat gca gaa aac aga     700
Ser Gln Gly Asn Val Leu Glu Arg Arg Gln Arg Asp Ala Glu Asn Arg
                 95                  100                 105 agc caa ggt aat gtt cta gag cgt cgt caa cgc gat gtt gag aat aag     748
Ser Gln Gly Asn Val Leu Glu Arg Arg Gln Arg Asp Val Glu Asn Lys
         110                 115                 120 agc caa ggc aat gtt cta gag cgt cgt caa cgc gat gtt gag aat aag     796
Ser Gln Gly Asn Val Leu Glu Arg Arg Gln Arg Asp Val Glu Asn Lys
     125                 130                 135 agc caa ggt aat gtt cta gag cgt cgt caa cgc gat gtt gag aat aag     844
Ser Gln Gly Asn Val Leu Glu Arg Arg Gln Arg Asp Val Glu Asn Lys
 140                 145                 150 agc caa ggt aat gtt cta gag cgt cgt caa cgt gat gcg gaa aac aag     892
Ser Gln Gly Asn Val Leu Glu Arg Arg Gln Arg Asp Ala Glu Asn Lys
155                 160                 165                 170 agc caa ggc aat gtt cta gag cgt cgt caa cgc gat gca gaa aac aga     940
Ser Gln Gly Asn Val Leu Glu Arg Arg Gln Arg Asp Ala Glu Asn Arg
                 175                 180                 185 agc caa ggt aat gtt tta gag cgt cgc caa cat gat gtt gag aat aag     988
Ser Gln Gly Asn Val Leu Glu Arg Arg Gln His Asp Val Glu Asn Lys
         190                 195                 200 agt caa gta ggt caa ctt ata ggg aaa aat cca ctt ttt tca aag tca    1036
Ser Gln Val Gly Gln Leu Ile Gly Lys Asn Pro Leu Phe Ser Lys Ser
     205                 210                 215 act gta tct aga gaa aat aat cac tct agt caa ggt gac tct aac aaa    1084
Thr Val Ser Arg Glu Asn Asn His Ser Ser Gln Gly Asp Ser Asn Lys
 220                 225                 230 cag tca ttc tct aaa aaa gta tct cag gtt act aat gta gct aat aga    1132
Gln Ser Phe Ser Lys Lys Val Ser Gln Val Thr Asn Val Ala Asn Arg
235                 240                 245                 250 ccg atg tta act aat aat tct aga aca att tca gtg ata aat aaa tta    1180
```

```
            Pro Met Leu Thr Asn Asn Ser Arg Thr Ile Ser Val Ile Asn Lys Leu
                        255                 260                 265 cct aaa aca ggt gat gat caa aat gtc att ttt aaa ctt gta ggt ttt      1228
Pro Lys Thr Gly Asp Asp Gln Asn Val Ile Phe Lys Leu Val Gly Phe
            270                 275                 280 ggt tta att tta tta aca agt ctc tgc ggt ttg aga cgc aat gaa aat      1276
Gly Leu Ile Leu Leu Thr Ser Leu Cys Gly Leu Arg Arg Asn Glu Asn
            285                 290                 295 taagtataat caaccattta gtaactatta taatgatata tgcaatcaat aaaaaggaa     1336 tcgaatacga gattcctttt tataattagg ttggttaggg tgactttttt catttggcta    1396
ttcttgaaag tttataaaaa tgtagtataa tagtcacatt aaaatgtttt gaaatattg     1456 atgaacaaca tcatcaaata gaggtcat                                       1484

<210> SEQ ID NO 274
<211> LENGTH: 298
<212> TYPE: PRT
<213> ORGANISM: Streptococcus agalactiae

<400> SEQUENCE: 274

Met Phe Asn Lys Ile Gly Phe Arg Thr Trp Lys Ser Gly Lys Leu Trp
1               5                   10                  15

Leu Tyr Met Gly Val Leu Gly Ser Thr Ile Ile Leu Gly Ser Ser Pro
            20                  25                  30

Val Ser Ala Met Asp Ser Val Gly Asn Gln Ser Gln Gly Asn Val Leu
        35                  40                  45

Glu Arg Arg Gln Arg Asp Ala Glu Asn Arg Ser Gln Gly Asn Val Leu
    50                  55                  60

Glu Arg Arg Gln Arg Asp Val Glu Asn Lys Ser Gln Gly Asn Val Leu
65                  70                  75                  80

Glu Arg Arg Gln Arg Asp Ala Glu Asn Lys Ser Gln Gly Asn Val Leu
                85                  90                  95

Glu Arg Arg Gln Arg Asp Ala Glu Asn Arg Ser Gln Gly Asn Val Leu
            100                 105                 110

Glu Arg Arg Gln Arg Asp Val Glu Asn Lys Ser Gln Gly Asn Val Leu
        115                 120                 125

Glu Arg Arg Gln Arg Asp Val Glu Asn Lys Ser Gln Gly Asn Val Leu
    130                 135                 140

Glu Arg Arg Gln Arg Asp Val Glu Asn Lys Ser Gln Gly Asn Val Leu
145                 150                 155                 160

Glu Arg Arg Gln Arg Asp Ala Glu Asn Lys Ser Gln Gly Asn Val Leu
                165                 170                 175

Glu Arg Arg Gln Arg Asp Ala Glu Asn Arg Ser Gln Gly Asn Val Leu
            180                 185                 190

Glu Arg Arg Gln His Asp Val Glu Asn Lys Ser Gln Val Gly Gln Leu
        195                 200                 205

Ile Gly Lys Asn Pro Leu Phe Ser Lys Ser Thr Val Ser Arg Glu Asn
    210                 215                 220

Asn His Ser Ser Gln Gly Asp Ser Asn Lys Gln Ser Phe Ser Lys Lys
225                 230                 235                 240

Val Ser Gln Val Thr Asn Val Ala Asn Arg Pro Met Leu Thr Asn Asn
                245                 250                 255

Ser Arg Thr Ile Ser Val Ile Asn Lys Leu Pro Lys Thr Gly Asp Asp
            260                 265                 270

Gln Asn Val Ile Phe Lys Leu Val Gly Phe Gly Leu Ile Leu Leu Thr
        275                 280                 285
```

```
Ser Leu Cys Gly Leu Arg Arg Asn Glu Asn
    290                 295

<210> SEQ ID NO 275
<211> LENGTH: 2446
<212> TYPE: DNA
<213> ORGANISM: Streptococcus agalactiae
<220> FEATURE:
<221> NAME/KEY: CDS
<222> LOCATION: (385)..(2238)

<400> SEQUENCE: 275
gcataaataa gtcacaattt ccttctaaaa attatgtctt tacttaactt taattgaata      60
tgctaccatc acattctttg taaaattttt aaataaccta gtttctgatg gtttagatga     120
agtattaaaa atatactatt atctcattgt aaatcctaat gttagtatga ctatctatca     180
tgttttataa tattgaagga aaatttaaaa atatcatgtt ttagatatca actatttaat     240
tttaaacata caaattaata ataaattgca attaaataac aaattacctt gacataaatt     300
ataaaatgat ttaatatata taatctaaat aaaaataata ataaaatgac tttaaaatt      360 taaaaaaagt aaggagaaaa ttaa ttg ttc aat aaa ata ggt ttt aga act         411
                         Met Phe Asn Lys Ile Gly Phe Arg Thr
                           1               5 tgg aaa tca gga aag ctt tgg ctt tat atg gga gtg cta gga tca act        459
Trp Lys Ser Gly Lys Leu Trp Leu Tyr Met Gly Val Leu Gly Ser Thr
 10              15                  20                  25 att att tta gga tca agt cct gta tct gct atg gat agt gtt gga aat       507
Ile Ile Leu Gly Ser Ser Pro Val Ser Ala Met Asp Ser Val Gly Asn
             30                  35                  40 caa agt caa ggt aat gtt cta gag cgt cgc caa cgt gat gcg gat aac       555
Gln Ser Gln Gly Asn Val Leu Glu Arg Arg Gln Arg Asp Ala Asp Asn
         45                  50                  55 aag agc caa ggt aat gtt tta gag cgt cgc caa cgt gat gca gat aac       603
Lys Ser Gln Gly Asn Val Leu Glu Arg Arg Gln Arg Asp Ala Asp Asn
     60                  65                  70 aaa agt cag ggc aat gtt cta gaa cgt cgc caa cgt gat gtt gat aac       651
Lys Ser Gln Gly Asn Val Leu Glu Arg Arg Gln Arg Asp Val Asp Asn
 75                  80                  85 aag agc caa ggt aac gtt cta gag cgt cgc caa cgc gat gct gat aac       699
Lys Ser Gln Gly Asn Val Leu Glu Arg Arg Gln Arg Asp Ala Asp Asn
 90                  95                 100                 105 aag agc caa ggt aat gtt tta gag cgc cgc caa cgc gat gca gat aac       747
Lys Ser Gln Gly Asn Val Leu Glu Arg Arg Gln Arg Asp Ala Asp Asn
             110                 115                 120 aaa agt caa ggt aat gtt cta gag cgt cgc caa cgc gat gtt gat aac       795
Lys Ser Gln Gly Asn Val Leu Glu Arg Arg Gln Arg Asp Val Asp Asn
         125                 130                 135 aag agc cag ggt aat gtt tta gag cgt cgc caa cgc gat gca gat aac       843
Lys Ser Gln Gly Asn Val Leu Glu Arg Arg Gln Arg Asp Ala Asp Asn
     140                 145                 150 aaa agt cag ggt aat gtt tta gag cgt cgc caa cgc gat gtt gat aac       891
Lys Ser Gln Gly Asn Val Leu Glu Arg Arg Gln Arg Asp Val Asp Asn
 155                 160                 165 aaa agc caa ggt aat gtt tta gag cgt cgc caa cgt gat gct gat aac       939
Lys Ser Gln Gly Asn Val Leu Glu Arg Arg Gln Arg Asp Ala Asp Asn
 170                 175                 180                 185 aaa agt cag ggc aat gtt cta gag cgt cgc caa cgt gat gcg gat aac       987
Lys Ser Gln Gly Asn Val Leu Glu Arg Arg Gln Arg Asp Ala Asp Asn
             190                 195                 200 aaa agc caa ggt aat gtt cta gag cgt cgc caa cgc gat gcg gat aac      1035
Lys Ser Gln Gly Asn Val Leu Glu Arg Arg Gln Arg Asp Ala Asp Asn
```

```
Lys Ser Gln Gly Asn Val Leu Glu Arg Arg Gln Arg Asp Ala Asp Asn
        205                 210                 215 aaa agt cag ggc aat gtt tta gag cgt cgc caa cgt gat gct gat aac    1083
Lys Ser Gln Gly Asn Val Leu Glu Arg Arg Gln Arg Asp Ala Asp Asn
        220                 225                 230 aaa agt caa ggt aat gtt cta gag cgt cgc caa cgc gat gca gat aac    1131
Lys Ser Gln Gly Asn Val Leu Glu Arg Arg Gln Arg Asp Ala Asp Asn
        235                 240                 245 aaa agc caa ggt aat gtt cta gag cgt cgc caa cgc gat gct gat aac    1179
Lys Ser Gln Gly Asn Val Leu Glu Arg Arg Gln Arg Asp Ala Asp Asn
250                 255                 260                 265 aaa agt caa ggt aat gtt cta gag cgt cgc caa cgt gat gct gat aac    1227
Lys Ser Gln Gly Asn Val Leu Glu Arg Arg Gln Arg Asp Ala Asp Asn
        270                 275                 280 aag agc caa ggc aat gtt ctt gag cgt cgt caa cgc gat gtc gat aac    1275
Lys Ser Gln Gly Asn Val Leu Glu Arg Arg Gln Arg Asp Val Asp Asn
        285                 290                 295 aaa agt cag ggt aat gtt tta gag cgt cgc caa cgt gat gcg gat aac    1323
Lys Ser Gln Gly Asn Val Leu Glu Arg Arg Gln Arg Asp Ala Asp Asn
        300                 305                 310 aag agt caa ggt aat gtt tta gag cgt cgc caa cgc gat gcg gat aac    1371
Lys Ser Gln Gly Asn Val Leu Glu Arg Arg Gln Arg Asp Ala Asp Asn
        315                 320                 325 aag agc caa ggt aat gtt tta gag cgt cgc caa cgc gat gcg gat aac    1419
Lys Ser Gln Gly Asn Val Leu Glu Arg Arg Gln Arg Asp Ala Asp Asn
330                 335                 340                 345 aag agt caa ggt aat gtt tta gag cgt cgc caa cgc gat gcg gat aac    1467
Lys Ser Gln Gly Asn Val Leu Glu Arg Arg Gln Arg Asp Ala Asp Asn
        350                 355                 360 aag agc caa ggt aat gtt tta gag cgt cgc caa cgc gat gca gat aac    1515
Lys Ser Gln Gly Asn Val Leu Glu Arg Arg Gln Arg Asp Ala Asp Asn
        365                 370                 375 aaa agt caa ggt aat gtt tta gag cgt cgc caa cgc gat gct gat aac    1563
Lys Ser Gln Gly Asn Val Leu Glu Arg Arg Gln Arg Asp Ala Asp Asn
        380                 385                 390 aag agc caa ggt aat gtt tta gag cgt cgt caa cgt gat gca gat aac    1611
Lys Ser Gln Gly Asn Val Leu Glu Arg Arg Gln Arg Asp Ala Asp Asn
        395                 400                 405 aaa agt cag ggc aat gtt tta gag cgt cgt caa cgt gat gcg gat aac    1659
Lys Ser Gln Gly Asn Val Leu Glu Arg Arg Gln Arg Asp Ala Asp Asn
410                 415                 420                 425 aag agc caa ggt aat gtt tta gag cgt cgc caa cgt gat gcg gat aac    1707
Lys Ser Gln Gly Asn Val Leu Glu Arg Arg Gln Arg Asp Ala Asp Asn
        430                 435                 440 aag agc cag ggc aat gtt cta gaa cgt cgt caa cgt gat gcg gat aac    1755
Lys Ser Gln Gly Asn Val Leu Glu Arg Arg Gln Arg Asp Ala Asp Asn
        445                 450                 455 aag agc caa ggt aac gtt tta gag cgt cgc caa cgt gat gcg gat aac    1803
Lys Ser Gln Gly Asn Val Leu Glu Arg Arg Gln Arg Asp Ala Asp Asn
        460                 465                 470 aag agc cag ggc aat gtt tta gag cgc cgc caa cgc gat gca gat aac    1851
Lys Ser Gln Gly Asn Val Leu Glu Arg Arg Gln Arg Asp Ala Asp Asn
        475                 480                 485 aaa agt caa ggt aat gtt cta gag cgt cgc caa cgc gat gca gat aac    1899
Lys Ser Gln Gly Asn Val Leu Glu Arg Arg Gln Arg Asp Ala Asp Asn
490                 495                 500                 505 aag agc cag ggt aat gtt cta gag cgt cgc caa cgc gat gcg gaa aac    1947
Lys Ser Gln Gly Asn Val Leu Glu Arg Arg Gln Arg Asp Ala Glu Asn
        510                 515                 520 aaa agt caa gta ggt caa ctt ata ggg aaa aat cca ctt ttt tca aag    1995
```

-continued

```
Lys Ser Gln Val Gly Gln Leu Ile Gly Lys Asn Pro Leu Phe Ser Lys
            525                 530                 535 tca act gta tct aga gaa aat aat cac tct agt caa ggt gac tct aac    2043
Ser Thr Val Ser Arg Glu Asn Asn His Ser Ser Gln Gly Asp Ser Asn
            540                 545                 550 aaa cag tca ttc tct aaa aaa ata tct cag gtt act aat gta gct aat    2091
Lys Gln Ser Phe Ser Lys Lys Ile Ser Gln Val Thr Asn Val Ala Asn
            555                 560                 565 gga ccg atg tta act aat aat tct aga aca att tca gtg ata aat aaa    2139
Gly Pro Met Leu Thr Asn Asn Ser Arg Thr Ile Ser Val Ile Asn Lys
570             575                 580                 585 tta cct aaa aca ggt gat gat caa aat gtc att ttt aaa ctt gta ggt    2187
Leu Pro Lys Thr Gly Asp Asp Gln Asn Val Ile Phe Lys Leu Val Gly
            590                 595                 600 ttt ggt tta att ttg tta aca agt ctc tgc ggt ttg aga cgc aat gaa    2235
Phe Gly Leu Ile Leu Leu Thr Ser Leu Cys Gly Leu Arg Arg Asn Glu
            605                 610                 615 aat taagtataat caaccattta gtaactatta taatgatata tgcaatcaat         2288
Asn aaaaaaggaa tcgaatacga gattccttt tataattagg ttggttaggg tgacttttt    2348 catttggcta ttcttgaaag tttataaaaa tgtagtataa tagtcacatt aaaatgtttt  2408 gaaatattg atgaacaaca tcatcaaata gaggtcat                           2446
```

<210> SEQ ID NO 276
<211> LENGTH: 618
<212> TYPE: PRT
<213> ORGANISM: Streptococcus agalactiae

<400> SEQUENCE: 276

```
Met Phe Asn Lys Ile Gly Phe Arg Thr Trp Lys Ser Gly Lys Leu Trp
1               5                   10                  15

Leu Tyr Met Gly Val Leu Gly Ser Thr Ile Ile Leu Gly Ser Ser Pro
            20                  25                  30

Val Ser Ala Met Asp Ser Val Gly Asn Gln Ser Gln Gly Asn Val Leu
        35                  40                  45

Glu Arg Arg Gln Arg Asp Ala Asp Asn Lys Ser Gln Gly Asn Val Leu
    50                  55                  60

Glu Arg Arg Gln Arg Asp Ala Asp Asn Lys Ser Gln Gly Asn Val Leu
65                  70                  75                  80

Glu Arg Arg Gln Arg Asp Val Asp Asn Lys Ser Gln Gly Asn Val Leu
                85                  90                  95

Glu Arg Arg Gln Arg Asp Ala Asp Asn Lys Ser Gln Gly Asn Val Leu
            100                 105                 110

Glu Arg Arg Gln Arg Asp Ala Asp Asn Lys Ser Gln Gly Asn Val Leu
        115                 120                 125

Glu Arg Arg Gln Arg Asp Val Asp Asn Lys Ser Gln Gly Asn Val Leu
    130                 135                 140

Glu Arg Arg Gln Arg Asp Ala Asp Asn Lys Ser Gln Gly Asn Val Leu
145                 150                 155                 160

Glu Arg Arg Gln Arg Asp Val Asp Asn Lys Ser Gln Gly Asn Val Leu
                165                 170                 175

Glu Arg Arg Gln Arg Asp Ala Asp Asn Lys Ser Gln Gly Asn Val Leu
            180                 185                 190

Glu Arg Arg Gln Arg Asp Ala Asp Asn Lys Ser Gln Gly Asn Val Leu
        195                 200                 205

Glu Arg Arg Gln Arg Asp Ala Asp Asn Lys Ser Gln Gly Asn Val Leu
```

```
                    210                 215                 220
Glu Arg Arg Gln Arg Asp Ala Asp Asn Lys Ser Gln Gly Asn Val Leu
225                 230                 235                 240

Glu Arg Arg Gln Arg Asp Ala Asp Asn Lys Ser Gln Gly Asn Val Leu
                245                 250                 255

Glu Arg Arg Gln Arg Asp Ala Asp Asn Lys Ser Gln Gly Asn Val Leu
            260                 265                 270

Glu Arg Arg Gln Arg Asp Ala Asp Asn Lys Ser Gln Gly Asn Val Leu
        275                 280                 285

Glu Arg Arg Gln Arg Asp Val Asp Asn Lys Ser Gln Gly Asn Val Leu
    290                 295                 300

Glu Arg Arg Gln Arg Asp Ala Asp Asn Lys Ser Gln Gly Asn Val Leu
305                 310                 315                 320

Glu Arg Arg Gln Arg Asp Ala Asp Asn Lys Ser Gln Gly Asn Val Leu
                325                 330                 335

Glu Arg Arg Gln Arg Asp Ala Asp Asn Lys Ser Gln Gly Asn Val Leu
            340                 345                 350

Glu Arg Arg Gln Arg Asp Ala Asp Asn Lys Ser Gln Gly Asn Val Leu
        355                 360                 365

Glu Arg Arg Gln Arg Asp Ala Asp Asn Lys Ser Gln Gly Asn Val Leu
    370                 375                 380

Glu Arg Arg Gln Arg Asp Ala Asp Asn Lys Ser Gln Gly Asn Val Leu
385                 390                 395                 400

Glu Arg Arg Gln Arg Asp Ala Asp Asn Lys Ser Gln Gly Asn Val Leu
                405                 410                 415

Glu Arg Arg Gln Arg Asp Ala Asp Asn Lys Ser Gln Gly Asn Val Leu
            420                 425                 430

Glu Arg Arg Gln Arg Asp Ala Asp Asn Lys Ser Gln Gly Asn Val Leu
        435                 440                 445

Glu Arg Arg Gln Arg Asp Ala Asp Asn Lys Ser Gln Gly Asn Val Leu
    450                 455                 460

Glu Arg Arg Gln Arg Asp Ala Asp Asn Lys Ser Gln Gly Asn Val Leu
465                 470                 475                 480

Glu Arg Arg Gln Arg Asp Ala Asp Asn Lys Ser Gln Gly Asn Val Leu
                485                 490                 495

Glu Arg Arg Gln Arg Asp Ala Asp Asn Lys Ser Gln Gly Asn Val Leu
            500                 505                 510

Glu Arg Arg Gln Arg Asp Ala Glu Asn Lys Ser Gln Val Gly Gln Leu
        515                 520                 525

Ile Gly Lys Asn Pro Leu Phe Ser Lys Ser Thr Val Ser Arg Glu Asn
    530                 535                 540

Asn His Ser Ser Gln Gly Asp Ser Asn Lys Gln Ser Phe Ser Lys Lys
545                 550                 555                 560

Ile Ser Gln Val Thr Asn Val Ala Asn Gly Pro Met Leu Thr Asn Asn
                565                 570                 575

Ser Arg Thr Ile Ser Val Ile Asn Lys Leu Pro Lys Thr Gly Asp Asp
            580                 585                 590

Gln Asn Val Ile Phe Lys Leu Val Gly Phe Gly Leu Ile Leu Leu Thr
        595                 600                 605

Ser Leu Cys Gly Leu Arg Arg Asn Glu Asn
    610                 615

<210> SEQ ID NO 277
<211> LENGTH: 5382
```

```
<212> TYPE: DNA
<213> ORGANISM: Streptococcus agalactiae
<220> FEATURE:
<221> NAME/KEY: CDS
<222> LOCATION: (259)..(2961)
<220> FEATURE:
<221> NAME/KEY: CDS
<222> LOCATION: (3087)..(5108)

<400> SEQUENCE: 277
```

| | |
|---|---:|
| atttttaagc aatattttaa aacataaaaa aagaaaaatc aactacttaa gctaattgaa | 60 |
| gtatttctaa gataataaaa aataagatta tcaataaaaa agaaaaatca ttcaaaaatt | 120 |
| gggaaaaaac tttaaaattc catacccttat aataagaaat tattgatatc ataataagtg | 180 |
| atagtttgta tattctagga tattctgtat ctgatcttag atttagaaac gacatttcgg | 240 |

```
cacaatagga gttgtaaa atg aga aaa tac caa aaa ttt tct aaa ata ttg      291
                    Met Arg Lys Tyr Gln Lys Phe Ser Lys Ile Leu
                     1               5                  10 acg tta agt ctt ttt tgt ttg tcg caa ata ccg ctt aat acc aat gtt      339
Thr Leu Ser Leu Phe Cys Leu Ser Gln Ile Pro Leu Asn Thr Asn Val
            15                  20                  25 tta ggg gaa agt acc gta ccg gaa aat ggt gct aaa gga aag tta gtt      387
Leu Gly Glu Ser Thr Val Pro Glu Asn Gly Ala Lys Gly Lys Leu Val
        30                  35                  40 gtt aaa aag aca gat gac cag aac aaa cca ctt tca aaa gct acc ttt      435
Val Lys Lys Thr Asp Asp Gln Asn Lys Pro Leu Ser Lys Ala Thr Phe
45                  50                  55 gtt tta aaa act act gct cat cca gaa agt aaa ata gaa aaa gta act      483
Val Leu Lys Thr Thr Ala His Pro Glu Ser Lys Ile Glu Lys Val Thr
60                  65                  70                  75 gct gag cta aca ggt gaa gct act ttt gat aat ctc ata cct gga gat      531
Ala Glu Leu Thr Gly Glu Ala Thr Phe Asp Asn Leu Ile Pro Gly Asp
            80                  85                  90 tat act tta tca gaa gaa aca gcg ccc gaa ggt tat aaa aag act aac      579
Tyr Thr Leu Ser Glu Glu Thr Ala Pro Glu Gly Tyr Lys Lys Thr Asn
        95                 100                 105 cag act tgg caa gtt aag gtt gag agt aat gga aaa act acg ata caa      627
Gln Thr Trp Gln Val Lys Val Glu Ser Asn Gly Lys Thr Thr Ile Gln
    110                 115                 120 aat agt ggt gat aaa aat tcc aca att gga caa aat cac gaa gaa cta      675
Asn Ser Gly Asp Lys Asn Ser Thr Ile Gly Gln Asn His Glu Glu Leu
125                 130                 135 gat aag cag tat ccc ccc aca gga att tat gaa gat aca aag gaa tct      723
Asp Lys Gln Tyr Pro Pro Thr Gly Ile Tyr Glu Asp Thr Lys Glu Ser
140                 145                 150                 155 tat aaa ctt gag cat gtt aaa ggt tca gtt cca aat gga aag tca gag      771
Tyr Lys Leu Glu His Val Lys Gly Ser Val Pro Asn Gly Lys Ser Glu
            160                 165                 170 gca aaa gca gtt aac cca tat tca agt gaa ggt gag cat ata aga gaa      819
Ala Lys Ala Val Asn Pro Tyr Ser Ser Glu Gly Glu His Ile Arg Glu
        175                 180                 185 att cca gag gga aca tta tct aaa cgt att tca gaa gta ggt gat tta      867
Ile Pro Glu Gly Thr Leu Ser Lys Arg Ile Ser Glu Val Gly Asp Leu
    190                 195                 200 gct cat aat aaa tat aaa att gag tta act gtc agt gga aaa acc ata      915
Ala His Asn Lys Tyr Lys Ile Glu Leu Thr Val Ser Gly Lys Thr Ile
205                 210                 215 gta aaa cca gtg gac aaa caa aag ccg tta gat gtt gtc ttc gta ctc      963
Val Lys Pro Val Asp Lys Gln Lys Pro Leu Asp Val Val Phe Val Leu
220                 225                 230                 235 gat aat tct aac tca atg aat aac gat ggc cca aat ttt caa agg cat     1011
```

-continued

| | | | | | | | | | | | | | | | |
|---|---|---|---|---|---|---|---|---|---|---|---|---|---|---|---|
| Asp | Asn | Ser | Asn | Ser | Met | Asn | Asn | Asp | Gly | Pro | Asn | Phe | Gln | Arg | His |
| | | | 240 | | | | | 245 | | | | | 250 | | |

```
aat aaa gcc aag aaa gct gcc gaa gct ctt ggg acc gca gta aaa gat    1059
Asn Lys Ala Lys Lys Ala Ala Glu Ala Leu Gly Thr Ala Val Lys Asp
            255             260             265 att tta gga gca aac agt gat aat agg gtt gca tta gtt acc tat ggt    1107
Ile Leu Gly Ala Asn Ser Asp Asn Arg Val Ala Leu Val Thr Tyr Gly
        270             275             280 tca gat att ttt gat ggt agg agt gta gat gtc gta aaa gga ttt aaa    1155
Ser Asp Ile Phe Asp Gly Arg Ser Val Asp Val Val Lys Gly Phe Lys
285             290             295 gaa gat gat aaa tat tat ggc ctt caa act aag ttc aca att cag aca    1203
Glu Asp Asp Lys Tyr Tyr Gly Leu Gln Thr Lys Phe Thr Ile Gln Thr
300             305             310             315 gag aat tat agt cat aaa caa tta aca aat aat gct gaa gag att ata    1251
Glu Asn Tyr Ser His Lys Gln Leu Thr Asn Asn Ala Glu Glu Ile Ile
            320             325             330 aaa agg att cct aca gaa gct cct aga gct aaa tgg gga tca act aca    1299
Lys Arg Ile Pro Thr Glu Ala Pro Arg Ala Lys Trp Gly Ser Thr Thr
        335             340             345 aac gga ctt act cca gag caa caa aag cag tac tat ctt agt aaa gta    1347
Asn Gly Leu Thr Pro Glu Gln Gln Lys Gln Tyr Tyr Leu Ser Lys Val
    350             355             360 ggg gaa aca ttt act atg aaa gcc ttc atg gag gca gat gat att ttg    1395
Gly Glu Thr Phe Thr Met Lys Ala Phe Met Glu Ala Asp Asp Ile Leu
365             370             375 agt caa gta gat cga aat agt caa aaa att att gtt cat ata act gat    1443
Ser Gln Val Asp Arg Asn Ser Gln Lys Ile Ile Val His Ile Thr Asp
380             385             390             395 ggt gtt cca aca aga tca tat gct att aat aat ttt aaa ttg ggt gca    1491
Gly Val Pro Thr Arg Ser Tyr Ala Ile Asn Asn Phe Lys Leu Gly Ala
            400             405             410 tca tat gaa agc caa ttt gaa caa atg aaa aaa aat gga tat cta aat    1539
Ser Tyr Glu Ser Gln Phe Glu Gln Met Lys Lys Asn Gly Tyr Leu Asn
        415             420             425 aaa agt aat ttt cta ctt act gat aag ccc gag gat ata aaa gga aat    1587
Lys Ser Asn Phe Leu Leu Thr Asp Lys Pro Glu Asp Ile Lys Gly Asn
    430             435             440 ggg gag agt tac ttt ttg ttt ccc tta gat agt tat caa aca cag ata    1635
Gly Glu Ser Tyr Phe Leu Phe Pro Leu Asp Ser Tyr Gln Thr Gln Ile
445             450             455 atc tct gga aac tta caa aaa ctt cat tat tta gat tta aat ctt aat    1683
Ile Ser Gly Asn Leu Gln Lys Leu His Tyr Leu Asp Leu Asn Leu Asn
460             465             470             475 tac cct aaa ggt aca att tat cga aat gga cca gta aga gaa cat gga    1731
Tyr Pro Lys Gly Thr Ile Tyr Arg Asn Gly Pro Val Arg Glu His Gly
            480             485             490 aca cca acc aaa ctt tat ata aat agt tta aaa cag aaa aat tat gac    1779
Thr Pro Thr Lys Leu Tyr Ile Asn Ser Leu Lys Gln Lys Asn Tyr Asp
        495             500             505 atc ttt aat ttt ggt ata gat ata tct gct ttt aga caa gtt tat aat    1827
Ile Phe Asn Phe Gly Ile Asp Ile Ser Ala Phe Arg Gln Val Tyr Asn
    510             515             520 gag gat tat aag aaa aat caa gat ggt act ttt caa aaa ttg aaa gag    1875
Glu Asp Tyr Lys Lys Asn Gln Asp Gly Thr Phe Gln Lys Leu Lys Glu
525             530             535 gaa gct ttt gaa ctt tca gat ggg gaa ata aca gaa cta atg aag tca    1923
Glu Ala Phe Glu Leu Ser Asp Gly Glu Ile Thr Glu Leu Met Lys Ser
540             545             550             555 ttc tct tct aaa cct gag tat tat acc ccg ata gta act tca tcc gat    1971
```

```
                Phe Ser Ser Lys Pro Glu Tyr Tyr Thr Pro Ile Val Thr Ser Ser Asp
                            560                 565                 570 gca tct aac aat gaa att tta tct aaa att cag caa caa ttt gaa aag         2019
Ala Ser Asn Asn Glu Ile Leu Ser Lys Ile Gln Gln Gln Phe Glu Lys
            575                 580                 585 gtt tta aca aaa gaa aac tca att gtt aat gga act ata gaa gat cct         2067
Val Leu Thr Lys Glu Asn Ser Ile Val Asn Gly Thr Ile Glu Asp Pro
            590                 595                 600 atg ggt gac aaa atc aat tta cag ctt ggc aac gga caa aca ttg caa         2115
Met Gly Asp Lys Ile Asn Leu Gln Leu Gly Asn Gly Gln Thr Leu Gln
        605                 610                 615 cca agt gat tat act tta cag gga aat gat gga agt ata atg aaa gat         2163
Pro Ser Asp Tyr Thr Leu Gln Gly Asn Asp Gly Ser Ile Met Lys Asp
620                 625                 630                 635 agc att gca act ggt ggg cct aat aat gat ggt gga ata ctt aaa ggg         2211
Ser Ile Ala Thr Gly Gly Pro Asn Asn Asp Gly Gly Ile Leu Lys Gly
                640                 645                 650 gtt aaa tta gaa tac atc aaa aat aaa ctc tac gtt aga ggt ttg aac         2259
Val Lys Leu Glu Tyr Ile Lys Asn Lys Leu Tyr Val Arg Gly Leu Asn
            655                 660                 665 tta ggg gag gga caa aaa gta aca ctc aca tat gat gtg aaa cta gat         2307
Leu Gly Glu Gly Gln Lys Val Thr Leu Thr Tyr Asp Val Lys Leu Asp
        670                 675                 680 gac agt ttt ata agt aac aaa ttc tat gac act aat ggt aga aca aca         2355
Asp Ser Phe Ile Ser Asn Lys Phe Tyr Asp Thr Asn Gly Arg Thr Thr
    685                 690                 695 ttg aat cct aaa tca gag gat cct aat aca ctt aga gat ttt cca atc         2403
Leu Asn Pro Lys Ser Glu Asp Pro Asn Thr Leu Arg Asp Phe Pro Ile
700                 705                 710                 715 cct aaa att cgt gat gtg aga gaa tat cct aca ata acg att aaa aac         2451
Pro Lys Ile Arg Asp Val Arg Glu Tyr Pro Thr Ile Thr Ile Lys Asn
                720                 725                 730 gag aag aag tta ggt gaa att gaa ttt aca aaa gtt gat aaa gat aat         2499
Glu Lys Lys Leu Gly Glu Ile Glu Phe Thr Lys Val Asp Lys Asp Asn
            735                 740                 745 aat aag ttg ctt ctc aaa gga gct acg ttt gaa ctt caa gaa ttt aat         2547
Asn Lys Leu Leu Leu Lys Gly Ala Thr Phe Glu Leu Gln Glu Phe Asn
        750                 755                 760 gaa gat tat aaa ctt tat tta cca ata aaa aat aat aat tca aaa gta         2595
Glu Asp Tyr Lys Leu Tyr Leu Pro Ile Lys Asn Asn Asn Ser Lys Val
    765                 770                 775 gtg acg gga gaa aac ggc aaa att tct tac aaa gat ttg aaa gat ggc         2643
Val Thr Gly Glu Asn Gly Lys Ile Ser Tyr Lys Asp Leu Lys Asp Gly
780                 785                 790                 795 aaa tat cag tta ata gaa gca gtt tcg ccg aag gat tat caa aaa att         2691
Lys Tyr Gln Leu Ile Glu Ala Val Ser Pro Lys Asp Tyr Gln Lys Ile
                800                 805                 810 act aat aaa cca att tta act ttt gaa gtt gtt aaa gga tcg ata caa         2739
Thr Asn Lys Pro Ile Leu Thr Phe Glu Val Val Lys Gly Ser Ile Gln
            815                 820                 825 aat ata ata gct gtt aat aaa cag att tct gaa tat cat gag gaa ggt         2787
Asn Ile Ile Ala Val Asn Lys Gln Ile Ser Glu Tyr His Glu Glu Gly
        830                 835                 840 gac aag cat tta att acc aac acg cat att cca cca aaa gga att att         2835
Asp Lys His Leu Ile Thr Asn Thr His Ile Pro Pro Lys Gly Ile Ile
    845                 850                 855 ccg atg aca ggt ggg aaa gga att cta tct ttc att tta ata ggt gga         2883
Pro Met Thr Gly Gly Lys Gly Ile Leu Ser Phe Ile Leu Ile Gly Gly
860                 865                 870                 875 tct atg atg tct att gca ggt gga att tat att tgg aaa aga tat aag         2931
```

-continued

| | |
|---|---|
| Ser Met Met Ser Ile Ala Gly Gly Ile Tyr Ile Trp Lys Arg Tyr Lys<br>880 885 890 | |
| aaa tct agt gat ata tct aga gaa aaa gat taagaatcat gtgttttagt<br>Lys Ser Ser Asp Ile Ser Arg Glu Lys Asp<br>895 900 | 2981 |
| attcttaatt aattaaatat aattcgaaag gagtggtgct gcggtaatat tataatccgt | 3041 |
| atattattat ctatgttgat taactagaat aagaaggaga tagaa atg aaa aaa atc<br>Met Lys Lys Ile<br>905 | 3098 |
| aac aaa tgt ctt aca gtg ttc tcg aca ctg cta ttg atc tta acg tca<br>Asn Lys Cys Leu Thr Val Phe Ser Thr Leu Leu Leu Ile Leu Thr Ser<br>910 915 920 | 3146 |
| cta ttc tca gtt gca cca gcg ttt gcg gac gac gta aca act gat act<br>Leu Phe Ser Val Ala Pro Ala Phe Ala Asp Asp Val Thr Thr Asp Thr<br>925 930 935 | 3194 |
| gtg acc ttg cac aag att gtc atg cca caa gct gca ttt gat aac ttt<br>Val Thr Leu His Lys Ile Val Met Pro Gln Ala Ala Phe Asp Asn Phe<br>940 945 950 | 3242 |
| act gaa ggt aca aaa ggt aag aat gat agc gat tat gtt ggc aaa caa<br>Thr Glu Gly Thr Lys Gly Lys Asn Asp Ser Asp Tyr Val Gly Lys Gln<br>955 960 965 | 3290 |
| att aat gac ctt aaa tct tat ttt ggc tca acc gat gct aaa gaa att<br>Ile Asn Asp Leu Lys Ser Tyr Phe Gly Ser Thr Asp Ala Lys Glu Ile<br>970 975 980 985 | 3338 |
| aag ggt gct ttc ttt gtt ttc aaa aat gaa act ggt aca aaa ttc att<br>Lys Gly Ala Phe Phe Val Phe Lys Asn Glu Thr Gly Thr Lys Phe Ile<br>990 995 1000 | 3386 |
| act gaa aat ggt aag gaa gtc gat act ttg gaa gct aaa gat gct<br>Thr Glu Asn Gly Lys Glu Val Asp Thr Leu Glu Ala Lys Asp Ala<br>1005 1010 1015 | 3431 |
| gaa ggt ggt gct gtt ctt tca ggg tta aca aaa gac act ggt ttt<br>Glu Gly Gly Ala Val Leu Ser Gly Leu Thr Lys Asp Thr Gly Phe<br>1020 1025 1030 | 3476 |
| gct ttt aac act gct aag tta aaa gga act tac caa atc gtt gaa<br>Ala Phe Asn Thr Ala Lys Leu Lys Gly Thr Tyr Gln Ile Val Glu<br>1035 1040 1045 | 3521 |
| ttg aaa gaa aaa tca aac tac gat aac aac ggt tct atc ttg gct<br>Leu Lys Glu Lys Ser Asn Tyr Asp Asn Asn Gly Ser Ile Leu Ala<br>1050 1055 1060 | 3566 |
| gat tca aaa gca gtt cca gtt aaa atc act ctg cca ttg gta aac<br>Asp Ser Lys Ala Val Pro Val Lys Ile Thr Leu Pro Leu Val Asn<br>1065 1070 1075 | 3611 |
| aac caa ggt gtt gtt aaa gat gct cac att tat cca aag aat act<br>Asn Gln Gly Val Val Lys Asp Ala His Ile Tyr Pro Lys Asn Thr<br>1080 1085 1090 | 3656 |
| gaa aca aaa cca caa gta gat aag aac ttt gca gat aaa gat ctt<br>Glu Thr Lys Pro Gln Val Asp Lys Asn Phe Ala Asp Lys Asp Leu<br>1095 1100 1105 | 3701 |
| gat tat act gac aac cga aaa gac aaa ggt gtt gtc tca gcg aca<br>Asp Tyr Thr Asp Asn Arg Lys Asp Lys Gly Val Val Ser Ala Thr<br>1110 1115 1120 | 3746 |
| gtt ggt gac aaa aaa gaa tac ata gtt gga aca aaa att ctt aaa<br>Val Gly Asp Lys Lys Glu Tyr Ile Val Gly Thr Lys Ile Leu Lys<br>1125 1130 1135 | 3791 |
| ggc tca gac tat aag aaa ctg gtt tgg act gat agc atg act aaa<br>Gly Ser Asp Tyr Lys Lys Leu Val Trp Thr Asp Ser Met Thr Lys<br>1140 1145 1150 | 3836 |
| ggt ttg acg ttc aac aac aac gtt aaa gta aca ttg gat ggt aaa<br>Gly Leu Thr Phe Asn Asn Asn Val Lys Val Thr Leu Asp Gly Lys<br>1155 1160 1165 | 3881 |

| | | | | | | | | | | | | |
|---|---|---|---|---|---|---|---|---|---|---|---|---|
| gat | ttt | cct | gtt | tta | aac | tac | aaa | ctc | gta | aca | gat | gac | caa | ggt | 3926 |
| Asp | Phe | Pro | Val | Leu | Asn | Tyr | Lys | Leu | Val | Thr | Asp | Asp | Gln | Gly | |
| | | | 1170 | | | | 1175 | | | | 1180 | | | | |

| ttc | cgt | ctt | gcc | ttg | aat | gca | aca | ggt | ctt | gca | gca | gta | gca | gct | 3971 |
| Phe | Arg | Leu | Ala | Leu | Asn | Ala | Thr | Gly | Leu | Ala | Ala | Val | Ala | Ala | |
| | 1185 | | | | 1190 | | | | 1195 | | | | | | |

| gct | gca | aaa | gac | aaa | gat | gtt | gaa | atc | aag | atc | act | tac | tca | gct | 4016 |
| Ala | Ala | Lys | Asp | Lys | Asp | Val | Glu | Ile | Lys | Ile | Thr | Tyr | Ser | Ala | |
| 1200 | | | | 1205 | | | | 1210 | | | | | | | |

| acg | gtg | aac | ggc | tcc | act | act | gtt | gaa | gtt | cca | gaa | acc | aat | gat | 4061 |
| Thr | Val | Asn | Gly | Ser | Thr | Thr | Val | Glu | Val | Pro | Glu | Thr | Asn | Asp | |
| | | 1215 | | | | 1220 | | | | 1225 | | | | | |

| gtt | aaa | ttg | gac | tat | ggt | aat | aac | cca | acg | gaa | gaa | agt | gaa | cca | 4106 |
| Val | Lys | Leu | Asp | Tyr | Gly | Asn | Asn | Pro | Thr | Glu | Glu | Ser | Glu | Pro | |
| | 1230 | | | | 1235 | | | | 1240 | | | | | | |

| caa | gaa | ggt | act | cca | gct | aac | caa | gaa | att | aaa | gtc | att | aaa | gac | 4151 |
| Gln | Glu | Gly | Thr | Pro | Ala | Asn | Gln | Glu | Ile | Lys | Val | Ile | Lys | Asp | |
| | | 1245 | | | | 1250 | | | | 1255 | | | | | |

| tgg | gca | gta | gat | ggt | aca | att | act | gat | gtt | aat | gtt | gca | gtt | aaa | 4196 |
| Trp | Ala | Val | Asp | Gly | Thr | Ile | Thr | Asp | Val | Asn | Val | Ala | Val | Lys | |
| | 1260 | | | | 1265 | | | | 1270 | | | | | | |

| gct | atc | ttt | acc | ttg | caa | gaa | aaa | caa | acg | gat | ggt | aca | tgg | gtg | 4241 |
| Ala | Ile | Phe | Thr | Leu | Gln | Glu | Lys | Gln | Thr | Asp | Gly | Thr | Trp | Val | |
| 1275 | | | | 1280 | | | | 1285 | | | | | | | |

| aac | gtt | gct | tca | cac | gaa | gca | aca | aaa | cca | tca | cgc | ttt | gaa | cat | 4286 |
| Asn | Val | Ala | Ser | His | Glu | Ala | Thr | Lys | Pro | Ser | Arg | Phe | Glu | His | |
| | | 1290 | | | | 1295 | | | | 1300 | | | | | |

| act | ttc | aca | ggt | ttg | gat | aat | act | aaa | act | tac | cgc | gtt | gtc | gaa | 4331 |
| Thr | Phe | Thr | Gly | Leu | Asp | Asn | Thr | Lys | Thr | Tyr | Arg | Val | Val | Glu | |
| | 1305 | | | | 1310 | | | | 1315 | | | | | | |

| cgt | gtt | agc | ggc | tac | act | cca | gaa | tat | gta | tca | ttt | aaa | aat | ggt | 4376 |
| Arg | Val | Ser | Gly | Tyr | Thr | Pro | Glu | Tyr | Val | Ser | Phe | Lys | Asn | Gly | |
| | 1320 | | | | 1325 | | | | 1330 | | | | | | |

| gtt | gtg | act | atc | aag | aac | aac | aaa | aac | tca | aat | gat | cca | act | cca | 4421 |
| Val | Val | Thr | Ile | Lys | Asn | Asn | Lys | Asn | Ser | Asn | Asp | Pro | Thr | Pro | |
| | | 1335 | | | | 1340 | | | | 1345 | | | | | |

| atc | aac | cca | tca | gaa | cca | aaa | gtg | gtg | act | tat | gga | cgt | aaa | ttt | 4466 |
| Ile | Asn | Pro | Ser | Glu | Pro | Lys | Val | Val | Thr | Tyr | Gly | Arg | Lys | Phe | |
| | 1350 | | | | 1355 | | | | 1360 | | | | | | |

| gtg | aaa | aca | aat | caa | gct | aac | act | gaa | cgc | ttg | gca | gga | gct | acc | 4511 |
| Val | Lys | Thr | Asn | Gln | Ala | Asn | Thr | Glu | Arg | Leu | Ala | Gly | Ala | Thr | |
| | 1365 | | | | 1370 | | | | 1375 | | | | | | |

| ttc | ctt | gtt | aag | aaa | gaa | gga | aaa | tac | ttg | gca | cgt | aaa | gca | ggt | 4556 |
| Phe | Leu | Val | Lys | Lys | Glu | Gly | Lys | Tyr | Leu | Ala | Arg | Lys | Ala | Gly | |
| 1380 | | | | 1385 | | | | 1390 | | | | | | | |

| gca | gca | act | gct | gaa | gca | aag | gca | gct | gta | aaa | act | gct | aaa | cta | 4601 |
| Ala | Ala | Thr | Ala | Glu | Ala | Lys | Ala | Ala | Val | Lys | Thr | Ala | Lys | Leu | |
| | | 1395 | | | | 1400 | | | | 1405 | | | | | |

| gca | ttg | gat | gaa | gct | gtt | aaa | gct | tat | aac | gac | ttg | act | aaa | gaa | 4646 |
| Ala | Leu | Asp | Glu | Ala | Val | Lys | Ala | Tyr | Asn | Asp | Leu | Thr | Lys | Glu | |
| | | 1410 | | | | 1415 | | | | 1420 | | | | | |

| aaa | caa | gaa | ggc | caa | gaa | ggt | aaa | aca | gca | ttg | gct | act | gtt | gat | 4691 |
| Lys | Gln | Glu | Gly | Gln | Glu | Gly | Lys | Thr | Ala | Leu | Ala | Thr | Val | Asp | |
| 1425 | | | | 1430 | | | | 1435 | | | | | | | |

| caa | aaa | caa | aaa | gct | tac | aat | gac | gct | ttt | gtt | aaa | gct | aac | tac | 4736 |
| Gln | Lys | Gln | Lys | Ala | Tyr | Asn | Asp | Ala | Phe | Val | Lys | Ala | Asn | Tyr | |
| | | | 1440 | | | | 1445 | | | | 1450 | | | | |

| tca | tat | gaa | tgg | gtt | gca | gat | aaa | aag | gct | gat | aat | gtt | gtt | aaa | 4781 |
| Ser | Tyr | Glu | Trp | Val | Ala | Asp | Lys | Lys | Ala | Asp | Asn | Val | Val | Lys | |
| | 1455 | | | | 1460 | | | | 1465 | | | | | | |

```
ttg atc tct aac gcc ggt ggt caa ttt gaa att act ggt ttg gat         4826
Leu Ile Ser Asn Ala Gly Gly Gln Phe Glu Ile Thr Gly Leu Asp
        1470                1475                1480 aaa ggc act tat agc ttg gaa gaa act caa gca cca gca ggt tat         4871
Lys Gly Thr Tyr Ser Leu Glu Glu Thr Gln Ala Pro Ala Gly Tyr
    1485                1490                1495 gcg aca ttg tca ggt gat gta aac ttt gaa gta act gcc aca tca         4916
Ala Thr Leu Ser Gly Asp Val Asn Phe Glu Val Thr Ala Thr Ser
1500                1505                1510 tat agc aaa ggg gct aca act gac atc gca tat gat aaa gga tct         4961
Tyr Ser Lys Gly Ala Thr Thr Asp Ile Ala Tyr Asp Lys Gly Ser
    1515                1520                1525 gta aaa aaa gat gcc caa caa gtt caa aac aaa aaa gta acc atc         5006
Val Lys Lys Asp Ala Gln Gln Val Gln Asn Lys Lys Val Thr Ile
1530                1535                1540 cca caa aca ggt ggt att ggt aca att ctt ttc aca att att ggt         5051
Pro Gln Thr Gly Gly Ile Gly Thr Ile Leu Phe Thr Ile Ile Gly
    1545                1550                1555 tta agc att atg ctt gga gca gta gtt gtc atg aaa aaa cgt caa         5096
Leu Ser Ile Met Leu Gly Ala Val Val Val Met Lys Lys Arg Gln
1560                1565                1570 tca gag gaa gct      taaggctagt ctttgatggt gtaagcac agttaaagct      5148
Ser Glu Glu Ala
    1575 gtgcttatga tctaagggta tttcagtaga agtactctta gatcataagc aagagccatt   5208 atttaggaga tgacgtgaag actaaaaata tcaacaaaaa aactaaaaag aagaagtcaa   5268 atcttccttt tatcattctt tttctaatag gtctatctat tttattgtat ccagtggtat   5328 cacgttttta ctatacgata gaatctaata atcaaacaca ggattttgag agag         5382

<210> SEQ ID NO 278
<211> LENGTH: 901
<212> TYPE: PRT
<213> ORGANISM: Streptococcus agalactiae

<400> SEQUENCE: 278

Met Arg Lys Tyr Gln Lys Phe Ser Lys Ile Leu Thr Leu Ser Leu Phe
1               5                   10                  15

Cys Leu Ser Gln Ile Pro Leu Asn Thr Asn Val Leu Gly Glu Ser Thr
            20                  25                  30

Val Pro Glu Asn Gly Ala Lys Gly Lys Leu Val Val Lys Lys Thr Asp
        35                  40                  45

Asp Gln Asn Lys Pro Leu Ser Lys Ala Thr Phe Val Leu Lys Thr Thr
    50                  55                  60

Ala His Pro Glu Ser Lys Ile Glu Lys Val Thr Ala Glu Leu Thr Gly
65                  70                  75                  80

Glu Ala Thr Phe Asp Asn Leu Ile Pro Gly Asp Tyr Thr Leu Ser Glu
                85                  90                  95

Glu Thr Ala Pro Glu Gly Tyr Lys Lys Thr Asn Gln Thr Trp Gln Val
            100                 105                 110

Lys Val Glu Ser Asn Gly Lys Thr Thr Ile Gln Asn Ser Gly Asp Lys
        115                 120                 125

Asn Ser Thr Ile Gly Gln Asn His Glu Glu Leu Asp Lys Gln Tyr Pro
    130                 135                 140

Pro Thr Gly Ile Tyr Glu Asp Thr Lys Glu Ser Tyr Lys Leu Glu His
145                 150                 155                 160

Val Lys Gly Ser Val Pro Asn Gly Lys Ser Glu Ala Lys Ala Val Asn
```

```
                       165                 170                 175
Pro Tyr Ser Ser Glu Gly Glu His Ile Arg Glu Ile Pro Glu Gly Thr
                   180                 185                 190

Leu Ser Lys Arg Ile Ser Glu Val Gly Asp Leu Ala His Asn Lys Tyr
               195                 200                 205

Lys Ile Glu Leu Thr Val Ser Gly Lys Thr Ile Val Lys Pro Val Asp
           210                 215                 220

Lys Gln Lys Pro Leu Asp Val Val Phe Val Leu Asp Asn Ser Asn Ser
225                 230                 235                 240

Met Asn Asn Asp Gly Pro Asn Phe Gln Arg His Asn Lys Ala Lys Lys
                   245                 250                 255

Ala Ala Glu Ala Leu Gly Thr Ala Val Lys Asp Ile Leu Gly Ala Asn
               260                 265                 270

Ser Asp Asn Arg Val Ala Leu Val Thr Tyr Gly Ser Asp Ile Phe Asp
           275                 280                 285

Gly Arg Ser Val Asp Val Val Lys Gly Phe Lys Glu Asp Asp Lys Tyr
       290                 295                 300

Tyr Gly Leu Gln Thr Lys Phe Thr Ile Gln Thr Glu Asn Tyr Ser His
305                 310                 315                 320

Lys Gln Leu Thr Asn Asn Ala Glu Glu Ile Ile Lys Arg Ile Pro Thr
                   325                 330                 335

Glu Ala Pro Arg Ala Lys Trp Gly Ser Thr Thr Asn Gly Leu Thr Pro
               340                 345                 350

Glu Gln Gln Lys Gln Tyr Tyr Leu Ser Lys Val Gly Glu Thr Phe Thr
           355                 360                 365

Met Lys Ala Phe Met Glu Ala Asp Asp Ile Leu Ser Gln Val Asp Arg
       370                 375                 380

Asn Ser Gln Lys Ile Ile Val His Ile Thr Asp Gly Val Pro Thr Arg
385                 390                 395                 400

Ser Tyr Ala Ile Asn Asn Phe Lys Leu Gly Ala Ser Tyr Glu Ser Gln
                   405                 410                 415

Phe Glu Gln Met Lys Lys Asn Gly Tyr Leu Asn Lys Ser Asn Phe Leu
               420                 425                 430

Leu Thr Asp Lys Pro Glu Asp Ile Lys Gly Asn Gly Glu Ser Tyr Phe
           435                 440                 445

Leu Phe Pro Leu Asp Ser Tyr Gln Thr Gln Ile Ile Ser Gly Asn Leu
       450                 455                 460

Gln Lys Leu His Tyr Leu Asp Leu Asn Leu Asn Tyr Pro Lys Gly Thr
465                 470                 475                 480

Ile Tyr Arg Asn Gly Pro Val Arg Glu His Gly Thr Pro Thr Lys Leu
                   485                 490                 495

Tyr Ile Asn Ser Leu Lys Gln Lys Asn Tyr Asp Ile Phe Asn Phe Gly
               500                 505                 510

Ile Asp Ile Ser Ala Phe Arg Gln Val Tyr Asn Glu Asp Tyr Lys Lys
           515                 520                 525

Asn Gln Asp Gly Thr Phe Gln Lys Leu Lys Glu Glu Ala Phe Glu Leu
       530                 535                 540

Ser Asp Gly Glu Ile Thr Glu Leu Met Lys Ser Phe Ser Ser Lys Pro
545                 550                 555                 560

Glu Tyr Tyr Thr Pro Ile Val Thr Ser Ser Asp Ala Ser Asn Asn Glu
                   565                 570                 575

Ile Leu Ser Lys Ile Gln Gln Phe Glu Lys Val Leu Thr Lys Glu
               580                 585                 590
```

Asn Ser Ile Val Asn Gly Thr Ile Glu Asp Pro Met Gly Asp Lys Ile
            595                 600                 605

Asn Leu Gln Leu Gly Asn Gly Gln Thr Leu Gln Pro Ser Asp Tyr Thr
        610                 615                 620

Leu Gln Gly Asn Asp Gly Ser Ile Met Lys Asp Ser Ile Ala Thr Gly
625                 630                 635                 640

Gly Pro Asn Asn Asp Gly Gly Ile Leu Lys Gly Val Lys Leu Glu Tyr
                645                 650                 655

Ile Lys Asn Lys Leu Tyr Val Arg Gly Leu Asn Leu Gly Glu Gly Gln
            660                 665                 670

Lys Val Thr Leu Thr Tyr Asp Val Lys Leu Asp Ser Phe Ile Ser
        675                 680                 685

Asn Lys Phe Tyr Asp Thr Asn Gly Arg Thr Thr Leu Asn Pro Lys Ser
        690                 695                 700

Glu Asp Pro Asn Thr Leu Arg Asp Phe Pro Ile Pro Lys Ile Arg Asp
705                 710                 715                 720

Val Arg Glu Tyr Pro Thr Ile Thr Ile Lys Asn Glu Lys Lys Leu Gly
                725                 730                 735

Glu Ile Glu Phe Thr Lys Val Asp Lys Asp Asn Asn Lys Leu Leu Leu
            740                 745                 750

Lys Gly Ala Thr Phe Glu Leu Gln Glu Phe Asn Glu Asp Tyr Lys Leu
        755                 760                 765

Tyr Leu Pro Ile Lys Asn Asn Asn Ser Lys Val Val Thr Gly Glu Asn
770                 775                 780

Gly Lys Ile Ser Tyr Lys Asp Leu Lys Asp Gly Lys Tyr Gln Leu Ile
785                 790                 795                 800

Glu Ala Val Ser Pro Lys Asp Tyr Gln Lys Ile Thr Asn Lys Pro Ile
                805                 810                 815

Leu Thr Phe Glu Val Val Lys Gly Ser Ile Gln Asn Ile Ile Ala Val
            820                 825                 830

Asn Lys Gln Ile Ser Glu Tyr His Glu Glu Gly Asp Lys His Leu Ile
        835                 840                 845

Thr Asn Thr His Ile Pro Pro Lys Gly Ile Ile Pro Met Thr Gly Gly
        850                 855                 860

Lys Gly Ile Leu Ser Phe Ile Leu Ile Gly Gly Ser Met Met Ser Ile
865                 870                 875                 880

Ala Gly Gly Ile Tyr Ile Trp Lys Arg Tyr Lys Lys Ser Ser Asp Ile
                885                 890                 895

Ser Arg Glu Lys Asp
            900

<210> SEQ ID NO 279
<211> LENGTH: 674
<212> TYPE: PRT
<213> ORGANISM: Streptococcus agalactiae

<400> SEQUENCE: 279

Met Lys Lys Ile Asn Lys Cys Leu Thr Val Phe Ser Thr Leu Leu Leu
1               5                   10                  15

Ile Leu Thr Ser Leu Phe Ser Val Ala Pro Ala Phe Ala Asp Asp Val
            20                  25                  30

Thr Thr Asp Thr Val Thr Leu His Lys Ile Val Met Pro Gln Ala Ala
        35                  40                  45

Phe Asp Asn Phe Thr Glu Gly Thr Lys Gly Lys Asn Asp Ser Asp Tyr
    50                  55                  60

```
Val Gly Lys Gln Ile Asn Asp Leu Lys Ser Tyr Phe Gly Ser Thr Asp
 65                  70                  75                  80

Ala Lys Glu Ile Lys Gly Ala Phe Phe Val Phe Lys Asn Glu Thr Gly
                 85                  90                  95

Thr Lys Phe Ile Thr Glu Asn Gly Lys Glu Val Asp Thr Leu Glu Ala
            100                 105                 110

Lys Asp Ala Glu Gly Gly Ala Val Leu Ser Gly Leu Thr Lys Asp Thr
        115                 120                 125

Gly Phe Ala Phe Asn Thr Ala Lys Leu Lys Gly Thr Tyr Gln Ile Val
130                 135                 140

Glu Leu Lys Glu Lys Ser Asn Tyr Asp Asn Gly Ser Ile Leu Ala
145                 150                 155                 160

Asp Ser Lys Ala Val Pro Val Lys Ile Thr Leu Pro Leu Val Asn Asn
                165                 170                 175

Gln Gly Val Val Lys Asp Ala His Ile Tyr Pro Lys Asn Thr Glu Thr
            180                 185                 190

Lys Pro Gln Val Asp Lys Asn Phe Ala Asp Lys Asp Leu Asp Tyr Thr
        195                 200                 205

Asp Asn Arg Lys Asp Lys Gly Val Val Ser Ala Thr Val Gly Asp Lys
210                 215                 220

Lys Glu Tyr Ile Val Gly Thr Lys Ile Leu Lys Gly Ser Asp Tyr Lys
225                 230                 235                 240

Lys Leu Val Trp Thr Asp Ser Met Thr Lys Gly Leu Thr Phe Asn Asn
                245                 250                 255

Asn Val Lys Val Thr Leu Asp Gly Lys Asp Phe Pro Val Leu Asn Tyr
            260                 265                 270

Lys Leu Val Thr Asp Asp Gln Gly Phe Arg Leu Ala Leu Asn Ala Thr
        275                 280                 285

Gly Leu Ala Ala Val Ala Ala Ala Lys Asp Lys Asp Val Glu Ile
290                 295                 300

Lys Ile Thr Tyr Ser Ala Thr Val Asn Gly Ser Thr Thr Val Glu Val
305                 310                 315                 320

Pro Glu Thr Asn Asp Val Lys Leu Asp Tyr Gly Asn Asn Pro Thr Glu
                325                 330                 335

Glu Ser Glu Pro Gln Glu Gly Thr Pro Ala Asn Gln Glu Ile Lys Val
            340                 345                 350

Ile Lys Asp Trp Ala Val Asp Gly Thr Ile Thr Asp Val Asn Val Ala
        355                 360                 365

Val Lys Ala Ile Phe Thr Leu Gln Glu Lys Gln Thr Asp Gly Thr Trp
370                 375                 380

Val Asn Val Ala Ser His Glu Ala Thr Lys Pro Ser Arg Phe Glu His
385                 390                 395                 400

Thr Phe Thr Gly Leu Asp Asn Thr Lys Thr Tyr Arg Val Val Glu Arg
                405                 410                 415

Val Ser Gly Tyr Thr Pro Glu Tyr Val Ser Phe Lys Asn Gly Val Val
            420                 425                 430

Thr Ile Lys Asn Asn Lys Asn Ser Asn Asp Pro Thr Pro Ile Asn Pro
        435                 440                 445

Ser Glu Pro Lys Val Val Thr Tyr Gly Arg Lys Phe Val Lys Thr Asn
450                 455                 460

Gln Ala Asn Thr Glu Arg Leu Ala Gly Ala Thr Phe Leu Val Lys Lys
465                 470                 475                 480

Glu Gly Lys Tyr Leu Ala Arg Lys Ala Gly Ala Thr Ala Glu Ala
                485                 490                 495
```

```
Lys Ala Ala Val Lys Thr Ala Lys Leu Ala Leu Asp Glu Ala Val Lys
            500                 505                 510

Ala Tyr Asn Asp Leu Thr Lys Glu Lys Gln Glu Gly Gln Glu Gly Lys
            515                 520                 525

Thr Ala Leu Ala Thr Val Asp Gln Lys Gln Lys Ala Tyr Asn Asp Ala
            530                 535                 540

Phe Val Lys Ala Asn Tyr Ser Tyr Glu Trp Val Ala Asp Lys Lys Ala
545                 550                 555                 560

Asp Asn Val Val Lys Leu Ile Ser Asn Ala Gly Gln Phe Glu Ile
                565                 570                 575

Thr Gly Leu Asp Lys Gly Thr Tyr Ser Leu Glu Glu Thr Gln Ala Pro
            580                 585                 590

Ala Gly Tyr Ala Thr Leu Ser Gly Asp Val Asn Phe Glu Val Thr Ala
            595                 600                 605

Thr Ser Tyr Ser Lys Gly Ala Thr Thr Asp Ile Ala Tyr Asp Lys Gly
            610                 615                 620

Ser Val Lys Lys Asp Ala Gln Gln Val Gln Asn Lys Lys Val Thr Ile
625                 630                 635                 640

Pro Gln Thr Gly Gly Ile Gly Thr Ile Leu Phe Thr Ile Ile Gly Leu
            645                 650                 655

Ser Ile Met Leu Gly Ala Val Val Met Lys Lys Arg Gln Ser Glu
            660                 665                 670

Glu Ala

<210> SEQ ID NO 280
<211> LENGTH: 3200
<212> TYPE: DNA
<213> ORGANISM: Streptococcus agalactiae
<220> FEATURE:
<221> NAME/KEY: CDS
<222> LOCATION: (487)..(2391)
<220> FEATURE:
<221> NAME/KEY: CDS
<222> LOCATION: (2461)..(3003)

<400> SEQUENCE: 280
gctcatgata atttatagaa catttataaa atcttataat aaactggtta agtataggaa        60
atactgcata tttcttgaaa atatggtgta tattgtgaat aaaatgatga ccaagttaat       120
tgaattttcc tatcgaaaaa ttttcaaaa aaataatttt cacgctcaaa tcatttgatt       180
gtcaaataaa tagagccttt ataaaaatat tatataagta taaatgtaa aaaaataaaa       240 aaatgatatt tttatttgat tcaaatgtat ttaataaaaa tacaaagttt ctaaaaagt       300 aaaaattcca tctcaataaa cagcgttagt tattataacc gaacattatt gtccttaaaa       360
cattaaaaca aaaacaaaag ttcgtaattt aattaatttg tcatgttact aatcttatgc       420
taatatatta tctcgtgata agttttgat gtaaaaatta tcatgaaaaa gaaagagag       480 atggaa atg aaa aaa caa ttt tta aaa tca gca gcg att cta tcg cta         528
       Met Lys Lys Gln Phe Leu Lys Ser Ala Ala Ile Leu Ser Leu
        1               5                   10 gca gta aca gca gta tct aca agt cag ccg gta gcc ggg ata act aaa       576
Ala Val Thr Ala Val Ser Thr Ser Gln Pro Val Ala Gly Ile Thr Lys
15              20                  25                  30 gat tat aat aac cga aat gaa aaa gta aaa aag tat tta caa gaa aat       624
Asp Tyr Asn Asn Arg Asn Glu Lys Val Lys Lys Tyr Leu Gln Glu Asn
                35                  40                  45 aat ttc ggt cat aaa ata gcg tat gga tgg aaa aat aaa gta gaa ttt       672
Asn Phe Gly His Lys Ile Ala Tyr Gly Trp Lys Asn Lys Val Glu Phe
```

|  |  |  |  |  |  |  |  |  |  |  |  |  |  |  |  |
|---|---|---|---|---|---|---|---|---|---|---|---|---|---|---|---|
|  |  |  |  | 50 |  |  |  | 55 |  |  |  | 60 |  |  |  |
| gat | ttt | cgt | tat | tta | ttg | gat | act | gct | aaa | tat | tta | gta | aat | aaa | gaa | 720 |
| Asp | Phe | Arg | Tyr | Leu | Leu | Asp | Thr | Ala | Lys | Tyr | Leu | Val | Asn | Lys | Glu |  |
|  |  | 65 |  |  |  |  | 70 |  |  |  |  | 75 |  |  |  |  |
| gaa | ttt | caa | gat | cct | tta | tat | aat | gat | gcg | cgc | gaa | gaa | ttg | ata | agt | 768 |
| Glu | Phe | Gln | Asp | Pro | Leu | Tyr | Asn | Asp | Ala | Arg | Glu | Glu | Leu | Ile | Ser |  |
|  | 80 |  |  |  |  | 85 |  |  |  |  | 90 |  |  |  |  |  |
| ttt | att | ttt | cct | tat | gag | aaa | ttt | tta | att | aac | aat | cgt | gac | ata | act | 816 |
| Phe | Ile | Phe | Pro | Tyr | Glu | Lys | Phe | Leu | Ile | Asn | Asn | Arg | Asp | Ile | Thr |  |
| 95 |  |  |  |  | 100 |  |  |  |  | 105 |  |  |  |  | 110 |  |
| aaa | tta | aca | gtt | aat | cag | tat | gaa | gcg | att | gtg | aat | aga | atg | agt | gtt | 864 |
| Lys | Leu | Thr | Val | Asn | Gln | Tyr | Glu | Ala | Ile | Val | Asn | Arg | Met | Ser | Val |  |
|  |  |  |  | 115 |  |  |  |  | 120 |  |  |  |  | 125 |  |  |
| gct | tta | caa | aaa | ttt | tca | aag | aat | att | ttt | gag | aaa | cag | aaa | gta | aat | 912 |
| Ala | Leu | Gln | Lys | Phe | Ser | Lys | Asn | Ile | Phe | Glu | Lys | Gln | Lys | Val | Asn |  |
|  |  | 130 |  |  |  |  | 135 |  |  |  |  | 140 |  |  |  |  |
| aaa | gat | tta | atc | cct | att | gcg | ttt | tgg | att | gag | aaa | agt | tac | aga | act | 960 |
| Lys | Asp | Leu | Ile | Pro | Ile | Ala | Phe | Trp | Ile | Glu | Lys | Ser | Tyr | Arg | Thr |  |
|  |  |  | 145 |  |  |  |  | 150 |  |  |  |  | 155 |  |  |  |
| gtt | gga | acg | aat | gaa | atc | gcc | gct | tct | gta | ggc | att | caa | gga | gga | ttt | 1008 |
| Val | Gly | Thr | Asn | Glu | Ile | Ala | Ala | Ser | Val | Gly | Ile | Gln | Gly | Gly | Phe |  |
|  | 160 |  |  |  |  | 165 |  |  |  |  | 170 |  |  |  |  |  |
| tat | caa | aac | ttc | cat | gat | tat | tat | aat | tat | tca | tat | cta | tta | aat | tct | 1056 |
| Tyr | Gln | Asn | Phe | His | Asp | Tyr | Tyr | Asn | Tyr | Ser | Tyr | Leu | Leu | Asn | Ser |  |
| 175 |  |  |  |  | 180 |  |  |  |  | 185 |  |  |  |  | 190 |  |
| tta | tgg | cat | gaa | gga | aat | gta | aaa | gaa | gta | gtt | aag | gat | tat | gaa | aac | 1104 |
| Leu | Trp | His | Glu | Gly | Asn | Val | Lys | Glu | Val | Val | Lys | Asp | Tyr | Glu | Asn |  |
|  |  |  |  | 195 |  |  |  |  | 200 |  |  |  |  | 205 |  |  |
| act | att | cgt | caa | ata | cta | tct | aaa | aag | cat | gag | att | gaa | aaa | att | ctt | 1152 |
| Thr | Ile | Arg | Gln | Ile | Leu | Ser | Lys | Lys | His | Glu | Ile | Glu | Lys | Ile | Leu |  |
|  |  |  | 210 |  |  |  |  | 215 |  |  |  |  | 220 |  |  |  |
| aat | cag | agc | act | tct | gat | atc | tct | ata | gat | gat | gat | gat | tac | gaa | aaa | 1200 |
| Asn | Gln | Ser | Thr | Ser | Asp | Ile | Ser | Ile | Asp | Asp | Asp | Asp | Tyr | Glu | Lys |  |
|  | 225 |  |  |  |  | 230 |  |  |  |  | 235 |  |  |  |  |  |
| gga | aat | aaa | gaa | ttg | cta | agg | gaa | aaa | tta | aat | att | att | cta | aat | ctt | 1248 |
| Gly | Asn | Lys | Glu | Leu | Leu | Arg | Glu | Lys | Leu | Asn | Ile | Ile | Leu | Asn | Leu |  |
| 240 |  |  |  |  | 245 |  |  |  |  | 250 |  |  |  |  |  |  |
| tca | aag | aga | gat | tac | aga | gta | act | cca | tac | tat | gaa | gtg | aat | aaa | cta | 1296 |
| Ser | Lys | Arg | Asp | Tyr | Arg | Val | Thr | Pro | Tyr | Tyr | Glu | Val | Asn | Lys | Leu |  |
| 255 |  |  |  |  | 260 |  |  |  |  | 265 |  |  |  |  | 270 |  |
| cat | aca | ggg | ctt | att | tta | ttg | gag | gat | gtc | cct | aat | tta | aag | att | gct | 1344 |
| His | Thr | Gly | Leu | Ile | Leu | Leu | Glu | Asp | Val | Pro | Asn | Leu | Lys | Ile | Ala |  |
|  |  |  | 275 |  |  |  |  | 280 |  |  |  |  | 285 |  |  |  |
| aag | gat | aag | ttg | ttc | tca | tta | gag | aat | tct | tta | aag | gaa | tac | aaa | gga | 1392 |
| Lys | Asp | Lys | Leu | Phe | Ser | Leu | Glu | Asn | Ser | Leu | Lys | Glu | Tyr | Lys | Gly |  |
|  | 290 |  |  |  |  | 295 |  |  |  |  | 300 |  |  |  |  |  |
| gag | aaa | gtt | aat | tat | gag | gaa | cta | aga | ttc | aat | acg | gaa | cct | tta | act | 1440 |
| Glu | Lys | Val | Asn | Tyr | Glu | Glu | Leu | Arg | Phe | Asn | Thr | Glu | Pro | Leu | Thr |  |
|  |  | 305 |  |  |  |  | 310 |  |  |  |  | 315 |  |  |  |  |
| agt | tac | tta | gaa | aat | aaa | gaa | aaa | ttt | tta | gtc | ccc | aat | att | cca | tat | 1488 |
| Ser | Tyr | Leu | Glu | Asn | Lys | Glu | Lys | Phe | Leu | Val | Pro | Asn | Ile | Pro | Tyr |  |
|  | 320 |  |  |  |  | 325 |  |  |  |  | 330 |  |  |  |  |  |
| aaa | aat | aaa | tta | att | tta | agg | gaa | gaa | gat | aaa | tat | agt | ttt | gaa | gat | 1536 |
| Lys | Asn | Lys | Leu | Ile | Leu | Arg | Glu | Glu | Asp | Lys | Tyr | Ser | Phe | Glu | Asp |  |
| 335 |  |  |  |  | 340 |  |  |  |  | 345 |  |  |  |  | 350 |  |
| gat | gaa | gaa | gag | ttt | gga | aat | gaa | ctt | cta | agt | tac | aat | aag | ctt | aag | 1584 |
| Asp | Glu | Glu | Glu | Phe | Gly | Asn | Glu | Leu | Leu | Ser | Tyr | Asn | Lys | Leu | Lys |  |
|  |  |  |  | 355 |  |  |  |  | 360 |  |  |  |  | 365 |  |  |
| aat | gaa | gtt | tta | cct | gtt | aat | att | aca | act | tct | act | ata | tta | aaa | ccg | 1632 |
| Asn | Glu | Val | Leu | Pro | Val | Asn | Ile | Thr | Thr | Ser | Thr | Ile | Leu | Lys | Pro |  |

```
                   370               375                380
ttt gaa cag aag aaa att gtg gaa gat ttt aat cct tat tct aat tta    1680
Phe Glu Gln Lys Lys Ile Val Glu Asp Phe Asn Pro Tyr Ser Asn Leu
            385                 390                395 gac aat tta gaa ata aaa aaa ata agg ttg aat ggc tcc caa aaa caa    1728
Asp Asn Leu Glu Ile Lys Lys Ile Arg Leu Asn Gly Ser Gln Lys Gln
400                 405                 410 aaa gta gaa cag gaa aaa act aaa tcg cca act cct caa aaa gag act    1776
Lys Val Glu Gln Glu Lys Thr Lys Ser Pro Thr Pro Gln Lys Glu Thr
415                 420                 425                 430 gtg aaa gaa caa act gag caa aaa gta tct gga aat act caa gag gta    1824
Val Lys Glu Gln Thr Glu Gln Lys Val Ser Gly Asn Thr Gln Glu Val
                435                 440                 445 gaa aag aaa tct gaa act gtg gca act tca caa caa agt tca gtt gcg    1872
Glu Lys Lys Ser Glu Thr Val Ala Thr Ser Gln Gln Ser Ser Val Ala
            450                 455                 460 caa act tct gtc caa cag ccg gct ccg gtt caa tca gtt gtt caa gaa    1920
Gln Thr Ser Val Gln Gln Pro Ala Pro Val Gln Ser Val Val Gln Glu
            465                 470                 475 tcc aaa gct tct caa gag gag att aat gca gca cac gat gct att tcg    1968
Ser Lys Ala Ser Gln Glu Glu Ile Asn Ala Ala His Asp Ala Ile Ser
480                 485                 490 gcg tat aaa tca aca gtc aat att gct aat aca gcc ggt gta aca act    2016
Ala Tyr Lys Ser Thr Val Asn Ile Ala Asn Thr Ala Gly Val Thr Thr
495                 500                 505                 510 gcg gaa atg acc acg ctc att aat act caa act tct aat ctt tct gat    2064
Ala Glu Met Thr Thr Leu Ile Asn Thr Gln Thr Ser Asn Leu Ser Asp
                515                 520                 525 gtt gag aaa gct tta gga aat aat aag gtt aat aat ggt gca gtc aat    2112
Val Glu Lys Ala Leu Gly Asn Asn Lys Val Asn Asn Gly Ala Val Asn
            530                 535                 540 gta ttg aga gaa gat aca gct cgt ctt gag aat atg att tgg aat cgt    2160
Val Leu Arg Glu Asp Thr Ala Arg Leu Glu Asn Met Ile Trp Asn Arg
            545                 550                 555 gct tac caa gct att gaa gaa ttc aac gtc gct cgt aat act tat aat    2208
Ala Tyr Gln Ala Ile Glu Glu Phe Asn Val Ala Arg Asn Thr Tyr Asn
            560                 565                 570 aac caa atc aag aca gaa aca gtt cca gtt gat aat gat att gaa gct    2256
Asn Gln Ile Lys Thr Glu Thr Val Pro Val Asp Asn Asp Ile Glu Ala
575                 580                 585                 590 att tta gca ggt tct caa gct aaa att agc cat ttg gac aat cgt atc    2304
Ile Leu Ala Gly Ser Gln Ala Lys Ile Ser His Leu Asp Asn Arg Ile
                595                 600                 605 gga gcg cgc cac atg gat caa gct ttt gta gct agt tta tta gaa gtt    2352
Gly Ala Arg His Met Asp Gln Ala Phe Val Ala Ser Leu Leu Glu Val
            610                 615                 620 act gag atg agt aaa tca atc tca tcg cgt ata aaa gag tagacactgc     2401
Thr Glu Met Ser Lys Ser Ile Ser Ser Arg Ile Lys Glu
            625                 630                 635 tatcaaggcg atcttaaact tttgtattaa actaacctaa aagatagaaa gagactaat  2460 atg aaa aaa ata aca act tta atc tta gct agt agc tta tta cta gtt    2508
Met Lys Lys Ile Thr Thr Leu Ile Leu Ala Ser Ser Leu Leu Leu Val
                640                 645                 650 gca acg aca tcg gtt aaa gct gat gat aac ttt gaa atg cca acg cgt    2556
Ala Thr Thr Ser Val Lys Ala Asp Asp Asn Phe Glu Met Pro Thr Arg
655                 660                 665 tat gtt aaa atg agt gaa aaa tca aaa gca ttt tat caa aga cta caa    2604
Tyr Val Lys Met Ser Glu Lys Ser Lys Ala Phe Tyr Gln Arg Leu Gln
                670                 675                 680
```

```
gaa aaa caa cgt aag gca cat act act gtg aag act ttt aat aat tca      2652
Glu Lys Gln Arg Lys Ala His Thr Thr Val Lys Thr Phe Asn Asn Ser
            685                 690                 695 gaa ata agg cat caa cta cct ctt aaa caa gaa aag gct aga aat gat      2700
Glu Ile Arg His Gln Leu Pro Leu Lys Gln Glu Lys Ala Arg Asn Asp
        700                 705                 710             715 atc tac aat tta ggc att ctt att tct cag gag tct aaa ggg ttc atc      2748
Ile Tyr Asn Leu Gly Ile Leu Ile Ser Gln Glu Ser Lys Gly Phe Ile
        720                 725                 730 caa cgt att gat aat gcc tat tct ttg gaa aat gtc tca gat att gtt      2796
Gln Arg Ile Asp Asn Ala Tyr Ser Leu Glu Asn Val Ser Asp Ile Val
735                 740                 745 aat gaa gct cag gct ttg tat aaa cgt aac tat gat tta ttt gaa aaa     2844
Asn Glu Ala Gln Ala Leu Tyr Lys Arg Asn Tyr Asp Leu Phe Glu Lys
                750                 755                 760 atc aaa tct aca cgt gat aag gtt caa gtc tta ctt gca tcg cat caa      2892
Ile Lys Ser Thr Arg Asp Lys Val Gln Val Leu Leu Ala Ser His Gln
        765                 770                 775 gat aat aca gac tta aaa aac ttt tat gct gag tta gat gat atg tat      2940
Asp Asn Thr Asp Leu Lys Asn Phe Tyr Ala Glu Leu Asp Asp Met Tyr
        780                 785                 790             795 gaa cat gtt tat ctc aat gaa agt aga gtg gag gcg ata aac aga aat      2988
Glu His Val Tyr Leu Asn Glu Ser Arg Val Glu Ala Ile Asn Arg Asn
        800                 805                 810 atc caa aaa tat aat tagtttctaa actaacaaac attcctaaat ataagatatt      3043
Ile Gln Lys Tyr Asn
815 aaaccctact tattgattag tgagtagggt tttactgttt taaatagctt tctgctcaga    3103 atgtaagcct tgtcatttca aaggaactat gttattattc ttaagtaaat taaataggac    3163 atttggggtg cgtaacagct gagattatac ccattga                             3200

<210> SEQ ID NO 281
<211> LENGTH: 635
<212> TYPE: PRT
<213> ORGANISM: Streptococcus agalactiae

<400> SEQUENCE: 281

Met Lys Lys Gln Phe Leu Lys Ser Ala Ala Ile Leu Ser Leu Ala Val
1               5                   10                  15

Thr Ala Val Ser Thr Ser Gln Pro Val Ala Gly Ile Thr Lys Asp Tyr
                20                  25                  30

Asn Asn Arg Asn Glu Lys Val Lys Lys Tyr Leu Gln Glu Asn Asn Phe
            35                  40                  45

Gly His Lys Ile Ala Tyr Gly Trp Lys Asn Lys Val Glu Phe Asp Phe
        50                  55                  60

Arg Tyr Leu Leu Asp Thr Ala Lys Tyr Leu Val Asn Lys Glu Glu Phe
65                  70                  75                  80

Gln Asp Pro Leu Tyr Asn Asp Ala Arg Glu Glu Leu Ile Ser Phe Ile
                85                  90                  95

Phe Pro Tyr Glu Lys Phe Leu Ile Asn Asn Arg Asp Ile Thr Lys Leu
            100                 105                 110

Thr Val Asn Gln Tyr Glu Ala Ile Val Asn Arg Met Ser Val Ala Leu
        115                 120                 125

Gln Lys Phe Ser Lys Asn Ile Phe Glu Lys Gln Lys Val Asn Lys Asp
    130                 135                 140

Leu Ile Pro Ile Ala Phe Trp Ile Glu Lys Ser Tyr Arg Thr Val Gly
145                 150                 155                 160
```

-continued

```
Thr Asn Glu Ile Ala Ala Ser Val Gly Ile Gln Gly Gly Phe Tyr Gln
                165                 170                 175

Asn Phe His Asp Tyr Tyr Asn Tyr Ser Tyr Leu Leu Asn Ser Leu Trp
            180                 185                 190

His Glu Gly Asn Val Lys Glu Val Val Lys Asp Tyr Glu Asn Thr Ile
        195                 200                 205

Arg Gln Ile Leu Ser Lys Lys His Glu Ile Glu Lys Ile Leu Asn Gln
    210                 215                 220

Ser Thr Ser Asp Ile Ser Ile Asp Asp Asp Tyr Glu Lys Gly Asn
225                 230                 235                 240

Lys Glu Leu Leu Arg Glu Lys Leu Asn Ile Ile Leu Asn Leu Ser Lys
                245                 250                 255

Arg Asp Tyr Arg Val Thr Pro Tyr Tyr Glu Val Asn Lys Leu His Thr
            260                 265                 270

Gly Leu Ile Leu Leu Glu Asp Val Pro Asn Leu Lys Ile Ala Lys Asp
        275                 280                 285

Lys Leu Phe Ser Leu Glu Asn Ser Leu Lys Glu Tyr Lys Gly Glu Lys
    290                 295                 300

Val Asn Tyr Glu Glu Leu Arg Phe Asn Thr Glu Pro Leu Thr Ser Tyr
305                 310                 315                 320

Leu Glu Asn Lys Glu Lys Phe Leu Val Pro Asn Ile Pro Tyr Lys Asn
                325                 330                 335

Lys Leu Ile Leu Arg Glu Glu Asp Lys Tyr Ser Phe Glu Asp Asp Glu
            340                 345                 350

Glu Glu Phe Gly Asn Glu Leu Leu Ser Tyr Asn Lys Leu Lys Asn Glu
        355                 360                 365

Val Leu Pro Val Asn Ile Thr Thr Ser Thr Ile Leu Lys Pro Phe Glu
    370                 375                 380

Gln Lys Lys Ile Val Glu Asp Phe Asn Pro Tyr Ser Asn Leu Asp Asn
385                 390                 395                 400

Leu Glu Ile Lys Lys Ile Arg Leu Asn Gly Ser Gln Lys Gln Lys Val
                405                 410                 415

Glu Gln Glu Lys Thr Lys Ser Pro Thr Pro Gln Lys Glu Thr Val Lys
            420                 425                 430

Glu Gln Thr Glu Gln Lys Val Ser Gly Asn Thr Gln Glu Val Glu Lys
        435                 440                 445

Lys Ser Glu Thr Val Ala Thr Ser Gln Gln Ser Ser Val Ala Gln Thr
    450                 455                 460

Ser Val Gln Gln Pro Ala Pro Val Gln Ser Val Gln Glu Ser Lys
465                 470                 475                 480

Ala Ser Gln Glu Glu Ile Asn Ala Ala His Asp Ala Ile Ser Ala Tyr
                485                 490                 495

Lys Ser Thr Val Asn Ile Ala Asn Thr Ala Gly Val Thr Thr Ala Glu
            500                 505                 510

Met Thr Thr Leu Ile Asn Thr Gln Thr Ser Asn Leu Ser Asp Val Glu
        515                 520                 525

Lys Ala Leu Gly Asn Asn Lys Val Asn Asn Gly Ala Val Asn Val Leu
    530                 535                 540

Arg Glu Asp Thr Ala Arg Leu Glu Asn Met Ile Trp Asn Arg Ala Tyr
545                 550                 555                 560

Gln Ala Ile Glu Glu Phe Asn Val Ala Arg Asn Thr Tyr Asn Asn Gln
                565                 570                 575

Ile Lys Thr Glu Thr Val Pro Val Asp Asn Asp Ile Glu Ala Ile Leu
            580                 585                 590
```

```
Ala Gly Ser Gln Ala Lys Ile Ser His Leu Asp Asn Arg Ile Gly Ala
            595                 600                 605

Arg His Met Asp Gln Ala Phe Val Ala Ser Leu Leu Glu Val Thr Glu
            610                 615                 620

Met Ser Lys Ser Ile Ser Ser Arg Ile Lys Glu
625                 630                 635

<210> SEQ ID NO 282
<211> LENGTH: 181
<212> TYPE: PRT
<213> ORGANISM: Streptococcus agalactiae

<400> SEQUENCE: 282

Met Lys Lys Ile Thr Thr Leu Ile Leu Ala Ser Ser Leu Leu Leu Val
1               5                   10                  15

Ala Thr Thr Ser Val Lys Ala Asp Asp Asn Phe Glu Met Pro Thr Arg
            20                  25                  30

Tyr Val Lys Met Ser Glu Lys Ser Lys Ala Phe Tyr Gln Arg Leu Gln
            35                  40                  45

Glu Lys Gln Arg Lys Ala His Thr Thr Val Lys Thr Phe Asn Asn Ser
50                  55                  60

Glu Ile Arg His Gln Leu Pro Leu Lys Gln Glu Lys Ala Arg Asn Asp
65                  70                  75                  80

Ile Tyr Asn Leu Gly Ile Leu Ile Ser Gln Glu Ser Lys Gly Phe Ile
            85                  90                  95

Gln Arg Ile Asp Asn Ala Tyr Ser Leu Glu Asn Val Ser Asp Ile Val
            100                 105                 110

Asn Glu Ala Gln Ala Leu Tyr Lys Arg Asn Tyr Asp Leu Phe Glu Lys
            115                 120                 125

Ile Lys Ser Thr Arg Asp Lys Val Gln Val Leu Leu Ala Ser His Gln
            130                 135                 140

Asp Asn Thr Asp Leu Lys Asn Phe Tyr Ala Glu Leu Asp Asp Met Tyr
145                 150                 155                 160

Glu His Val Tyr Leu Asn Glu Ser Arg Val Glu Ala Ile Asn Arg Asn
            165                 170                 175

Ile Gln Lys Tyr Asn
            180

<210> SEQ ID NO 283
<211> LENGTH: 643
<212> TYPE: PRT
<213> ORGANISM: Streptococcus agalactiae

<400> SEQUENCE: 283

Met Lys Lys Lys Arg Glu Met Glu Met Lys Lys Gln Phe Leu Lys Ser
1               5                   10                  15

Ala Ala Ile Leu Ser Leu Ala Val Thr Ala Val Ser Thr Ser Gln Pro
            20                  25                  30

Val Ala Gly Ile Thr Lys Asp Tyr Asn Asn Arg Asn Glu Lys Val Lys
            35                  40                  45

Lys Tyr Leu Gln Glu Asn Asn Phe Gly His Lys Ile Ala Tyr Gly Trp
            50                  55                  60

Lys Asn Lys Val Glu Phe Asp Phe Arg Tyr Leu Leu Asp Thr Ala Lys
65                  70                  75                  80

Tyr Leu Val Asn Lys Glu Glu Phe Gln Asp Pro Leu Tyr Asn Asp Ala
            85                  90                  95
```

```
Arg Glu Glu Leu Ile Ser Phe Ile Phe Pro Tyr Lys Phe Leu Ile
            100                 105                 110

Asn Asn Arg Asp Ile Thr Lys Leu Thr Val Asn Gln Tyr Glu Ala Ile
        115                 120                 125

Val Asn Arg Met Ser Val Ala Leu Gln Lys Phe Ser Lys Asn Ile Phe
    130                 135                 140

Glu Lys Gln Lys Val Asn Lys Asp Leu Ile Pro Ile Ala Phe Trp Ile
145                 150                 155                 160

Glu Lys Ser Tyr Arg Thr Val Gly Thr Asn Glu Ile Ala Ala Ser Val
                165                 170                 175

Gly Ile Gln Gly Gly Phe Tyr Gln Asn Phe His Asp Tyr Tyr Asn Tyr
            180                 185                 190

Ser Tyr Leu Leu Asn Ser Leu Trp His Glu Gly Asn Val Lys Glu Val
        195                 200                 205

Val Lys Asp Tyr Glu Asn Thr Ile Arg Gln Ile Leu Ser Lys Lys His
    210                 215                 220

Glu Ile Glu Lys Ile Leu Asn Gln Ser Thr Ser Asp Ile Ser Ile Asp
225                 230                 235                 240

Asp Asp Asp Tyr Glu Lys Gly Asn Lys Glu Leu Leu Arg Glu Lys Leu
                245                 250                 255

Asn Ile Ile Leu Asn Leu Ser Lys Arg Asp Tyr Arg Val Thr Pro Tyr
            260                 265                 270

Tyr Glu Val Asn Lys Leu His Thr Gly Leu Ile Leu Leu Glu Asp Val
        275                 280                 285

Pro Asn Leu Lys Ile Ala Lys Asp Lys Leu Phe Ser Leu Glu Asn Ser
    290                 295                 300

Leu Lys Glu Tyr Lys Gly Glu Lys Val Asn Tyr Glu Glu Leu Arg Phe
305                 310                 315                 320

Asn Thr Glu Pro Leu Thr Ser Tyr Leu Glu Asn Lys Glu Lys Phe Leu
                325                 330                 335

Val Pro Asn Ile Pro Tyr Lys Asn Lys Leu Ile Leu Arg Glu Glu Asp
            340                 345                 350

Lys Tyr Ser Phe Glu Asp Asp Glu Glu Glu Phe Gly Asn Glu Leu Leu
        355                 360                 365

Ser Tyr Asn Lys Leu Lys Asn Glu Val Leu Pro Val Asn Ile Thr Thr
    370                 375                 380

Ser Thr Ile Leu Lys Pro Phe Glu Gln Lys Lys Ile Val Glu Asp Phe
385                 390                 395                 400

Asn Pro Tyr Ser Asn Leu Asp Asn Leu Glu Ile Lys Lys Ile Arg Leu
                405                 410                 415

Asn Gly Ser Gln Lys Gln Lys Val Glu Gln Glu Lys Thr Lys Ser Pro
            420                 425                 430

Thr Pro Gln Lys Glu Thr Val Lys Glu Gln Glu Gln Lys Val Ser
        435                 440                 445

Gly Asn Thr Gln Glu Val Glu Lys Lys Ser Glu Thr Val Ala Thr Ser
    450                 455                 460

Gln Gln Ser Ser Val Ala Gln Thr Ser Val Gln Pro Ala Pro Val
465                 470                 475                 480

Gln Ser Val Val Gln Glu Ser Lys Ala Ser Gln Glu Glu Ile Asn Ala
                485                 490                 495

Ala His Asp Ala Ile Ser Ala Tyr Lys Ser Thr Val Asn Ile Ala Asn
            500                 505                 510

Thr Ala Gly Val Thr Thr Ala Glu Met Thr Thr Leu Ile Asn Thr Gln
        515                 520                 525
```

```
Thr Ser Asn Leu Ser Asp Val Glu Lys Ala Leu Gly Asn Asn Lys Val
    530                 535                 540

Asn Asn Gly Ala Val Asn Val Leu Arg Glu Asp Thr Ala Arg Leu Glu
545                 550                 555                 560

Asn Met Ile Trp Asn Arg Ala Tyr Gln Ala Ile Glu Glu Phe Asn Val
                565                 570                 575

Ala Arg Asn Thr Tyr Asn Asn Gln Ile Lys Thr Glu Thr Val Pro Val
            580                 585                 590

Asp Asn Asp Ile Glu Ala Ile Leu Ala Gly Ser Gln Ala Lys Ile Ser
        595                 600                 605

His Leu Asp Asn Arg Ile Gly Ala Arg His Met Asp Gln Ala Phe Val
    610                 615                 620

Ala Ser Leu Leu Glu Val Thr Glu Met Ser Lys Ser Ile Ser Ser Arg
625                 630                 635                 640

Ile Lys Glu

<210> SEQ ID NO 284
<211> LENGTH: 635
<212> TYPE: PRT
<213> ORGANISM: Streptococcus agalactiae

<400> SEQUENCE: 284

Met Lys Lys Gln Phe Leu Lys Ser Ala Ala Ile Leu Ser Leu Ala Val
1               5                   10                  15

Thr Ala Val Ser Thr Ser Gln Pro Val Ala Gly Ile Thr Lys Asp Tyr
            20                  25                  30

Asn Asn Arg Asn Glu Lys Val Lys Lys Tyr Leu Gln Glu Asn Asn Phe
        35                  40                  45

Gly His Lys Ile Ala Tyr Gly Trp Lys Asn Lys Val Glu Phe Asp Phe
    50                  55                  60

Arg Tyr Leu Leu Asp Thr Ala Lys Tyr Leu Val Asn Lys Glu Glu Phe
65                  70                  75                  80

Gln Asp Pro Leu Tyr Asn Asp Ala Arg Glu Glu Leu Ile Ser Phe Ile
                85                  90                  95

Phe Pro Tyr Glu Lys Phe Leu Ile Asn Asn Arg Asp Ile Thr Lys Leu
            100                 105                 110

Thr Val Asn Gln Tyr Glu Ala Ile Val Asn Arg Met Ser Val Ala Leu
        115                 120                 125

Gln Lys Phe Ser Lys Asn Ile Phe Glu Lys Gln Lys Val Asn Lys Asp
130                 135                 140

Leu Ile Pro Ile Ala Phe Trp Ile Glu Lys Ser Tyr Arg Thr Val Gly
145                 150                 155                 160

Thr Asn Glu Ile Ala Ala Ser Val Gly Ile Gln Gly Gly Phe Tyr Gln
                165                 170                 175

Asn Phe His Asp Tyr Tyr Asn Tyr Ser Tyr Leu Leu Asn Ser Leu Trp
            180                 185                 190

His Glu Gly Asn Val Lys Glu Val Val Lys Asp Tyr Glu Asn Thr Ile
        195                 200                 205

Arg Gln Ile Leu Ser Lys Lys His Glu Ile Lys Ile Leu Asn Gln
    210                 215                 220

Ser Thr Ser Asp Ile Ser Ile Asp Asp Asp Tyr Glu Lys Gly Asn
225                 230                 235                 240

Lys Glu Leu Leu Arg Glu Lys Leu Asn Ile Ile Leu Asn Leu Ser Lys
                245                 250                 255
```

Arg Asp Tyr Arg Val Thr Pro Tyr Tyr Glu Val Asn Lys Leu His Thr
             260                 265                 270

Gly Leu Ile Leu Leu Glu Asp Val Pro Asn Leu Lys Ile Ala Lys Asp
             275                 280                 285

Lys Leu Phe Ser Leu Glu Asn Ser Leu Lys Glu Tyr Lys Gly Glu Lys
             290                 295                 300

Val Asn Tyr Glu Glu Leu Arg Phe Asn Thr Glu Pro Leu Thr Ser Tyr
305                 310                 315                 320

Leu Glu Asn Lys Glu Lys Phe Leu Val Pro Asn Ile Pro Tyr Lys Asn
             325                 330                 335

Lys Leu Ile Leu Arg Glu Glu Asp Lys Tyr Ser Phe Glu Asp Asp Glu
             340                 345                 350

Glu Glu Phe Gly Asn Glu Leu Leu Ser Tyr Asn Lys Leu Lys Asn Glu
             355                 360                 365

Val Leu Pro Val Asn Ile Thr Thr Ser Thr Ile Leu Lys Pro Phe Glu
             370                 375                 380

Gln Lys Lys Ile Val Glu Asp Phe Asn Pro Tyr Ser Asn Leu Asp Asn
385                 390                 395                 400

Leu Glu Ile Lys Lys Ile Arg Leu Asn Gly Ser Gln Lys Gln Lys Val
             405                 410                 415

Glu Gln Glu Lys Thr Lys Ser Pro Thr Pro Gln Lys Glu Thr Val Lys
             420                 425                 430

Glu Gln Thr Glu Gln Lys Val Ser Gly Asn Thr Gln Glu Val Glu Lys
             435                 440                 445

Lys Ser Glu Thr Val Ala Thr Ser Gln Gln Ser Ser Val Ala Gln Thr
450                 455                 460

Ser Val Gln Gln Pro Ala Pro Val Gln Ser Val Val Gln Glu Ser Lys
465                 470                 475                 480

Ala Ser Gln Glu Glu Ile Asn Ala Ala His Asp Ala Ile Ser Ala Tyr
             485                 490                 495

Lys Ser Thr Val Asn Ile Ala Asn Thr Ala Gly Val Thr Thr Ala Glu
             500                 505                 510

Met Thr Thr Leu Ile Asn Thr Gln Thr Ser Asn Leu Ser Asp Val Glu
             515                 520                 525

Lys Ala Leu Gly Asn Asn Lys Val Asn Asn Gly Ala Val Asn Val Leu
             530                 535                 540

Arg Glu Asp Thr Ala Arg Leu Glu Asn Met Ile Trp Asn Arg Ala Tyr
545                 550                 555                 560

Gln Ala Ile Glu Glu Phe Asn Val Ala Arg Asn Thr Tyr Asn Asn Gln
             565                 570                 575

Ile Lys Thr Glu Thr Val Pro Val Asp Asn Asp Ile Glu Ala Ile Leu
             580                 585                 590

Ala Gly Ser Gln Ala Lys Ile Ser His Leu Asp Asn Arg Ile Gly Ala
             595                 600                 605

Arg His Met Asp Gln Ala Phe Val Ala Ser Leu Leu Glu Val Thr Glu
             610                 615                 620

Met Ser Lys Ser Ile Ser Ser Arg Ile Lys Glu
625                 630                 635

<210> SEQ ID NO 285
<211> LENGTH: 753
<212> TYPE: PRT
<213> ORGANISM: Streptococcus agalactiae

<400> SEQUENCE: 285

-continued

```
Met Lys Lys Gln Phe Leu Lys Ser Ala Ala Ile Leu Ser Leu Ala Val
  1               5                  10                  15

Thr Ala Val Ser Thr Ser Gln Pro Val Gly Ala Ile Val Gly Lys Asp
             20                  25                  30

Glu Thr Lys Leu Arg Gln Gln Leu Gly Tyr Ile Asp Ser Lys Lys Ser
         35                  40                  45

Gly Lys Lys Ile Asp Glu Arg Trp Gly Glu Lys Ile Tyr Asn Tyr Leu
 50                  55                  60

Ser Tyr Glu Leu Ile Glu Ala Asn Glu Trp Ile Asn Arg Ser Glu Phe
 65                  70                  75                  80

Gln Glu Pro Glu Tyr Arg Thr Ile Leu Ser Gly Phe Lys Asp Lys Ile
                 85                  90                  95

Asp Ser Ile Glu Tyr Tyr Leu Ile Asn Leu Ser Asn Ile Ala Lys Glu
                100                 105                 110

Asp Ala His Gln Arg Asn Ile Leu Gln Ser Leu Asp Lys Tyr Glu Lys
            115                 120                 125

Ser Gly Ile Tyr Asn Leu Asp Gln Gly Val Tyr Asn Tyr Ile Tyr Gln
        130                 135                 140

Glu Ile Ser Ser Ala Lys His Lys Phe Ser Asp Gly Val Asp Lys Ile
145                 150                 155                 160

Tyr Arg Leu Asp Ser Thr Leu Phe Pro Phe Ser Val Trp Tyr Asp Lys
                165                 170                 175

His Leu Asp Asn Asn Asp Asn Tyr Lys Asp Asn Lys Asp Phe Lys Glu
            180                 185                 190

Tyr Ile Ala Leu Leu Asn Glu Ile Thr Arg Lys Ala Arg Leu Gly Tyr
        195                 200                 205

Gln Ile Val Asn Asn His Lys Asp Gly Glu His Lys Asp Glu Ala Glu
    210                 215                 220

Ile Leu Asp Ile Leu Ile Arg Asp Ile Thr Phe Val Ser Lys Asp Ala
225                 230                 235                 240

Pro Gly Tyr Lys Tyr Ile Pro Asn Lys Arg Ile Ala Ala Lys Ile Ile
                245                 250                 255

Glu Asp Leu Asp Gly Ile Ile Asn Asp Phe Lys Asn Thr Gly Lys
            260                 265                 270

Asp Lys Pro Ser Leu Glu Lys Leu Lys Asp Thr Glu Phe His Lys Lys
        275                 280                 285

Tyr Leu Asn Ser Thr Glu Pro Tyr Ser Ile Glu Thr Asn Leu Pro Ser
    290                 295                 300

Asn Tyr Lys Glu Leu Lys Glu Lys Gln Ile Lys Leu Glu Tyr Gly
305                 310                 315                 320

Tyr Lys Lys Ser Ser Lys Ile Tyr Thr Ser Ala His Tyr Ala Leu Tyr
                325                 330                 335

Ser Glu Glu Ile Asp Ala Ala Lys Glu Leu Leu Gln Lys Val Lys Ile
            340                 345                 350

Ala Lys Asp Asn Tyr Asn Glu Ile Lys Ser Met Asn Leu Ser Pro Ser
        355                 360                 365

Ile Phe Asn Gln Tyr Leu Gln Leu Leu Gln Ile Val Ile Ser Ser Glu
    370                 375                 380

Ile Asn Leu Lys Lys Ala Leu Asp Asn Thr Val Asp Leu Pro Ile Glu
385                 390                 395                 400

Asn Asn Phe Asn Thr Leu Asp Ile Gln Tyr Asn Lys Leu Asp Thr Ala
                405                 410                 415

Ile Lys Ser Leu Arg Lys Phe Val Thr Lys Tyr Lys Gln Glu Val Arg
            420                 425                 430
```

-continued

```
Lys Ala Thr Lys Ser Tyr Ser Lys Lys Glu Leu Val Asn Ala Glu Leu
            435                 440                 445
Thr Lys Val Ile Ser Asn Asp Asn Ile Leu Leu Asp Met Gln Ala Ile
    450                 455                 460
Ser Ser Asn Tyr Gly Ser Thr Lys Lys Phe Val Tyr Ser Val Lys Arg
465                 470                 475                 480
Leu Pro Tyr Val Pro Gln Val Ile Met Thr Thr Thr Ser Asn Val Leu
                485                 490                 495
Met Pro Gln Lys Gln Val Glu Lys Val Lys Leu Leu Thr Pro Phe Thr
            500                 505                 510
Ile Ser Asn Lys Glu Val Leu Asn His Asp Ser Leu Val Glu Asn Asp
            515                 520                 525
Ala Gln Lys Gln Lys Val Glu Gln Glu Lys Thr Lys Ser Leu Ala Pro
            530                 535                 540
Gln Lys Gly Ala Val Lys Glu Gln Thr Glu Gln Lys Val Ser Gly Asn
545                 550                 555                 560
Thr Gln Glu Ile Glu Lys Lys Ser Glu Thr Val Ala Thr Pro Gln Gln
                565                 570                 575
Ser Ser Val Ala Gln Thr Ser Val Gln Gln Pro Ala Pro Val Gln Ser
            580                 585                 590
Val Val Gln Glu Ser Lys Ala Ser Gln Glu Glu Ile Asn Ala Ala His
            595                 600                 605
Asp Ala Ile Ser Ala Tyr Lys Ser Thr Val Asn Ile Ala Asn Thr Ala
            610                 615                 620
Gly Val Thr Thr Ala Glu Met Thr Thr Leu Ile Asn Thr Gln Thr Ser
625                 630                 635                 640
Asn Leu Ser Asp Val Glu Lys Ala Leu Gly Asn Asn Lys Val Asn Asn
                645                 650                 655
Gly Ala Val Asn Val Leu Arg Glu Asp Thr Ala Arg Leu Glu Asn Met
                660                 665                 670
Ile Trp Asn Arg Ala Tyr Gln Ala Ile Glu Glu Phe Asn Val Ala Arg
            675                 680                 685
Asn Thr Tyr Asn Asn Gln Ile Lys Thr Glu Thr Val Pro Val Asp Asn
            690                 695                 700
Asp Ile Glu Ala Ile Leu Ala Gly Ser Gln Ala Lys Ile Ser His Leu
705                 710                 715                 720
Asp Asn Arg Ile Gly Ala Arg His Met Asp Gln Ala Phe Val Ala Ser
                725                 730                 735
Leu Leu Glu Val Thr Glu Met Ser Lys Ser Ile Ser Ser Arg Ile Lys
            740                 745                 750
Glu
```